US011447493B2

(12) United States Patent
Kanouni et al.

(10) Patent No.: US 11,447,493 B2
(45) Date of Patent: Sep. 20, 2022

(54) INHIBITORS OF CYCLIN-DEPENDENT KINASES

(71) Applicant: Kinnate Biopharma Inc., San Diego, CA (US)

(72) Inventors: Toufike Kanouni, Rancho Santa Fe, CA (US); Lee Arnold, Rancho Santa Fe, CA (US); Stephen W. Kaldor, San Diego, CA (US); Eric A. Murphy, San Marcos, CA (US)

( * ) Notice: Subject to any disclaimer, the term of this patent is extended or adjusted under 35 U.S.C. 154(b) by 18 days.

(21) Appl. No.: 17/052,162

(22) PCT Filed: May 2, 2019

(86) PCT No.: PCT/US2019/030409
§ 371 (c)(1),
(2) Date: Oct. 30, 2020

(87) PCT Pub. No.: WO2019/213403
PCT Pub. Date: Nov. 7, 2019

(65) Prior Publication Data
US 2021/0053969 A1 Feb. 25, 2021

Related U.S. Application Data

(60) Provisional application No. 62/666,024, filed on May 2, 2018.

(51) Int. Cl.
| | | |
|---|---|---|
| C07D 471/04 | (2006.01) |
| C07D 401/12 | (2006.01) |
| C07D 403/12 | (2006.01) |
| C07D 413/14 | (2006.01) |
| A61K 9/00 | (2006.01) |
| A61K 9/08 | (2006.01) |
| A61K 9/48 | (2006.01) |
| C07D 401/14 | (2006.01) |

(52) U.S. Cl.
CPC .......... *C07D 471/04* (2013.01); *A61K 9/0019* (2013.01); *A61K 9/08* (2013.01); *A61K 9/4825* (2013.01); *C07D 401/12* (2013.01); *C07D 401/14* (2013.01); *C07D 403/12* (2013.01); *C07D 413/14* (2013.01)

(58) Field of Classification Search
CPC .. C07D 471/04; C07D 401/12; C07D 401/14; C07D 403/12; C07D 413/14
See application file for complete search history.

(56) References Cited

U.S. PATENT DOCUMENTS

| | | | |
|---|---|---|---|
| 5,846,514 A | 12/1998 | Foster et al. |
| 6,334,997 B1 | 1/2002 | Foster et al. |
| 2007/0004763 A1 | 1/2007 | Baindur et al. |
| 2014/0309184 A1 | 10/2014 | Rocconi et al. |
| 2014/0309249 A1 | 10/2014 | Gray et al. |
| 2015/0087664 A1 | 3/2015 | Blake et al. |
| 2016/0264552 A1 | 9/2016 | Ciblat et al. |
| 2020/0024266 A1 | 1/2020 | Kanouni et al. |
| 2021/0130340 A1 | 5/2021 | Kanouni et al. |

FOREIGN PATENT DOCUMENTS

| | | |
|---|---|---|
| WO | WO-2015058126 A1 | 4/2015 |
| WO | WO-2015058163 A2 | 4/2015 |
| WO | WO-2015124941 A1 | 8/2015 |
| WO | WO-2016073620 A1 | 5/2016 |
| WO | WO-2016105528 A2 | 6/2016 |
| WO | WO-2016160617 A2 | 10/2016 |
| WO | WO-2016193939 A1 | 12/2016 |
| WO | WO-2016201370 A1 | 12/2016 |
| WO | WO-2016210296 A1 | 12/2016 |
| WO | WO-2017044858 A2 | 3/2017 |
| WO | WO-2017163076 A1 | 9/2017 |
| WO | WO-2018118793 A1 | 6/2018 |
| WO | WO-2019035866 A1 | 2/2019 |
| WO | WO-2019058132 A1 | 3/2019 |
| WO | WO-2019213403 A1 | 11/2019 |
| WO | WO-2020006497 A1 | 1/2020 |
| WO | WO-2021011796 A1 | 1/2021 |
| WO | WO-2021138215 A1 | 7/2021 |

OTHER PUBLICATIONS

Golub et al. Science, vol. 286, Oct. 15, 1999, pp. 531-537.*
Ali et al. The development of a selective cyclin-dependent kinase inhibitor that shows antitumor activity. Cancer Res. 69(15):6208-6215 (2009).
Bajrami et al. Genome-wide profiling of genetic synthetic lethality identifies CDK12 as a novel determinant of PARP1/2 inhibitor sensitivity. Cancer Res. 74(1):287-297 (2014).
Berge et al. Pharmaceutical Salts. Journal of Pharmaceutical Sciences 66(1):1-19 (Jan. 1977).
Berro et al. CDK13, a new potential human immunodeficiency virus type 1 inhibitory factor regulating viral mRNA splicing. J. Virol. 82:7155-7166 (2008).
Brägelmann et al. Systematic Kinase Inhibitor Profiling Identifies CDK9 as a Synthetic Lethal Target in NUT Midline Carcinoma. Cell Rep. 20(12):2833-2845 (2017).
Cancer Genome Atlas Network, Comprehensive molecular portraits of human breast tumours, Nature, 490:61-70 (2012).
Cancer Genome Atlas Research Network, Integrated genomic analyses of ovarian carcinoma, Nature, 474:609-615 (2011).
Cao et al. Phylogenetic analysis of CDK and cyclin proteins in premetazoan lineages. BMC Evol. Biol. 14:10-26 (2014).
Cayrol et al. THZ1 targeting CDK7 suppresses STAT transcriptional activity and sensitizes T-cell lymphomas to BCL2 inhibitors. Nature Commun. 8:14290 (2017).

(Continued)

*Primary Examiner* — Samira J Jean-Louis
(74) *Attorney, Agent, or Firm* — Wilson Sonsini Goodrich & Rosati

(57) ABSTRACT

Provided herein are inhibitors of cyclin-dependent kinases (CDKs), pharmaceutical compositions comprising said compounds, and methods for using said compounds for the treatment of diseases.

19 Claims, No Drawings

(56) References Cited

OTHER PUBLICATIONS

Cerami et al. The eBio cancer genomics portal: an open platform for exploring multidimensional cancer genomics data. Cancer Discov. 2:401-404 (2012).
Chemical Structure Search. (51 pgs.) (2018).
Chen et al. Cdk12 and Cdk13 regulate axonal elongation through a common signaling pathway that modulates Cdk5 expression. Exp. Neurol. 261:10-21 (2014).
Christensen et al. Targeting transcriptional addictions in small cell lung cancer with a covalent CDK7 inhibitor. Cancer Cell 26(6):909-922 (2014).
Coleman et al. Chapter 17. Chemical Inhibitors of Cyclin-dependent Kinases. Annual Reports in Medicinal Chemistry 32:171-179 (1997).
Dey et al. Voruciclib, a clinical stage oral CDK9 inhibitor, represses MCL-1 and sensitizes high-risk Diffuse Large B-cell Lymphoma to BCL2 inhibition. Sci. Rep. 7(1):18007 (2017).
Enke et al. The CDK-activating kinase (Cak1p) from budding yeast has an unusual ATP-binding pocket. J. Biol. Chem. 274(4):1949-1956 (1999).
Evan et al. Re-engineering the Pancreas Tumor Microenvironment: A "Regenerative Program" Hacked. Clin. Cancer Res. 23(7):1647-1655 (2017).
Evans. Synthesis of radiolabeled compounds. J Radioanal Chem 64(1-2):9-32 (1981).
Ficarra et al. Leveraging Gas-Phase Fragmentation Pathways for Improved Identification and Selective Detection of Targets Modified by Covalent Probes. Anal. Chem. 88(24):12248-12254.
Gao et al. Overcoming Resistance to the THZ Series of Covalent Transcriptional CDK Inhibitors. Cell Chem. Biol. 25(2):135-142.
Greenall et al. Cyclin-dependent kinase 7 is a therapeutic target in high-grade glioma. Oncogenesis 6(5):e336 (2017).
Greifenberg et al. Structural and Functional Analysis of the Cdk13/Cyclin K Complex. Cell Rep. 14:320-331 (2016).
Hamilton et al. Heterozygous mutations affecting the protein kinase domain of CDK13 cause a syndromic form of developmental delay and intellectual disability. J. Med. Genet. 55(1):28-38 (2017).
He et al. Cdk7 Is Required for Activity-Dependent Neuronal Gene Expression, Long-Lasting Synaptic Plasticity and Long-Term Memory. Front. Mol. Neurosci. 10:365-377 (2017).
Hong et al. CDK7 inhibition suppresses rheumatoid arthritis inflammation via blockage of NF-κB activation and IL-1 p/IL-6 secretion. J. Cell. Mol. Med. 22:1292-1301 (2017).
Iniguez et al. EWS/FLI Confers Tumor Cell Synthetic Lethality to CDK12 Inhibition in Ewing Sarcoma. Cancer Cell 33(2):202-216 (2018).
Iversen et al. A comparison of assay performance measures in screening assays: signal window, Z' factor, and assay variability ratio. J. Biomol. Screen. 3:247-252 (2006).
Johnson et al. CDK12 Inhibition Reverses De Novo and Acquired PARP Inhibitor Resistance in BRCA Wild-Type and Mutated Models of Triple-Negative Breast Cancer. Cell Rep. 17(9):2367-2381 (2016).
Kabalka et al. The Synthesis of Radiolabeled Compounds via Organometallic Intermediates. Tetrahedron 45(21):6601-6621 (1989).
Kalan et al. Activation of the p53 Transcriptional Program Sensitizes Cancer Cells to Cdk7 Inhibitors. Cell Reports 21(2):467-481 (2017).
Kandoth et al. Mutational landscape and significance across 12 major cancer types. Nature 502(7471):333-339 (2013).
Kwiatkowski et al. Targeting transcription regulation in cancer with a covalent CDK7 inhibitor. Nature 511(7511):616-620 (2014).
Lam et al. Targeting RNA transcription and translation in ovarian cancer cells with pharmacological inhibitor CDKI-73. Oncotarget 5:7691-7704 (2014).
Li et al. Therapeutic Rationale to Target Highly Expressed CDK7 Conferring Poor Outcomes in Triple-Negative Breast Cancer. Cancer Res. 77(14):3834-3845 (2017).
Lim et al. Cdks, cyclins and CKIs: roles beyond cell cycle regulation. Development 140:3079-3093 (2013).
Lucking. Identification of Atuveciclib (BAY 1143572), the First Highly Selective, Clinical PTEFb/CDK9 Inhibitor for the Treatment of Cancer. ChemMedChem. 12(21):1776-1793 (2017).
Malumbres. Cyclin-dependent kinases. Genome Biol. 15(6):122-132 (2014).
Mertins et al. Proteogenomics connects somatic mutations to signalling in breast cancer. Nature 534(7605):55-62 (2016).
Nagaraja et al. Transcriptional Dependencies in Diffuse Intrinsic Pontine Glioma. Cancer Cell31(5):635-652 (2017).
Naidoo et al. Evaluation of CDK12 Protein Expression as a Potential Novel Biomarker for DNA Damage Response-Targeted Therapies in Breast Cancer. Mol. Cancer Ther. 17(1):306-315 (2017).
Paculova et al. The emerging roles ofCDK12 in tumorigenesis. Cell Div. 12 :7-17 (2017).
Pang et al. miR-206 inhibits the growth of hepatocellular carcinoma cells via targeting CDK9. Cancer Med. 6(10):2398-2409 (2017).
PCT/US2019/030409 International Search Report and Written Opinion dated Jul. 2, 2019.
PCT/US2019/039959 International Invitation to Pay Additional Fees dated Aug. 19, 2019.
PCT/US2019/039959 International Search Report and Written Opinion dated Oct. 29, 2019.
PCT/US2020/042371 International Search Report and Written Opinion dated Oct. 16, 2020.
PubChem CID 118976958 https://pubchem.ncbi.nlm.nih.gov/compound/118976958 (2016).
PubChem CID 153314224 https://pubchem.ncbi.nlm.nih.gov/compound/153314224 (2020).
PubChem CID 68429631. Create date Nov. 30, 2012 (7 pgs).
Tien et al. CDK12 regulates alternative last exon mRNA splicing and promotes breast cancer cell invasion. Nucleic Acids Res. 45(11):6698-6716 (2017).
U.S. Appl. No. 16/457,400 Office Action dated Apr. 17, 2020 .
U.S. Appl. No. 16/457,400 Office Action dated Nov. 27, 2019.
Zhang et al. A Simple Statistical Parameter for Use in Evaluation and Validation of High Throughput Screening Assays. J. Biomol. Screen. 2:67-73 (1999).
Zhang et al. Covalent targeting of remote cysteine residues to develop CDK12 and CDK13 inhibitors. Nature Chem. Biol. 12(10):876-884 (2016).
PCT/US2020/066967 International Search Report and Written Opinion dated Mar. 15, 2021.
PubChem SID 325943755 [https://pubchem.ncbi.nlm.nih.gov/substance/325943755] (2017).
Golub et al. Molecular Classification of Cancer: Class Discovery and Class Prediction by Gene Expression Monitoring. Science 286:531-537 (1999).
U.S. Appl. No. 17/052,162 Office Action dated Mar. 31, 2022.
U.S. Appl. No. 17/095,672 Office Action dated Nov. 17, 2021.

\* cited by examiner

INHIBITORS OF CYCLIN-DEPENDENT KINASES

CROSS REFERENCE TO RELATED APPLICATIONS

This application is the U.S. National Stage application of International Application No. PCT/US2019/030409, filed on May 2, 2019, and claims the benefit of U.S. Provisional Application No. 62/666,024, filed on May 2, 2018, all of which are incorporated by reference herein in their entireties.

BACKGROUND

Cyclin-dependent kinases (CDKs) are a family of multifunctional enzymes that modify various protein substrates involved in cell cycle progression. Specifically, CDKs phosphorylate their substrates by transferring phosphate groups from ATP to specific stretches of amino acids in the substrates. The deregulation of CDKs is involved in the etiology of many human diseases, including cancers.

BRIEF SUMMARY OF THE INVENTION

Provided herein are inhibitors of cyclin-dependent kinases (CDKs), pharmaceutical compositions comprising said compounds, and methods for using said compounds for the treatment of diseases.

One embodiment provides a compound, or pharmaceutically acceptable salt or solvate thereof, having the structure of Formula (I):

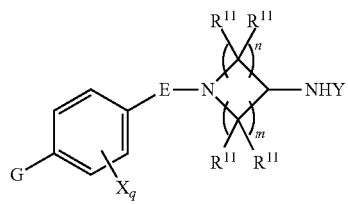

(I)

wherein,
E is selected from a bond, —SO$_2$—, —C(O)—, —CH$_2$—, —CH(R$^4$)—, or —C(R$^4$)$_2$—;
G is selected from a group having the structure:

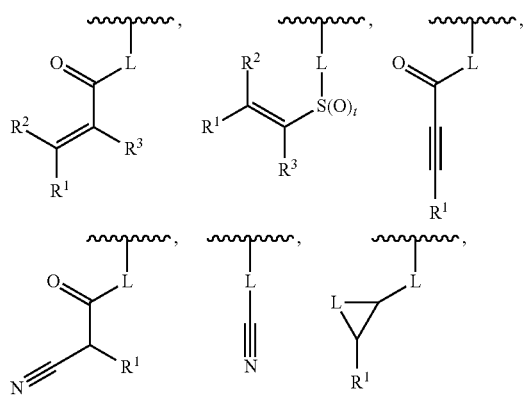

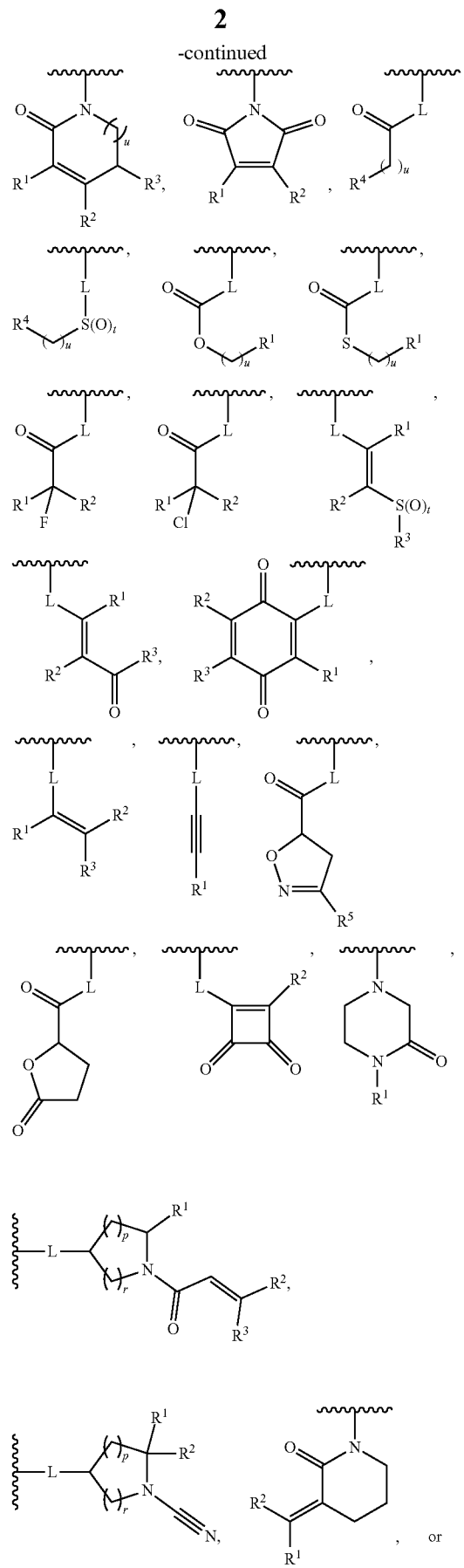

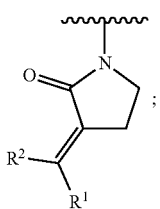

wherein,
L is O, NH, or N (optionally substituted C1-C4 alkyl);
t is 0, 1, or 2;
u is 1, or 2;
p is 0, 1, or 2;
r is 0, 1, or 2;
$R^1$ is selected from hydrogen, optionally substituted C1-C4 alkyl, or optionally substituted heterocyclylalkyl;
$R^2$ is selected from hydrogen, or optionally substituted C1-C4 alkyl;
$R^3$ is selected from hydrogen, —CN, or optionally substituted C1-C4 alkyl;
each $R^4$ is independently selected from optionally substituted C1-C4 alkyl, or optionally substituted heterocyclylalkyl;
$R^5$ is optionally substituted C1-C4 alkyl, or optionally substituted heterocyclylalkyl;
each $R^{11}$ is independently selected from hydrogen, halogen, optionally substituted C1-C6 alkyl, or both $R^{11}$ groups form an oxo;
q is 0, 1, 2, or 3; n is 0, 1, 2, or 3; m is 0, 1, 2, or 3;
X is halogen, optionally substituted C1-C4 alkyl, or optionally substituted C1-C4 alkoxy;
Y is a group selected from:

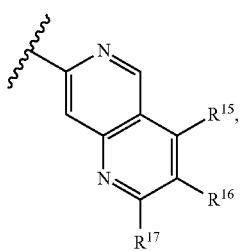

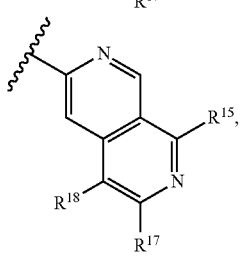

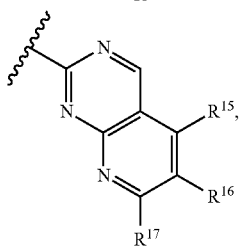

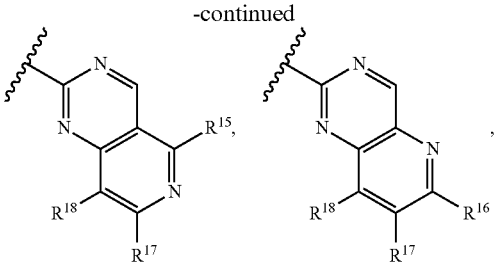

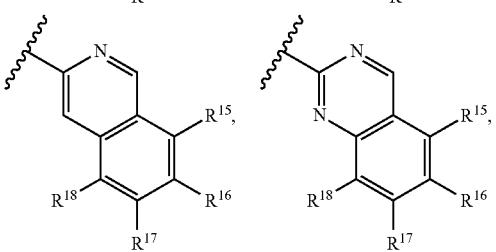

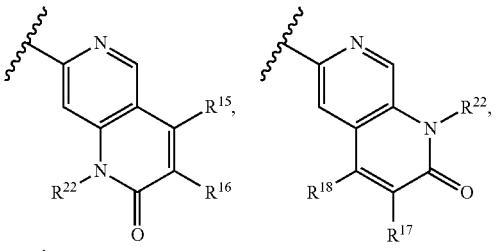

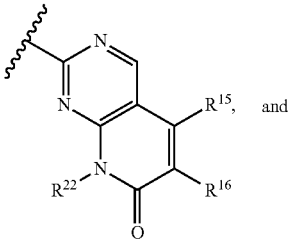

and

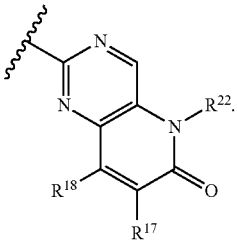

wherein,
$R^{15}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N$(R^{22})_2$, —SO$_2R^{21}$, —N$(R^{22})$SO$_2R^{21}$, —SO$_2$N$(R^{22})_2$, —N$(R^{22})$SO$_2$N$(R^{22})_2$, —CON$(R^{22})_2$, —N$(R^{22})$CO$_2R^{21}$, —N$(R^{22})$CON$(R^{22})_2$, —N$(R^{22})$COR$^{21}$, —OC(O)N$(R^{22})_2$, —OSO$_2$N$(R^{22})_2$, or —N$(R^{22})$SO$_3R^{21}$;
$R^{16}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

R$^{17}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

R$^{18}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

each R$^{21}$ is independently selected from alkyl, cycloalkyl, cycloalkylalkyl, aryl, aralkyl, heterocyclyl, heterocyclylalkyl, heteroaryl, or heteroarylalkyl; and each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

One embodiment provides a compound, or pharmaceutically acceptable salt or solvate thereof, having the structure of Formula (II):

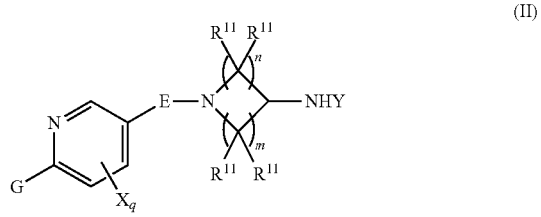

(II)

wherein,

E is selected from a bond, —SO$_2$—, —C(O)—, —CH$_2$—, —CH(R$^4$)—, or —C(R$^4$)$_2$—;

G is selected from a group having the structure:

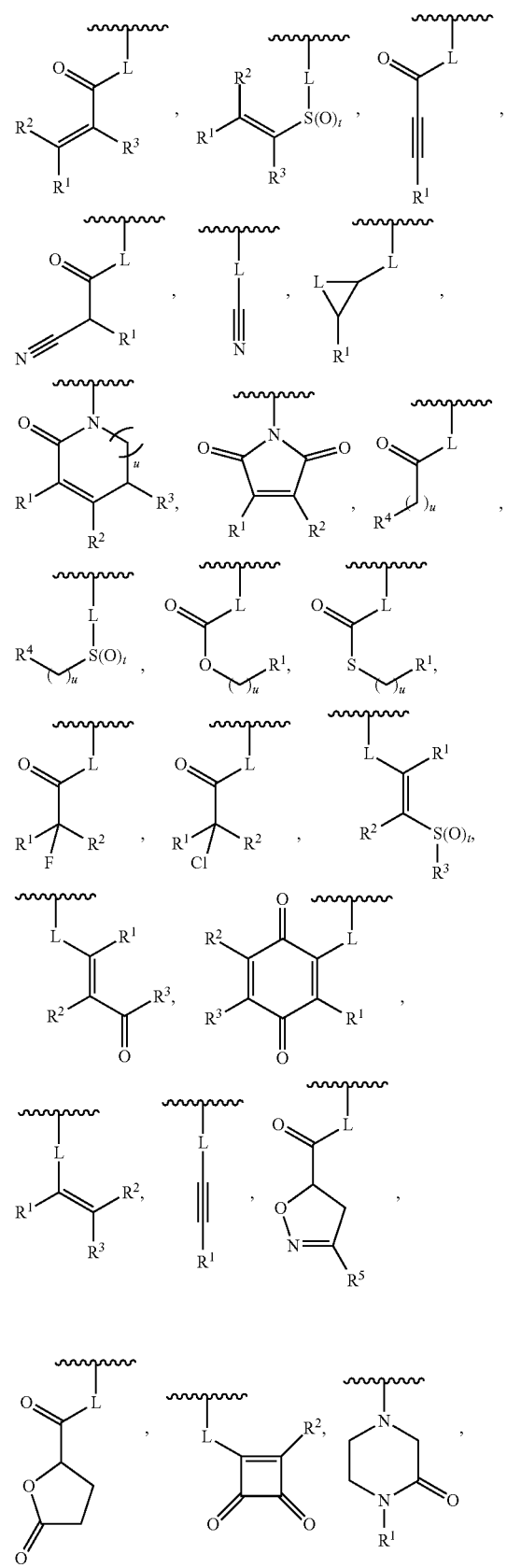

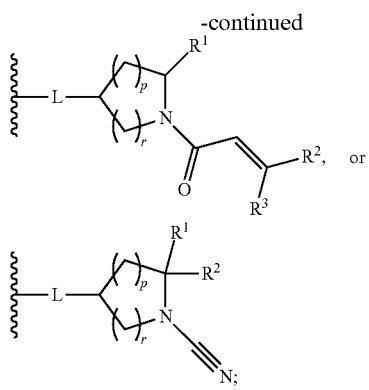

wherein,

L is O, NH, or N (optionally substituted C1-C4 alkyl);

t is 0, 1, or 2;

u is 1 or 2;

p is 0, 1, or 2;

r is 0, 1, or 2;

$R^1$ is selected from hydrogen, optionally substituted C1-C4 alkyl, or optionally substituted heterocyclylalkyl;

$R^2$ is selected from hydrogen, or optionally substituted C1-C4 alkyl;

$R^3$ is selected from hydrogen, —CN, or optionally substituted C1-C4 alkyl;

each $R^4$ is independently selected from optionally substituted C1-C4 alkyl, or optionally substituted heterocyclylalkyl;

$R^5$ is optionally substituted C1-C4 alkyl, or optionally substituted heterocyclylalkyl;

each $R^{11}$ is independently selected from hydrogen, halogen, optionally substituted C1-C6 alkyl, or both $R^{11}$ groups form an oxo;

q is 0, 1, or 2; n is 0, 1, 2, or 3; m is 0, 1, 2, or 3;

X is halogen, optionally substituted C1-C4 alkyl, or optionally substituted C1-C4 alkoxy;

Y is a group selected from:

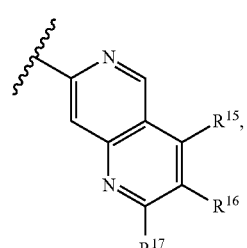 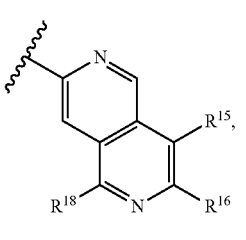

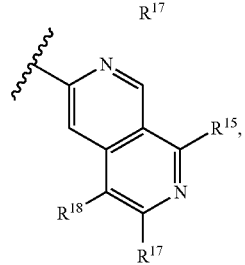

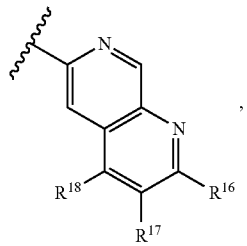

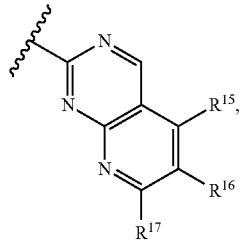

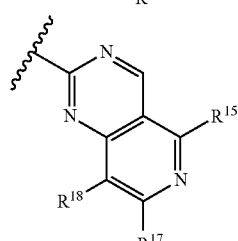

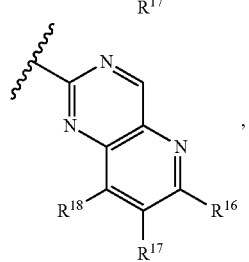

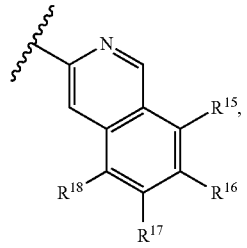

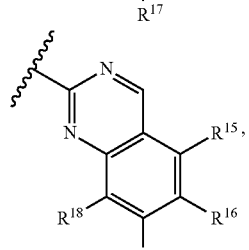

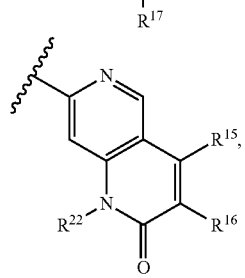

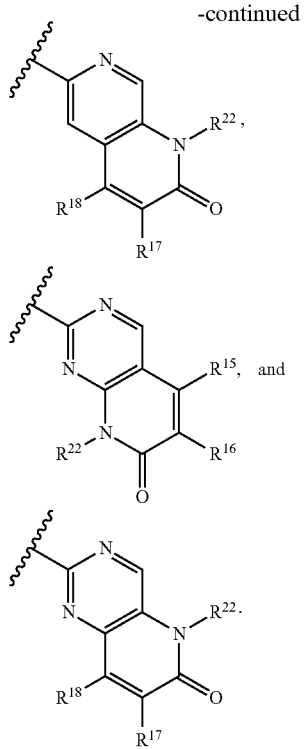

wherein,

R$^{15}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

R$^{16}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

R$^{17}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

R$^{18}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

each R$^{21}$ is independently selected from alkyl, cycloalkyl, cycloalkylalkyl, aryl, aralkyl, heterocyclyl, heterocyclylalkyl, heteroaryl, or heteroarylalkyl; and each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

One embodiment provides a pharmaceutical composition comprising a compound of Formula (I), or pharmaceutically acceptable salt or solvate thereof, and at least one pharmaceutically acceptable excipient.

One embodiment provides a method of treating a disease or disorder in a patient in need thereof comprising administering to the patient a compound of Formula (I), or pharmaceutically acceptable salt or solvate thereof. Another embodiment provides the method wherein the disease or disorder is cancer.

One embodiment provides a pharmaceutical composition comprising a compound of Formula (II), or pharmaceutically acceptable salt or solvate thereof, and at least one pharmaceutically acceptable excipient.

One embodiment provides a method of treating a disease or disorder in a patient in need thereof comprising administering to the patient a compound of Formula (II), or pharmaceutically acceptable salt or solvate thereof. Another embodiment provides the method wherein the disease or disorder is cancer.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises two carbon atoms (e.g., $C_2$ alkenylene). In other embodiments, an alkenylene comprises five to eight carbon atoms (e.g., $C_5$-$C_8$ alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

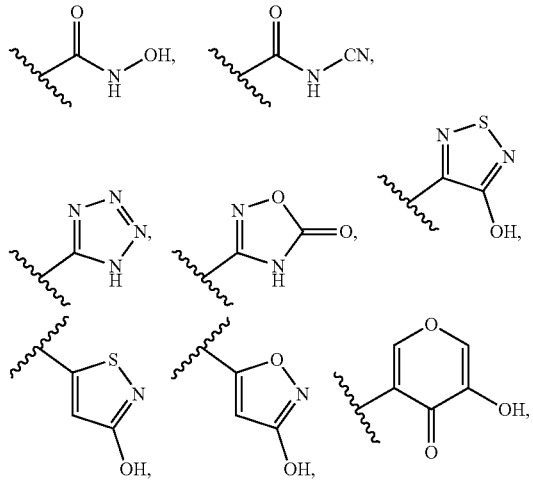

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^a$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —R$^c$-heterocyclyl where R$^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—R$^c$-heterocyclyl where R$^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{35}S$, $^{36}S$, $^{35}Cl$, $^{37}Cl$, $^{79}Br$, $^{81}Br$, $^{125}I$ are all contemplated. In some embodiments, isotopic substitution with $^{18}F$ is contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [Curr., Pharm. Des., 2000; 6(10)] 2000, 110 pp; George W.; Varma, Rajender S. The Synthesis of Radiolabeled Compounds via Organometallic Intermediates, Tetra-

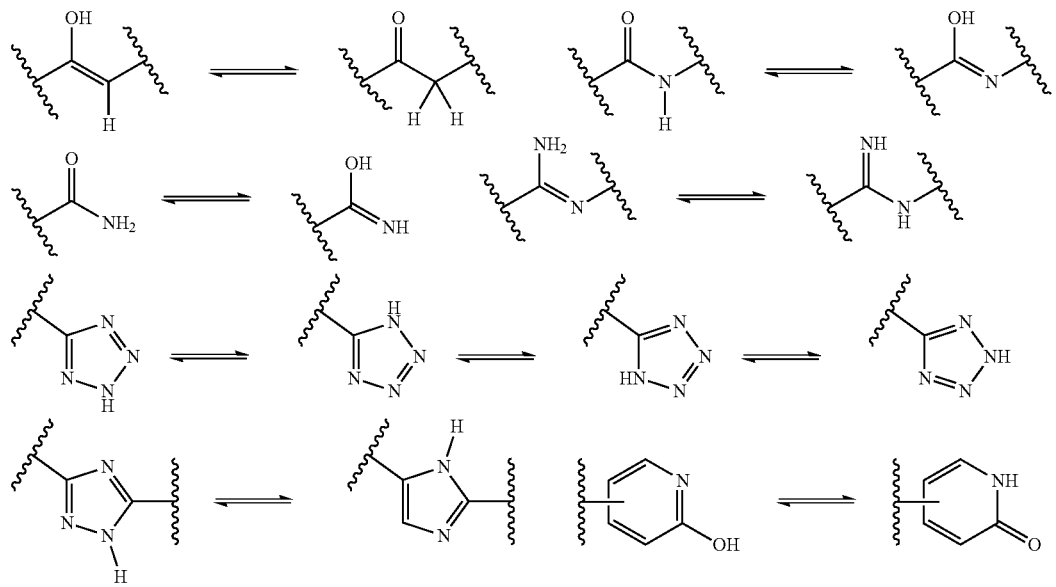

hedron, 1989, 45(21), 6601-21; and Evans, E. Anthony. Synthesis of radiolabeled compounds, J. Radioanal. Chem., 1981, 64(1-2), 9-32.

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-$d_3$ ($CD_3I$), are readily available and may be employed to transfer a deuterium-substituted carbon atom under nucleophilic substitution reaction conditions to the reaction substrate. The use of $CD_3I$ is illustrated, by way of example only, in the reaction schemes below.

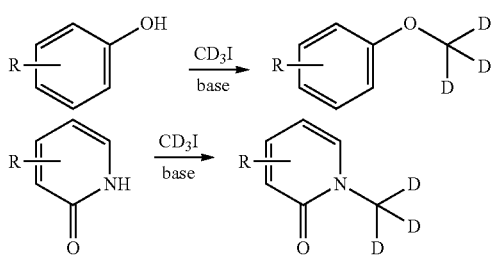

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

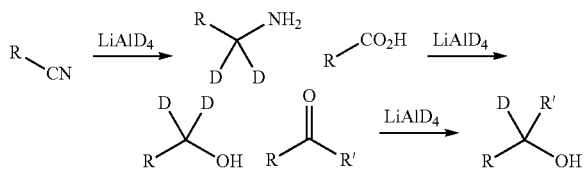

Deuterium gas and palladium catalyst are employed to reduce unsaturated carbon-carbon linkages and to perform a reductive substitution of aryl carbon-halogen bonds as illustrated, by way of example only, in the reaction schemes below.

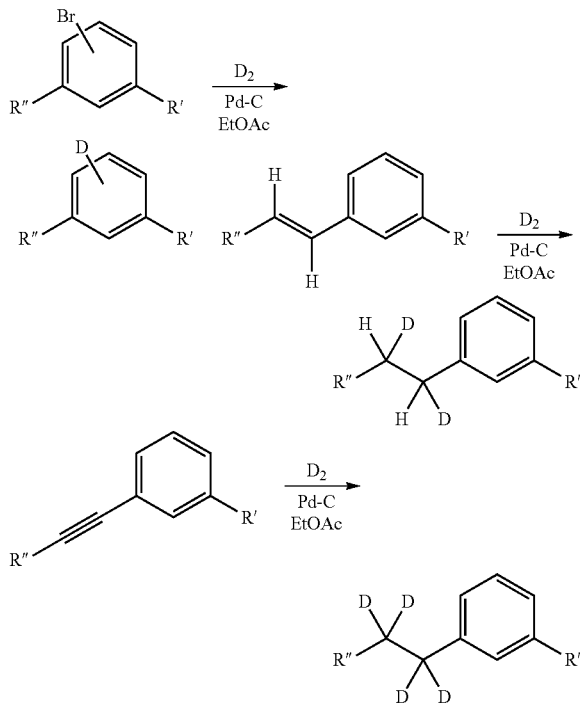

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the inhibitor of cyclin-dependent kinases (CDKs) compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein optionally exist in either unsolvated as well as solvated forms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

Cyclin-Dependent Kinases

Cyclin-dependent kinases (CDKs) are a family of serine/threonine protein kinases that are known to function in the processes of cell cycle regulation, metabolism, gene transcription, RNA processing, and DNA repair, with each CDK playing a distinct role (Malumbres, M., 2014, Genome Biol. 15(6), 122-132; Lim et al., 2013, Development 140, 3079-3093). Inhibition of CDKs has long been of therapeutic interest in the treatment of conditions characterized by cellular hyperproliferation, such as cancer, psoriasis, and fungal infections (Coleman, K. G. et al., 1997, Annual Reports in Medicinal Chemistry 32, 171-179).

CDKs are characterized by as being dependent on one or more separate catalytic cyclin subunits in order to carry out specific functions (Malumbres, 2014). Structurally, CDKs comprise a conserved catalytic core containing an ATP-binding pocket, a cyclin binding domain, and an activating T-loop motif (Coleman, 1997; Enke et al., 1999, J. Biol. Chem. 274(4), 1949-1956).

Human cells are known to have at least 20 CDKs and 29 cyclins, which can be grouped into 8 subfamilies (Lim, 2013; Cao et al., 2014, BMC Evol. Biol. 14, 10-26). Therapies known in the art include selective inhibition of specific CDKs.

CDK7 and CDK9 are part of the subfamily of transcriptional CDKs which regulate gene transcription via the phosphorylation of the carboxy-terminal domain of RNA polymerase II (Lucking, U., 2017, Chem Med Chem. 12(21), 1776-1793). Inhibitors of CDK7 and CDK9 are recognized in the art as being therapeutically beneficial against various types of cancers.

CDK7 is known to be required for activity-dependent neuronal gene expression, synaptic plasticity, and long-term memory (He et al., 2017, Front. Mol. Neurosci. 10, 365-377). CDK7 inhibition is known to suppress rheumatoid arthritis inflammation via blocking NF-kB activation and IL-1β/IL-6 secretion (Hong et al., 2017, J. Cell. Mol. Med. 22, 1292-1301), and has been shown to disrupt the cell cycle of high-grade glioma (Greenall et al., 2017, Oncogenesis 6(5), e336). The CDK7 inhibitor THZ1 has been shown to significantly affect transcription in T cell leukemia, neuroblastoma, small-cell lung cancer and triple-negative breast cancer cells in vitro (Gao et al., 2017, Cell Chem. Biol. 25, 1-8; Kwiatkowski et al., 2014, Nature 511(7511), 616-620). When screened against a panel of 1,151 cancer cell lines, a THZ1 concentration less than 200 nM exhibited an IC50 in 52% of those lines (Kwiatkowski, 2014, see Table 3a).

CDK9 is known to regulate the expression of antiapoptotic proteins for the survival of cancer cells (Pang et al., 2017, Cancer Med. 6(10), 2398-2409) and is known to regulate the DNA damage response in complex with cyclin-K (Lim, 2013). Inhibitors of CDK9 have been shown to repress transcription of genes associated with B-cell lymphoma, the most common form of non-Hodgkin lymphoma (Dey et al., 2017, Sci. Rep. 7(1), 18007), hepatocellular carcinoma (Pang, 2017), NUT midline carcinoma (Bragelmann et al., 2017, Cell Rep. 20(12), 2833-2845), ovarian cancer, epithelial carcinoma, colorectal carcinoma, cervical carcinoma, prostate adenocarcinoma, breast adenocarcinoma, and pancreatic carcinoma (Lam et al., 2014, Oncotarget 5, 7691-7704).

CDK12 and CDK13 are transcription-associated CDKs, and are known to regulate RNA polymerase II transcription in complex with cyclin K (Lim, 2013), as well as axonal and transcriptional elongation (Chen et al., 2014, Exp. Neurol. 261, 10-21; Paculova et al., 2017, Cell Div. 12, 7-17).

It has been suggested that CDK12 has oncogenic properties, and is mutated or overexpressed in various types of cancer, leading to dysregulation of cell proliferation (Paculova, 2017). CDK12 inhibitors have been found to reduce gene expression in BRCA cells (Johnson et al., 2016, Cell Rep. 17(9), 2367-2381). Mutations of CDK12 have been shown to disrupt DNA repair, contributing to hyperproliferation and the pathogenesis of breast tumor cells (Tien et al., 2017, Nucleic Acids Res. 45(11), 6698-6716). It is estimated that CDK12 mutations are present in 13% of breast cancers and 5% of ovarian cancers (Tien, 2017; Cerami et al., 2012, Cancer Discov. 2, 401-404; Cancer Genome Atlas Research Network, 2011, Nature, 474, 609-615; Kandoth et al., 2013, Nature 502, 333-339; Cancer Genome Atlas Network, 2012, Nature 490, 61-70).

CDK13 is known to regulate processes associated with growth signaling (Greifenberg et al., 2016, Cell Rep. 14, 320-331). CDK13 mutations affecting the protein kinase domain have been linked to congenital heart disease, developmental delay and intellectual disability (Hamilton et al., 2017, J. Med. Genet. 55(1), 28-38). CDK13 is known to interact with the splicing factor SRSF1 and regulate alternative splicing of HIV mRNA (Berro et al., 2008, J. Virol. 82, 7155-7166).

CDK inhibitory compounds have been described in the literature. See, for example: Gao et al., 2018, Cell Chem. Biol. 25(2), 135-142; WO 2017/044858; WO 2016/210296; WO 2016/201370; Ficarro et al., 2016, Anal. Chem. 88(24), 12248-12254; WO 2016/160617; Zhang et al., 2016, Nature Chem. Biol. 12(10), 876-884; WO 2016/105528; WO 2015/058126; and WO 2015/058163. Other examples include: WO 2015/124941; Ali et al., 2009, Cancer Res. 69(15), 6208-6215; WO 2016/193939; Bajrami et al., 2014, Cancer Res. 74(1), 287-297; Li et al., 2017, Cancer Res. 77(14), 3834-3845; Cayrol et al., 2017, Nature Commun. 8:14290, 1-11; Johnson et al., 2016, Cell Reports 17(9), 2367-2381; Kalan et al., 2017, Cell Reports 21(2), 467-481; Christensen et al., 2014, Cancer Cell 26(6), 909-922; Iniguez et al., 2018, Cancer Cell 33(2), 202-216; Mertins et al., 2016, Nature 534(7605), 55-62; Nagaraja et al., 2017, Cancer Cell 31(5), 635-652; Naidoo et al., 2017, Mol. Cancer Ther. 17(1), 306-315; Paculova et al., 2017, Cell Div. 12:7, 1-10; and Evan et al., 2017, Clin. Cancer Res. 23(7), 1647-1655.

Based on the role of CDKs in the processes of cell cycle regulation, metabolism, gene transcription, RNA processing, and DNA repair, compounds which alter CDKs activity are considered to be useful in treating or preventing various disorders, including cancer. In some embodiments, described herein is a small molecule inhibitor of cyclin-dependent kinases (CDKs). In some embodiments, described herein is a pharmaceutical composition comprising a small molecule inhibitor of cyclin-dependent kinases (CDKs). In other embodiments, a small molecule inhibitor of cyclin-dependent kinases (CDKs) is used to treat or prevent a disease or condition in a subject in need thereof.

In some embodiments, a heteroaromatic CDK inhibitory compound as described herein is used to treat or prevent cancer in a subject in need thereof. In some embodiments, a pharmaceutical composition comprising a heteroaromatic CDK inhibitory compound as described herein is used to treat or prevent cancer in a subject in need thereof. In some embodiments, disclosed herein is a method of treating cancer comprising administering to a subject in need thereof a therapeutically effective amount of a heteroaromatic CDK inhibitory compound as described herein. In some embodiments, disclosed herein is a method of treating cancer comprising administering to a subject in need thereof a therapeutically effective amount of a pharmaceutical composition comprising a heteroaromatic CDK inhibitory compound as described herein. In some embodiments, disclosed herein is a method of treating cancer comprising administering to a subject having been previously diagnosed with cancer a therapeutically effective amount of a heteroaromatic CDK inhibitory compound as described herein.

Myotonic dystrophy is a rare genetic disorder that affects muscle function. Symptoms include gradually worsening muscle loss and weakness. There are two main types: type 1 (DM1) due to mutations in the dystrophia myotonica protein kinase (DMPK) gene, and type 2 (DM2) due to mutations in the CNBP gene. Myotonic dystrophy type 1 is caused by a repeat expansion mutation in the 3'-untranslated region of the DMPK gene. When expressed the DMPK expansion transcripts remain in the nucleus where they form foci. Hayes et al. (WO 2017/163076 and WO 2019/058132) have found CDK12 inhibitors useful in the treatment of disorders caused by the generation of RNA repeat expansion transcripts.

In some embodiments, a heteroaromatic CDK inhibitory compound is a heteroaromatic CDK7, CDK9, CDK12, and CDK13 inhibitory compound. In some embodiments, a heteroaromatic CDK inhibitory compound is a heteroaromatic CDK7 inhibitory compound. In some embodiments, a heteroaromatic CDK inhibitory compound is a heteroaromatic CDK9 inhibitory compound. In some embodiments, a heteroaromatic CDK inhibitory compound is a heteroaromatic CDK12 inhibitory compound. In some embodiments, a heteroaromatic CDK inhibitory compound is a heteroaromatic CDK13 inhibitory compound. In some embodiments, a heteroaromatic CDK inhibitory compound is a heteroaromatic CDK7 and CDK9 inhibitory compound. In some embodiments, a heteroaromatic CDK inhibitory compound is a heteroaromatic CDK7 and CDK12 inhibitory compound. In some embodiments, a heteroaromatic CDK inhibitory compound is a heteroaromatic CDK7 and CDK13 inhibitory compound. In some embodiments, a heteroaromatic CDK inhibitory compound is a heteroaromatic CDK9 and CDK12 inhibitory compound. In some embodiments, a heteroaromatic CDK inhibitory compound is a heteroaromatic CDK9 and CDK13 inhibitory compound. In some embodiments, a heteroaromatic CDK inhibitory compound is a heteroaromatic CDK12 and CDK13 inhibitory compound. In some embodiments, a heteroaromatic CDK inhibitory compound is a heteroaromatic CDK7, CDK9, and CDK12 inhibitory compound.

In some embodiments, a heteroaromatic CDK inhibitory compound is a heteroaromatic CDK7, CDK9, and CDK13 inhibitory compound. In some embodiments, a heteroaromatic CDK inhibitory compound is a heteroaromatic CDK7, CDK12, and CDK13 inhibitory compound. In some embodiments, a heteroaromatic CDK inhibitory compound is a heteroaromatic CDK9, CDK12, and CDK13 inhibitory compound.

Heteroaromatic CDK Inhibitory Compounds

In one aspect, provided herein is a heteroaromatic CDK inhibitory compound.

One embodiment provides a compound, or pharmaceutically acceptable salt or solvate thereof, having the structure of Formula (I):

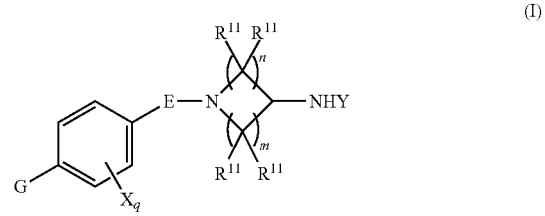

wherein,
E is selected from a bond, —SO$_2$—, —C(O)—, —CH$_2$—, —CH(R$^4$)—, or —C(R$^4$)$_2$—;
G is selected from a group having the structure:

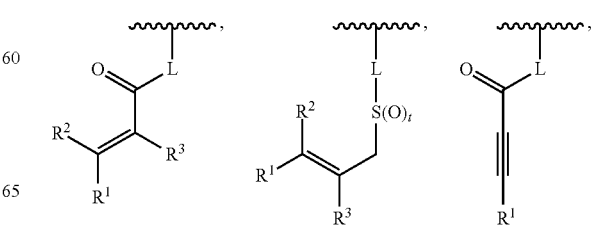

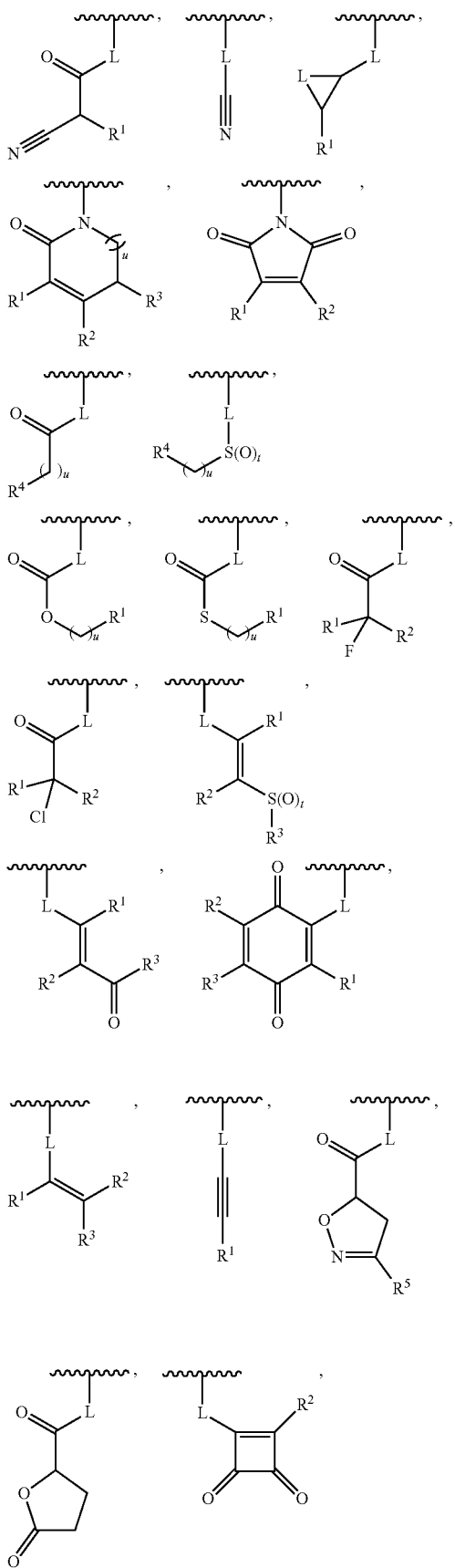

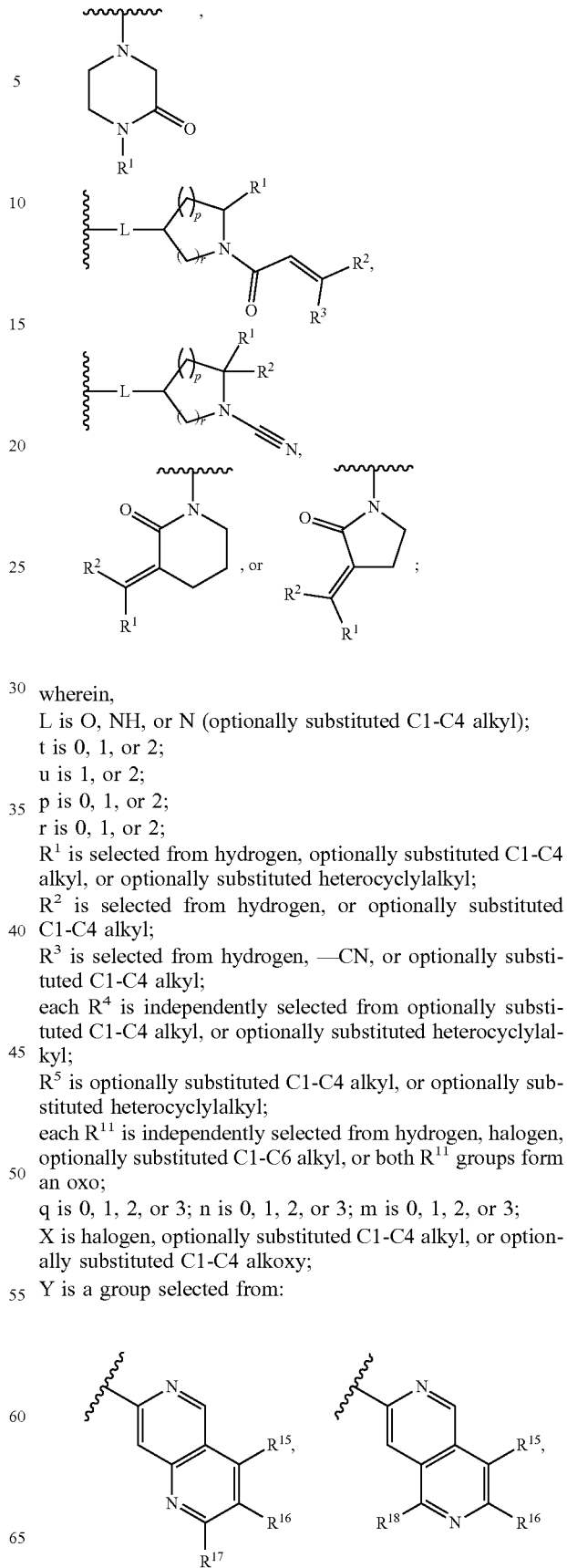

wherein,
L is O, NH, or N (optionally substituted C1-C4 alkyl);
t is 0, 1, or 2;
u is 1, or 2;
p is 0, 1, or 2;
r is 0, 1, or 2;
$R^1$ is selected from hydrogen, optionally substituted C1-C4 alkyl, or optionally substituted heterocyclylalkyl;
$R^2$ is selected from hydrogen, or optionally substituted C1-C4 alkyl;
$R^3$ is selected from hydrogen, —CN, or optionally substituted C1-C4 alkyl;
each $R^4$ is independently selected from optionally substituted C1-C4 alkyl, or optionally substituted heterocyclylalkyl;
$R^5$ is optionally substituted C1-C4 alkyl, or optionally substituted heterocyclylalkyl;
each $R^{11}$ is independently selected from hydrogen, halogen, optionally substituted C1-C6 alkyl, or both $R^{11}$ groups form an oxo;
q is 0, 1, 2, or 3; n is 0, 1, 2, or 3; m is 0, 1, 2, or 3;
X is halogen, optionally substituted C1-C4 alkyl, or optionally substituted C1-C4 alkoxy;
Y is a group selected from:

-continued

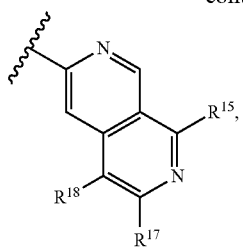

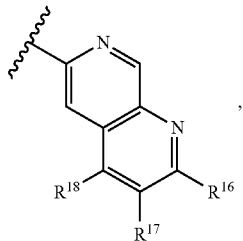

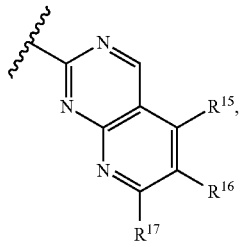  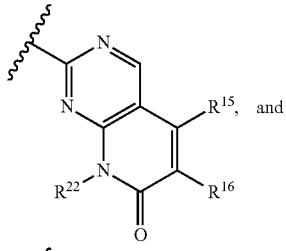

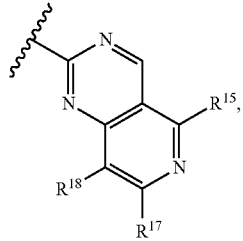

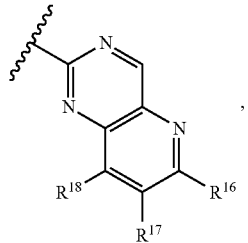

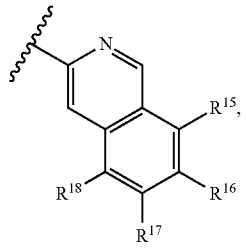

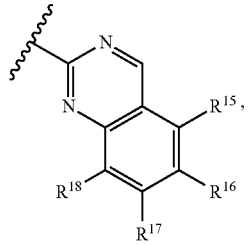

-continued

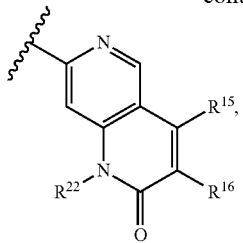

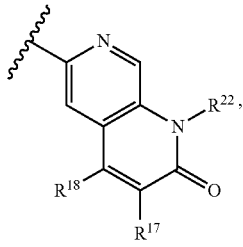

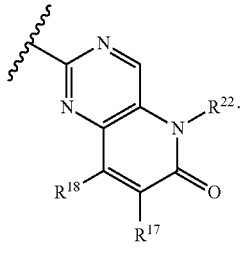, and

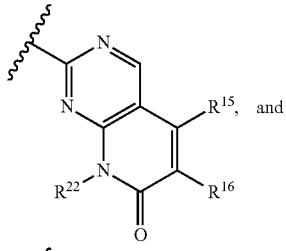

wherein, $R^{15}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N($R^{22}$)$_2$, —SO$_2$$R^{21}$, —N($R^{22}$)SO$_2$$R^{21}$, —SO$_2$N($R^{22}$)$_2$, —N($R^{22}$)SO$_2$N($R^{22}$)$_2$, —CON($R^{22}$)$_2$, —N($R^{22}$)CO$_2$$R^{21}$, —N($R^{22}$)CON($R^{22}$)$_2$, —N($R^{22}$)COR$^{21}$, —OC(O)N($R^{22}$)$_2$, —OSO$_2$N($R^{22}$)$_2$, or —N($R^{22}$)SO$_3$$R^{21}$;

$R^{16}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N($R^{22}$)$_2$, —SO$_2$$R^{21}$, —N($R^{22}$)SO$_2$$R^{21}$, —SO$_2$N($R^{22}$)$_2$, —N($R^{22}$)SO$_2$N($R^{22}$)$_2$, —CON($R^{22}$)$_2$, —N($R^{22}$)CO$_2$$R^{21}$, —N($R^{22}$)CON($R^{22}$)$_2$, —N($R^{22}$)COR$^{21}$, —OC(O)N($R^{22}$)$_2$, —OSO$_2$N($R^{22}$)$_2$, or —N($R^{22}$)SO$_3$$R^{21}$;

$R^{17}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N($R^{22}$)$_2$, —SO$_2$$R^{21}$, —N($R^{22}$)SO$_2$$R^{21}$, —SO$_2$N($R^{22}$)$_2$, —N($R^{22}$)SO$_2$N($R^{22}$)$_2$, —CON($R^{22}$)$_2$, —N($R^{22}$)CO$_2$$R^{21}$, —N($R^{22}$)CON($R^{22}$)$_2$, —N($R^{22}$)COR$^{21}$, —OC(O)N($R^{22}$)$_2$, —OSO$_2$N($R^{22}$)$_2$, or —N($R^{22}$)SO$_3$$R^{21}$;

$R^{18}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N($R^{22}$)$_2$, —SO$_2$$R^{21}$, —N($R^{22}$)SO$_2$$R^{21}$, —SO$_2$N($R^{22}$)$_2$, —N($R^{22}$)SO$_2$N($R^{22}$)$_2$, —CON($R^{22}$)$_2$, —N($R^{22}$)CO$_2$$R^{21}$, —N($R^{22}$)CON($R^{22}$)$_2$, —N($R^{22}$)COR$^{21}$, —OC(O)N($R^{22}$)$_2$, —OSO$_2$N($R^{22}$)$_2$, or —N($R^{22}$)SO$_3$$R^{21}$;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (I), or pharmaceutically acceptable salt or solvate thereof, wherein G is

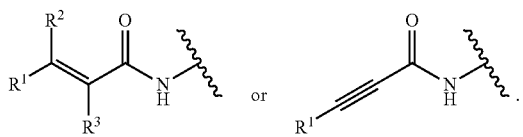

Another embodiment provides a compound of Formula (I), or pharmaceutically acceptable salt or solvate thereof, wherein G is

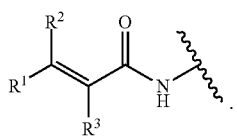

Another embodiment provides a compound of Formula (I), or pharmaceutically acceptable salt or solvate thereof, wherein $R^3$ is hydrogen or —CN.

Another embodiment provides a compound of Formula (I), or pharmaceutically acceptable salt or solvate thereof, wherein L is NH.

Another embodiment provides a compound of Formula (I), or pharmaceutically acceptable salt or solvate thereof, wherein t is 2.

Another embodiment provides a compound of Formula (I), or pharmaceutically acceptable salt or solvate thereof, wherein q is 0, 1, or 2.

Another embodiment provides a compound of Formula (I), or pharmaceutically acceptable salt or solvate thereof, wherein q is 0, or 1.

Another embodiment provides a compound of Formula (I), or pharmaceutically acceptable salt or solvate thereof, wherein X is a halogen.

Another embodiment provides a compound of Formula (I), or pharmaceutically acceptable salt or solvate thereof, wherein $R^2$ is hydrogen. Another embodiment provides a compound of Formula (I), or pharmaceutically acceptable salt or solvate thereof, wherein $R^3$ is hydrogen. Another embodiment provides a compound of Formula (I), or pharmaceutically acceptable salt or solvate thereof, wherein $R^2$ and $R^3$ is hydrogen.

Another embodiment provides a compound of Formula (I), or pharmaceutically acceptable salt or solvate thereof, wherein $R^1$ is hydrogen.

Another embodiment provides a compound of Formula (I), or pharmaceutically acceptable salt or solvate thereof, wherein $R^1$ is optionally substituted C1-C4 alkyl.

Another embodiment provides a compound of Formula (I), or pharmaceutically acceptable salt or solvate thereof, wherein $R^1$ is optionally substituted C1-C2 alkyl.

Another embodiment provides a compound of Formula (I), or pharmaceutically acceptable salt or solvate thereof, wherein $R^1$ is optionally substituted C1 alkyl. Another embodiment provides a compound of Formula (I), or pharmaceutically acceptable salt or solvate thereof, wherein $R^1$ is optionally substituted C1 alkyl and the C1 alkyl is substituted with an optionally substituted amino group. Another embodiment provides the compound wherein the optionally substituted amino group is a dimethylamino. Another embodiment provides a compound of Formula (I), or pharmaceutically acceptable salt or solvate thereof, wherein $R^1$ is —CH$_2$—N(Me)$_2$.

Another embodiment provides a compound of Formula (I), or pharmaceutically acceptable salt or solvate thereof, wherein $R^1$ is optionally substituted heterocyclylalkyl. Another embodiment provides a compound of Formula (I), or pharmaceutically acceptable salt or solvate thereof, wherein the optionally substituted heterocyclylalkyl comprises an optionally substituted C1 alkyl. Another embodiment provides a compound of Formula (I), or pharmaceutically acceptable salt or solvate thereof, wherein the optionally substituted heterocyclylalkyl comprises an optionally substituted N-linked heterocyclyl. Another embodiment provides a compound of Formula (I), or pharmaceutically acceptable salt or solvate thereof, wherein the optionally substituted N-linked heterocyclyl is an N-linked pyrrolidine or piperidine.

Another embodiment provides a compound of Formula (I), or pharmaceutically acceptable salt or solvate thereof, wherein n is 1 and m is 1. Another embodiment provides a compound of Formula (I), or pharmaceutically acceptable salt or solvate thereof, wherein n is 1 and m is 2. Another embodiment provides a compound of Formula (I), or pharmaceutically acceptable salt or solvate thereof, wherein n is 1 and m is 3.

Another embodiment provides a compound of Formula (I), or pharmaceutically acceptable salt or solvate thereof, wherein $R^{11}$ is hydrogen. Another embodiment provides a compound of Formula (I), or pharmaceutically acceptable salt or solvate thereof, wherein $R^{11}$ is halogen. Another embodiment provides a compound of Formula (I), or pharmaceutically acceptable salt or solvate thereof, wherein $R^{11}$ is optionally substituted C1-C6 alkyl. Another embodiment provides a compound of Formula (I), or pharmaceutically acceptable salt or solvate thereof, wherein both $R^{11}$ groups form an oxo.

Another embodiment provides a compound of Formula (I), or pharmaceutically acceptable salt or solvate thereof, wherein Y is selected from:

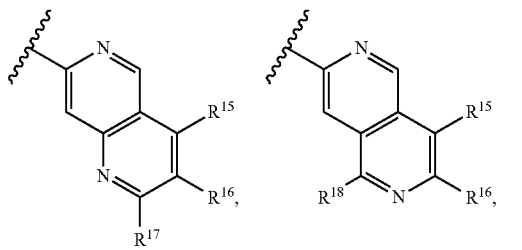

Another embodiment provides a compound of Formula (I), or pharmaceutically acceptable salt or solvate thereof, wherein Y is selected from:

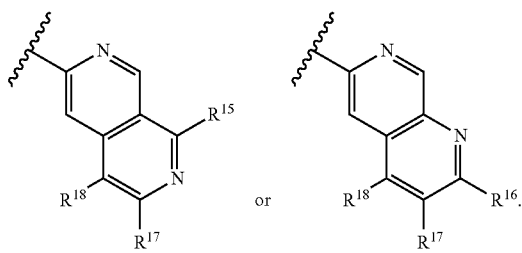

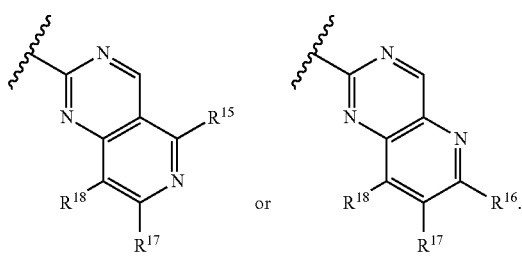

Another embodiment provides a compound of Formula (I), or pharmaceutically acceptable salt or solvate thereof, wherein Y is:

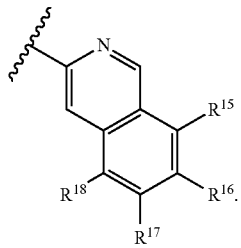

Another embodiment provides a compound of Formula (I), or pharmaceutically acceptable salt or solvate thereof, wherein Y is:

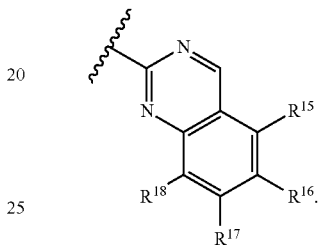

Another embodiment provides a compound of Formula (I), or pharmaceutically acceptable salt or solvate thereof, wherein $R^{15}$ is hydrogen.

Another embodiment provides a compound of Formula (I), or pharmaceutically acceptable salt or solvate thereof, wherein $R^{16}$ is hydrogen.

Another embodiment provides a compound of Formula (I), or pharmaceutically acceptable salt or solvate thereof, wherein $R^{17}$ is hydrogen.

Another embodiment provides a compound of Formula (I), or pharmaceutically acceptable salt or solvate thereof, wherein $R^{18}$ is hydrogen.

Another embodiment provides a compound of Formula (I), or pharmaceutically acceptable salt or solvate thereof, wherein $R^{15}$ and $R^{16}$ are hydrogen.

Another embodiment provides a compound of Formula (I), or pharmaceutically acceptable salt or solvate thereof, wherein E is a bond.

Another embodiment provides a compound of Formula (I), or pharmaceutically acceptable salt or solvate thereof, wherein E is —SO$_2$—.

Another embodiment provides a compound of Formula (I), or pharmaceutically acceptable salt or solvate thereof, wherein E is —C(O)—.

Another embodiment provides a compound of Formula (I), or pharmaceutically acceptable salt or solvate thereof, wherein E is —CH$_2$—.

Another embodiment provides a compound of Formula (I), or pharmaceutically acceptable salt or solvate thereof, wherein E is —CH($R^4$)—.

Another embodiment provides a compound of Formula (I), or pharmaceutically acceptable salt or solvate thereof, wherein E is —C($R^4$)$_2$—.

One embodiment provides a compound, or pharmaceutically acceptable salt or solvate thereof, having the structure of Formula (II):

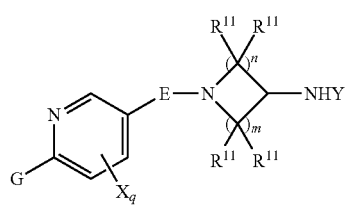

(II)

wherein,

E is selected from a bond, —SO$_2$—, —C(O)—, —CH$_2$—, —CH(R$^4$)—, or —C(R$^4$)$_2$—;

G is selected from a group having the structure:

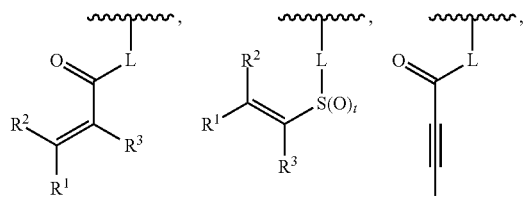

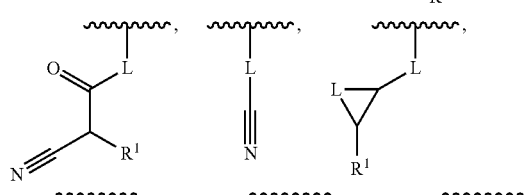

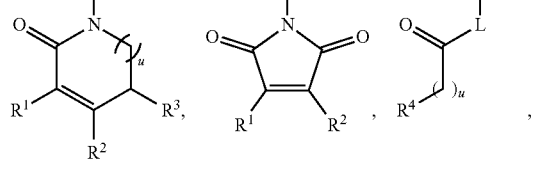

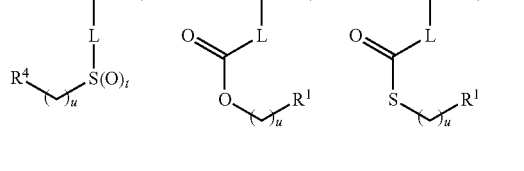

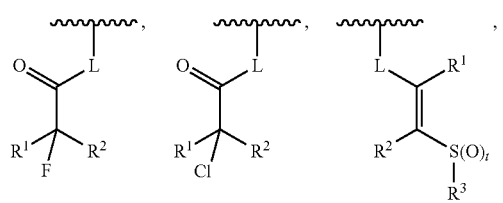

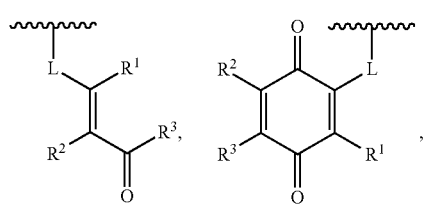

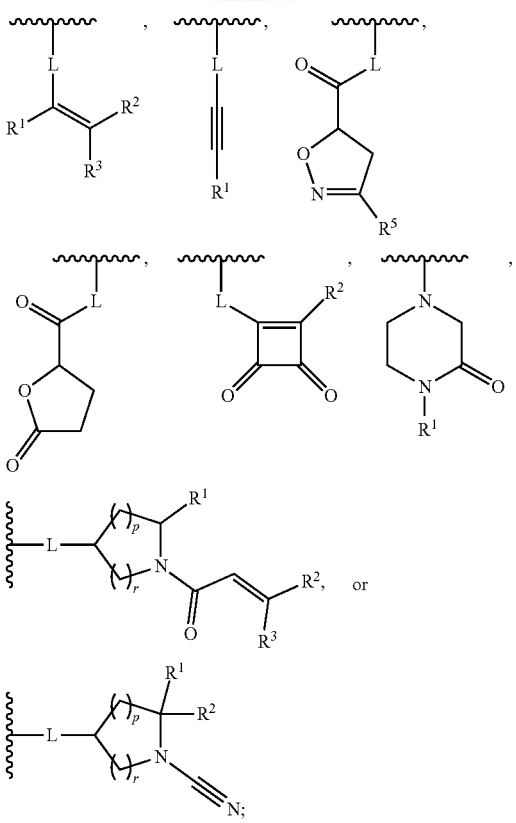

wherein,

L is O, NH, or N (optionally substituted C1-C4 alkyl);

t is 0, 1, or 2;

u is 1 or 2;

p is 0, 1, or 2;

r is 0, 1, or 2;

R$^1$ is selected from hydrogen, optionally substituted C1-C4 alkyl, or optionally substituted heterocyclylalkyl;

R$^2$ is selected from hydrogen, or optionally substituted C1-C4 alkyl;

R$^3$ is selected from hydrogen, —CN, or optionally substituted C1-C4 alkyl;

each R$^4$ is independently selected from optionally substituted C1-C4 alkyl, or optionally substituted heterocyclylalkyl;

R$^5$ is optionally substituted C1-C4 alkyl, or optionally substituted heterocyclylalkyl;

each R$^{11}$ is independently selected from hydrogen, halogen, optionally substituted C1-C6 alkyl, or both R$^{11}$ groups form an oxo;

q is 0, 1, or 2; n is 0, 1, 2, or 3; m is 0, 1, 2, or 3;

X is halogen, optionally substituted C1-C4 alkyl, or optionally substituted C1-C4 alkoxy;

Y is a group selected from:

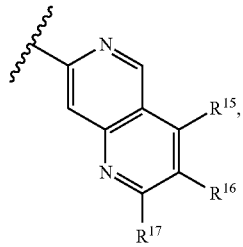 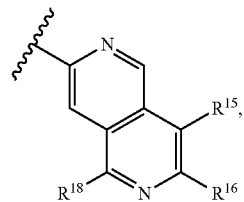 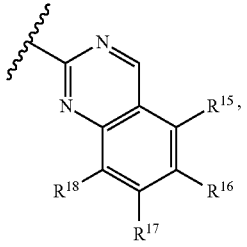

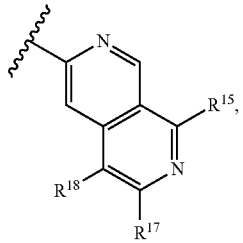 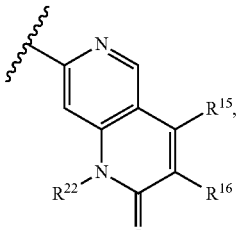

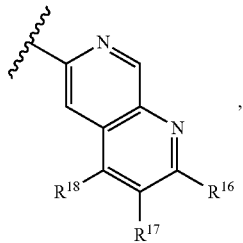 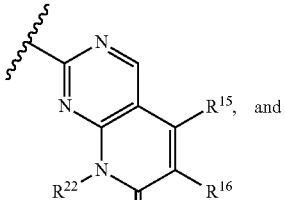

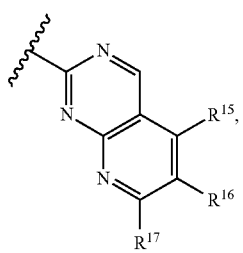 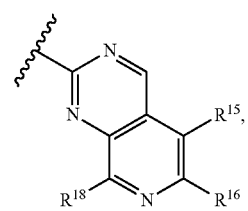

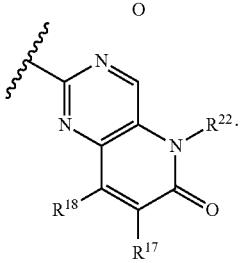

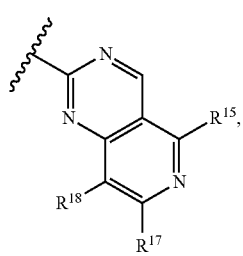

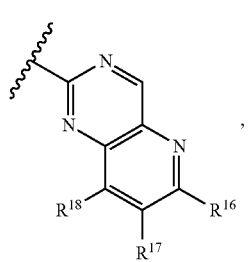

wherein, $R^{15}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

R$^{16}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

R$^{17}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

R$^{18}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

each R$^{21}$ is independently selected from alkyl, cycloalkyl, cycloalkylalkyl, aryl, aralkyl, heterocyclyl, heterocyclylalkyl, heteroaryl, or heteroarylalkyl; and each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (II), or pharmaceutically acceptable salt or solvate thereof, wherein G is

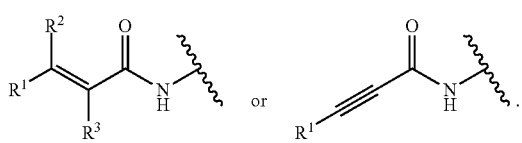

Another embodiment provides a compound of Formula (II), or pharmaceutically acceptable salt or solvate thereof, wherein G is

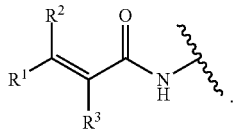

Another embodiment provides a compound of Formula (II), or pharmaceutically acceptable salt or solvate thereof, wherein R$^3$ is hydrogen or —CN.

Another embodiment provides a compound of Formula (II), or pharmaceutically acceptable salt or solvate thereof, wherein L is NH.

Another embodiment provides a compound of Formula (II), or pharmaceutically acceptable salt or solvate thereof, wherein t is 2.

Another embodiment provides a compound of Formula (II), or pharmaceutically acceptable salt or solvate thereof, wherein q is 0, or 1.

Another embodiment provides a compound of Formula (II), or pharmaceutically acceptable salt or solvate thereof, wherein q is 0.

Another embodiment provides a compound of Formula (II), or pharmaceutically acceptable salt or solvate thereof, wherein X is a halogen.

Another embodiment provides a compound of Formula (II), or pharmaceutically acceptable salt or solvate thereof, wherein R$^2$ is hydrogen.

Another embodiment provides a compound of Formula (II), or pharmaceutically acceptable salt or solvate thereof, wherein R$^3$ is hydrogen.

Another embodiment provides a compound of Formula (II), or pharmaceutically acceptable salt or solvate thereof, wherein R$^2$ and R$^3$ is hydrogen.

Another embodiment provides a compound of Formula (II), or pharmaceutically acceptable salt or solvate thereof, wherein R$^1$ is hydrogen.

Another embodiment provides a compound of Formula (II), or pharmaceutically acceptable salt or solvate thereof, wherein R$^1$ is optionally substituted C1-C4 alkyl.

Another embodiment provides a compound of Formula (II), or pharmaceutically acceptable salt or solvate thereof, wherein R$^1$ is optionally substituted C1-C2 alkyl.

Another embodiment provides a compound of Formula (II), or pharmaceutically acceptable salt or solvate thereof, wherein R$^1$ is optionally substituted C1 alkyl. Another embodiment provides a compound of Formula (II), or pharmaceutically acceptable salt or solvate thereof, wherein R$^1$ is optionally substituted C1 alkyl and the C1 alkyl is substituted with an optionally substituted amino group. Another embodiment provides a compound of Formula (II), or pharmaceutically acceptable salt or solvate thereof, wherein R$^1$ is optionally substituted C1 alkyl, the C1 alkyl is substituted with an optionally substituted amino group, and the optionally substituted amino group is a dimethylamino. Another embodiment provides a compound of Formula (II), or pharmaceutically acceptable salt or solvate thereof, wherein R$^1$ is —CH$_2$—N(Me)$_2$.

Another embodiment provides a compound of Formula (II), or pharmaceutically acceptable salt or solvate thereof, wherein R$^1$ is optionally substituted heterocyclylalkyl.

Another embodiment provides a compound of Formula (II), or pharmaceutically acceptable salt or solvate thereof, wherein R$^1$ is optionally substituted heterocyclylalkyl, and the optionally substituted heterocyclylalkyl comprises an optionally substituted C1 alkyl.

Another embodiment provides a compound of Formula (II), or pharmaceutically acceptable salt or solvate thereof, wherein $R^1$ is optionally substituted heterocyclylalkyl, and the optionally substituted heterocyclylalkyl comprises an optionally substituted N-linked heterocyclyl.

Another embodiment provides a compound of Formula (II), or pharmaceutically acceptable salt or solvate thereof, wherein $R^1$ is optionally substituted heterocyclylalkyl, the optionally substituted heterocyclylalkyl comprises an optionally substituted N-linked heterocyclyl, and the optionally substituted N-linked heterocyclyl is an N-linked pyrrolidine or piperidine.

Another embodiment provides a compound of Formula (II), or pharmaceutically acceptable salt or solvate thereof, wherein n is 1 and m is 1. Another embodiment provides a compound of Formula (II), or pharmaceutically acceptable salt or solvate thereof, wherein n is 1 and m is 2. Another embodiment provides a compound of Formula (II), or pharmaceutically acceptable salt or solvate thereof, wherein n is 1 and m is 3.

Another embodiment provides a compound of Formula (II), or pharmaceutically acceptable salt or solvate thereof, wherein $R^{11}$ is hydrogen. Another embodiment provides a compound of Formula (II), or pharmaceutically acceptable salt or solvate thereof, wherein $R^{11}$ is halogen. Another embodiment provides a compound of Formula (II), or pharmaceutically acceptable salt or solvate thereof, wherein $R^{11}$ is optionally substituted C1-C6 alkyl. Another embodiment provides a compound of Formula (II), or pharmaceutically acceptable salt or solvate thereof, wherein both $R^{11}$ groups form an oxo.

Another embodiment provides a compound of Formula (II), or pharmaceutically acceptable salt or solvate thereof, wherein Y is selected from:

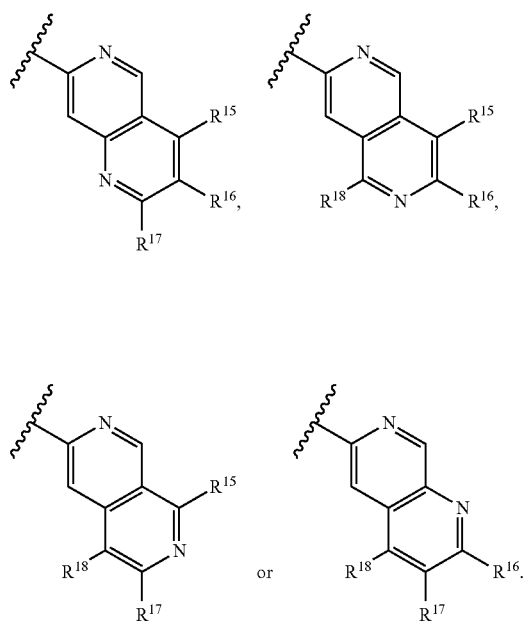

Another embodiment provides a compound of Formula (II), or pharmaceutically acceptable salt or solvate thereof, wherein Y is selected from:

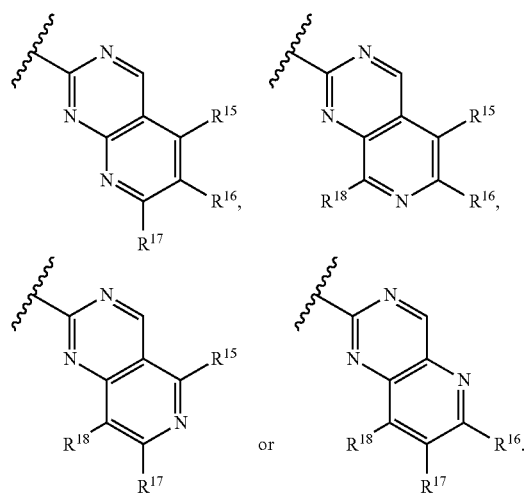

Another embodiment provides a compound of Formula (II), or pharmaceutically acceptable salt or solvate thereof, wherein Y is:

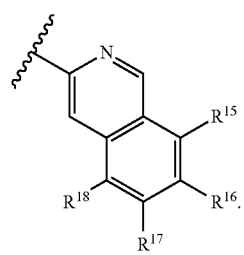

Another embodiment provides a compound of Formula (II), or pharmaceutically acceptable salt or solvate thereof, wherein Y is:

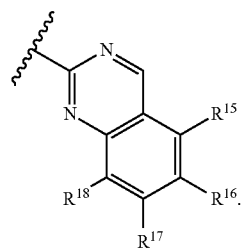

Another embodiment provides a compound of Formula (II), or pharmaceutically acceptable salt or solvate thereof, wherein $R^{15}$ is hydrogen.

Another embodiment provides a compound of Formula (II), or pharmaceutically acceptable salt or solvate thereof, wherein $R^{16}$ is hydrogen.

Another embodiment provides a compound of Formula (II), or pharmaceutically acceptable salt or solvate thereof, wherein $R^{17}$ is hydrogen.

Another embodiment provides a compound of Formula (II), or pharmaceutically acceptable salt or solvate thereof, wherein $R^{18}$ is hydrogen.

Another embodiment provides a compound of Formula (II), or pharmaceutically acceptable salt or solvate thereof, wherein $R^{15}$ and $R^{16}$ are hydrogen.

Another embodiment provides a compound of Formula (II), or pharmaceutically acceptable salt or solvate thereof, wherein E is a bond.

Another embodiment provides a compound of Formula (II), or pharmaceutically acceptable salt or solvate thereof, wherein E is —SO$_2$—.

Another embodiment provides a compound of Formula (II), or pharmaceutically acceptable salt or solvate thereof, wherein E is —C(O)—.

Another embodiment provides a compound of Formula (II), or pharmaceutically acceptable salt or solvate thereof, wherein E is —CH$_2$—.

Another embodiment provides a compound of Formula (II), or pharmaceutically acceptable salt or solvate thereof, wherein E is —CH(R$^4$)—.

Another embodiment provides a compound of Formula (II), or pharmaceutically acceptable salt or solvate thereof, wherein E is —C(R$^4$)$_2$—.

One embodiment provides a compound, or pharmaceutically acceptable salt or solvate thereof, having the structure of Formula (Ia):

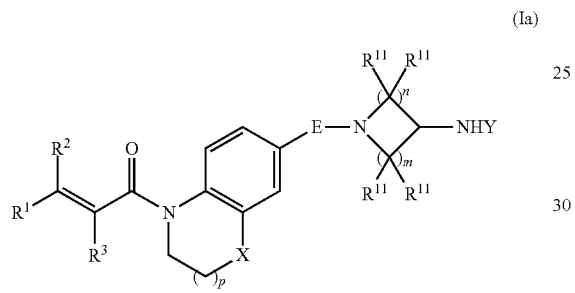

(Ia)

wherein,
E is selected from a bond, —SO$_2$—, —C(O)—, —CH$_2$—, —CH(R$^4$)—, or —C(R$^4$)$_2$—;
X is O, NH, —C(R$^{11}$)$_2$—;
wherein,
R$^1$ is selected from hydrogen, optionally substituted C1-C4 alkyl, or optionally substituted heterocyclylalkyl;
R$^2$ is selected from hydrogen, or optionally substituted C1-C4 alkyl;
R$^3$ is selected from hydrogen, —CN, or optionally substituted C1-C4 alkyl;
R$^5$ is optionally substituted C1-C4 alkyl, or optionally substituted heterocyclylalkyl;
each R$^{11}$ is independently selected from hydrogen, halogen, optionally substituted C1-C6 alkyl, or both R$^{11}$ groups form an oxo;
p is 0, 1, or 2; q is 0, 1, 2, or 3; n is 0, 1, 2, or 3; m is 0, 1, 2, or 3;
X is halogen, optionally substituted C1-C4 alkyl, or optionally substituted C1-C4 alkoxy;
Y is a group selected from:

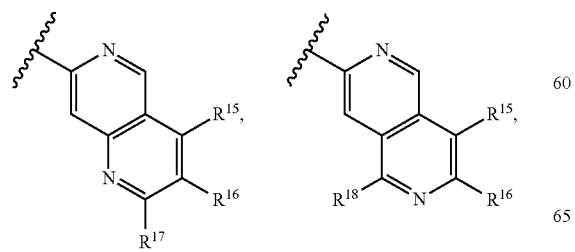

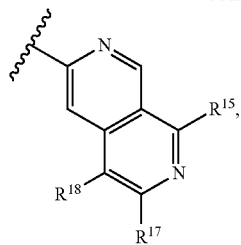

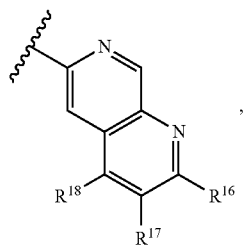

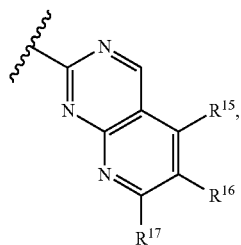

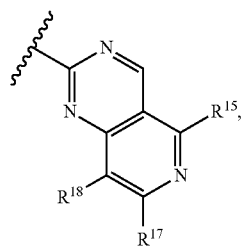

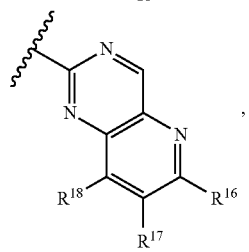

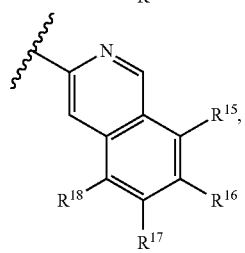

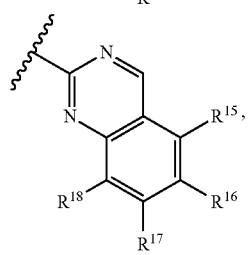

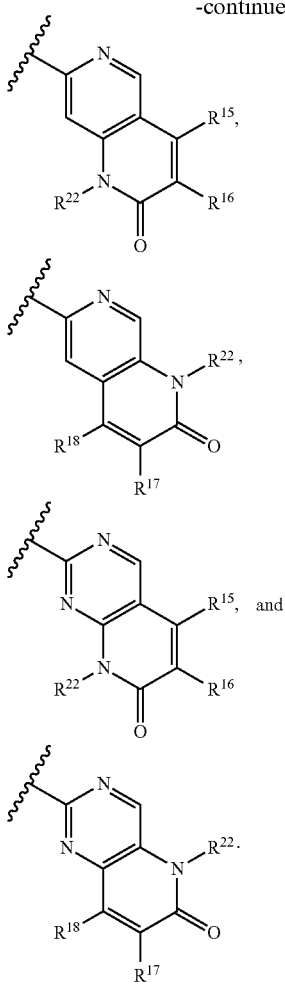

wherein, $R^{15}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N($R^{22}$)$_2$, —SO$_2R^{21}$, —N($R^{22}$)SO$_2R^{21}$, —SO$_2$N($R^{22}$)$_2$, —N($R^{22}$)SO$_2$N($R^{22}$)$_2$, —CON($R^{22}$)$_2$, —N($R^{22}$)CO$_2R^{21}$, —N($R^{22}$)CON($R^{22}$)$_2$, —N($R^{22}$)COR$^{21}$, —OC(O)N($R^{22}$)$_2$, —OSO$_2$N($R^{22}$)$_2$, or —N($R^{22}$)SO$_3R^{21}$;

$R^{16}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N($R^{22}$)$_2$, —SO$_2R^{21}$, —N($R^{22}$)SO$_2R^{21}$, —SO$_2$N($R^{22}$)$_2$, —N($R^{22}$)SO$_2$N($R^{22}$)$_2$, —CON($R^{22}$)$_2$, —N($R^{22}$)CO$_2R^{21}$, —N($R^{22}$)CON($R^{22}$)$_2$, —N($R^{22}$)COR$^{21}$, —OC(O)N($R^{22}$)$_2$, —OSO$_2$N($R^{22}$)$_2$, or —N($R^{22}$)SO$_3R^{21}$;

$R^{17}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N($R^{22}$)$_2$, —SO$_2R^{21}$, —N($R^{22}$)SO$_2R^{21}$, —SO$_2$N($R^{22}$)$_2$, —N($R^{22}$)SO$_2$N($R^{22}$)$_2$, —CON($R^{22}$)$_2$, —N($R^{22}$)CO$_2R^{21}$, —N($R^{22}$)CON($R^{22}$)$_2$, —N($R^{22}$)COR$^{21}$, —OC(O)N($R^{22}$)$_2$, —OSO$_2$N($R^{22}$)$_2$, or —N($R^{22}$)SO$_3R^{21}$;

$R^{18}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N($R^{22}$)$_2$, —SO$_2R^{21}$, —N($R^{22}$)SO$_2R^{21}$, —SO$_2$N($R^{22}$)$_2$, —N($R^{22}$)SO$_2$N($R^{22}$)$_2$, —CON($R^{22}$)$_2$, —N($R^{22}$)CO$_2R^{21}$, —N($R^{22}$)CON($R^{22}$)$_2$, —N($R^{22}$)COR$^{21}$, —OC(O)N($R^{22}$)$_2$, —OSO$_2$N($R^{22}$)$_2$, or —N($R^{22}$)SO$_3R^{21}$;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (Ia), or pharmaceutically acceptable salt or solvate thereof, wherein $R^3$ is hydrogen or —CN.

Another embodiment provides a compound of Formula (Ia), or pharmaceutically acceptable salt or solvate thereof, wherein q is 0, 1, or 2.

Another embodiment provides a compound of Formula (Ia), or pharmaceutically acceptable salt or solvate thereof, wherein q is 0, or 1.

Another embodiment provides a compound of Formula (Ia), or pharmaceutically acceptable salt or solvate thereof, wherein X is a halogen.

Another embodiment provides a compound of Formula (Ia), or pharmaceutically acceptable salt or solvate thereof, wherein $R^2$ is hydrogen. Another embodiment provides a compound of Formula (IV), or pharmaceutically acceptable salt or solvate thereof, wherein $R^3$ is hydrogen. Another embodiment provides a compound of Formula (Ia), or pharmaceutically acceptable salt or solvate thereof, wherein $R^2$ and $R^3$ is hydrogen.

Another embodiment provides a compound of Formula (Ia), or pharmaceutically acceptable salt or solvate thereof, wherein $R^1$ is hydrogen.

Another embodiment provides a compound of Formula (Ia), or pharmaceutically acceptable salt or solvate thereof, wherein $R^1$ is optionally substituted C1-C4 alkyl.

Another embodiment provides a compound of Formula (Ia), or pharmaceutically acceptable salt or solvate thereof, wherein $R^1$ is optionally substituted C1-C2 alkyl.

Another embodiment provides a compound of Formula (Ia), or pharmaceutically acceptable salt or solvate thereof, wherein $R^1$ is optionally substituted C1 alkyl. Another embodiment provides a compound of Formula (Ia), or pharmaceutically acceptable salt or solvate thereof, wherein $R^1$ is optionally substituted C1 alkyl and the C1 alkyl is substituted with an optionally substituted amino group. Another embodiment provides the compound wherein the optionally substituted amino group is a dimethylamino. Another embodiment provides a compound of Formula (Ia), or pharmaceutically acceptable salt or solvate thereof, wherein $R^1$ is —$CH_2$—$N(Me)_2$.

Another embodiment provides a compound of Formula (Ia), or pharmaceutically acceptable salt or solvate thereof, wherein $R^1$ is optionally substituted heterocyclylalkyl. Another embodiment provides a compound of Formula (Ia), or pharmaceutically acceptable salt or solvate thereof, wherein the optionally substituted heterocyclylalkyl comprises an optionally substituted C1 alkyl. Another embodiment provides a compound of Formula (Ia), or pharmaceutically acceptable salt or solvate thereof, wherein the optionally substituted heterocyclylalkyl comprises an optionally substituted N-linked heterocyclyl. Another embodiment provides a compound of Formula (Ia), or pharmaceutically acceptable salt or solvate thereof, wherein the optionally substituted N-linked heterocyclyl is an N-linked pyrrolidine or piperidine.

Another embodiment provides a compound of Formula (Ia), or pharmaceutically acceptable salt or solvate thereof, wherein n is 1 and m is 1. Another embodiment provides a compound of Formula (Ia), or pharmaceutically acceptable salt or solvate thereof, wherein n is 1 and m is 2. Another embodiment provides a compound of Formula (Ia), or pharmaceutically acceptable salt or solvate thereof, wherein n is 1 and m is 3.

Another embodiment provides a compound of Formula (Ia), or pharmaceutically acceptable salt or solvate thereof, wherein $R^{11}$ is hydrogen. Another embodiment provides a compound of Formula (Ia), or pharmaceutically acceptable salt or solvate thereof, wherein $R^{11}$ is halogen. Another embodiment provides a compound of Formula (Ia), or pharmaceutically acceptable salt or solvate thereof, wherein $R^{11}$ is optionally substituted C1-C6 alkyl. Another embodiment provides a compound of Formula (Ia), or pharmaceutically acceptable salt or solvate thereof, wherein both $R^{11}$ groups form an oxo.

Another embodiment provides a compound of Formula (Ia), or pharmaceutically acceptable salt or solvate thereof, wherein Y is selected from:

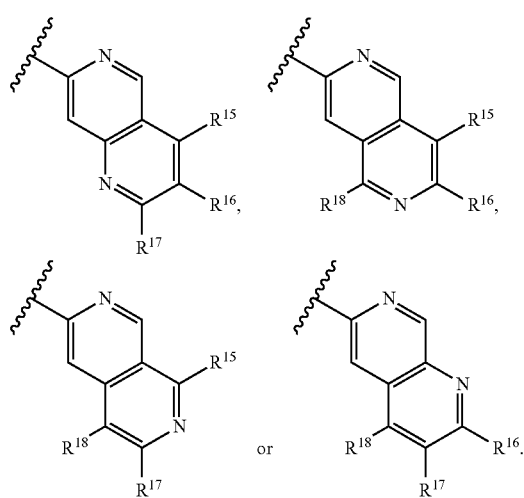

Another embodiment provides a compound of Formula (Ia), or pharmaceutically acceptable salt or solvate thereof, wherein Y is selected from:

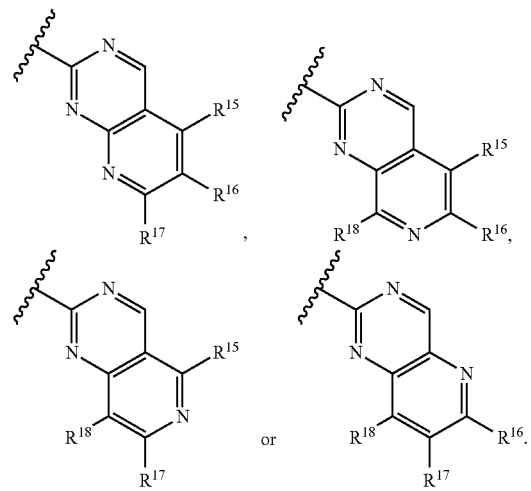

Another embodiment provides a compound of Formula (Ia), or pharmaceutically acceptable salt or solvate thereof, wherein Y is:

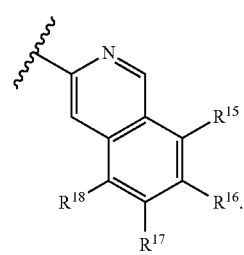

Another embodiment provides a compound of Formula (Ia), or pharmaceutically acceptable salt or solvate thereof, wherein Y is:

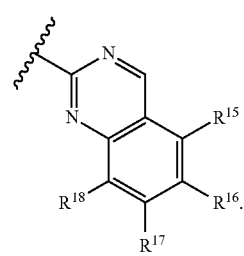

Another embodiment provides a compound of Formula (Ia), or pharmaceutically acceptable salt or solvate thereof, wherein $R^{15}$ is hydrogen.

Another embodiment provides a compound of Formula (Ia), or pharmaceutically acceptable salt or solvate thereof, wherein $R^{16}$ is hydrogen.

Another embodiment provides a compound of Formula (Ia), or pharmaceutically acceptable salt or solvate thereof, wherein $R^{17}$ is hydrogen.

Another embodiment provides a compound of Formula (Ia), or pharmaceutically acceptable salt or solvate thereof, wherein $R^{18}$ is hydrogen.

Another embodiment provides a compound of Formula (Ia), or pharmaceutically acceptable salt or solvate thereof, wherein $R^{15}$ and $R^{16}$ are hydrogen.

Another embodiment provides a compound of Formula (Ia), or pharmaceutically acceptable salt or solvate thereof, wherein E is a bond.

Another embodiment provides a compound of Formula (Ia), or pharmaceutically acceptable salt or solvate thereof, wherein E is —SO$_2$—.

Another embodiment provides a compound of Formula (Ia), or pharmaceutically acceptable salt or solvate thereof, wherein E is —C(O)—.

Another embodiment provides a compound of Formula (Ia), or pharmaceutically acceptable salt or solvate thereof, wherein E is —CH$_2$—.

Another embodiment provides a compound of Formula (Ia), or pharmaceutically acceptable salt or solvate thereof, wherein E is —CH(R$^4$)—.

Another embodiment provides a compound of Formula (Ia), or pharmaceutically acceptable salt or solvate thereof, wherein E is —C(R$^4$)$_2$—.

Another embodiment provides a compound of Formula (Ia), or pharmaceutically acceptable salt or solvate thereof, wherein X is O.

Another embodiment provides a compound of Formula (Ia), or pharmaceutically acceptable salt or solvate thereof, wherein X is NH.

Another embodiment provides a compound of Formula (Ia), or pharmaceutically acceptable salt or solvate thereof, wherein X is —C(R$^{11}$)$_2$—.

Another embodiment provides a compound of Formula (Ia), or pharmaceutically acceptable salt or solvate thereof, wherein p is 0.

Another embodiment provides a compound of Formula (Ia), or pharmaceutically acceptable salt or solvate thereof, wherein p is 1.

Another embodiment provides a compound of Formula (Ia), or pharmaceutically acceptable salt or solvate thereof, wherein p is 2.

In some embodiments, the heteroaromatic CDK inhibitory compound of Formula (I), Formula (II), or Formula (Ia) described herein has a structure provided in Table 1.

TABLE 1

| Synthetic Chemistry Example | Compound Structure | Compound Name |
|---|---|---|
| 1 | 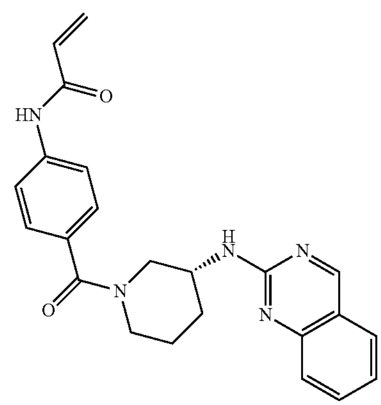 [SMILES: C=CC(=O)Nc1ccc(C(=O)N2CCC[C@@H](Nc3ncc4ccccc4n3)C2)cc1] | (R)-N-(4-(3-(quinazolin-2-ylamino)piperidine-1-carbonyl)phenyl)acrylamide |
| 2 | 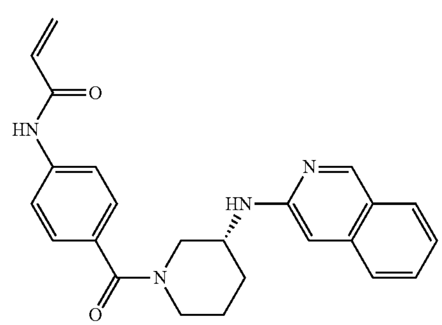 [SMILES: C=CC(=O)Nc1ccc(C(=O)N2CCC[C@@H](Nc3cc4ccccc4cn3)C2)cc1] | (R)-N-(4-(3-(isoquinolin-3-ylamino)piperidine-1-carbonyl)phenyl)acrylamide |

TABLE 1-continued

| Synthetic Chemistry Example | Compound Structure | Compound Name |
|---|---|---|
| 3 | 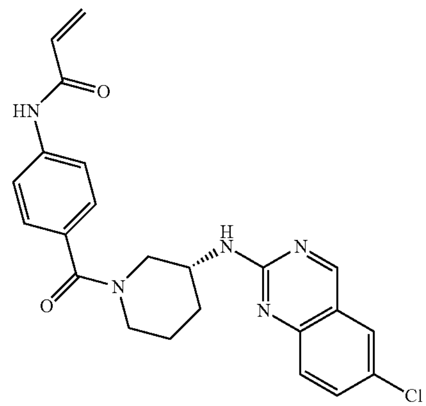 [SMILES: C=CC(=O)Nc1ccc(C(=O)N2CCC[C@@H](Nc3ncc4cc(Cl)ccc4n3)C2)cc1] | (R)-N-(4-(3-((6-chloroquinazolin-2-yl)amino)piperidine-1-carbonyl)phenyl)acrylamide |
| 4 | 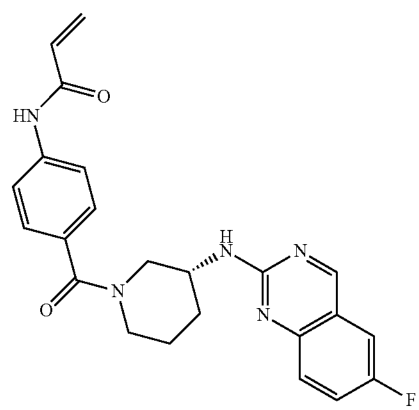 [SMILES: C=CC(=O)Nc1ccc(C(=O)N2CCC[C@@H](Nc3ncc4cc(F)ccc4n3)C2)cc1] | (R)-N-(4-(3-((6-fluoroquinazolin-2-yl)amino)piperidine-1-carbonyl)phenyl)acrylamide |
| 5 | 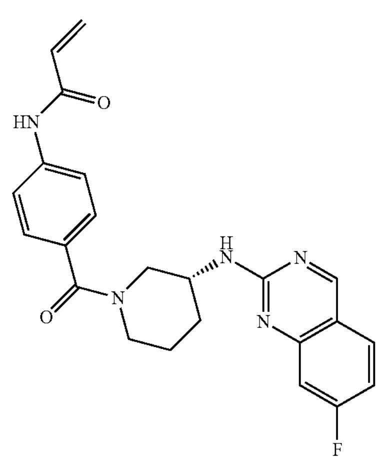 [SMILES: C=CC(=O)Nc1ccc(C(=O)N2CCC[C@@H](Nc3ncc4ccc(F)cc4n3)C2)cc1] | (R)-N-(4-(3-((7-fluoroquinazolin-2-yl)amino)piperidine-1-carbonyl)phenyl)acrylamide |

TABLE 1-continued

| Synthetic Chemistry Example | Compound Structure | Compound Name |
|---|---|---|
| 6 | 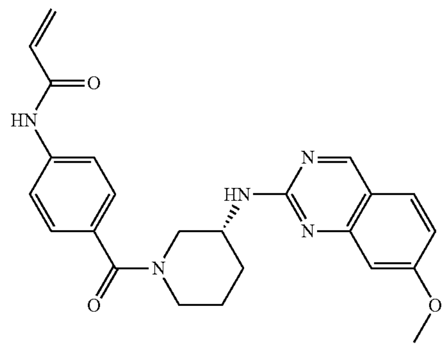 [SMILES: C=CC(=O)Nc1ccc(C(=O)N2CCC[C@@H](Nc3ncc4ccc(OC)cc4n3)C2)cc1] | (R)-N-(4-(3-((7-methoxyquinazolin-2-yl)amino)piperidine-1-carbonyl)phenyl)acrylamide |
| 7 | 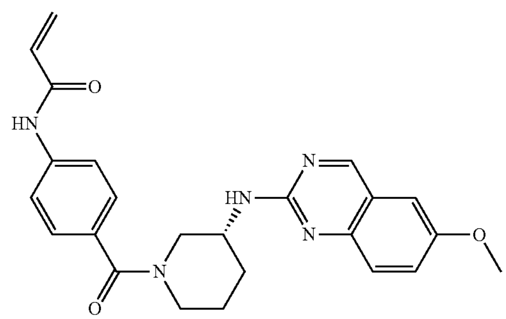 [SMILES: C=CC(=O)Nc1ccc(C(=O)N2CCC[C@@H](Nc3ncc4cc(OC)ccc4n3)C2)cc1] | (R)-N-(4-(3-((6-methoxyquinazolin-2-yl)amino)piperidine-1-carbonyl)phenyl)acrylamide |
| 8 | 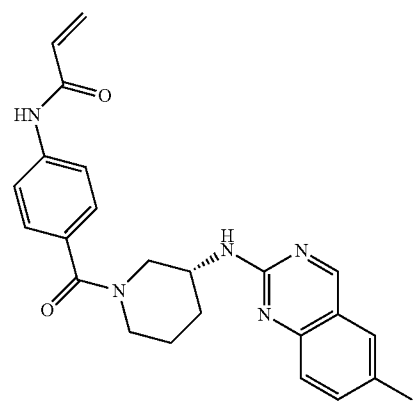 [SMILES: C=CC(=O)Nc1ccc(C(=O)N2CCC[C@@H](Nc3ncc4cc(C)ccc4n3)C2)cc1] | (R)-N-(4-(3-((6-methylquinazolin-2-yl)amino)piperidine-1-carbonyl)phenyl)acrylamide |
| 9 | 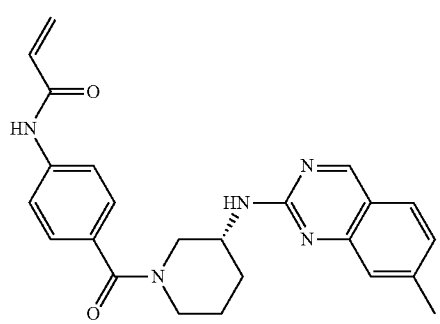 [SMILES: C=CC(=O)Nc1ccc(C(=O)N2CCC[C@@H](Nc3ncc4ccc(C)cc4n3)C2)cc1] | (R)-N-(4-(3-((7-methylquinazolin-2-yl)amino)piperidine-1-carbonyl)phenyl)acrylamide |

TABLE 1-continued

| Synthetic Chemistry Example | Compound Structure | Compound Name |
|---|---|---|
| 10 | 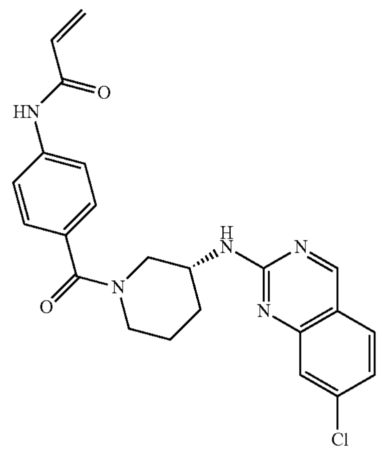 [SMILES: C=CC(=O)Nc1ccc(C(=O)N2CCC[C@@H](Nc3ncc4ccc(Cl)cc4n3)C2)cc1] | (R)-N-(4-(3-((7-chloroquinazolin-2-yl)amino)piperidine-1-carbonyl)phenyl)acrylamide |
| 11 | 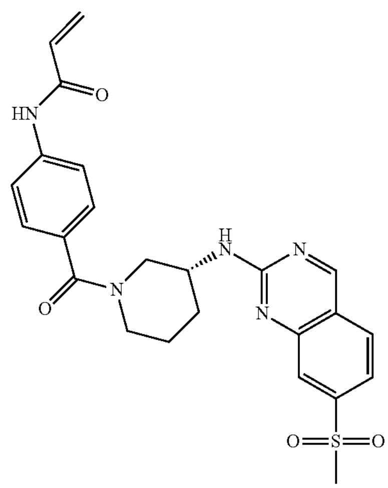 [SMILES: C=CC(=O)Nc1ccc(C(=O)N2CCC[C@@H](Nc3ncc4ccc(S(C)(=O)=O)cc4n3)C2)cc1] | (R)-N-(4-(3-((7-(methylsulfonyl)quinazolin-2-yl)amino)piperidine-1-carbonyl)phenyl)acrylamide |
| 12 | 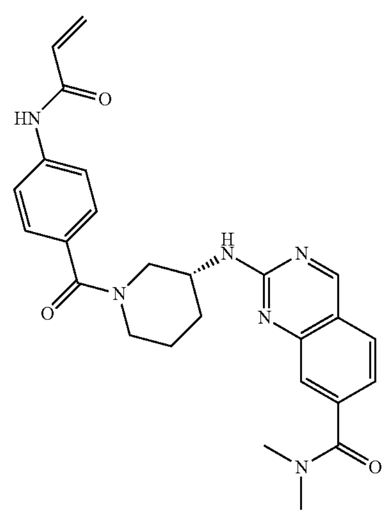 [SMILES: C=CC(=O)Nc1ccc(C(=O)N2CCC[C@@H](Nc3ncc4ccc(C(=O)N(C)C)cc4n3)C2)cc1] | (R)-2-((1-(4-acrylamidobenzoyl)piperidin-3-yl)amino)-N,N-dimethylquinazoline-7-carboxamide |

TABLE 1-continued

| Synthetic Chemistry Example | Compound Structure | Compound Name |
|---|---|---|
| 13 | 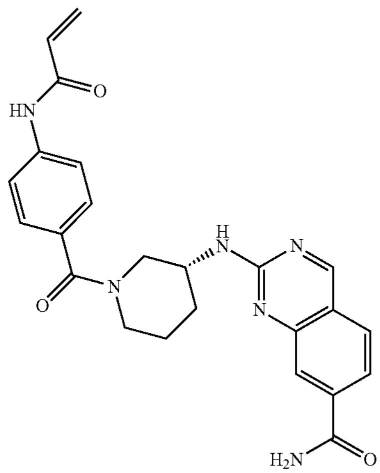 [SMILES: C=CC(=O)Nc1ccc(C(=O)N2CCC[C@@H](Nc3ncc4ccc(C(N)=O)cc4n3)C2)cc1] | (R)-2-((1-(4-acrylamidobenzoyl)piperidin-3-yl)amino)quinazoline-7-carboxamide |
| 14 | 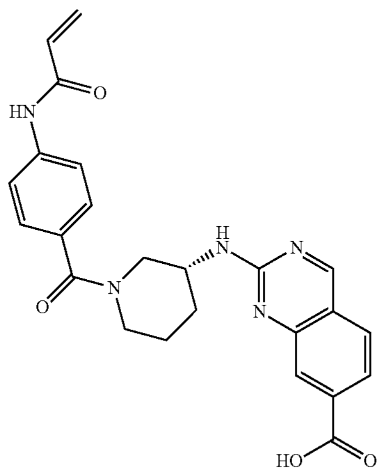 [SMILES: C=CC(=O)Nc1ccc(C(=O)N2CCC[C@@H](Nc3ncc4ccc(C(=O)O)cc4n3)C2)cc1] | (R)-2-((1-(4-acrylamidobenzoyl)piperidin-3-yl)amino)quinazoline-7-carboxylic acid |
| 15 | 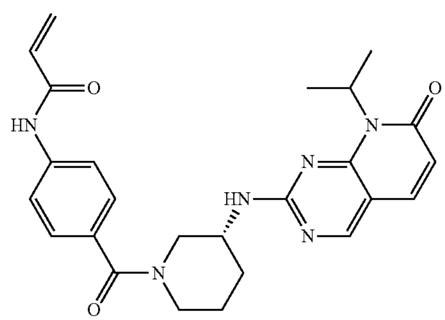 [SMILES: C=CC(=O)Nc1ccc(C(=O)N2CCC[C@@H](Nc3ncc4ccc(=O)n(C(C)C)c4n3)C2)cc1] | (R)-N-(4-(3-((8-isopropyl-7-oxo-7,8-dihydropyrido[2,3-d]pyrimidin-2-yl)amino)piperidine-1-carbonyl)phenyl)acrylamide |
| 16 | 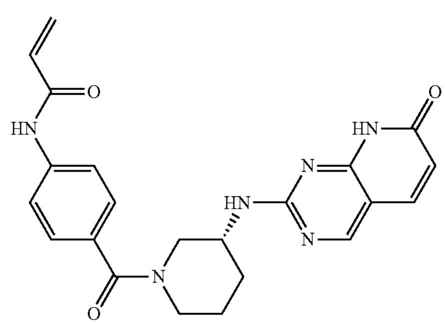 [SMILES: C=CC(=O)Nc1ccc(C(=O)N2CCC[C@@H](Nc3ncc4ccc(=O)[nH]c4n3)C2)cc1] | (R)-N-(4-(3-((7-oxo-7,8-dihydropyrido[2,3-d]pyrimidin-2-yl)amino)piperidine-1-carbonyl)phenyl)acrylamide |

TABLE 1-continued

| Synthetic Chemistry Example | Compound Structure | Compound Name |
|---|---|---|
| 25 | 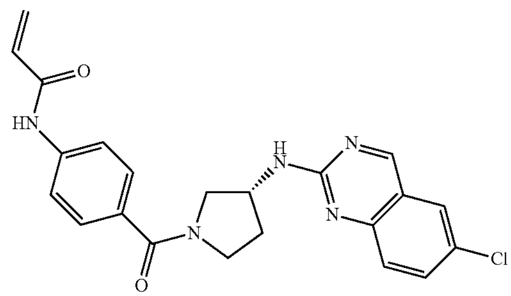 [SMILES: C=CC(=O)Nc1ccc(C(=O)N2CC[C@@H](Nc3ncc4cc(Cl)ccc4n3)C2)cc1] | (R)-N-(4-(3-((6-chloroquinazolin-2-yl)amino)pyrrolidine-1-carbonyl)phenyl)acrylamide |
| 26 | 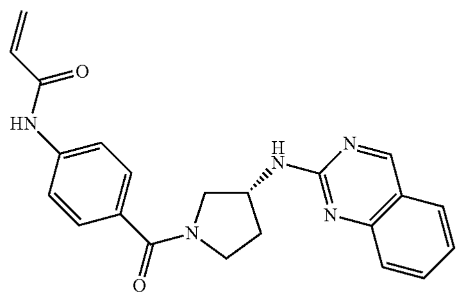 [SMILES: C=CC(=O)Nc1ccc(C(=O)N2CC[C@@H](Nc3ncc4ccccc4n3)C2)cc1] | (R)-N-(4-(3-(quinazolin-2-ylamino)pyrrolidine-1-carbonyl)phenyl)acrylamide |
| 27 | 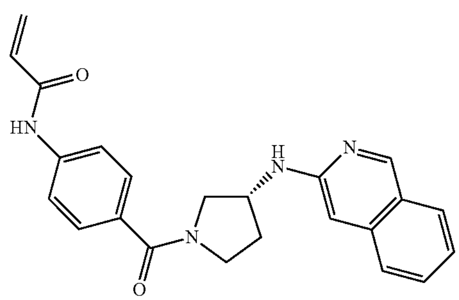 | (R)-N-(4-(3-(isoquinolin-3-ylamino)pyrrolidine-1-carbonyl)phenyl)acrylamide |
| 28 | 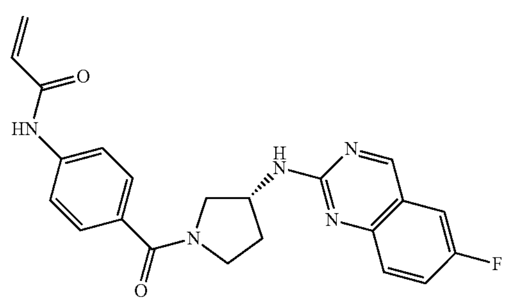 [SMILES: C=CC(=O)Nc1ccc(C(=O)N2CC[C@@H](Nc3ncc4cc(F)ccc4n3)C2)cc1] | (R)-N-(4-(3-((6-fluoroquinazolin-2-yl)amino)pyrrolidine-1-carbonyl)phenyl)acrylamide |
| 29 | 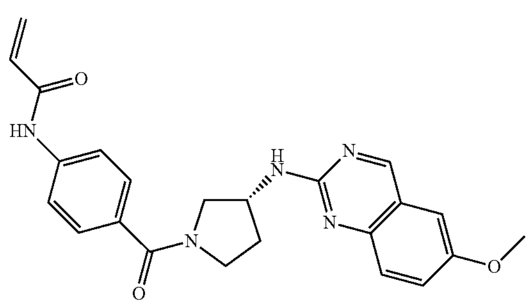 [SMILES: C=CC(=O)Nc1ccc(C(=O)N2CC[C@@H](Nc3ncc4cc(OC)ccc4n3)C2)cc1] | (R)-N-(4-(3-((6-methoxyquinazolin-2-yl)amino)pyrrolidine-1-carbonyl)phenyl)acrylamide |

TABLE 1-continued

| Synthetic Chemistry Example | Compound Structure | Compound Name |
|---|---|---|
| 30 | 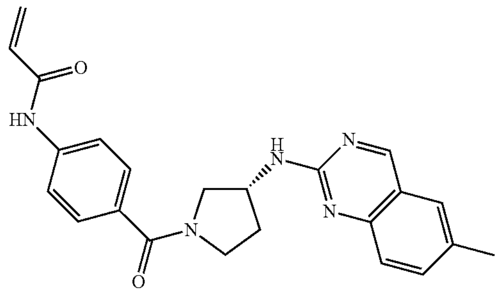 [SMILES: C=CC(=O)Nc1ccc(C(=O)N2CC[C@@H](Nc3ncc4cc(C)ccc4n3)C2)cc1] | (R)-N-(4-(3-((6-methylquinazolin-2-yl)amino)pyrrolidine-1-carbonyl)phenyl)acrylamide |
| 31 | 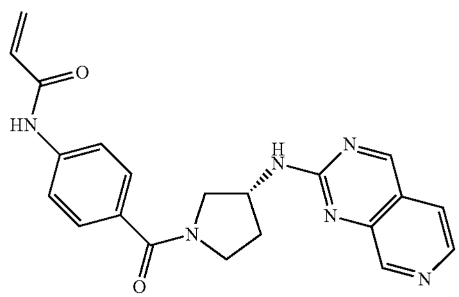 [SMILES: C=CC(=O)Nc1ccc(C(=O)N2CC[C@@H](Nc3ncc4ccncc4n3)C2)cc1] | (R)-N-(4-(3-(pyrido[3,4-d]pyrimidin-2-ylamino)pyrrolidine-1-carbonyl)phenyl)acrylamide |
| 32 | 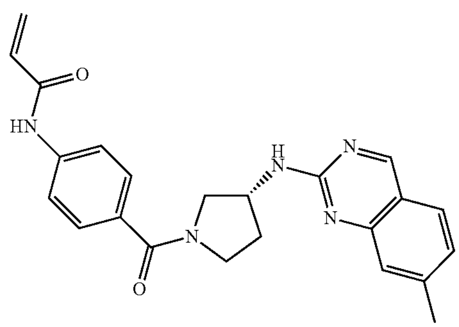 [SMILES: C=CC(=O)Nc1ccc(C(=O)N2CC[C@@H](Nc3ncc4ccc(C)cc4n3)C2)cc1] | (R)-N-(4-(3-((7-methylquinazolin-2-yl)amino)pyrrolidine-1-carbonyl)phenyl)acrylamide |
| 33 | 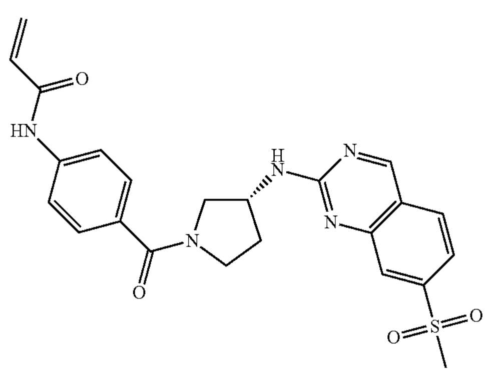 [SMILES: C=CC(=O)Nc1ccc(C(=O)N2CC[C@@H](Nc3ncc4ccc(S(C)(=O)=O)cc4n3)C2)cc1] | (R)-N-(4-(3-((7-(methylsulfonyl)quinazolin-2-yl)amino)pyrrolidine-1-carbonyl)phenyl)acrylamide |

TABLE 1-continued

| Synthetic Chemistry Example | Compound Structure | Compound Name |
|---|---|---|
| 34 | 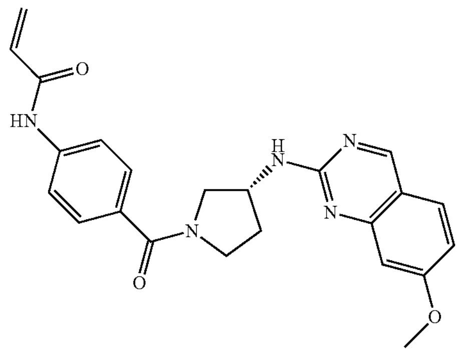 [SMILES: C=CC(=O)Nc1ccc(C(=O)N2CC[C@@H](Nc3ncc4ccc(OC)cc4n3)C2)cc1] | (R)-N-(4-(3-((7-methoxyquinazolin-2-yl)amino)pyrrolidine-1-carbonyl)phenyl)acrylamide |
| 35 | 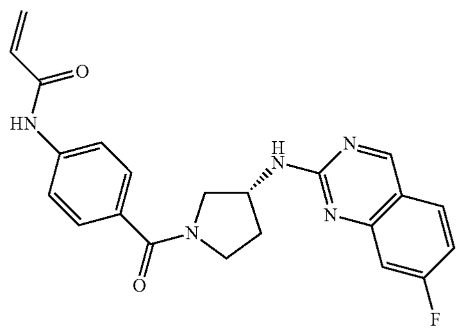 [SMILES: C=CC(=O)Nc1ccc(C(=O)N2CC[C@@H](Nc3ncc4ccc(F)cc4n3)C2)cc1] | (R)-N-(4-(3-((7-fluoroquinazolin-2-yl)amino)pyrrolidine-1-carbonyl)phenyl)acrylamide |
| 36 | 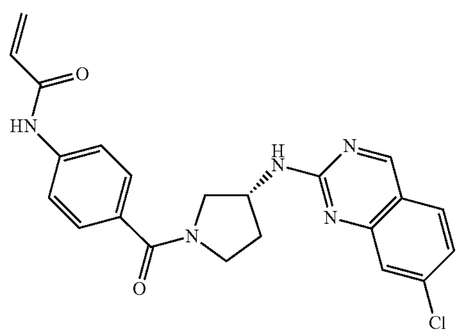 | (R)-N-(4-(3-((7-chloroquinazolin-2-yl)amino)pyrrolidine-1-carbonyl)phenyl)acrylamide |
| 37 | 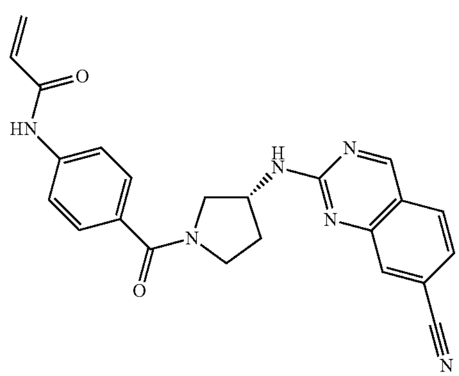 [SMILES: C=CC(=O)Nc1ccc(C(=O)N2CC[C@@H](Nc3ncc4ccc(C#N)cc4n3)C2)cc1] | (R)-N-(4-(3-((7-cyanoquinazolin-2-yl)amino)pyrrolidine-1-carbonyl)phenyl)acrylamide |

TABLE 1-continued

| Synthetic Chemistry Example | Compound Structure | Compound Name |
|---|---|---|
| 38 | 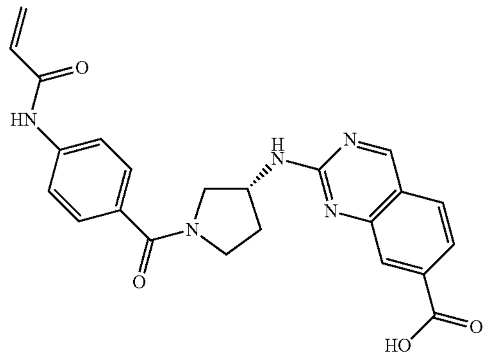 [SMILES: C=CC(=O)Nc1ccc(C(=O)N2CC[C@@H](Nc3ncc4ccc(C(=O)O)cc4n3)C2)cc1] | (R)-2-((1-(4-acrylamidobenzoyl)pyrrolidin-3-yl)amino)quinazoline-7-carboxylic acid |
| 39 | 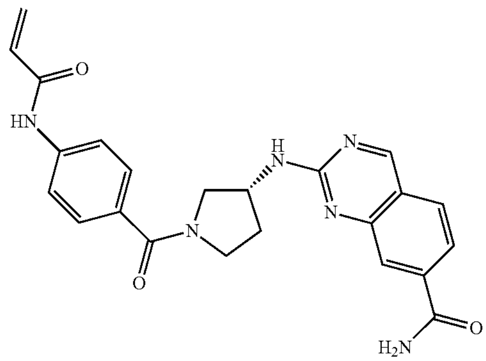 [SMILES: C=CC(=O)Nc1ccc(C(=O)N2CC[C@@H](Nc3ncc4ccc(C(N)=O)cc4n3)C2)cc1] | (R)-2-((1-(4-acrylamidobenzoyl)pyrrolidin-3-yl)amino)quinazoline-7-carboxamide |
| 40 | 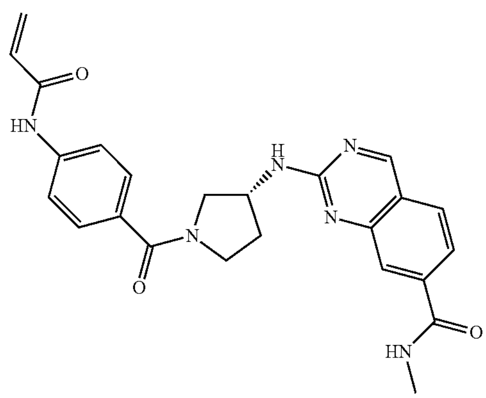 [SMILES: C=CC(=O)Nc1ccc(C(=O)N2CC[C@@H](Nc3ncc4ccc(C(=O)NC)cc4n3)C2)cc1] | (R)-2-((1-(4-acrylamidobenzoyl)pyrrolidin-3-yl)amino)-N-methylquinazoline-7-carboxamide |
| 41 | 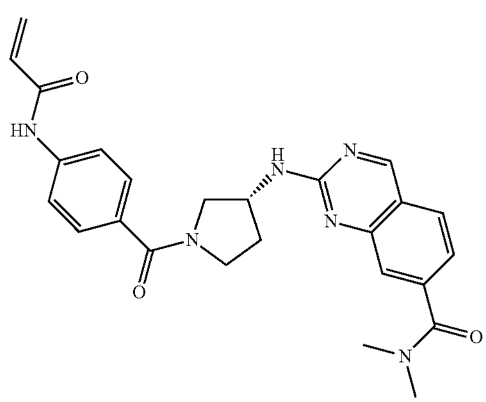 [SMILES: C=CC(=O)Nc1ccc(C(=O)N2CC[C@@H](Nc3ncc4ccc(C(=O)N(C)C)cc4n3)C2)cc1] | (R)-2-((1-(4-acrylamidobenzoyl)pyrrolidin-3-yl)amino)-N,N-dimethylquinazoline-7-carboxamide |

TABLE 1-continued

| Synthetic Chemistry Example | Compound Structure | Compound Name |
|---|---|---|
| 42 | 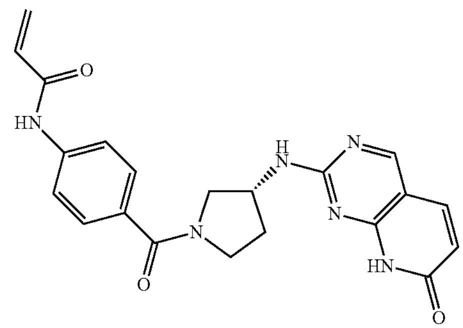 [SMILES: C=CC(=O)Nc1ccc(C(=O)N2CC[C@@H](Nc3ncc4ccc(=O)[nH]c4n3)C2)cc1] | (R)-N-(4-(3-((7-oxo-7,8-dihydropyrido[2,3-d]pyrimidin-2-yl)amino)pyrrolidine-1-carbonyl)phenyl)acrylamide |
| 43 | 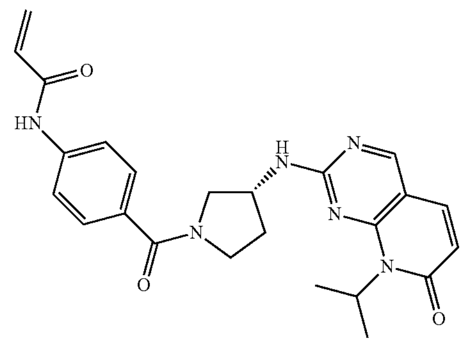 [SMILES: C=CC(=O)Nc1ccc(C(=O)N2CC[C@@H](Nc3ncc4ccc(=O)n(C(C)C)c4n3)C2)cc1] | (R)-N-(4-(3-((8-isopropyl-7-oxo-7,8-dihydropyrido[2,3-d]pyrimidin-2-yl)amino)pyrrolidine-1-carbonyl)phenyl)acrylamide |
| 58 | 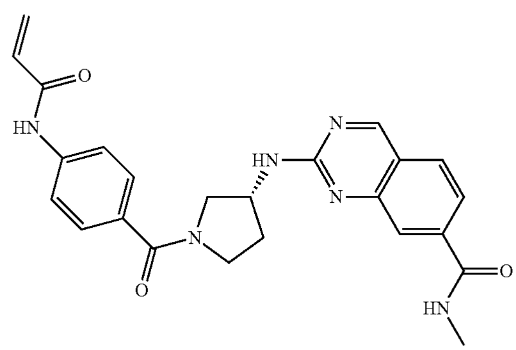 [SMILES: C=CC(=O)Nc1ccc(C(=O)N2CC[C@@H](Nc3ncc4ccc(C(=O)NC)cc4n3)C2)cc1] | (R)-2-((1-(4-acrylamidobenzoyl)pyrrolidin-3-yl)amino)-N-methylquinazoline-7-carboxamide |
| 62 | 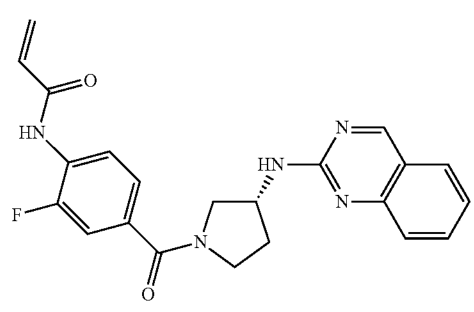 [SMILES: C=CC(=O)Nc1ccc(C(=O)N2CC[C@@H](Nc3ncc4ccccc4n3)C2)cc1F] | (R)-N-(2-fluoro-4-(3-(quinazolin-2-ylamino)pyrrolidine-1-carbonyl)phenyl)acrylamide |

TABLE 1-continued

| Synthetic Chemistry Example | Compound Structure | Compound Name |
|---|---|---|
| 63 | 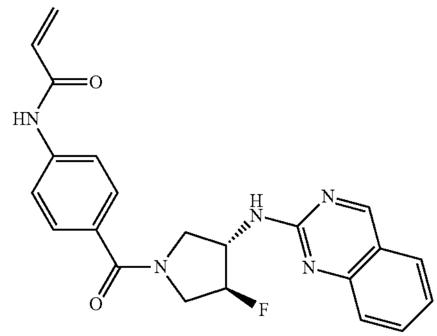 [SMILES: C=CC(=O)Nc1ccc(C(=O)N2C[C@H](Nc3ncc4ccccc4n3)[C@@H](F)C2)cc1] | N-(4-((3S,4S)-3-fluoro-4-(quinazolin-2-ylamino)pyrrolidine-1-carbonyl)phenyl)acrylamide |
| 64 | 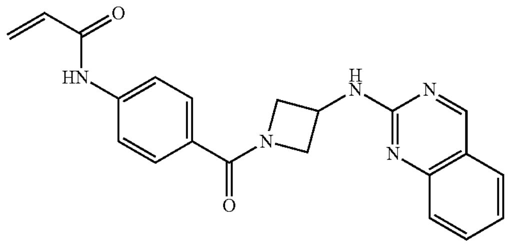 [SMILES: C=CC(=O)Nc1ccc(C(=O)N2CC(Nc3ncc4ccccc4n3)C2)cc1] | N-(4-(3-(quinazolin-2-ylamino)azetidine-1-carbonyl)phenyl)acrylamide |
| 65 | 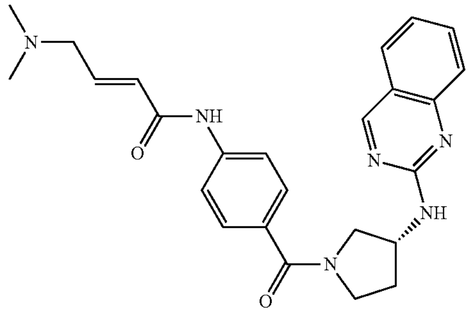 [SMILES: CN(C)C/C=C/C(=O)Nc1ccc(C(=O)N2CC[C@@H](Nc3ncc4ccccc4n3)C2)cc1] | (R,E)-4-(dimethylamino)-N-(4-(3-(quinazolin-2-ylamino)pyrrolidine-1-carbonyl)phenyl)but-2-enamide |
| 66 | 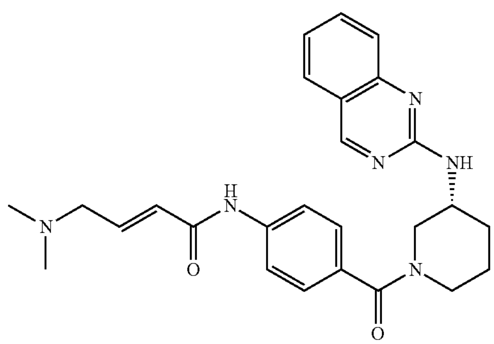 [SMILES: CN(C)C/C=C/C(=O)Nc1ccc(C(=O)N2CCC[C@@H](Nc3ncc4ccccc4n3)C2)cc1] | (R,E)-4-(dimethylamino)-N-(4-(3-(quinazolin-2-ylamino)piperidine-1-carbonyl)phenyl)but-2-enamide |
| 67 | 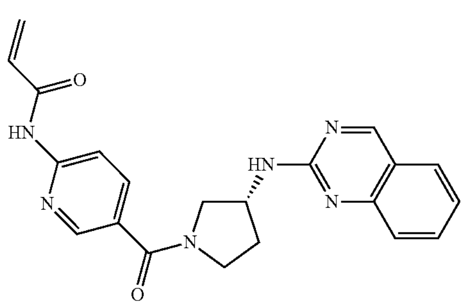 [SMILES: C=CC(=O)Nc1ccc(C(=O)N2CC[C@@H](Nc3ncc4ccccc4n3)C2)cn1] | (R)-N-(5-(3-(quinazolin-2-ylamino)pyrrolidine-1-carbonyl)pyridin-2-yl)acrylamide |

TABLE 1-continued

| Synthetic Chemistry Example | Compound Structure | Compound Name |
|---|---|---|
| 68 | 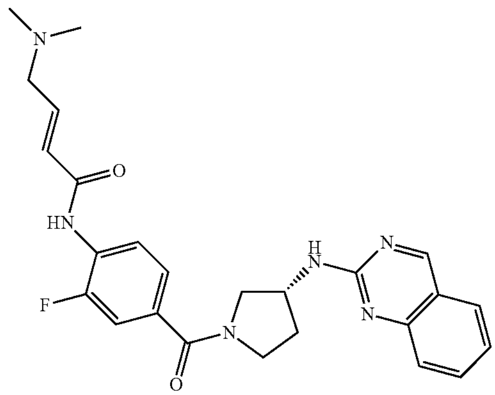 [SMILES: CN(C)C/C=C/C(=O)Nc1ccc(C(=O)N2CC[C@@H](Nc3ncc4ccccc4n3)C2)cc1F] | (R,E)-4-(dimethylamino)-N-(2-fluoro-4-(3-(quinazolin-2-ylamino)pyrrolidine-1-carbonyl)phenyl)but-2-enamide |
| 69 | 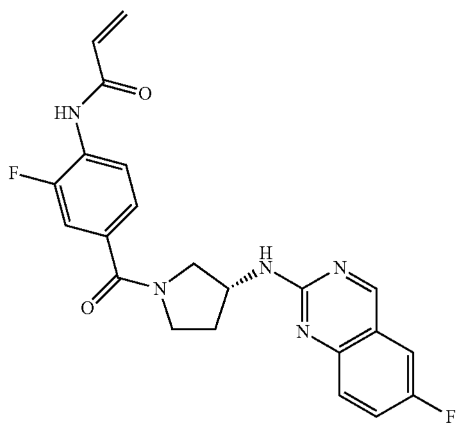 [SMILES: C=CC(=O)Nc1ccc(C(=O)N2CC[C@@H](Nc3ncc4cc(F)ccc4n3)C2)cc1F] | (R)-N-(2-fluoro-4-(3-((6-fluoroquinazolin-2-yl)amino)pyrrolidine-1-carbonyl)phenyl)acrylamide |
| 70 | 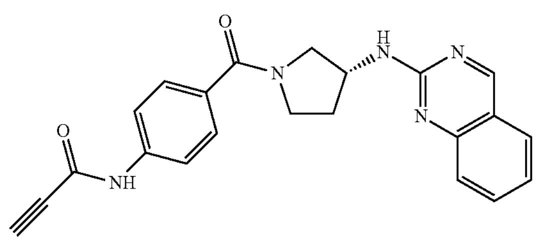 [SMILES: C#CC(=O)Nc1ccc(C(=O)N2CC[C@@H](Nc3ncc4ccccc4n3)C2)cc1] | (R)-N-(4-(3-(quinazolin-2-ylamino)pyrrolidine-1-carbonyl)phenyl)propiolamide |
| 71 | 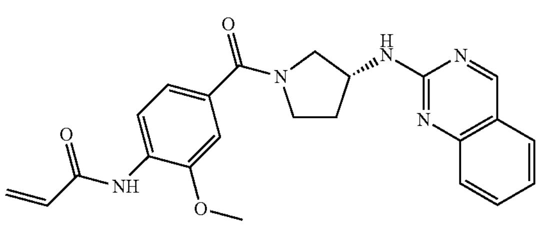 [SMILES: C=CC(=O)Nc1ccc(C(=O)N2CC[C@@H](Nc3ncc4ccccc4n3)C2)cc1OC] | (R)-N-(2-methoxy-4-(3-(quinazolin-2-ylamino)pyrrolidine-1-carbonyl)phenyl)acrylamide |
| 72 | 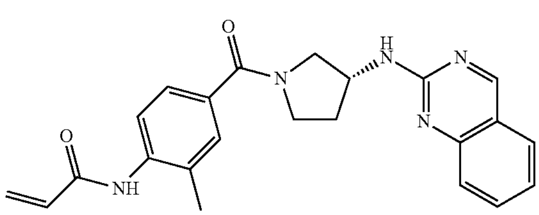 [SMILES: C=CC(=O)Nc1ccc(C(=O)N2CC[C@@H](Nc3ncc4ccccc4n3)C2)cc1C] | (R)-N-(2-methyl-4-(3-(quinazolin-2-ylamino)pyrrolidine-1-carbonyl)phenyl)acrylamide |

TABLE 1-continued

| Synthetic Chemistry Example | Compound Structure | Compound Name |
|---|---|---|
| 73 | 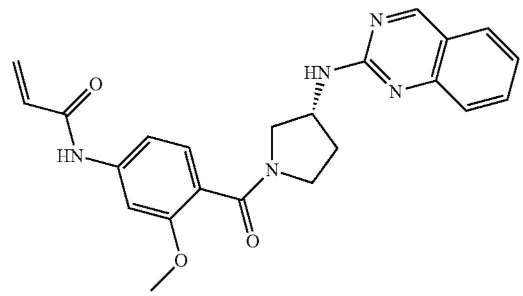 [SMILES: C=CC(=O)Nc1ccc(C(=O)N2CC[C@@H](Nc3ncc4ccccc4n3)C2)c(OC)c1] | N-{3-Methoxy-4-[3-(quinazolin-2-ylamino)-pyrrolidine-1-carbonyl]-phenyl}-acrylamide |
| 74 | 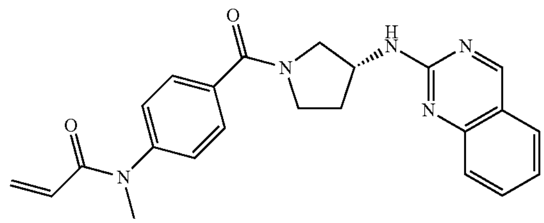 [SMILES: C=CC(=O)N(C)c1ccc(C(=O)N2CC[C@@H](Nc3ncc4ccccc4n3)C2)cc1] | (R)-N-methyl-N-(4-(3-(quinazolin-2-ylamino)pyrrolidine-1-carbonyl)phenyl)acrylamide |
| 75 | 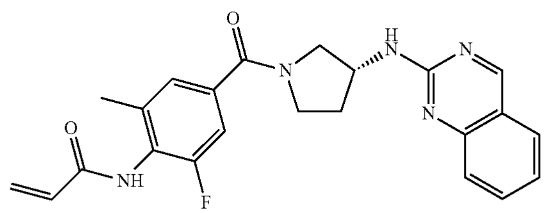 [SMILES: C=CC(=O)Nc1c(C)cc(C(=O)N2CC[C@@H](Nc3ncc4ccccc4n3)C2)cc1F] | (R)-N-(2-fluoro-6-methyl-4-(3-(quinazolin-2-ylamino)pyrrolidine-1-carbonyl)phenyl)acrylamide |
| 76 | 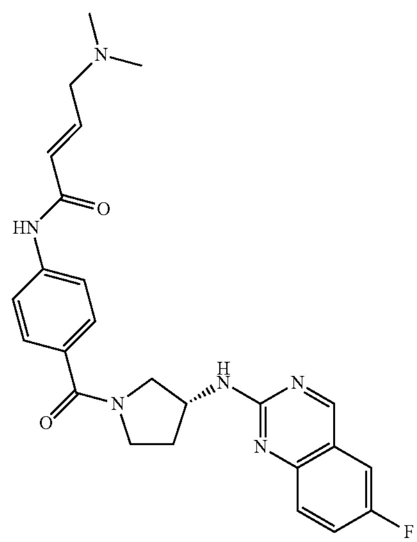 [SMILES: CN(C)C/C=C/C(=O)Nc1ccc(C(=O)N2CC[C@@H](Nc3ncc4cc(F)ccc4n3)C2)cc1] | (R,E)-4-(dimethylamino)-N-(4-(3-((6-fluoroquinazolin-2-yl)amino)pyrrolidine-1-carbonyl)phenyl)but-2-enamide |
| 77 | 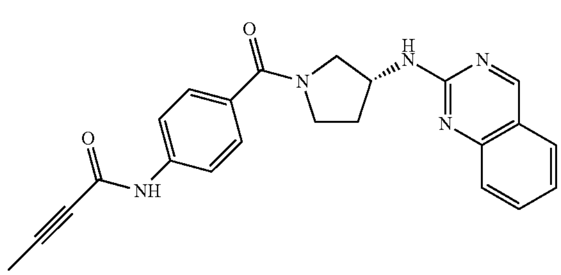 [SMILES: CC#CC(=O)Nc1ccc(C(=O)N2CC[C@@H](Nc3ncc4ccccc4n3)C2)cc1] | (R)-N-(4-(3-(quinazolin-2-ylamino)pyrrolidine-1-carbonyl)phenyl)but-2-ynamide |

TABLE 1-continued

| Synthetic Chemistry Example | Compound Structure | Compound Name |
|---|---|---|
| 78 | 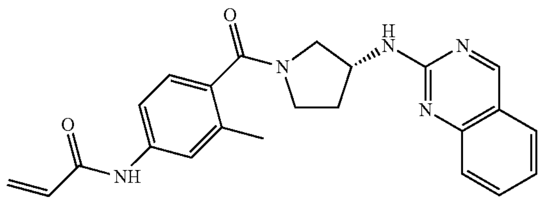 [SMILES: C=CC(=O)Nc1ccc(C(=O)N2CC[C@@H](Nc3ncc4ccccc4n3)C2)c(C)c1] | (R)-N-(3-methyl-4-(3-(quinazolin-2-ylamino)pyrrolidine-1-carbonyl)phenyl)acrylamide |
| 79 | 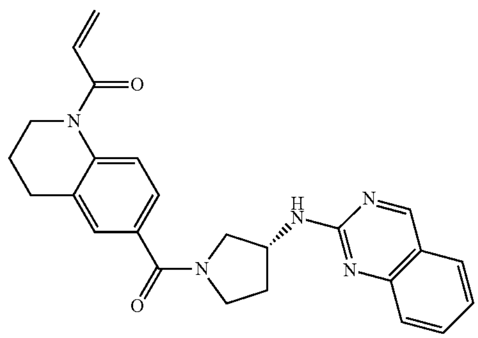 [SMILES: C=CC(=O)N1CCCc2cc(C(=O)N3CC[C@@H](Nc4ncc5ccccc5n4)C3)ccc21] | (R)-1-(6-(3-(quinazolin-2-ylamino)pyrrolidine-1-carbonyl)-3,4-dihydroquinolin-1(2H)-yl)prop-2-en-1-one |
| 80 | 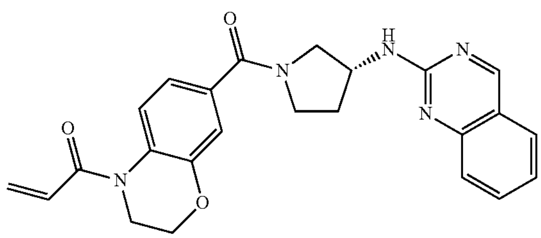 [SMILES: C=CC(=O)N1CCOc2cc(C(=O)N3CC[C@@H](Nc4ncc5ccccc5n4)C3)ccc21] | (R)-1-(7-(3-(quinazolin-2-ylamino)pyrrolidine-1-carbonyl)-2H-benzo[b][1,4]oxazin-4(3H)-yl)prop-2-en-1-one |
| 81 | 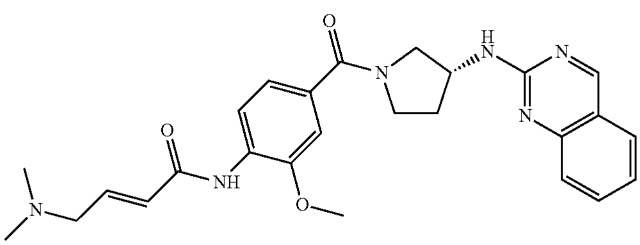 [SMILES: COc1cc(C(=O)N2CC[C@@H](Nc3ncc4ccccc4n3)C2)ccc1NC(=O)/C=C/CN(C)C] | (R,E)-4-(dimethylamino)-N-(2-methoxy-4-(3-(quinazolin-2-ylamino)pyrrolidine-1-carbonyl)phenyl)but-2-enamide |
| 82 | 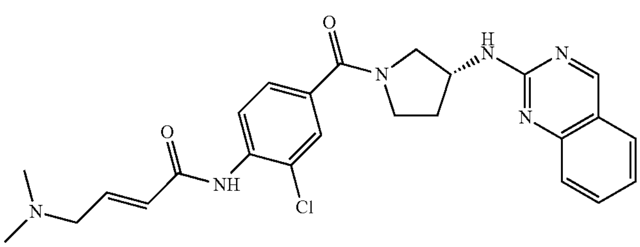 | (R,E)-N-(2-chloro-4-(3-(quinazolin-2-ylamino)pyrrolidine-1-carbonyl)phenyl)-4-(dimethylamino)but-2-enamide |
| 83 | 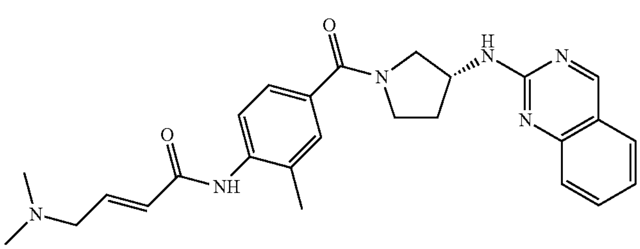 [SMILES: Cc1cc(C(=O)N2CC[C@@H](Nc3ncc4ccccc4n3)C2)ccc1NC(=O)/C=C/CN(C)C] | (R,E)-4-(dimethylamino)-N-(2-methyl-4-(3-(quinazolin-2-ylamino)pyrrolidine-1-carbonyl)phenyl)but-2-enamide |

TABLE 1-continued

| Synthetic Chemistry Example | Compound Structure | Compound Name |
|---|---|---|
| 84 | 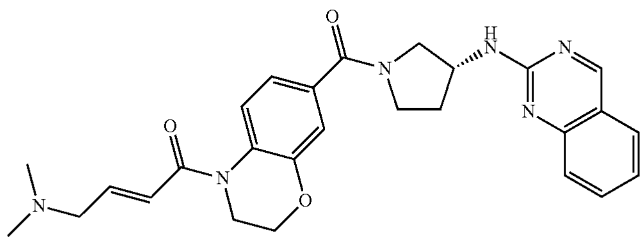 [SMILES: CN(C)C/C=C/C(=O)N1CCOc2cc(C(=O)N3CC[C@@H](Nc4ncc5ccccc5n4)C3)ccc21] | (R,E)-4-(dimethylamino)-1-(7-(3-(quinazolin-2-ylamino)pyrrolidine-1-carbonyl)-2H-benzo[b][1,4]oxazin-4(3H)-yl)but-2-en-1-one |
| 85 | 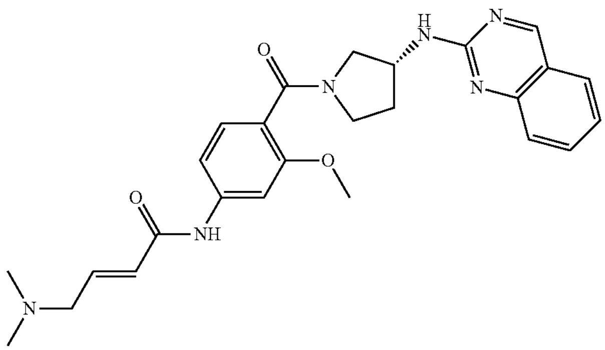 [SMILES: COc1cc(NC(=O)/C=C/CN(C)C)ccc1C(=O)N1CC[C@@H](Nc2ncc3ccccc3n2)C1] | 4-Dimethylamino-but-2-enoic acid {3-methoxy-4-[3-(quinazolin-2-ylamino)-pyrrolidine-1-carbonyl]-phenyl}-amide |
| 86 | 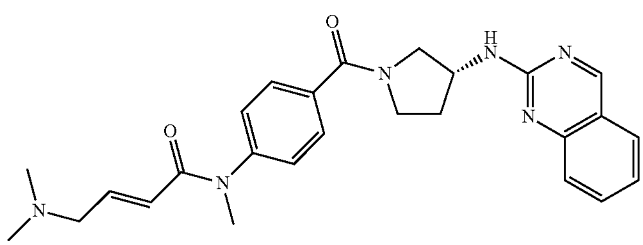 [SMILES: CN(C)C/C=C/C(=O)N(C)c1ccc(C(=O)N2CC[C@@H](Nc3ncc4ccccc4n3)C2)cc1] | (R,E)-4-(dimethylamino)-N-methyl-N-(4-(3-(quinazolin-2-ylamino)pyrrolidine-1-carbonyl)phenyl)but-2-enamide |
| 87 | 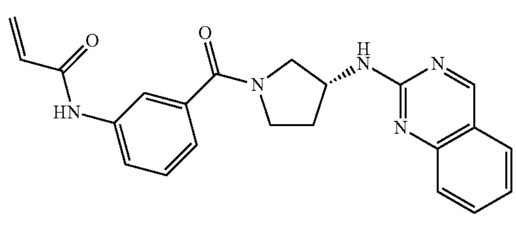 [SMILES: C=CC(=O)Nc1cccc(C(=O)N2CC[C@@H](Nc3ncc4ccccc4n3)C2)c1] | (R)-N-(3-(3-(quinazolin-2-ylamino)pyrrolidine-1-carbonyl)phenyl)acrylamide |
| 88 | 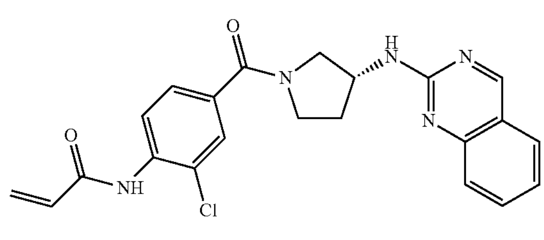 [SMILES: C=CC(=O)Nc1ccc(C(=O)N2CC[C@@H](Nc3ncc4ccccc4n3)C2)cc1Cl] | (R)-N-(2-chloro-4-(3-(quinazolin-2-ylamino)pyrrolidine-1-carbonyl)phenyl)acrylamide |

TABLE 1-continued

| Synthetic Chemistry Example | Compound Structure | Compound Name |
|---|---|---|
| 89 | 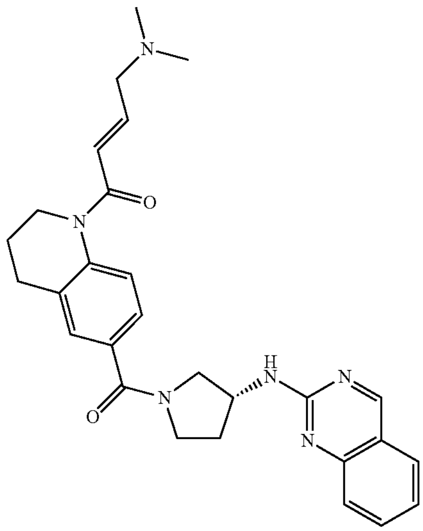 [SMILES: CN(C)C/C=C/C(=O)N1CCCc2cc(C(=O)N3CC[C@@H](Nc4ncc5ccccc5n4)C3)ccc21] | (R,E)-4-(dimethylamino)-1-(6-(3-(quinazolin-2-ylamino)pyrrolidine-1-carbonyl)-3,4-dihydroquinolin-1(2H)-yl)but-2-en-1-one |
| 90 | 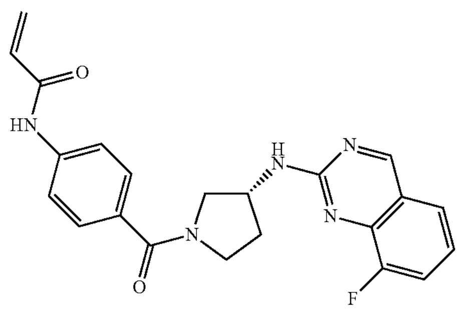 [SMILES: C=CC(=O)Nc1ccc(C(=O)N2CC[C@@H](Nc3ncc4cccc(F)c4n3)C2)cc1] | (R)-N-(4-(3-((8-fluoroquinazolin-2-yl)amino)pyrrolidine-1-carbonyl)phenyl)acrylamide |
| 91 | 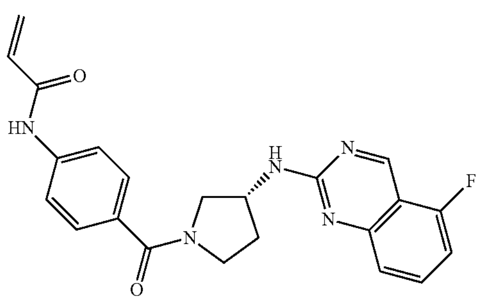 [SMILES: C=CC(=O)Nc1ccc(C(=O)N2CC[C@@H](Nc3ncc4c(F)cccc4n3)C2)cc1] | (R)-N-(4-(3-((5-fluoroquinazolin-2-yl)amino)pyrrolidine-1-carbonyl)phenyl)acrylamide |
| 92 | 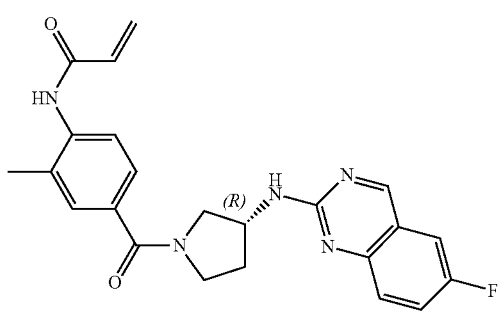 | (R)-N-(4-(3-((6-fluoroquinazolin-2-yl)amino)pyrrolidine-1-carbonyl)-2-methylphenyl)acrylamide |

TABLE 1-continued

| Synthetic Chemistry Example | Compound Structure | Compound Name |
|---|---|---|
| 93 | 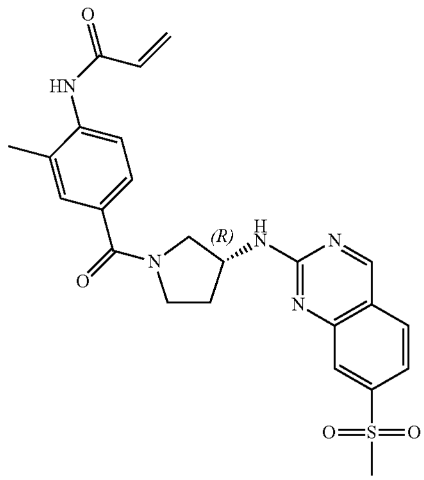 | (R)-N-(2-methyl-4-(3-((7-(methylsulfonyl)quinazolin-2-yl)amino)pyrrolidine-1-carbonyl)phenyl)acrylamide |
| 94 | 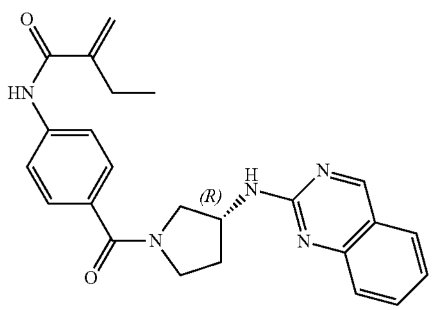 | (R)-2-methylene-N-(4-(3-(quinazolin-2-ylamino)pyrrolidine-1-carbonyl)phenyl)butanamide |
| 95 | 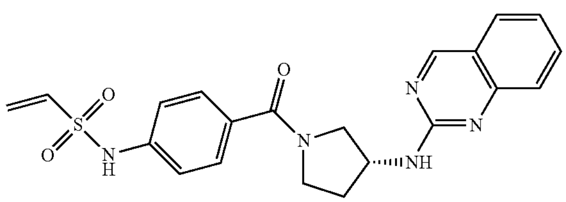 [SMILES: C=CS(=O)(=O)Nc1ccc(C(=O)N2CC[C@@H](Nc3ncc4ccccc4n3)C2)cc1] | (R)-N-(4-(3-(quinazolin-2-ylamino)pyrrolidine-1-carbonyl)phenyl)ethenesulfonamide |
| 96 | 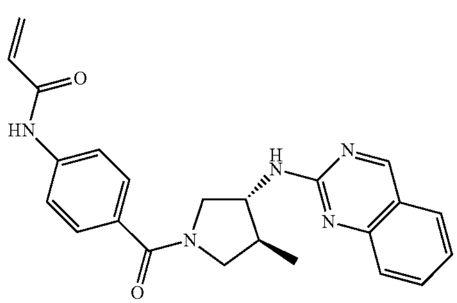 [SMILES: C=CC(=O)Nc1ccc(C(=O)N2C[C@H](Nc3ncc4ccccc4n3)[C@@H](C)C2)cc1] | N-(4-((3S,4R)-3-methyl-4-(quinazolin-2-ylamino)pyrrolidine-1-carbonyl)phenyl)acrylamide |

One embodiment provides a compound, or pharmaceutically acceptable salt or solvate thereof, having the structure of Formula (III):

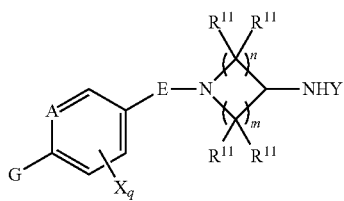
(III)

wherein,
A is C—H, or N;
E is selected from a bond, —SO$_2$—, —C(O)—, —CH$_2$—, —CH(R$^4$)—, or —C(R$^4$)$_2$—; A is C—H or N;
G is selected from a group having the structure:

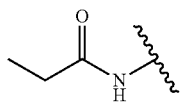

wherein,
r is 0, 1, or 2;
each R$^{11}$ is independently selected from hydrogen, halogen, optionally substituted C1-C6 alkyl, or both R$^{11}$ groups form an oxo;
q is 0, 1, or 2; n is 0, 1, 2, or 3; m is 0, 1, 2, or 3;
X is halogen, optionally substituted C1-C4 alkyl, or optionally substituted C1-C4 alkoxy;
Y is a group selected from:

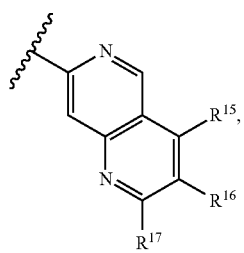

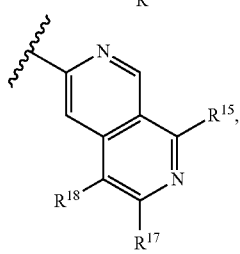

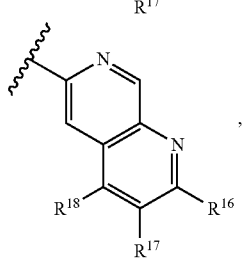

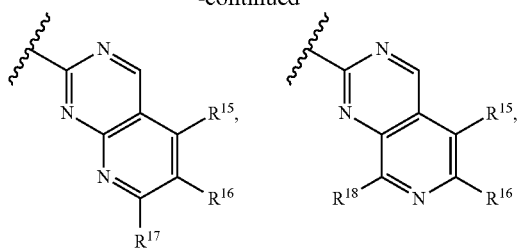

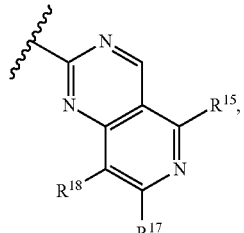

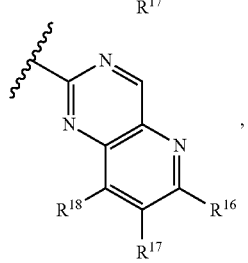

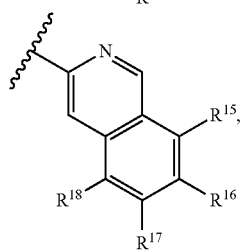

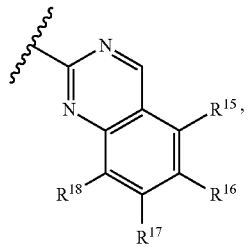

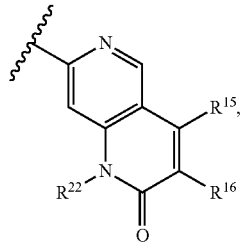

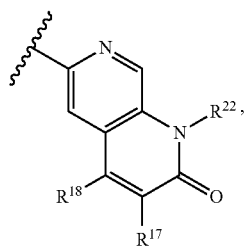

-continued

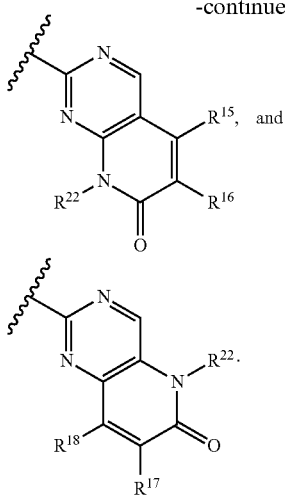

wherein, $R^{15}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N($R^{22}$)$_2$, —SO$_2$$R^{21}$, —N($R^{22}$)SO$_2$$R^{21}$, —SO$_2$N($R^{22}$)$_2$, —N($R^{22}$)SO$_2$N($R^{22}$)$_2$, —CON($R^{22}$)$_2$, —N($R^{22}$)CO$_2$$R^{21}$, —N($R^{22}$)CON($R^{22}$)$_2$, —N($R^{22}$)COR$^{21}$, —OC(O)N($R^{22}$)$_2$, —OSO$_2$N($R^{22}$)$_2$, or —N($R^{22}$)SO$_3$$R^{21}$;

$R^{16}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N($R^{22}$)$_2$, —SO$_2$$R^{21}$, —N($R^{22}$)SO$_2$$R^{21}$, —SO$_2$N($R^{22}$)$_2$, —N($R^{22}$)SO$_2$N($R^{22}$)$_2$, —CON($R^{22}$)$_2$, —N($R^{22}$)CO$_2$$R^{21}$, —N($R^{22}$)CON($R^{22}$)$_2$, —N($R^{22}$)COR$^{21}$, —OC(O)N($R^{22}$)$_2$, —OSO$_2$N($R^{22}$)$_2$, or —N($R^{22}$)SO$_3$$R^{21}$;

$R^{17}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N($R^{22}$)$_2$, —SO$_2$$R^{21}$, —N($R^{22}$)SO$_2$$R^{21}$, —SO$_2$N($R^{22}$)$_2$, —N($R^{22}$)SO$_2$N($R^{22}$)$_2$, —CON($R^{22}$)$_2$, —N($R^{22}$)CO$_2$$R^{21}$, —N($R^{22}$)CON($R^{22}$)$_2$, —N($R^{22}$)COR$^{21}$, —OC(O)N($R^{22}$)$_2$, —OSO$_2$N($R^{22}$)$_2$, or —N($R^{22}$)SO$_3$$R^{21}$;

$R^{18}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N($R^{22}$)$_2$, —SO$_2$$R^{21}$, —N($R^{22}$)SO$_2$$R^{21}$, —SO$_2$N($R^{22}$)$_2$, —N($R^{22}$)SO$_2$N($R^{22}$)$_2$, —CON($R^{22}$)$_2$, —N($R^{22}$)CO$_2$$R^{21}$, —N($R^{22}$)CON($R^{22}$)$_2$, —N($R^{22}$)COR$^{21}$, —OC(O)N($R^{22}$)$_2$, —OSO$_2$N($R^{22}$)$_2$, or —N($R^{22}$)SO$_3$$R^{21}$;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

In some embodiments, the heteroaromatic CDK inhibitory compound of Formula (III) as described herein has a structure provided in Table 2.

TABLE 2

| Synthetic Chemistry Example | Compound Structure | Compound Name |
|---|---|---|
| 17 | 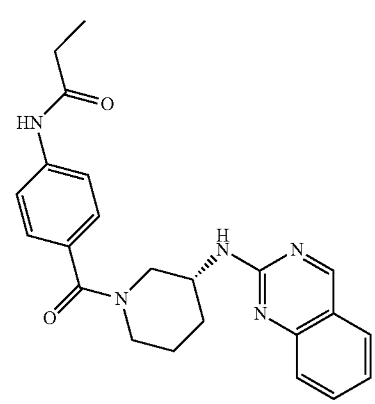 [SMILES: CCC(=O)Nc1ccc(C(=O)N2CCC[C@@H](Nc3ncc4ccccc4n3)C2)cc1] | (R)-N-(4-(3-(quinazolin-2-ylamino)piperidine-1-carbonyl)phenyl)propionamide |

TABLE 2-continued

| Synthetic Chemistry Example | Compound Structure | Compound Name |
|---|---|---|
| 18 | 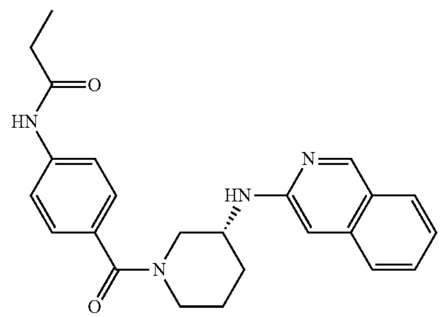 [SMILES: CCC(=O)Nc1ccc(C(=O)N2CCC[C@@H](Nc3cc4ccccc4cn3)C2)cc1] | (R)-N-(4-(3-(isoquinolin-3-ylamino)piperidine-1-carbonyl)phenyl)propionamide |
| 19 | 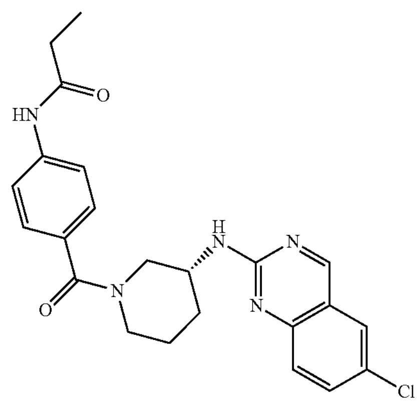 [SMILES: CCC(=O)Nc1ccc(C(=O)N2CCC[C@@H](Nc3ncc4cc(Cl)ccc4n3)C2)cc1] | (R)-N-(4-(3-((6-chloroquinazolin-2-yl)amino)piperidine-1-carbonyl)phenyl)propionamide |
| 20 | 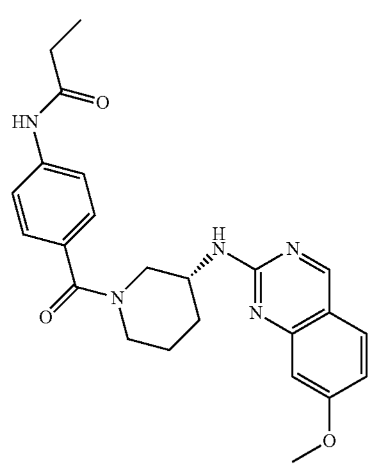 [SMILES: CCC(=O)Nc1ccc(C(=O)N2CCC[C@@H](Nc3ncc4ccc(OC)cc4n3)C2)cc1] | (R)-N-(4-(3-((7-methoxyquinazolin-2-yl)amino)piperidine-1-carbonyl)phenyl)propionamide |

TABLE 2-continued

| Synthetic Chemistry Example | Compound Structure | Compound Name |
|---|---|---|
| 21 | 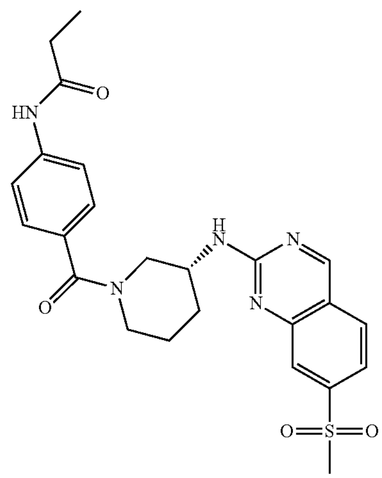 [SMILES: CCC(=O)Nc1ccc(C(=O)N2CCC[C@@H](Nc3ncc4ccc(S(C)(=O)=O)cc4n3)C2)cc1] | (R)-N-(4-(3-((7-(methylsulfonyl)quinazolin-2-yl)amino)piperidine-1-carbonyl)phenyl)propionamide |
| 22 | 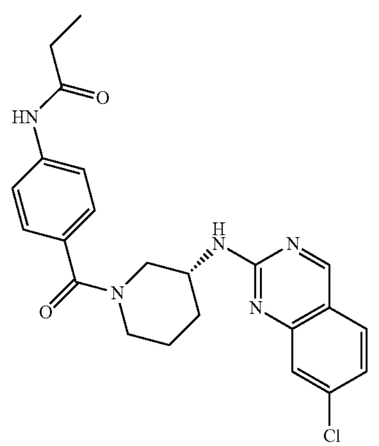 | (R)-N-(4-(3-((7-chloroquinazolin-2-yl)amino)piperidine-1-carbonyl)phenyl)propionamide |
| 23 | 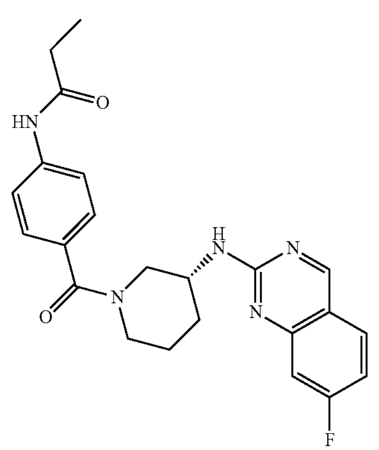 | (R)-N-(4-(3-((7-fluoroquinazolin-2-yl)amino)piperidine-1-carbonyl)phenyl)propionamide |

TABLE 2-continued

| Synthetic Chemistry Example | Compound Structure | Compound Name |
|---|---|---|
| 24 | 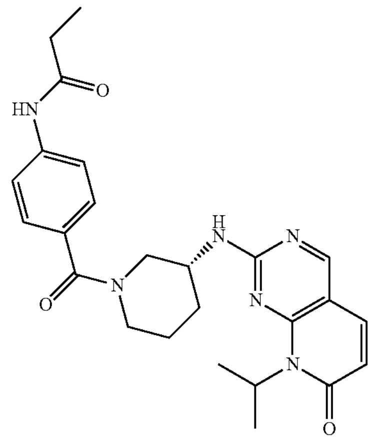 [SMILES: CCC(=O)Nc1ccc(C(=O)N2CCC[C@@H](Nc3ncc4ccc(=O)n(C(C)C)c4n3)C2)cc1] | (R)-N-(4-(3-((8-isopropyl-7-oxo-7,8-dihydropyrido[2,3-d]pyrimidin-2-yl)amino)piperidine-1-carbonyl)phenyl)propionamide |
| 44 | 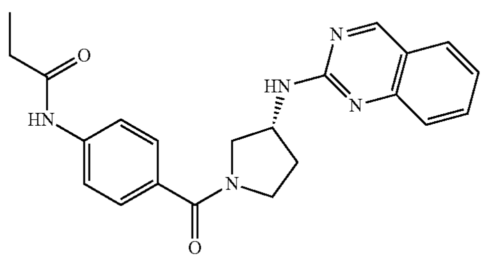 [SMILES: CCC(=O)Nc1ccc(C(=O)N2CC[C@@H](Nc3ncc4ccccc4n3)C2)cc1] | (R)-N-(4-(3-(quinazolin-2-ylamino)pyrrolidine-1-carbonyl)phenyl)propionamide |
| 45 | 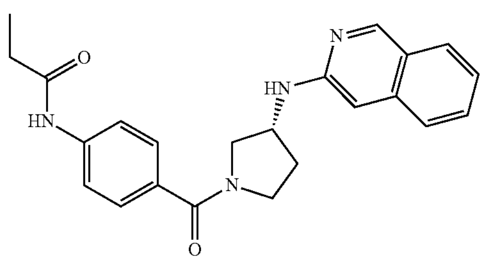 [SMILES: CCC(=O)Nc1ccc(C(=O)N2CC[C@@H](Nc3cc4ccccc4cn3)C2)cc1] | (R)-N-(4-(3-(isoquinolin-3-ylamino)pyrrolidine-1-carbonyl)phenyl)propionamide |
| 46 | 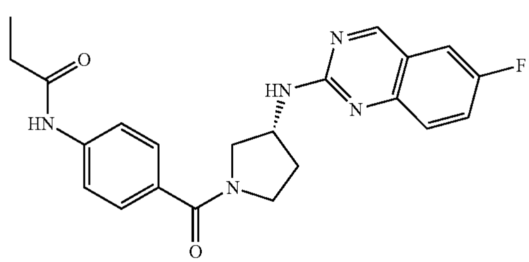 [SMILES: CCC(=O)Nc1ccc(C(=O)N2CC[C@@H](Nc3ncc4cc(F)ccc4n3)C2)cc1] | (R)-N-(4-(3-((6-fluoroquinazolin-2-yl)amino)pyrrolidine-1-carbonyl)phenyl)propionamide |
| 47 | 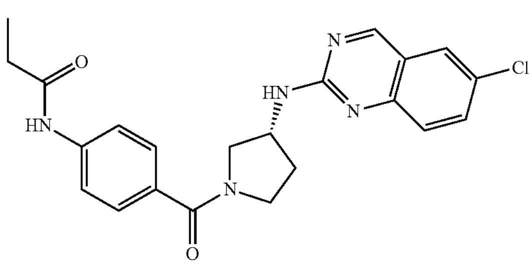 [SMILES: CCC(=O)Nc1ccc(C(=O)N2CC[C@@H](Nc3ncc4cc(Cl)ccc4n3)C2)cc1] | (R)-N-(4-(3-((6-chloroquinazolin-2-yl)amino)pyrrolidine-1-carbonyl)phenyl)propionamide |

TABLE 2-continued

| Synthetic Chemistry Example | Compound Structure | Compound Name |
|---|---|---|
| 48 | 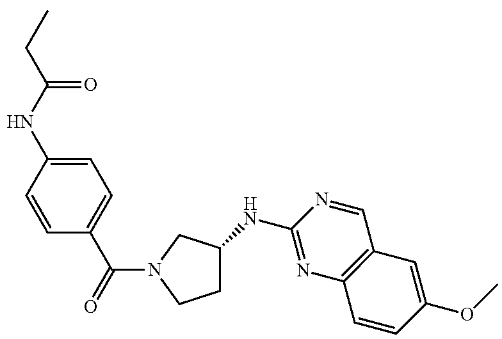 [SMILES: CCC(=O)Nc1ccc(C(=O)N2CC[C@@H](Nc3ncc4cc(OC)ccc4n3)C2)cc1] | (R)-N-(4-(3-((6-methoxyquinazolin-2-yl)amino)pyrrolidine-1-carbonyl)phenyl)propionamide |
| 49 | 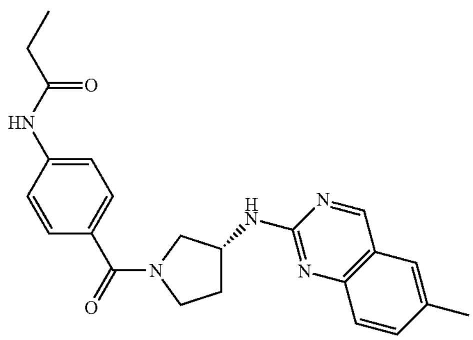 [SMILES: CCC(=O)Nc1ccc(C(=O)N2CC[C@@H](Nc3ncc4cc(C)ccc4n3)C2)cc1] | (R)-N-(4-(3-((6-methylquinazolin-2-yl)amino)pyrrolidine-1-carbonyl)phenyl)propionamide |
| 50 | 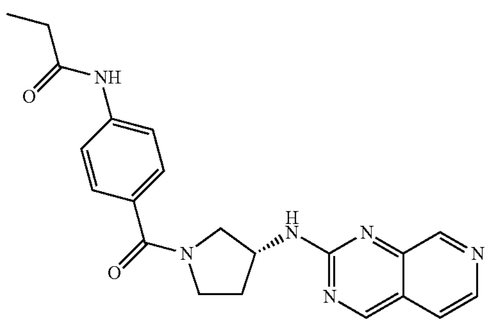 [SMILES: CCC(=O)Nc1ccc(C(=O)N2CC[C@@H](Nc3ncc4ccncc4n3)C2)cc1] | (R)-N-(4-(3-(pyrido[3,4-d]pyrimidin-2-ylamino)pyrrolidine-1-carbonyl)phenyl)propionamide |
| 51 | 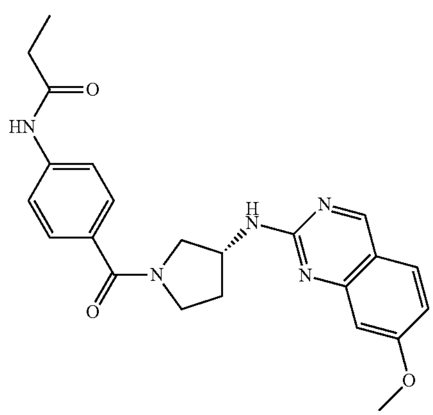 [SMILES: CCC(=O)Nc1ccc(C(=O)N2CC[C@@H](Nc3ncc4ccc(OC)cc4n3)C2)cc1] | (R)-N-(4-(3-((7-methoxyquinazolin-2-yl)amino)pyrrolidine-1-carbonyl)phenyl)propionamide |

TABLE 2-continued

| Synthetic Chemistry Example | Compound Structure | Compound Name |
| --- | --- | --- |
| 52 | 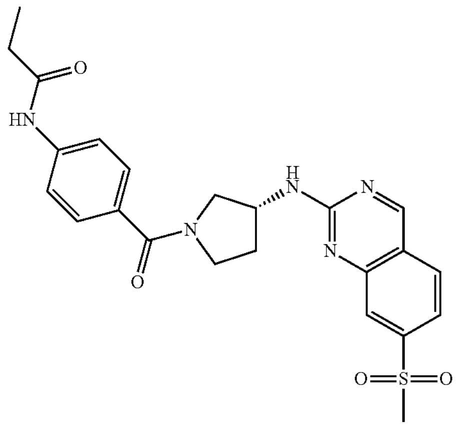 [SMILES: CCC(=O)Nc1ccc(C(=O)N2CC[C@@H](Nc3ncc4ccc(S(C)(=O)=O)cc4n3)C2)cc1] | (R)-N-(4-(3-((7-(methylsulfonyl)quinazolin-2-yl)amino)pyrrolidine-1-carbonyl)phenyl)propionamide |
| 53 | 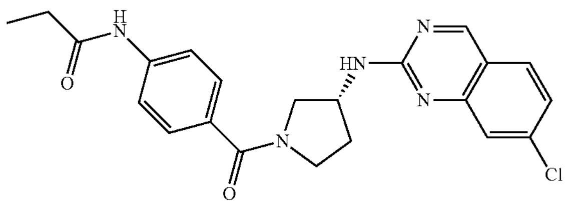 [SMILES: CCC(=O)Nc1ccc(C(=O)N2CC[C@@H](Nc3ncc4ccc(Cl)cc4n3)C2)cc1] | (R)-N-(4-(3-((7-methoxyquinazolin-2-yl)amino)pyrrolidine-1-carbonyl)phenyl)propionamide |
| 54 | 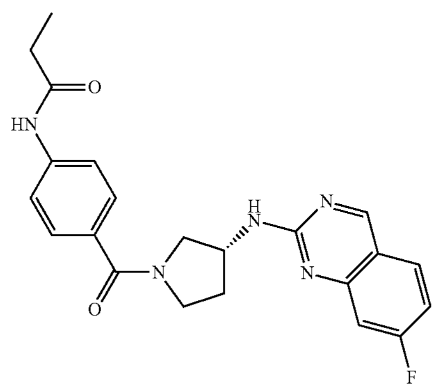 [SMILES: CCC(=O)Nc1ccc(C(=O)N2CC[C@@H](Nc3ncc4ccc(F)cc4n3)C2)cc1] | (R)-N-(4-(3-((7-fluoroquinazolin-2-yl)amino)pyrrolidine-1-carbonyl)phenyl)propionamide |
| 55 | 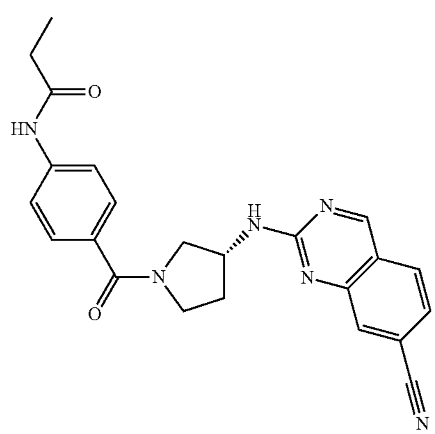 [SMILES: CCC(=O)Nc1ccc(C(=O)N2CC[C@@H](Nc3ncc4ccc(C#N)cc4n3)C2)cc1] | (R)-N-(4-(3-((7-cyanoquinazolin-2-yl)amino)pyrrolidine-1-carbonyl)phenyl)propionamide |

TABLE 2-continued

| Synthetic Chemistry Example | Compound Structure | Compound Name |
|---|---|---|
| 56 | 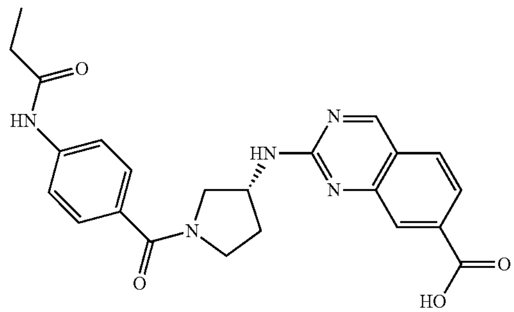 [SMILES: CCC(=O)Nc1ccc(C(=O)N2CC[C@@H](Nc3ncc4ccc(C(=O)O)cc4n3)C2)cc1] | (R)-2-((1-(4-propionamidobenzoyl)pyrrolidin-3-yl)amino)quinazoline-7-carboxylic acid |
| 57 | 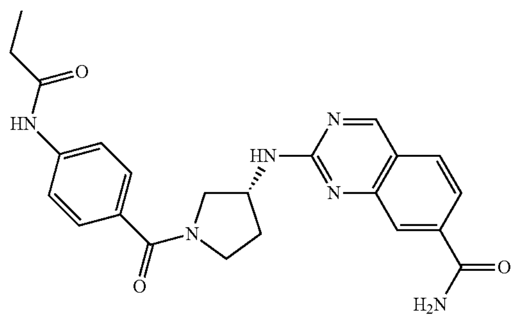 [SMILES: CCC(=O)Nc1ccc(C(=O)N2CC[C@@H](Nc3ncc4ccc(C(N)=O)cc4n3)C2)cc1] | (R)-2-((1-(4-propionamidobenzoyl)pyrrolidin-3-yl)amino)quinazoline-7-carboxamide |
| 59 | 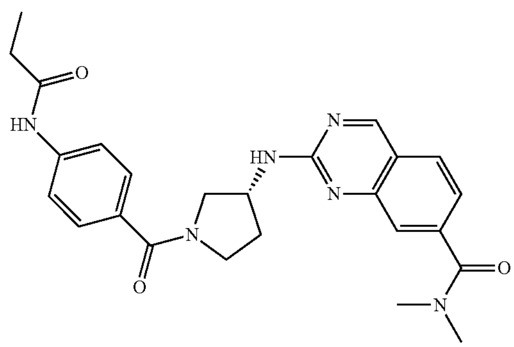 [SMILES: CCC(=O)Nc1ccc(C(=O)N2CC[C@@H](Nc3ncc4ccc(C(=O)N(C)C)cc4n3)C2)cc1] | (R)-N,N-dimethyl-2-((1-(4-propionamidobenzoyl)pyrrolidin-3-yl)amino)quinazoline-7-carboxamide |
| 60 | 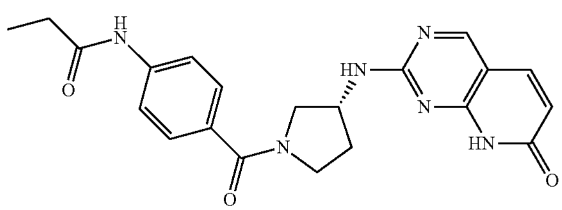 [SMILES: CCC(=O)Nc1ccc(C(=O)N2CC[C@@H](Nc3ncc4ccc(=O)[nH]c4n3)C2)cc1] | (R)-N-(4-(3-((7-oxo-7,8-dihydropyrido[2,3-d]pyrimidin-2-yl)amino)pyrrolidine-1-carbonyl)phenyl)propionamide |
| 61 | 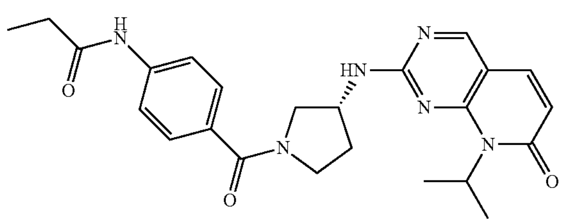 [SMILES: CCC(=O)Nc1ccc(C(=O)N2CC[C@@H](Nc3ncc4ccc(=O)n(C(C)C)c4n3)C2)cc1] | (R)-N-(4-(3-((8-isopropyl-7-oxo-7,8-dihydropyrido[2,3-d]pyrimidin-2-yl)amino)pyrrolidine-1-carbonyl)phenyl)propionamide |

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the heteroaromatic CDK inhibitory compounds described herein is P. H. Stahl & C. G. Wermuth "Handbook of Pharmaceutical Salts", Verlag Helvetica Chimica Acta, Zurich, 2002.

Modification of Cyclin-Dependent Kinase

One embodiment provides a method of inhibiting a CDK enzyme comprising contacting the enzyme with a compound of Formula (I), (II), (Ia) or a compound disclosed in Table 1. One embodiment provides the method wherein the CDK enzyme is selected from CDK7, CDK9, CDK12, or CDK13, or a combination thereof.

One embodiment provides a modified CDK12 polypeptide wherein the active site cysteine of unmodified CDK12 has been modified with a substituent having the structure of Formula (IV):

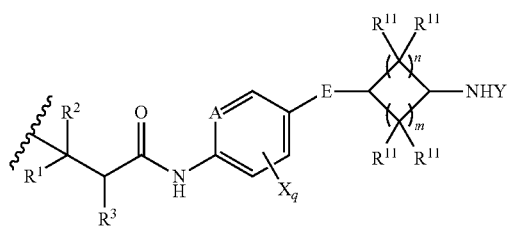

wherein,
A is C—H or N;
E is selected from a bond, —SO$_2$—, —C(O)—, —CH$_2$—, —CH(R$^4$)—, or —C(R$^4$)$_2$—;
R$^1$ is selected from hydrogen, optionally substituted C1-C4 alkyl, or optionally substituted heterocyclylalkyl;
R$^2$ is selected from hydrogen, or optionally substituted C1-C4 alkyl;
R$^3$ is selected from hydrogen, —CN, or optionally substituted C1-C4 alkyl;
each R$^4$ is independently selected from optionally substituted C1-C4 alkyl, or optionally substituted heterocyclylalkyl;
each R$^{11}$ is independently selected from hydrogen, halogen, optionally substituted C1-C6 alkyl, or both R$^{11}$ groups form an oxo;
q is 0, 1, or 2; n is 0, 1, 2, or 3; m is 0, 1, 2, or 3;
X is halogen, optionally substituted C1-C4 alkyl, or optionally substituted C1-C4 alkoxy;
Y is an optionally substituted 10-atom bicyclic heteroaryl with at least one nitrogen atom.

Another embodiment provides the modified CDK12 polypeptide wherein the unmodified CDK12 polypeptide is isoform 1 (*Homo sapiens*).

Another embodiment provides the modified CDK12 polypeptide wherein the unmodified CDK12 polypeptide is isoform 2 (*Homo sapiens*).

Another embodiment provides the modified CDK12 polypeptide wherein the unmodified CDK12 polypeptide is an isoform 1 (*Homo sapiens*) variant. Another embodiment provides the modified CDK12 polypeptide wherein the unmodified CDK12 polypeptide is isoform 1 (*Homo sapiens*) variant I1131V. Another embodiment provides the modified CDK12 polypeptide wherein the unmodified CDK12 polypeptide is isoform 1 (*Homo sapiens*) variant L1189Q. Another embodiment provides the modified CDK12 polypeptide wherein the unmodified CDK12 polypeptide is isoform 1 (*Homo sapiens*) variant T1195M.

Another embodiment provides the modified CDK12 polypeptide wherein the unmodified CDK12 polypeptide is a SEQID selected from a SEQID provided in Table 3 or 4.

TABLE 3

CDK12 Sequences

| SEQ ID NO | Ensembl Protein ID (Accession Number) | Amino Acid Sequence |
|---|---|---|
| 1 | ENSP00000398880 (NP_057591.2) | MPNSERHGGKKDGSGGASGTLQPSSGGGSSNSRERHRLVSKHKRHK SKHSKDMGLVTPEAASLGTVIKPLVEYDDISSDSDTFSDDMAFKLDR RENDERRGSDRSDRLHKHRHHQHRRSRDLLKAKQTEKEKSQEVSSK SGSMKDRISGSSKRSNEETDDYGKAQVAKSSSKESRSSKLHKEKTRK ERELKSGHKDRSKSHRKRETPKSYKTVDSPKRRSRSPHRKWSDSSKQ DDSPSGASYGQDYDLSPSRSHTSSNYDSYKKSPGSTSRRQSVSPPYKE PSAYQSSTRSPSPYSRRQRSVSPYSRRRSSSYERSGSYSGRSPSPYGRR RSSSPFLSKRSLSRSPLPSRKSMKSRSRSPAYSRHSSSHSKKKRSSSRS RHSSISPVRLPLNSSLGAELSRKKKERAAAAAAAKMDGKESKGSPVF LPRKENSSVEAKDSGLESKKLPRSVKLEKSAPDTELVNVTHLNTEVK NSSDTGKVKLDENSEKHLVKDLKAQGTRDSKPIALKEEIVTPKETETS EKETPPPLPTIASPPPPLPTTTPPPQTPPLPPLPPIPALPQQPPLPPSQPAF SQVPASSTSTLPPSTHSKTSAVSSQANSQPPVQVSVKTQVSVTAAIPH LKTSTLPPLPLPPLLPGDDDMDSPKETLPSKPVKKEKEQRTRHLLTDL PLPPELPGGDLSPPDSPEPKAITPPQQPYKKRPKICCPRYGERRQTESD WGKRCVDKFDIIGIIGEGTYGQVYKAKDKDTGELVALKKVRLDNEK EGFPITAIREIKILRQLIHRSVVNMKEIVTDKQDALDFKKDKGAFYLV FEYMDHDLMGLLESGLVHFSEDHIKSFMKQLMEGLEYCHKKNFLHR DIKCSNILLNNSGQIKLADFGLARLYNSEESRPYTNKVITLWYRPPEL LLGEERYTPAIDVWSCGCILGELFTKKPIFQANLELAQLELISRLCGSP CPAVWPDVIKLPYFNTMKPKKQYRRRLREEFSFIPSAALDLLDHMLT LDPSKRCTAEQTLQSDFLKDVELSKMAPPDLPHWQDCHELWSKKRR RQRQSGVVEEPPPSKTSRKETTSGTSTEPVKNSSPAPPQPAPGKVES GAGDAIGLADITQQLNQSELAVLLNLLQSQTDLSIPQMAQLLNIHSNP EMQQQLEALNQSISALTEATSQQQDSETMAPEESLKEAPSAPVILPSA EQTTLEASSTPADMQNILAVLLSQLMKTQEPAGSLEENNSDKNSGPQ GPRRTPTMPQEEAAACPPHILPPEKRPPEPPGPPPPPPPPPLVEGDLSSA PQELNPAVTAALLQLLSQPEAEPPGHLPHEHQALRPMEYSTRPRPNR TYGNTDGPETGFSAIDTDERNSGPALTESLVQTLVKNRTFSGSLSHLG ESSSYQGTGSVQFPGDQDLRFARVPLALHPVVGQPFLKAEGSSNSVV HAETKLQNYGELGPGTTGASSSGAGLHWGGPTQSSAYGKLYRGPTR VPPRGGRGRGVPY |
| 2 | ENSP00000407720 (NP_055898.1) | MPNSERHGGKKDGSGGASGTLQPSSGGGSSNSRERHRLVSKHKRHK SKHSKDMGLVTPEAASLGTVIKPLVEYDDISSDSDTFSDDMAFKLDR RENDERRGSDRSDRLHKHRHHQHRRSRDLLKAKQTEKEKSQEVSSK SGSMKDRISGSSKRSNEETDDYGKAQVAKSSSKESRSSKLHKEKTRK ERELKSGHKDRSKSHRKRETPKSYKTVDSPKRRSRSPHRKWSDSSKQ DDSPSGASYGQDYDLSPSRSHTSSNYDSYKKSPGSTSRRQSVSPPYKE PSAYQSSTRSPSPYSRRQRSVSPYSRRRSSSYERSGSYSGRSPSPYGRR RSSSPFLSKRSLSRSPLPSRKSMKSRSRSPAYSRHSSSHSKKKRSSSRS RHSSISPVRLPLNSSLGAELSRKKKERAAAAAAAKMDGKESKGSPVF LPRKENSSVEAKDSGLESKKLPRSVKLEKSAPDTELVNVTHLNTEVK NSSDTGKVKLDENSEKHLVKDLKAQGTRDSKPIALKEEIVTPKETETS EKETPPPLPTIASPPPPLPTTTPPPQTPPLPPLPPIPALPQQPPLPPSQPAF SQVPASSTSTLPPSTHSKTSAVSSQANSQPPVQVSVKTQVSVTAAIPH LKTSTLPPLPLPPLLPGDDDMDSPKETLPSKPVKKEKEQRTRHLLTDL PLPPELPGGDLSPPDSPEPKAITPPQQPYKKRPKICCPRYGERRQTESD WGKRCVDKFDIIGIIGEGTYGQVYKAKDKDTGELVALKKVRLDNEK EGFPITAIREIKILRQLIHRSVVNMKEIVTDKQDALDFKKDKGAFYLV FEYMDHDLMGLLESGLVHFSEDHIKSFMKQLMEGLEYCHKKNFLHR DIKCSNILLNNSGQIKLADFGLARLYNSEESRPYTNKVITLWYRPPEL LLGEERYTPAIDVWSCGCILGELFTKKPIFQANLELAQLELISRLCGSP CPAVWPDVIKLPYFNTMKPKKQYRRRLREEFSFIPSAALDLLDHMLT LDPSKRCTAEQTLQSDFLKDVELSKMAPPDLPHWQDCHELWSKKRR RQRQSGVVEEPPPSKTSRKETTSGTSTEPVKNSSPAPPQPAPGKVES GAGDAIGLADITQQLNQSELAVLLNLLQSQTDLSIPQMAQLLNIHSNP EMQQQLEALNQSISALTEATSQQQDSETMAPEESLKEAPSAPVILPSA EQTTLEASSTPADMQNILAVLLSQLMKTQEPAGSLEENNSDKNSGPQ GPRRTPTMPQEEAAEKRPPEPPGPPPPPPPPLVEGDLSSAPQELNPAV TAALLQLLSQPEAEPPGHLPHEHQALRPMEYSTRPRPNRTYGNTDGP ETGFSAIDTDERNSGPALTESLVQTLVKNRTFSGSLSHLGESSSYQGT GSVQFPGDQDLRFARVPLALHPVVGQPFLKAEGSSNSVVHAETKLQ NYGELGPGTTGASSSGAGLHWGGPTQSSAYGKLYRGPTRVPPRGGR GRGVPY |
| 3 | ENSP00000464641 | MPNSERHGGKKDGSGGASGTLQPSSGGGSSNSRERHRLVSKHKRHK SKHSKDMGLVTPEAASLGTVIKPLVEYDDISSDSDTFSDDMAFKLDR RENDERRGSDRSDRLHKHRHHQHRRSRDLLKAKQTEKEKSQEVSSK SGSMKDRISGSSKRSNEETDDYGKAQVAKSSSKESRSSKLHKEKTRK ERELKSGHKDRSKSHRKRETPKSYKTVDSPKRRSRSPHRKWSDSSKQ DDSPSGASYGQDYDLSPSRSHTSSNYDSYKKSPGSTSRRQSVSPPYKE PSAYQSSTRSPSPYSRRQRSVSPYSRRRSSSYERSGSYSGRSPSPYGRR |

TABLE 3-continued

CDK12 Sequences

| SEQ ID NO | Ensembl Protein ID (Accession Number) | Amino Acid Sequence |
|---|---|---|
| | | RSSSPFLSKRSLSRSPLPRKSMKSRSRSPAYSRHSSSHSKKKRSSSRSR HSSISPVRLPLNSSLGAELSRKKKERAAAAAAAKMDGKESKGSPVFL PRKENSSVEAKDSGLESKKLPRSVKLEKSAPDTELVNVTHLNTEVKN SSDTGKVKLDENSEKHLVKDLKAQGTRDSKPIALKEEIVTPKETETSE KETPPPLPTIASPPPPLPTTTPPPQTPPLPPLPPIPALPQQPPLPPSQPAFS QVPASSTSTLPPSTHSKTSAVSSQANSQPPVQVSVKTQVSVTAAIPHL KTSTLPPLPLPPLLPGDDDMDSPKETLPSKPVKKEKEQRTRHLLTDLP LPPELPGGDLSPPDSPEPKAITPPQQPYKKRPKICCPRYGERRQTESDW GKRCVDKFDIIGIIGEGTYGQVYKAKDKDTGELVALKKVRLDNEKE GFPITAIREIKILRQLIHRSVVNMKEIVTDKQDALDFKKDKGAFYLVF EYMDHDLMGLLESGLVHFSEDHIKSFMKQLMEGLEYCHKKNFLHR DIKCSNILLNNSGQIKLADFGLARLYNSEESRPYTNKVITLWYRPPEL LLGEERYTPAIDVWSCGCILGELFTKKPIFQANLELAQLELISRLCGSP CPAVWPDVIKLPYFNTMKPKKQYRRRLREEFSFIPSAALDLLDHMLT LDPSKRCTAEQTLQSDFLKDVELSKMAPPDLPHWQDCHELWSKKRR RQRQSGVVVEEPPPSKTSRKETTSGTSTEPVKNSSPAPPQPAPGKVES GAGDAIGLADITQQLNQSELAVLLNLLQSQTDLSIPQMAQLLNIHSNP EMQQQLEALNQSISALTEATSQQQDSETMAPEESLKEAPSAPVILPSA EQTTLEASST |
| 4 | ENSP00000453329 | XADITQQLNQSELAVLLNLLQSQTDLSIPQMAQLLNIHSNPEMQQQL EALNQSISALTEATSQQQDSETMAPEESLKEAPSAPVILPSAEQTTLEA SSTPADMQNILAVLLSQLMKTQEPAGSLEENNSDKNSGPQGPRRTPT MPQEEAAGRSNGGNAL |

TABLE 4

Variant CDK12 Sequences

| SEQ ID NO | Amino Acid Sequence |
|---|---|
| 5 | MPNSERHGGKKDGSGGASGTLQPSSGGGSSNSRERHRLVSKHKRHKSKHSKDMG LVTPEAASLGTVIKPLVEYDDISSDSDTFSDDMAFKLDRRENDERRGSDRSDRLHK HRHHQHRRSRDLLKAKQTEKEKSQEVSSKSGSMKDRISGSSKRSNEETDDYGKAQ VAKSSSKESRSSKLHKEKTRKERELKSGHKDRSKSHRKRETPKSYKTVDSPKRRSR SPHRKWSDSSKQDDSPSGASYGQDYDLSPSRSHTSSNYDSYKKSPGSTSRRQSVSP PYKEPSAYQSSTRSPSPYSRRQRSVSPYSRRRSSSYERSGSYSGRSPSPYGRRRSSSP FLSKRSLSRSPLPSRKSMKSRSRSPAYSRHSSSHSKKKRSSSRSRHSSISPVRLPLNSS LGAELSRKKKERAAAAAAAKMDGKESKGSPVFLPRKENSSVEAKDSGLESKKLP RSVKLEKSAPDTELVNVTHLNTEVKNSSDTGKVKLDENSEKHLVKDLKAQGTRD SKPIALKEEIVTPKETETSEKETPPPLPTIASPPPPLPTTTPPPQTPPLPPLPPIPALPQQP PLPPSQPAFSQVPASSTSTLPPSTHSKTSAVSSQANSQPPVQVSVKTQVSVTAAIPHL KTSTLPPLPLPPLLPGDDDMDSPKETLPSKPVKKEKEQRTRHLLTDLPLPPELPGGD LSPPDSPEPKAITPPQQPYKKRPKICCPRYGERRQTESDWGKRCVDKFDIIGIIGEGT YGQVYKAKDKDTGELVALKKVRLDNEKEGFPITAIREIKILRQLIHRSVVNMKEIV TDKQDALDFKKDKGAFYLVFEYMDHDLMGLLESGLVHFSEDHIKSFMKQLMEGL EYCHKKNFLHRDIKCSNILLNNSGQIKLADFGLARLYNSEESRPYTNKVITLWYRP PELLLGEERYTPAIDVWSCGCILGELFTKKPIFQANLELAQLELISRLCGSPCPAVW PDVIKLPYFNTMKPKKQYRRRLREEFSFIPSAALDLLDHMLTLDPSKRCTAEQTLQ SDFLKDVELSKMAPPDLPHWQDCHELWSKKRRRQRQSGVVVEEPPPSKTSRKETT SGTSTEPVKNSSPAPPQPAPGKVESGAGDAIGLADITQQLNQSELAVLLNLLQSQT DLSVPQMAQLLNIHSNPEMQQQLEALNQSISALTEATSQQQDSETMAPEESLKEAP SAPVILPSAEQTTLEASSTPADMQNILAVLLSQLMKTQEPAGSLEENNSDKNSGPQ GPRRTPTMPQEEAAACPPHILPPEKRPPEPPGPPPPPPPPPLVEGDLSSAPQELNPAV TAALLQLLSQPEAEPPGHLPHEHQALRPMEYSTRPRPNRTYGNTDGPETGFSAIDT DERNSGPALTESLVQTLVKNRTFSGSLSHLGESSSYQGTGSVQFPGDQDLRFARVP LALHPVVGQPFLKAEGSSNSVVHAETKLQNYGELGPGTTGASSSGAGLHWGGPT QSSAYGKLYRGPTRVPPRGGRGRGVPY |
| 6 | MPNSERHGGKKDGSGGASGTLQPSSGGGSSNSRERHRLVSKHKRHKSKHSKDMG LVTPEAASLGTVIKPLVEYDDISSDSDTFSDDMAFKLDRRENDERRGSDRSDRLHK HRHHQHRRSRDLLKAKQTEKEKSQEVSSKSGSMKDRISGSSKRSNEETDDYGKAQ VAKSSSKESRSSKLHKEKTRKERELKSGHKDRSKSHRKRETPKSYKTVDSPKRRSR SPHRKWSDSSKQDDSPSGASYGQDYDLSPSRSHTSSNYDSYKKSPGSTSRRQSVSP PYKEPSAYQSSTRSPSPYSRRQRSVSPYSRRRSSSYERSGSYSGRSPSPYGRRRSSSP FLSKRSLSRSPLPSRKSMKSRSRSPAYSRHSSSHSKKKRSSSRSRHSSISPVRLPLNSS LGAELSRKKKERAAAAAAAKMDGKESKGSPVFLPRKENSSVEAKDSGLESKKLP RSVKLEKSAPDTELVNVTHLNTEVKNSSDTGKVKLDENSEKHLVKDLKAQGTRD SKPIALKEEIVTPKETETSEKETPPPLPTIASPPPPLPTTTPPPQTPPLPPLPPIPALPQQP |

TABLE 4-continued

Variant CDK12 Sequences

| SEQ ID NO | Amino Acid Sequence |
|---|---|
|  | PLPPSQPAFSQVPASSTSTLPPSTHSKTSAVSSQANSQPPVQVSVKTQVSVTAAIPHL<br>KTSTLPPLPLPPLLPGDDDMDSPKETLPSKPVKKEKEQRTREILLTDLPLPPELPGGD<br>LSPPDSPEPKAITPPQQPYKKRPKICCPRYGERRQTESDWGKRCVDKFDIIGIIGEGT<br>YGQVYKAKDKDTGELVALKKVRLDNEKEGFPITAIREIKILRQLIHRSVVNMKEIV<br>TDKQDALDFKKDKGAFYLVFEYMDHDLMGLLESGLVHFSEDHIKSFMKQLMEGL<br>EYCHKKNFLHRDIKCSNILLNNSGQIKLADFGLARLYNSEESRPYTNKVITLWYRP<br>PELLLGEERYTPAIDVWSCGCILGELFTKKPIFQANLELAQLELISRLCGSPCPAVW<br>PDVIKLPYFNTMKPKKQYRRRLREEFSFIPSAALDLLDHMLTLDPSKRCTAEQTLQ<br>SDFLKDVELSKMAPPDLPHWQDCHELWSKKRRRQRQSGVVVEEPPPSKTSRKETT<br>SGTSTEPVKNSSPAPPQPAPGKVESGAGDAIGLADITQQLNQSELAVLLNLLQSQT<br>DLSIPQMAQLLNIHSNPEMQQQLEALNQSISALTEATSQQQDSETMAPEESLKEAP<br>SAPVIQPSAEQTTLEASSTPADMQNILAVLLSQLMKTQEPAGSLEENNSDKNSGPQ<br>GPRRTPTMPQEEAAACPPHILPPEKRPPEPPGPPPPPPPPLVEGDLSSAPQELNPAV<br>TAALLQLLSQPEAEPPGHLPHEHQALRPMEYSTRPRPNRTYGNTDGPETGFSAIDT<br>DERNSGPALTESLVQTLVKNRTFSGSLSHLGESSSYQGTGSVQFPGDQDLRFARVP<br>LALHPVVGQPFLKAEGSSNSVVHAETKLQNYGELGPGTTGASSSGAGLHWGGPT<br>QSSAYGKLYRGPTRVPPRGGRGRGVPY |
| 7 | MPNSERHGGKKDGSGGASGTLQPSSGGGSSNSRERHRLVSKHKRHKSKHSKDMG<br>LVTPEAASLGTVIKPLVEYDDISSDSDTFSDDMAFKLDRRENDERRGSDRSDRLHK<br>HRHHQHRRSRDLLKAKQTEKEKSQEVSSKSGSMKDRISGSSKRSNEETDDYGKAQ<br>VAKSSSKESRSSKLHKEKTRKERELKSGHKDRSKSHRKRETPKSYKTVDSPKRRSR<br>SPHRKWSDSSKQDDSPSGASYGQDYDLSPSRSHTSSNYDSYKKSPGSTSRRQSVSP<br>PYKEPSAYQSSTRSPSPYSRRQRSVSPYSRRRSSSYERSGSYSGRSPSPYGRRRSSSP<br>FLSKRSLSRSPLPSRKSMKSRSPAYSRHSSSHSKKKRSSSRSRHSSISPVRLPLNSS<br>LGAELSRKKKERAAAAAAAKMDGKESKGSPVFLPRKENSSVEAKDSGLESKKLP<br>RSVKLEKSAPDTELVNVTHLNTEVKNSSDTGKVKLDENSEKHLVKDLKAQGTRD<br>SKPIALKEEIVTPKETETSEKETPPPLPTIASPPPPLPTTTPPPQTPPLPPLPPIPALPQQP<br>PLPPSQPAFSQVPASSTSTLPPSTHSKTSAVSSQANSQPPVQVSVKTQVSVTAAIPHL<br>KTSTLPPLPLPPLLPGDDDMDSPKETLPSKPVKKEKEQRTRHLLTDLPLPPELPGGD<br>LSPPDSPEPKAITPPQQPYKKRPKICCPRYGERRQTESDWGKRCVDKFDIIGIIGEGT<br>YGQVYKAKDKDTGELVALKKVRLDNEKEGFPITAIREIKILRQLIHRSVVNMKEIV<br>TDKQDALDFKKDKGAFYLVFEYMDHDLMGLLESGLVHFSEDHIKSFMKQLMEGL<br>EYCHKKNFLHRDIKCSNILLNNSGQIKLADFGLARLYNSEESRPYTNKVITLWYRP<br>PELLLGEERYTPAIDVWSCGCILGELFTKKPIFQANLELAQLELISRLCGSPCPAVW<br>PDVIKLPYFNTMKPKKQYRRRLREEFSFIPSAALDLLDHMLTLDPSKRCTAEQTLQ<br>SDFLKDVELSKMAPPDLPHWQDCHELWSKKRRRQRQSGVVVEEPPPSKTSRKETT<br>SGTSTEPVKNSSPAPPQPAPGKVESGAGDAIGLADITQQLNQSELAVLLNLLQSQT<br>DLSIPQMAQLLNIHSNPEMQQQLEALNQSISALTEATSQQQDSETMAPEESLKEAP<br>SAPVILPSAEQMTLEASSTPADMQNILAVLLSQLMKTQEPAGSLEENNSDKNSGPQ<br>GPRRTPTMPQEEAAACPPHILPPEKRPPEPPGPPPPPPPPLVEGDLSSAPQELNPAV<br>TAALLQLLSQPEAEPPGHLPHEHQALRPMEYSTRPRPNRTYGNTDGPETGFSAIDT<br>DERNSGPALTESLVQTLVKNRTFSGSLSHLGESSSYQGTGSVQFPGDQDLRFARVP<br>LALHPVVGQPFLKAEGSSNSVVHAETKLQNYGELGPGTTGASSSGAGLHWGGPT<br>QSSAYGKLYRGPTRVPPRGGRGRGVPY |
| 8 | MPNSERHGGKKDGSGGASGTLQPSSGGGSSNSRERHRLVSKHKRHKSKHSKDMG<br>LVTPEAASLGTVIKPLVEYDDISSDSDTFSDDMAFKLDRRENDERRGSDRSDRLHK<br>HRHHQHRRSRDLLKAKQTEKEKSQEVSSKSGSMKDRISGSSKRSNEETDDYGKAQ<br>VAKSSSKESRSSKLHKEKTRKERELKSGHKDRSKSHRKRETPKSYKTVDSPKRRSR<br>SPHRKWSDSSKQDDSPSGASYGQDYDLSPSRSHTSSNYDSYKKSPGSTSRRQSVSP<br>PYKEPSAYQSSTRSPSPYSRRQRSVSPYSRRRSSSYERSGSYSGRSPSPYGRRRSSSP<br>FLSKRSLSRSPLPSRKSMKSRSPAYSRHSSSHSKKKRSSSRSRHSSISPVRLPLNSS<br>LGAELSRKKKERAAAAAAAKMDGKESKGSPVFLPRKENSSVEAKDSGLESKKLP<br>RSVKLEKSAPDTELVNVTHLNTEVKNSSDTGKVKLDENSEKHLVKDLKAQGTRD<br>SKPIALKEEIVTPKETETSEKETPPPLPTIASPPPPLPTTTPPPQTPPLPPLPPIPALPQQP<br>PLPPSQPAFSQVPASSTSTLPPSTHSKTSAVSSQANSQPPVQVSVKTQVSVTAAIPHL<br>KTSTLPPLPLPPLLPGDDDMDSPKETLPSKPVKKEKEQRTRHLLTDLPLPPELPGGD<br>LSPPDSPEPKAITPPQQPYKKRPKICCPRYGERRQTESDWGKRCVDKFDIIGIIGEGT<br>YGQVYKAKDKDTGELVALKKVRLDNEKEGFPITAIREIKILRQLIHRSVVNMKEIV<br>TDKQDALDFKKDKGAFYLVFEYMDHDLMGLLESGLVHF'SEDHIKSFMKQLMEGL<br>EYCHKKNFLHRDIKCSNILLNNSGQIKLADFGLARLYNSEESRPYTNKVITLWYRP<br>PELLLGEERYTPAIDVWSCGCILGELFTKKPIFQANLELAQLELISRLCGSPCPAVW<br>PDVIKLPYENTMKPKKQYRRRLREEFSFIPSAALDLLDHMLTLDPSKRCTAEQTLQ<br>SDFLKDVELSKMAPPDLPHWQDCHELWSKKRRRQRQSGVVVEEPPPSKTSRKETT<br>SGTSTEPVKNSSPAPPQPAPGKVESGAGDAIGLADITQQLNQSELAVLLNLLQSQT<br>DLSVPQMAQLLNIHSNPEMQQQLEALNQSISALTEATSQQQDSETMAPEESLKEAP<br>SAPVILPSAEQTTLEASSTPADMQNILAVLLSQLMKTQEPAGSLEENNSDKNSGPQ<br>GPRRTPTMPQEEAAEKRPPEPPGPPPPPPPPLVEGDLSSAPQELNPAVTAALLQLL<br>SQPEAEPPGHLPHEHQALRPMEYSTRPRPNRTYGNTDGPETGFSAIDTDERNSGPA<br>LTESLVQTLVKNRTFSGSLSHLGESSSYQGTGSVQFPGDQDLRFARVPLALHPVVG<br>QPFLKAEGSSNSVVHAETKLQNYGELGPGTTGASSSGAGLHWGGPTQSSAYGKL<br>YRGPTRVPPRGGRGRGVPY |

TABLE 4-continued

Variant CDK12 Sequences

| SEQ ID NO | Amino Acid Sequence |
|---|---|
| 9 | MPNSERHGGKKDGSGGASGTLQPSSGGGSSNSRERHRLVSKHKRHKSKHSKDMG<br>LVTPEAASLGTVIKPLVEYDDISSDSDTFSDDMAFKLDRRENDERRGSDRSDRLHK<br>HRHHQHRRSRDLLKAKQTEKEKSQEVSSKSGSMKDRISGSSKRSNEETDDYGKAQ<br>VAKSSSKESRSSKLHKEKTRKERELKSGHKDRSKSHRKRETPKSYKTVDSPKRRSR<br>SPHRKWSDSSKQDDSPSGASYGQDYDLSPSRSHTSSNYDSYKKSPGSTSRRQSVSP<br>PYKEPSAYQSSTRSPSPYSRRQRSVSPYSRRRSSSYERSGSYSGRSPSPYGRRRSSSP<br>FLSKRSLSRSPLPSRKSMKSRSRSPAYSRHSSSHSKKKRSSSRSRHSSISPVRLPLNSS<br>LGAELSRKKKERAAAAAAAKMDGKESKGSPVFLPRKENSSVEAKDSGLESKKLP<br>RSVKLEKSAPDTELVNVTHLNTEVKNSSDTGKVKLDENSEKHLVKDLKAQGTRD<br>SKPIALKEEIVTPKETETSEKETPPPLPTIASPPPPLPTTTPPPQTPPLPPLPPIPALPQQP<br>PLPPSQPAFSQVPASSTSTLPPSTHSKTSAVSSQANSQPPVQVSVKTQVSVTAAIPHL<br>KTSTLPPLPLPPLLPGDDDMDSPKETLPSKPVKKEKEQRTREILLTDLPLPPELPGGD<br>LSPPDSPEPKAITPPQQPYKKRPKICCPRYGERRQTESDWGKRCVDKFDIIGIIGEGT<br>YGQVYKAKDKDTGELVALKKVRLDNEKEGFPITAIREIKILRQLIHRSVVNMKEIV<br>TDKQDALDFKKDKGAFYLVFEYMDHDLMGLLESGLVHFSEDHIKSFMKQLMEGL<br>EYCHKKNFLHRDIKCSNILLNNSGQIKLADFGLARLYNSEESRPYTNKVITLWYRP<br>PELLLGEERYTPAIDVWSCGCILGELFTKKPIFQANLELAQLELISRLCGSPCPAVW<br>PDVIKLPYFNTMKPKKQYRRRLREEFSFIPSAALDLLDHMLTLDPSKRCTAEQTLQ<br>SDFLKDVELSKMAPPDLPHWQDCHELWSKKRRRQRQSGVVVEEPPPSKTSRKETT<br>SGTSTEPVKNSSPAPPQPAPGKVESGAGDAIGLADITQQLNQSELAVLLNLLQSQT<br>DLSIPQMAQLLNIHSNPEMQQQLEALNQSISALTEATSQQQDSETMAPEESLKEAP<br>SAPVI<u>Q</u>PSAEQTTLEASSTPADMQNILAVLLSQLMKTQEPAGSLEENNSDKNSGPQ<br>GPRRTPTMPQEEAAEKRPPEPPGPPPPPPPPPLVEGDLSSAPQELNPAVTAALLQLL<br>SQPEAEPPGHLPHEHQALRPMEYSTRPRPNRTYGNTDGPETGFSAIDTDERNSGPA<br>LTESLVQTLVKNRTFSGSLSHLGESSSYQGTGSVQFPGDQDLRFARVPLALHPVVG<br>QPPFLKAEGSSNSVVHAETKLQNYGELGPGTTGASSSGAGLHWGGPTQSSAYGKL<br>YRGPTRVPPRGGRGRGVPY |
| 10 | MPNSERHGGKKDGSGGASGTLQPSSGGGSSNSRERHRLVSKHKRHKSKHSKDMG<br>LVTPEAASLGTVIKPLVEYDDISSDSDTFSDDMAFKLDRRENDERRGSDRSDRLHK<br>HRHHQHRRSRDLLKAKQTEKEKSQEVSSKSGSMKDRISGSSKRSNEETDDYGKAQ<br>VAKSSSKESRSSKLHKEKTRKERELKSGHKDRSKSHRKRETPKSYKTVDSPKRRSR<br>SPHRKWSDSSKQDDSPSGASYGQDYDLSPSRSHTSSNYDSYKKSPGSTSRRQSVSP<br>PYKEPSAYQSSTRSPSPYSRRQRSVSPYSRRRSSSYERSGSYSGRSPSPYGRRRSSSP<br>FLSKRSLSRSPLPSRKSMKSRSRSPAYSRHSSSHSKKKRSSSRSRHSSISPVRLPLNSS<br>LGAELSRKKKERAAAAAAAKMDGKESKGSPVFLPRKENSSVEAKDSGLESKKLP<br>RSVKLEKSAPDTELVNVTHLNTEVKNSSDTGKVKLDENSEKHLVKDLKAQGTRD<br>SKPIALKEEIVTPKETETSEKETPPPLPTIASPPPPLPTTTPPPQTPPLPPLPPIPALPQQP<br>PLPPSQPAFSQVPASSTSTLPPSTHSKTSAVSSQANSQPPVQVSVKTQVSVTAAIPHL<br>KTSTLPPLPLPPLLPGDDDMDSPKETLPSKPVKKEKEQRTREILLTDLPLPPELPGGD<br>LSPPDSPEPKAITPPQQPYKKRPKICCPRYGERRQTESDWGKRCVDKFDIIGIIGEGT<br>YGQVYKAKDKDTGELVALKKVRLDNEKEGFPITAIREIKILRQLIHRSVVNMKEIV<br>TDKQDALDFKKDKGAFYLVFEYMDHDLMGLLESGLVHFSEDHIKSFMKQLMEGL<br>EYCHKKNFLHRDIKCSNILLNNSGQIKLADFGLARLYNSEESRPYTNKVITLWYRP<br>PELLLGEERYTPAIDVWSCGCILGELFTKKPIFQANLELAQLELISRLCGSPCPAVW<br>PDVIKLPYFNTMKPKKQYRRRLREEFSFIPSAALDLLDHMLTLDPSKRCTAEQTLQ<br>SDFLKDVELSKMAPPDLPHWQDCHELWSKKRRRQRQSGVVVEEPPPSKTSRKETT<br>SGTSTEPVKNSSPAPPQPAPGKVESGAGDAIGLADITQQLNQSELAVLLNLLQSQT<br>DLSIPQMAQLLNIHSNPEMQQQLEALNQSISALTEATSQQQDSETMAPEESLKEAP<br>SAPVILPSAEQ<u>M</u>TLEASSTPADMQNILAVLLSQLMKTQEPAGSLEENNSDKNSGPQ<br>GPRRTPTMPQEEAAEKRPPEPPGPPPPPPPPPLVEGDLSSAPQELNPAVTAALLQLL<br>SQPEAEPPGHLPHEHQALRPMEYSTRPRPNRTYGNTDGPETGFSAIDTDERNSGPA<br>LTESLVQTLVKNRTFSGSLSHLGESSSYQGTGSVQFPGDQDLRFARVPLALHPVVG<br>QPPFLKAEGSSNSVVHAETKLQNYGELGPGTTGASSSGAGLHWGGPTQSSAYGKL<br>YRGPTRVPPRGGRGRGVPY |
| 11 | MPNSERHGGKKDGSGGASGTLQPSSGGGSSNSRERHRLVSKHKRHKSKHSKDMG<br>LVTPEAASLGTVIKPLVEYDDISSDSDTFSDDMAFKLDRRENDERRGSDRSDRLHK<br>HRHHQHRRSRDLLKAKQTEKEKSQEVSSKSGSMKDRISGSSKRSNEETDDYGKAQ<br>VAKSSSKESRSSKLHKEKTRKERELKSGHKDRSKSHRKRETPKSYKTVDSPKRRSR<br>SPHRKWSDSSKQDDSPSGASYGQDYDLSPSRSHTSSNYDSYKKSPGSTSRRQSVSP<br>PYKEPSAYQSSTRSPSPYSRRQRSVSPYSRRRSSSYERSGSYSGRSPSPYGRRRSSSP<br>FLSKRSLSRSPLPRKSMKSRSRSPAYSRHSSSHSKKKRSSSRSRHSSISPVRLPLNSSL<br>GAELSRKKKERAAAAAAAKMDGKESKGSPVFLPRKENSSVEAKDSGLESKKLPRS<br>VKLEKSAPDTELVNVTHLNTEVKNSSDTGKVKLDENSEKHLVKDLKAQGTRDSK<br>PIALKEEIVTPKETETSEKETPPPLPTIASPPPPLPTTTPPPQTPPLPPLPPIPALPQQPPL<br>PPSQPAFSQVPASSTSTLPPSTHSKTSAVSSQANSQPPVQVSVKTQVSVTAAIPHLK<br>TSTLPPLPLPPLLPGDDDMDSPKETLPSKPVKKEKEQRTRHLLTDLPLPPELPGGDL<br>SPPDSPEPKAITPPQQPYKKRPKICCPRYGERRQTESDWGKRCVDKFDIIGIIGEGTY<br>GQVYKAKDKDTGELVALKKVRLDNEKEGFPITAIREIKILRQLIHRSVVNMKEIVT<br>DKQDALDFKKDKGAFYLVFEYMDHDLMGLLESGLVHFSEDHIKSFMKQLMEGLE<br>YCHKKNFLHRDIKCSNILLNNSGQIKLADFGLARLYNSEESRPYTNKVITLWYRPP<br>ELLLGEERYTPAIDVWSCGCILGELFTKKPIFQANLELAQLELISRLCGSPCPAVWP<br>DVIKLPYFNTMKPKKQYRRRLREEFSFIPSAALDLLDHMLTLDPSKRCTAEQTLQS<br>DFLKDVELSKMAPPDLPHWQDCHELWSKKRRRQRQSGVVVEEPPPSKTSRKETTS |

TABLE 4-continued

Variant CDK12 Sequences

| SEQ ID NO | Amino Acid Sequence |
|---|---|
|  | GTSTEPVKNSSPAPPQPAPGKVESGAGDAIGLADITQQLNQSELAVLLNLLQSQTD<br>LSVPQMAQLLNIHSNPEMQQQLEALNQSISALTEATSQQQDSETMAPEESLKEAPS<br>APVILPSAEQTTLEASST |
| 12 | MPNSERHGGKKDGSGGASGTLQPSSGGGSSNSRERHRLVSKHKRHKSKHSKDMG<br>LVTPEAASLGTVIKPLVEYDDISSDSDTFSDDMAFKLDRRENDERRGSDRSDRLHK<br>HRHHQHRRSRDLLKAKQTEKEKSQEVSSKSGSMKDRISGSSKRSNEETDDYGKAQ<br>VAKSSSKESRSSKLHKEKTRKERELKSGHKDRSKSHRKRETPKSYKTVDSPKRRSR<br>SPHRKWSDSSKQDDSPSGASYGQDYDLSPSRSHTSSNYDSYKKSPGSTSRRQSVSP<br>PYKEPSAYQSSTRSPSPYSRRQRSVSPYSRRSSSYERSGSYSGRSPSPYGRRRSSSP<br>FLSKRSLSRSPLPRKSMKSRSRSPAYSRHSSSHSKKKRSSSRSRHSSISPVRLPLNSSL<br>GAELSRKKKERAAAAAAAKMDGKESKGSPVFLPRKENSSVEAKDSGLESKKLPRS<br>VKLEKSAPDTELVNVTHLNTEVKNSSDTGKVKLDENSEKHLVKDLKAQGTRDSK<br>PIALKEEIVTPKETETSEKETPPPLPTIASPPPPLPTTTPPPQTPPLPPLPPIPALPQQPPL<br>PPSQPAFSQVPASSTSTLPPSTHSKTSAVSSQANSQPPVQVSVKTQVSVTAAIPHLK<br>TSTLPPLPLPPLLPGDDDMDSPKETLPSKPVKKEKEQRTREILLTDLPLPPELPGGDL<br>SPPDSPEPKAITPPQQPYKKRPKICCPRYGERRQTESDWGKRCVDKFDIIGIIGEGTY<br>GQVYKAKDKDTGELVALKKVRLDNEKEGFPITAIREIKILRQLIHRSVVNMKEIVT<br>DKQDALDFKKDKGAFYLVFEYMDHDLMGLLESGLVHFSEDHIKSFMKQLMEGLE<br>YCHKKNFLHRDIKCSNILLNNSGQIKLADFGLARLYNSEESRPYTNKVITLWYRPP<br>ELLLGEERYTPAIDVWSCGCILGELFTKKPIFQANLELAQLELISRLCGSPCPAVWP<br>DVIKLPYFNTMKPKKQYRRRLREEFSFIPSAALDLLDHMLTLDPSKRCTAEQTLQS<br>DFLKDVELSKMAPPDLPHWQDCHELWSKKRRRQRQSGVVVEEPPPSKTSRKETTS<br>GTSTEPVKNSSPAPPQPAPGKVESGAGDAIGLADITQQLNQSELAVLLNLLQSQTD<br>LSIPQMAQLLNIHSNPEMQQQLEALNQSISALTEATSQQQDSETMAPEESLKEAPS<br>APVIQPSAEQTTLEASST |
| 13 | MPNSERHGGKKDGSGGASGTLQPSSGGGSSNSRERHRLVSKHKRHKSKHSKDMG<br>LVTPEAASLGTVIKPLVEYDDISSDSDTFSDDMAFKLDRRENDERRGSDRSDRLHK<br>HRHHQHRRSRDLLKAKQTEKEKSQEVSSKSGSMKDRISGSSKRSNEETDDYGKAQ<br>VAKSSSKESRSSKLHKEKTRKERELKSGHKDRSKSHRKRETPKSYKTVDSPKRRSR<br>SPHRKWSDSSKQDDSPSGASYGQDYDLSPSRSHTSSNYDSYKKSPGSTSRRQSVSP<br>PYKEPSAYQSSTRSPSPYSRRQRSVSPYSRRSSSYERSGSYSGRSPSPYGRRRSSSP<br>FLSKRSLSRSPLPRKSMKSRSRSPAYSRHSSSHSKKKRSSSRSRHSSISPVRLPLNSSL<br>GAELSRKKKERAAAAAAAKMDGKESKGSPVFLPRKENSSVEAKDSGLESKKLPRS<br>VKLEKSAPDTELVNVTHLNTEVKNSSDTGKVKLDENSEKHLVKDLKAQGTRDSK<br>PIALKEEIVTPKETETSEKETPPPLPTIASPPPPLPTTTPPPQTPPLPPLPPIPALPQQPPL<br>PPSQPAFSQVPASSTSTLPPSTHSKTSAVSSQANSQPPVQVSVKTQVSVTAAIPHLK<br>TSTLPPLPLPPLLPGDDDMDSPKETLPSKPVKKEKEQRTRHLLTDLPLPPELPGGDL<br>SPPDSPEPKAITPPQQPYKKRPKICCPRYGERRQTESDWGKRCVDKFDIIGIIGEGTY<br>GQVYKAKDKDTGELVALKKVRLDNEKEGFPITAIREIKILRQLIHRSVVNMKEIVT<br>DKQDALDFKKDKGAFYLVFEYMDHDLMGLLESGLVHFSEDHIKSFMKQLMEGLE<br>YCHKKNFLHRDIKCSNILLNNSGQIKLADFGLARLYNSEESRPYTNKVITLWYRPP<br>ELLLGEERYTPAIDVWSCGCILGELFTKKPIFQANLELAQLELISRLCGSPCPAVWP<br>DVIKLPYFNTMKPKKQYRRRLREEFSFIPSAALDLLDHMLTLDPSKRCTAEQTLQS<br>DFLKDVELSKMAPPDLPHWQDCHELWSKKRRRQRQSGVVVEEPPPSKTSRKETTS<br>GTSTEPVKNSSPAPPQPAPGKVESGAGDAIGLADITQQLNQSELAVLLNLLQSQTD<br>LSIPQMAQLLNIHSNPEMQQQLEALNQSISALTEATSQQQDSETMAPEESLKEAPS<br>APVILPSAEQMTLEASST |
| 14 | XADITQQLNQSELAVLLNLLQSQTDLSVPQMAQLLNIHSNPEMQQQLEALNQSISA<br>LTEATSQQQDSETMAPEESLKEAPSAPVILPSAEQTTLEASSTPADMQNILAVLLSQ<br>LMKTQEPAGSLEENNSDKNSGPQGPRRTPTMPQEEAAGRSNGGNAL |
| 15 | XADITQQLNQSELAVLLNLLQSQTDLSIPQMAQLLNIHSNPEMQQQLEALNQSISA<br>LTEATSQQQDSETMAPEESLKEAPSAPVIQSAEQTTLEASSTPADMQNILAVLLSQ<br>LMKTQEPAGSLEENNSDKNSGPQGPRRTPTMPQEEAAGRSNGGNAL |
| 16 | XADITQQLNQSELAVLLNLLQSQTDLSIPQMAQLLNIHSNPEMQQQLEALNQSISA<br>LTEATSQQQDSETMAPEESLKEAPSAPVILPSAEQMTLEASSTPADMQNILAVLLS<br>QLMKTQEPAGSLEENNSDKNSGPQGPRRTPTMPQEEAAGRSNGGNAL |

One embodiment provides a modified CDK13 polypeptide wherein the active site cysteine of unmodified CDK13 has been modified with a substituent having the structure of Formula (IV):

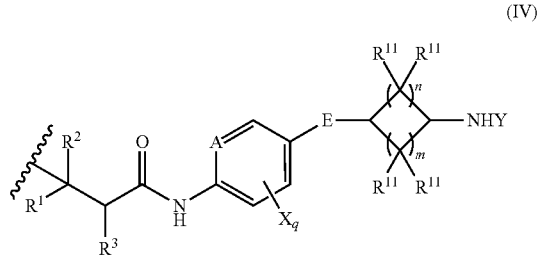

wherein,
A is C—H or N;
E is selected from a bond, —SO$_2$—, —C(O)—, —CH$_2$—, —CH(R$^4$)—, or —C(R$^4$)$_2$—;
R$^1$ is selected from hydrogen, optionally substituted C1-C4 alkyl, or optionally substituted heterocyclylalkyl;
R$^2$ is selected from hydrogen, or optionally substituted C1-C4 alkyl;
R$^3$ is selected from hydrogen, —CN, or optionally substituted C1-C4 alkyl;
each R$^4$ is independently selected from optionally substituted C1-C4 alkyl, or optionally substituted heterocyclylalkyl;
each R$^{11}$ is independently selected from hydrogen, halogen, optionally substituted C1-C6 alkyl, or both R$^{11}$ groups form an oxo;
q is 0, 1, or 2; n is 0, 1, 2, or 3; m is 0, 1, 2, or 3;
X is halogen, optionally substituted C1-C4 alkyl, or optionally substituted C1-C4 alkoxy;
Y is an optionally substituted 10-atom bicyclic heteroaryl with at least one nitrogen atom.

Another embodiment provides the modified CDK13 polypeptide wherein the unmodified CDK13 polypeptide is isoform 1 (*Homo sapiens*).

Another embodiment provides the modified CDK13 polypeptide wherein the unmodified CDK13 polypeptide is isoform 2 (*Homo sapiens*).

Another embodiment provides the modified CDK13 polypeptide wherein the unmodified CDK13 polypeptide is an isoform 1 (*Homo sapiens*) variant. Another embodiment provides the modified CDK13 polypeptide wherein the unmodified CDK13 polypeptide is isoform 1 (*Homo sapiens*) variant L403F. Another embodiment provides the modified CDK13 polypeptide wherein the unmodified CDK13 polypeptide is isoform 1 (*Homo sapiens*) variant T500A.

Another embodiment provides the modified CDK13 polypeptide wherein the unmodified CDK13 polypeptide is a SEQID selected from a SEQID provided in Table 5 or 6.

TABLE 5

CDK13 Sequences

| SEQ ID NO | Ensembl Protein ID (Accession Number) | Amino Acid Sequence |
|---|---|---|
| 17 | ENSP00000181839 (NP_003709.3) | MPSSSDTALGGGGGLSWAEKKLEERRKRRRFLSPQQPPLLLPLLQPQ LLQPPPPPPPLLFLAAPGTAAAAAAAAAASSSCFSPGPPLEVKRLARG KRRAGGRQKRRRGPRAGQEAEKRRVFSLPQPQQDGGGGASSGGGV TPLVEYEDVSSQSEQGLLLGGASAATAATAAGGTGGSGGSPASSSGT QRRGEGSERRPRRDRRSSSGRSKERHREHRRRDGQRGGSEASKSRSR HSHSGEERAEVAKSGSSSSSGGRRKSASATSSSSSSRKDRDSKAHRSR TKSSKEPPSAYKEPPKAYREDKTEPKAYRRRRSLSPLGGRDDSPVSH RASQSLRSRKSPSPAGGGSSPYSRRLPRSPSPYSRRRSPSYSRHSSYER GGDVSPSPYSSSSWRRSRSPYSPVLRRSGKSRSRSPYSSRHSRSRSRHR LSRSRSRHSSISPSTLTLKSSLAAELNKNKKARAAEAARAAEAAKAA EATKAAEAAAKAAKASNTSTPTKGNTETSASASQTNHVKDVKKIKIE HAPSPSSGGTLKNDKAKTKPPLQVTKVENNLIVDKATKKAVIVGKES KSAATKEESVSLKEKTKPLTPSIGAKEKEQHVALVTSTLPPLPLPPML PEDKEADSLRGNISVKAVKKEVEKKLRCLLADLPLPPELPGGDDLSK SPEEKKTATQLHSKRRPKICGPRYGETKEKDIDWGKRCVDKFDIIGII GEGTYGQVYKARDKDTGEMVALKKVRLDNEKEGFPITAIREIKILRQ LTHQSIINMKEIVTDKEDALDFKKDKGAFYLVFEYMDHDLMGLLES GLVHFNENHIKSFMRQLMEGLDYCHKKNFLHRDIKCSNILLNNRGQI KLADFGLARLYSSEESRPYTNKVITLWYRPPELLLGEERYTPAIDVWS CGCILGELFTKKPIFQANQELAQLELISRICGSPCPAVWPDVIKLPYEN TMKPKKQYRRKLREEFVFIPAAALDLFDYMLALDPSKRCTAEQALQ CEFLRDVEPSKMPPPDLPLWQDCHELWSKKRRRQKQMGMTDDVSTI KAPRKDLSLGLDDSRTNTPQGVLPSSQLKSQGSSNVAPVKTGPGQHL NHSELAILLNLLQSKTSVNMADFVQVLNIKVNSETQQQLNKINLPAGI LATGEKQTDPSTPQQESSKPLGGIQPSSQTIQPKVETDAAQAAVQSAF AVLLTQLIKAQQSKQKDVLLEERENGSGHEASLQLRPPPEPSTPVSGQ DDLIQHQDMRILELTPEPDRPRILPPDQRPPEPPEPPPVTEEDLDYRTE NQHVPTTSSSLTDPHAGVKAALLQLLAQHQPQDDPKREGGIDYQAG DTYVSTSDYKDNFGSSSFSSAPYVSNDGLGSSSAPPLERRSFIGNSDIQ SLDNYSTASSHSGGPPQPSAFSESFPSSVAGYGDIYLNAGPMLFSGDK DHRFEYSHGPIAVLANSSDPSTGPESTHPLPAKMHNYNYGGNLQENP SGPSLMHGQTWTSPAQGPGYSQGYRGHISTSTGRGRGRGLPY |
| 18 | ENSP00000340557 (NP_112557.2) | MPSSSDTALGGGGGLSWAEKKLEERRKRRRFLSPQQPPLLLPLLQPQ LLQPPPPPPPLLFLAAPGTAAAAAAAAAASSSCFSPGPPLEVKRLARG KRRAGGRQKRRRGPRAGQEAEKRRVFSLPQPQQDGGGGASSGGGV TPLVEYEDVSSQSEQGLLLGGASAATAATAAGGTGGSGGSPASSSGT |

TABLE 5-continued

CDK13 Sequences

| SEQ ID NO | Ensembl Protein ID (Accession Number) | Amino Acid Sequence |
|---|---|---|
| | | QRRGEGSERRPRRDRRSSSGRSKERHREHRRRDGQRGGSEASKSRSR HSHSGEERAEVAKSGSSSSSGGRRKSASATSSSSSSRKDRDSKAHRSR TKSSKEPPSAYKEPPKAYREDKTEPKAYRRRRSLSPLGGRDDSPVSH RASQSLRSRKSPSPAGGGSSPYSRRLPRSPSPYSRRRSPSYSRHSSYER GGDVSPSPYSSSSWRRSRSPYSPVLRRSGKSRSRSPYSSRHSRSRSRHR LSRSRSRHSSISPSTLTLKSSLAAELNKNKKARAAEAARAAEAAKAA EATKAAEAAAKAAKASNTSTPTKGNTETSASASQTNHVKDVKKIKIE HAPSPSSGGTLKNDKAKTKPPLQVTKVENNLIVDKATKKAVIVGKES KSAATKEESVSLKEKTKPLTPSIGAKEKEQHVALVTSTLPPLPLPPML PEDKEADSLRGNISVKAVKKEVEKKLRCLLADLPLPPELPGGDDLSK SPEEKKTATQLHSKRRPKICGPRYGETKEKDIDWGKRCVDKFDIIGII GEGTYGQVYKARDKDTGEMVALKKVRLDNEKEGFPITAIREIKILRQ LTHQSIINMKEIVTDKEDALDFKKDKGAFYLVFEYMDHDLMGLLES GLVHFNENHIKSFIVIRQLMEGLDYCHKKNELHRDIKCSNILLNNRGQI KLADFGLARLYSSEESRPYTNKVITLWYRPPELLLGEERYTPAIDVWS CGCILGELFTKKPIFQANQELAQLELISRICGSPCPAVWPDVIKLPYFN TMKPKKQYRRKLREEFVFIPAAALDLFDYMLALDPSKRCTAEQALQ CEFLRDVEPSKMPPPDLPLWQDCHELWSKKRRRQKQMGMTDDVSTI KAPRKDLSLGLDDSRTNTPQGVLPSSQLKSQGSSNVAPGEKQTDPST PQQESSKPLGGIQPSSQTIQPKVETDAAQAAVQSAFAVLLTQLIKAQQ SKQKDVLLEERENGSGHEASLQLRPPPEPSTPVSGQDDLIQHQDMRIL ELTPEPDRPRILPPDQRPPEPPEPPPVTEEDLDYRTENQHVPTTSSSLTD PHAGVKAALLQLLAQHQPQDDPKREGGIDYQAGDTYVSTSDYKDNF GSSSFSSAPYVSNDGLGSSSAPPLERRSFIGNSDIQSLDNYSTASSHSG GPPQPSAFSESFPSSVAGYGDIYLNAGPMLFSGDKDHRFEYSHGPIAV LANSSDPSTGPESTHPLPAKMHNYNYGGNLQENPSGPSLMHGQTWT SPAQGPGYSQGYRGHISTSTGRGRGRGLPY |
| 19 | ENSP00000494206 | XAKAAKASNTSTPTKGNTETSASASQTNHVKDVKKIKIEHAPSPSSG GTLKNDKAKTKPPLQVTKVENNLIVDKATKKAVIVGKESKSAATKE ESVSLKEKTKPLTPSIGAKEKEQHVALVTSTLPPLPLPPMLPEDKEAD SLRGNISVKAVKKEVEKKLRCLLADLPLPPELPGGDDLSKSPEEKKT ATQLHSKRRPKICGPRYGETKEKDIDWGKRCVDKFDIIGIIGEGTYGQ VYKARDKDTGEMVALKKVRLDNEKEGFPITAIREIKILRQLTHQSIIN MKEIVTDKEDALDFKKDKGAFYLVFEYMDHDLMGLLESGLVHFNE NHIKSFIVIRQLMEGLDYCHKKNELHRDIKCSNILLNNRGQIKLADFGL ARLYSSEESRPYTNKVITLWYRPPELLLGEERYTPAIDVWSCGCILGE LFTKKPIFQANQELAQLELIRHEENEVSDKQI |
| 20 | ENSP00000494168 | GQRGGSEASKSRSRHSHSGEERAEVAKSGSSSSSGGRRKSASATSSSS SSRKDRDSKAHRSRTKSSKEPPSAYKEPPKAYREDKTEPKAYRRRRS LSPLGGRDDSPVSHRASQSLRSRKSPSPAGGGSSPYSRRLPRSPSPYSR RRSPSYSRHSSYERGGDVSPSPYSSSSWRRSRSPYSPVLRRSGKSRSRS PYSSRHSRSRSRHRLSRSRSRHSSISPSTLTLKSSLAAELNKNKKARAA EEAARAAEAAKAAEATKAAEAAAKAAKASNTSTPTKGNTETSASASQ TNHVKDVKKIKIEHAPSPSSGGTLKNDKAKTKPPLQVTKVENNLIVD KATKKAVIVGKESKSAATKEESVSLKEKTKPLTPSIGAKEKEQHVAL VTSTLPPLPLPPMLPEDKEADSLRGNISVKAVKKEVEKKLRCLLADLP LPPELPGGDDLSKSPEEKKTATQLHSKRRPKICGPRYGETKEKDIDW GKRCVDKFDIIGIIGEGTYGQVYKARDKDTGEMVALKKVRLDNEKE GFPITAIREIKILRQLTHQSIINMKEIVTDKEDALDFKKDKGAFYLVFE YMDHDLMGLLESGLVHFNENHIKSFMRQLMEGLDYCHKKNFLHRDI KCSNILLNNRGQIKLADFGLARLYSSEESRPYTNKVITLWYRPPELLL GEERYTPAIDVWSCGCILGELFTKKPIFQANQELAQLELISRICGSPCP AVWPDVIKLPYENTMKPKKQYRRKLREEFVFIPAAALDLEDYMLAL DPSKRCTAEQALQCEFLRDVEPSKMPPPERFLHAEAMHHSKMAESLP LWQDCHELWSKKRRRQKQMGMTDDVSTIKAPRKDLSLGLDDSRTN TPQGVLPSSQLKSQGSSNVAPVKTGPGQHLNHSELAILLNLLQSKTSV NMADFVQVLNIKVNSETQQQLNKINLPAGILATGEKQTDPSTPQQES SKPLGGIQPSSQTIQPKVETDAAQAAVQSAFAVLLTQLIKAQQSKQK DVLLEERENGSGHEASLQLRPPPEPSTPVSGQDDLIQHQDMRILELTP EPDRPRILPPDQRPPEPPEPPPVTEEDLDYRTENQHVPTTSSSLTDPHA GVKAALLQLLAQHQPQDDPKREGGIDYQAGDTYVSTSDYKDNFGSS SFSSAPYVSNDGLGSSSAPPLERRSFIGNSDIQSLDNYSTASSHSGGPP QPSAFSESFPSSVAGYGDIYLNAGPMLFSGDKDHRFEYSHGPIAVLAN SSDPSTGPESTHPLPAKMHNYNYGGNLQENPSGPSLMHGQTWTSPA QGPGYSQGYRGHISTSTGRGRGRGLPY |
| 21 | ENSP00000496440 | XSRHSSYERGGDVSPSPYSSSSWRRSRSPYSPVLRRSGKSRSRSPYSSR HSRSRSRHRLSRSRSRHSSISPSTLTLKSSLAAELNKNKKARAAEAAR AAEAAKAAEATKAAEAAAKAAKASNTSTPTKGNTETSASASQTNHV KDVKKIKIEHAPSPSSGGTLKNDKAKTKPPLQVTKVENNLIVDKATK KAVIVGKESKSAATKEESVSLKEKTKPLTPSIGAKEKEQHVALVTSTL |

TABLE 5-continued

CDK13 Sequences

| SEQ ID NO | Ensembl Protein ID (Accession Number) | Amino Acid Sequence |
|---|---|---|
| | | PPLPLPPMLPEDKEADSLRGNISVKAVKKEVEKKLRCLLADLPLPPEL PGGDDLSKSPEEKKTATQLHSKRRPKICGPRYGETKEKDIDWGKRCV DKFDIIGIIGEGTYGQVYKARDKDTGEMVALKKVRLDNEKEGFPITAI REIKILRQLTHQSIINMKEIVTDKEDALDFKKDKGAFYLVFEYMDHD LMGLLESGLVHFNENHIKSFMRQLMEGLDYCHKKNFLHRDIKCSNIL LNNRGQIKLADFGLARLYSSEESRPYTNKVITLWYRPPELLLGEERYT PAIDVWSCGCILGELFTKKPIFQANQELAQLELISRICGSPCPAVWPDV IKLPYFNTMKPKKQYRRKLREEFVFIPAAALDLFDYMLALDPSKRCT AEQALQCEFLRDVEPSKMPPPERFLHAEAMHHSKMAESLPLWQDCH ELWSKKRRRQKQMGMTDDVSTIKAPRKDLSLGLDDSRTNTPQGVLP SSQLKSQGSSNVAPGEKQTDPSTPQQESSKPLGGIQPSSQTIQPKVETD AAQAAVQSAFAVLLTQLIKAQQSKQKDVLLEERENGSGHEASLQLR PPPEPSTPVSGQDDLIQHQDMRILELTPEPDRPRILPPDQRPPEPEPPP VTEEDLDYRTENQHVPTTSSSLTDPHAGVKAALLQLLAQHQPQDDP KREGGIDYQAGDTYVSTSDYKDNFGSSSFSSAPYVSNDGLGSSSAPPL ERRSFIGNSDIQSLDNYSTASSHSGGPPQPSAFSESFPSSVAGYGDIYL NAGPMLFSGDKDHRFEYSHGPIAVLANSSDPSTGPESTHPLPAKMHN YNYGGNLQENPSGPSLMHGQTWTSPAQGPGYSQGYRGHISTSTGRG RGRGLPY |
| 22 | ENSP00000496187 | IVGKESKSAATKEESVSLKEKTKPLTPSIGAKEKEQHVALVTSTLPPLP LPPMLPEDKEADSLRGNISVKAVKKEVEKKLRCLLADLPLPPELPGG DDLSKSPEEKKTATQLHSKRRPKICGPRYGETKEKDIDWGKRCVDKF DIIGIIGEGTYGQVYKARDKDTGEMVALKKVRLDNEKEGFPITAIREI KILRQLTHQSIINMKEIVTDKEDALDFKKDKGAFYLVFEYMDHDLM GLLESGLVHFNENHIKSFMRQLMEGLDYCHKKNFLHRDIKCSNILLN NRGQIKLADFGLARLYSSEESRPYTNKVITLWYRPPELLLGEERYTPA IDVWSCGCILGELFTKKPIFQANQELAQLELIRASLCCQAGVQWRNL GSLQPLPPRENRICGSPCPAVWPDVIKLPYENTMKPKKQYRRKLREEF VFIPAAALDLFDYMLALDPSKRCTAEQALQCEFLRDVEPSKMPPPDL PLWQDCHELWSKKRRRQKQMGMTDDVSTIKAPRKDLSLGLDDSRT NTPQGVLPSSQLKSQGSSNVAPGEKQTDPSTPQQESSKPLGGIQPSSQ TIQPKVETDAAQAAVQSAFAVLLTQLIKAQQSKQKDVLLEERENGSG HEASLQLRPPPEPSTPVSGQDDLIQHQDMRILELTPEPDRPRILPPDQR PPEPPEPPPVTEEDLDYRTENQHVPTTSSSLTDPHAGVKAALLQLLAQ HQPQDDPKREGGIDYQAGDTYVSTSDYKDNFGSSSFSSAPYVSNDGL GSSSAPPLERRSFIGNSDIQSLDNYSTASSHSGGPPQPSAFSESFPSSVA GYGDIYLNAGPMLFSGDKDHRFEYSHGPIAVLANSSDPSTGPESTHPL PAKMHNYNYGGNLQENPSGPSLMHGQTWTSPAQGPGYSQGYRGHI STSTGRGRGRGLPY |
| 23 | ENSP00000480835 | MLPEDKEADSLRGNISVKAVKKEVEKKLRCLLADLPLPPELPGGDDL SKSPEEKKTATQLHSKRRPKICGPRYGETKEKDIDWGKRCVDKFDII GIIGEGTYGQVYKARDKDTGEMVALKKVRLDNEKEGFPITAIREIKILR QLTHQSIINMKEIVTDKEDALDFKKDKGAFYLVFEYMDHDLMGLLE SGLVHFNENHIKSFMRQLMEGLDYCHKKNFLHRDIKCSNILLNNRGQ IKLADFGLARLYSSEESRPYTNKVITLWYRPPELLLGEERYTPAIDVW SCGCILGELFTKKPIFQANQELAQLELIRHEENEVSDKQI |
| 24 | ENSP00000484610 | MLPEDKEADSLRGNISVKAVKKEVEKKLRCLLADLPLPPELPGGDDL SKSPEEKKTATQLHSKRRPKICGPRYGETKEKDIDWGKRCVDKFDIIG IIGEGTYGQVYKARDKDTGEMVALKKVRLDNEKEGFPITAIREIKILR QLTHQSIINMKEIVTDKEDALDFKKDKGAFYLVFEYMDHDLMGLLE SGLVHFNENHIKSFMRQLMEGLDYCHKKNFLHRDIKCSNILLNNRGQ IKLADFGLARLYSSEESRPYTNKVITLWYRPPELLLGEERYTPAIDVW SCGCILGELFTKKPIFQANQELAQLELISRICGSPCPAVWPDVIKLPYF NTMKPKKQYRRKLREEFVFIPAAALDLFDYMLALDPSKRCTAEQAL QCEFLRDVEPSKCLHQISLYGKIVMSYGVKSEEDRSRWA |
| 25 | ENSP00000495083 | XQQDGGGGASSGGGVTPLVEYEDVSSQSEQGLLLGGASAATAATAA GGTGGSGGSPASSSGTQRRGEGSERRPRRDRRSSSGRSKERHREHRR RDGQRGGSEASKSRSRHSHSGEERAEVAKSGSSSSSGGRRKSASATS SSSSSSRKDRDSKAHRSRTKSSKEPPSAYKEPPKAYREDKTEPKAYRR RRSLSPLGGRDDSPVSHRASQSLRSRKSPSPAGGGSSPYSRRLPRSPSP YSRRRSPSYSRHSSYERGGDVSPSPYSSSWRRSRSPYSPVLR |
| 26 | ENSP00000493853 | XRSGKSRSRSPYSSRHSRSRSRHRLSRSRSRHSSISPSTLTLKSSLAAEL NKNKKARAAEAARAAEAAKAAEEATKAAEAAAKAAKASNTSTPTKG NTETSASASQTNHVKDVKKIKIEHAPSSSGGTLKNDKAKTKPPLQV TKVENNLIVDKATKKAVIVGKESKSAATKEESVSLKEKTKPLTPSIGA KEKEQHVALVTSTLPPLPLPPMLPEDKEADSLRGNISVKAVKKEVEK KLRCLLADLPLPPELPGGDDLSKSPEEKKTATQLHSKRRPKYVLAFY LLLN |

TABLE 5-continued

CDK13 Sequences

| SEQ ID NO | Ensembl Protein ID (Accession Number) | Amino Acid Sequence |
|---|---|---|
| 27 | ENSP00000494207 | XFMRQLMEGLDYCHKKNFLHRDIKCSNILLNNRGQIKLADFGLARL YSSEESRPYTNKVITLWYRPPELLLGEERYTPAIDVWSCGCILGELFT KKPIFQANQELAQLELISTGWVRWLTPVIAALWEAKTGGSLEPRSSR PD |
| 28 | ENSP00000495036 | KEKDIDWGKRCVDKFDIIGIIGEGTYGQVYKARDKDTGEMVALKKV RLDNEKEGFPITAIREIKILRQLTHQSIINMKEIVTDKEDALDFKKDKG AFYLVFEYMDHDLMGLLESGLVHFNENHIKSFMRQLMEGLDYCHK KNFLHRDIKCSNILLNNRGQIKLADFGLARLYSSEESRPYTNKVITLW YRPPELLLGEERYTPAIDVWSCGCILGELFTKKPIFQANQELAQLELIR FT |
| 29 | ENSP00000496618 | XAEAARAAEAAKAAEATKAAEAAAKAAKASNTSTPTKGNTETSAS ASQTNHVKDVKKIKIEHAPSPSSGGTLKNDKAKTKPPLQVTKVENNL IVDKATKKAVIVGKESKSAATKEESVSLKEKTKPLTPSIGAKEKEQHV ALVTSTLPPLPLPPMLPEDKEADSLRGNISVKAVKKEVEKKLRCLLA DLPLPPELPGGDDLSKSPEEKKTATQLHSKRRPKTIFDRICGPRYGET KEKDIDWGKRCVDKFDIIGIIG |

TABLE 6

CDK13 Variants

| SEQ ID NO | Amino Acid Sequence |
|---|---|
| 30 | MPSSSDTALGGGGGLSWAEKKLEERRKRRRFLSPQQPPLLLPLLQPQLLQPPPPPPP LLFLAAPGTAAAAAAAAASSSCFSPGPPLEVKRLARGKRRAGGRQKRRRGPRAG QEAEKRRVFSLPQPQQDGGGGASSGGGVTPLVEYEDVSSQSEQGLLLGGASAATA ATAAGGTGGSGGSPASSSGTQRRGEGSERRPRRDRRSSSGRSKERHREHRRRDGQ RGGSEASKSRSRHSHSGEERAEVAKSGSSSSSGGRRKSASATSSSSSSRKDRDSKA HRSRTKSSKEPPSAYKEPPKAYREDKTEPKAYRRRRSLSPLGGRDDSPVSHRASQS LRSRKSPSPAGGGSSPYSRRLPRSPSPYSRRRSPSYSRHSSYERGGDVSPSPYSSSSW RRSRSPYSPVFRRSGKSRSPYSSRHSRSRSRHRLSRSRSRHSSISPSTLTLKSSLAA ELNKNKKARAAEAARAAEAAKAAEATKAAEAAAKAAKASNTSTPTKGNTETSA SASQTNHVKDVKKIKIEHAPSPSSGGTLKNDKAKTKPPLQVTKVENNLIVDKATK KAVIVGKESKSAATKEESVSLKEKTKPLTPSIGAKEKEQHVALVTSTLPPLPLPPML PEDKEADSLRGNISVKAVKKEVEKKLRCLLADLPLPPELPGGDDLSKSPEEKKTAT QLHSKRRPKICGPRYGETKEKDIDWGKRCVDKFDIIGIIGEGTYGQVYKARDKDTG EMVALKKVRLDNEKEGFPITAIREIKILRQLTHQSIINMKEIVTDKEDALDFKKDKG AFYLVFEYMDHDLMGLLESGLVHFNENHIKSFMRQLMEGLDYCHKKNFLHRDIK CSNILLNNRGQIKLADFGLARLYSSEESRPYTNKVITLWYRPPELLLGEERYTPAID VWSCGCILGELFTKKPIFQANQELAQLELISRICGSPCPAVWPDVIKLPYFNTMKPK KQYRRKLREEFVFIPAAALDLFDYMLALDPSKRCTAEQALQCEFLRDVEPSKMPPP DLPLWQDCHELWSKKRRRQKQMGMTDDVSTIKAPRKDLSLGLDDSRTNTPQGVL PSSQLKSQGSSNVAPVKTGPGQHLNHSELAILLNLLQSKTSVNMADFVQVLNIKV NSETQQQLNKINLPAGILATGEKQTDPSTPQQESSKPLGGIQPSSQTIQPKVETDAA QAAVQSAFAVLLTQLIKAQQSKQKDVLLEERENGSGHEASLQLRPPPEPSTPVSGQ DDLIQHQDMRILELTPEPDRPRILPPDQRPPEPPEPPPVTEEDLDYRTENQHVPTTSS SLTDPHAGVKAALLQLLAQHQPQDDPKREGGIDYQAGDTYVSTSDYKDNFGSSSF SSAPYVSNDGLGSSSAPPLERRSFIGNSDIQSLDNYSTASSHSGGPPQPSAFSESFPSS VAGYGDIYLNAGPMLFSGDKDHRFEYSHGPIAVLANSSDPSTGPESTHPLPAKMH NYNYGGNLQENPSGPSLMHGQTWTSPAQGPGYSQGYRGHISTSTGRGRGRGLPY |
| 31 | MPSSSDTALGGGGGLSWAEKKLEERRKRRRFLSPQQPPLLLPLLQPQLLQPPPPPPP LLFLAAPGTAAAAAAAAASSSCFSPGPPLEVKRLARGKRRAGGRQKRRRGPRAG QEAEKRRVFSLPQPQQDGGGGASSGGGVTPLVEYEDVSSQSEQGLLLGGASAATA ATAAGGTGGSGGSPASSSGTQRRGEGSERRPRRDRRSSSGRSKERHREHRRRDGQ RGGSEASKSRSRHSHSGEERAEVAKSGSSSSSGGRRKSASATSSSSSSRKDRDSKA HRSRTKSSKEPPSAYKEPPKAYREDKTEPKAYRRRRSLSPLGGRDDSPVSHRASQS LRSRKSPSPAGGGSSPYSRRLPRSPSPYSRRRSPSYSRHSSYERGGDVSPSPYSSSSW RRSRSPYSPVLRRSGKSRSRSPYSSRHSRSRSRHRLSRSRSRHSSISPSTLTLKSSLAA ELNKNKKARAAEAARAAEAAKAAEATKAAEAAAKAAKASNTSTPTKGNAETSA SASQTNHVKDVKKIKIEHAPSPSSGGTLKNDKAKTKPPLQVTKVENNLIVDKATK KAVIVGKESKSAATKEESVSLKEKTKPLTPSIGAKEKEQHVALVTSTLPPLPLPPML PEDKEADSLRGNISVKAVKKEVEKKLRCLLADLPLPPELPGGDDLSKSPEEKKTAT QLHSKRRPKICGPRYGETKEKDIDWGKRCVDKFDIIGIIGEGTYGQVYKARDKDTG EMVALKKVRLDNEKEGFPITAIREIKILRQLTHQSIINMKEIVTDKEDALDFKKDKG AFYLVFEYMDHDLMGLLESGLVHF'NENHIKSFMRQLMEGLDYCHKKNELHRDIK |

TABLE 6-continued

CDK13 Variants

| SEQ ID NO | Amino Acid Sequence |
|---|---|
|  | CSNILLNNRGQIKLADFGLARLYSSEESRPYTNKVITLWYRPPELLLGEERYTPAID VWSCGCILGELFTKKPIFQANQELAQLELISRICGSPCAVWPDVIKLPYFNTMKPK KQYRRKLREEFVFIPAAALDLFDYMLALDPSKRCTAEQALQCEFLRDVEPSKMPPP DLPLWQDCHELWSKKRRRQKQMGMTDDVSTIKAPRKDLSLGLDDSRTNTPQGVL PSSQLKSQGSSNVAPVKTGPGQHLNSELAILLNLLQSKTSVNMADFVQVLNIKV NSETQQQLNKINLPAGILATGEKQTDPSTPQQESSKPLGGIQPSSQTIQPKVETDAA QAAVQSAFAVLLTQLIKAQQSKQKDVLLEERENGSGHEASLQLRPPPEPSTPVSGQ DDLIQHQDMRILELTPEPDRPRILPPDQRPPEPPEPPPVTEEDLDYRTENQHVPTTSS SLTDPHAGVKAALLQLLAQHQPQDDPKREGGIDYQAGDTYVSTSDYKDNFGSSSF SSAPYVSNDGLGSSSAPPLERRSFIGNSDIQSLDNYSTASSHSGGPPQPSAFSESFPSS VAGYGDIYLNAGPMLFSGDKDHRFEYSHGPIAVLANSSDPSTGPESTHPLPAKMH NYNYGGNLQENPSGPSLMHGQTWTSPAQGPGYSQGYRGHISTSTGRGRGRGLPY |
| 32 | MPSSSDTALGGGGGLSWAEKKLEERRKRRRFLSPQQPPLLLPLLQPQLLQPPPPPPP LLFLAAPGTAAAAAAAAAASSSCFSPGPPLEVKRLARGKRRAGGRQKRRRGPRAG QEAEKRRVFSLPQPQQDGGGGASSGGGVTPLVEYEDVSSQSEQGLLLGGASAATA ATAAGGTGGSGGSPASSSGTQRRGEGSERRPRRDRRSSSGRSKERHREHRRRDGQ RGGSEASKSRSRHSHSGEERAEVAKSGSSSSSGGRRKSASATSSSSSSRKDRDSKA HRSRTKSSKEPPSAYKEPPKAYREDKTEPKAYRRRRSLSPLGGRDDSPVSHRASQS LRSRKSPSPAGGGSSPYSRRLPRSPSPYSRRRSPSYSRHSSYERGGDVSPSPYSSSSW RRSRSPYSPVFRRSGKSRSRSPYSSRHSRSRSRHRLSRSRSRHSSISPSTLTLKSSLAA ELNKNKKARAAEAARAAEAAKAAEATKAAEAAAKAAKASNTSTPTKGNTETSA SASQTNHVKDVKKIKIEHAPSPSSGGTLKNDKAKTKPPLQVTKVENNLIVDKATK KAVIVGKESKSAATKEESVSLKEKTKPLTPSIGAKEKEQHVALVTSTLPPLPPPML PEDKEADSLRGNISVKAVKKEVEKKLRCLLADLPLPPELPGGDDLSKSPEEKKTAT QLHSKRRPKICGPRYGETKEKDIDWGKRCVDKFDIIGIIGEGTYGQVYKARDKDTG EMVALKKVRLDNEKEGFPITAIREIKILRQLTHQSIINMKEIVTDKEDALDFKKDKG AFYLVFEYMDHDLMGLLESGLVHF'NENHIKSFMRQLMEGLDYCHKKNELHRDIK CSNILLNNRGQIKLADFGLARLYSSEESRPYTNKVITLWYRPPELLLGEERYTPAID VWSCGCILGELFTKKPIFQANQELAQLELISRICGSPCAVWPDVIKLPYFNTMKPK KQYRRKLREEFVFIPAAALDLFDYMLALDPSKRCTAEQALQCEFLRDVEPSKMPPP DLPLWQDCHELWSKKRRRQKQMGMTDDVSTIKAPRKDLSLGLDDSRTNTPQGVL PSSQLKSQGSSNVAPGEKQTDPSTPQQESSKPLGGIQPSSQTIQPKVETDAAQAAVQ SAFAVLLTQLIKAQQSKQKDVLLEERENGSGHEASLQLRPPPEPSTPVSGQDDLIQ HQDMRILELTPEPDRPRILPPDQRPPEPPEPPPVTEEDLDYRTENQHVPTTSSSLTDP HAGVKAALLQLLAQHQPQDDPKREGGIDYQAGDTYVSTSDYKDNFGSSSFSSAPY VSNDGLGSSSAPPLERRSFIGNSDIQSLDNYSTASSHSGGPPQPSAFSESFPSSVAGY GDIYLNAGPMLFSGDKDHRFEYSHGPIAVLANSSDPSTGPESTHPLPAKMHNYNY GGNLQENPSGPSLMHGQTWTSPAQGPGYSQGYRGHISTSTGRGRGRGLPY |
| 33 | MPSSSDTALGGGGGLSWAEKKLEERRKRRRFLSPQQPPLLLPLLQPQLLQPPPPPPP LLFLAAPGTAAAAAAAAAASSSCFSPGPPLEVKRLARGKRRAGGRQKRRRGPRAG QEAEKRRVFSLPQPQQDGGGGASSGGGVTPLVEYEDVSSQSEQGLLLGGASAATA ATAAGGTGGSGGSPASSSGTQRRGEGSERRPRRDRRSSSGRSKERHREHRRRDGQ RGGSEASKSRSRHSHSGEERAEVAKSGSSSSSGGRRKSASATSSSSSSRKDRDSKA HRSRTKSSKEPPSAYKEPPKAYREDKTEPKAYRRRRSLSPLGGRDDSPVSHRASQS LRSRKSPSPAGGGSSPYSRRLPRSPSPYSRRRSPSYSRHSSYERGGDVSPSPYSSSSW RRSRSPYSPVLRRSGKSRSRSPYSSRHSRSRSRHRLSRSRSRHSSISPSTLTLKSSLAA ELNKNKKARAAEAARAAEAAKAAEATKAAEAAAKAAKASNTSTPTKGNAETSA SASQTNHVKDVKKIKIEHAPSPSSGGTLKNDKAKTKPPLQVTKVENNLIVDKATK KAVIVGKESKSAATKEESVSLKEKTKPLTPSIGAKEKEQHVALVTSTLPPLPLPPPML PEDKEADSLRGNISVKAVKKEVEKKLRCLLADLPLPPELPGGDDLSKSPEEKKTAT QLHSKRRPKICGPRYGETKEKDIDWGKRCVDKFDIIGIIGEGTYGQVYKARDKDTG EMVALKKVRLDNEKEGFPITAIREIKILRQLTHQSIINMKEIVTDKEDALDFKKDKG AFYLVFEYMDHDLMGLLESGLVHFNENHIKSFMRQLMEGLDYCHKKNFLHRDIK CSNILLNNRGQIKLADFGLARLYSSEESRPYTNKVITLWYRPPELLLGEERYTPAID VWSCGCILGELFTKKPIFQANQELAQLELISRICGSPCAVWPDVIKLPYFNTMKPK KQYRRKLREEFVFIPAAALDLFDYMLALDPSKRCTAEQALQCEFLRDVEPSKMPPP DLPLWQDCHELWSKKRRRQKQMGMTDDVSTIKAPRKDLSLGLDDSRTNTPQGVL PSSQLKSQGSSNVAPGEKQTDPSTPQQESSKPLGGIQPSSQTIQPKVETDAAQAAVQ SAFAVLLTQLIKAQQSKQKDVLLEERENGSGHEASLQLRPPPEPSTPVSGQDDLIQ HQDMRILELTPEPDRPRILPPDQRPPEPPEPPPVTEEDLDYRTENQHVPTTSSSLTDP HAGVKAALLQLLAQHQPQDDPKREGGIDYQAGDTYVSTSDYKDNFGSSSFSSAPY VSNDGLGSSSAPPLERRSFIGNSDIQSLDNYSTASSHSGGPPQPSAFSESFPSSVAGY GDIYLNAGPMLFSGDKDHRFEYSHGPIAVLANSSDPSTGPESTHPLPAKMHNYNY GGNLQENPSGPSLMHGQTWTSPAQGPGYSQGYRGHISTSTGRGRGRGLPY |
| 34 | XAKAAKASNTSTPTKGNAETSASASQTNHVKDVKKIKIEHAPSPSSGGTLKNDKA KTKPPLQVTKVENNLIVDKATKKAVIVGKESKSAATKEESVSLKEKTKPLTPSIGA KEKEQHVALVTSTLPPLPLPPPMLPEDKEADSLRGNISVKAVKKEVEKKLRCLLADL PLPPELPGGDDLSKSPEEKKTATQLHSKRRPKICGPRYGETKEKDIDWGKRCVDKF |

TABLE 6-continued

CDK13 Variants

| SEQ ID NO | Amino Acid Sequence |
|---|---|
| | DIIGIIGEGTYGQVYKARDKDTGEMVALKKVRLDNEKEGFPITAIREIKILRQLTHQ<br>SIINMKEIVTDKEDALDFKKDKGAFYLVFEYMDHDLMGLLESGLVHFNENHIKSF<br>MRQLMEGLDYCHKKNFLHRDIKCSNILLNNRGQIKLADFGLARLYSSEESRPYTN<br>KVITLWYRPPELLLGEERYTPAIDVWSCGCILGELFTKKPIFQANQELAQLELIRHE<br>ENEVSDKQI |
| 35 | MLPEDKEADSLRGNISVKAVKKEVEKKLRCLLADLPLPPELPGGDDLSKSPEEKKT<br>ATQLHSKRRPKICGPRYGETKEKDIDWGKRCVDKFDIIGIIGEGTYGQVYKARDKD<br>TGEMVALKKVRLDNEKEGFPITAIREIKILRQLTHQSIINMKEIVTDKEDALDFKKD<br>KGAFYLVFEYMDHDLMGLLESGLVHFNENHIKSFMRQLMEGLDYCHKKNFLHR<br>DIKCSNILLNNRGQIKLADFGLARLYSSEESRPYTNKVITLWYRPPELLLGEERYTP<br>AIDVWSCGCILGELFTKKPIFQANQELAQLELISRICGSPCPAVWPDVIKLPYFNTM<br>KPKKQYRRKLREEFVFIPAAALDLFDYMLALDPSKRCTAEQALQCEFLRDVEPSK<br>CLHQISLYGKIVMSYGVKNEEDRSRWA |
| 36 | XRSGKSRSRSPYSSRHSRSRSRHRLSRSRSRHSSISPSTLTLKSSLAAELNKNKKAR<br>AAEAARAAEAAKAAEATKAAEAAAKAAKASNTSTPTKGNAETSASASQTNHVK<br>DVKKIKIEHAPSPSSGGTLKNDKAKTKPPLQVTKVENNLIVDKATKKAVIVGKESK<br>SAATKEESVSLKEKTKPLTPSIGAKEKEQHVALVTSTLPPLPLPPMLPEDKEADSLR<br>GNISVKAVKKEVEKKLRCLLADLPLPPELPGGDDLSKSPEEKKTATQLHSKRRPKY<br>VLAFYLLLN |
| 37 | XSRHSSYERGGDVSPSPYSSSSWRRSRSPYSPVFRRSGKSRSRSPYSSRHSRSRH<br>RLSRSRSRHSSISPSTLTLKSSLAAELNKNKKARAAEAARAAEAAKAAEATKAAE<br>AAAKAAKASNTSTPTKGNTETSASASQTNHVKDVKKIKIEHAPSPSSGGTLKNDK<br>AKTKPPLQVTKVENNLIVDKATKKAVIVGKESKSAATKEESVSLKEKTKPLTPSIG<br>AKEKEQHVALVTSTLPPLPLPPMLPEDKEADSLRGNISVKAVKKEVEKKLRCLLA<br>DLPLPPELPGGDDLSKSPEEKKTATQLHSKRRPKICGPRYGETKEKDIDWGKRCVD<br>KEDIIGIIGEGTYGQVYKARDKDTGEMVALKKVRLDNEKEGFPITAIREIKILRQLT<br>HQSIINMKEIVTDKEDALDFKKDKGAFYLVFEYMDHDLMGLLESGLVHFNENHIK<br>SFIVIRQLMEGLDYCHKKNELHRDIKCSNILLNNRGQIKLADFGLARLYSSEESRPYT<br>NKVITLWYRPPELLLGEERYTPAIDVWSCGCILGELFTKKPIFQANQELAQLELISRI<br>CGSPCPAVWPDVIKLPYENTMKPKKQYRRKLREEFVFIPAAALDLEDYMLALDPS<br>KRCTAEQALQCEFLRDVEPSKMPPPERFLHAEAMHHSKMAESLPLWQDCHELWS<br>KKRRRQKQMGMTDDVSTIKAPRKDLSLGLDDSRTNTPQGVLPSSQLKSQGSSNVA<br>PGEKQTDPSTPQQESSKPLGGIQPSSQTIQPKVETDAAQAAVQSAFAVLLTQLIKAQ<br>QSKQKDVLLEERENGSGHEASLQLRPPPEPSTPVSGQDDLIQHQDMRILELTPEPDR<br>PRILPPDQRPPEPPEPPPVTEEDLDYRTENQHVPTTSSSLTDPHAGVKAALLQLLAQ<br>HQPDDPKREGGIDYQAGDTYVSTSDYKDNFGSSSFSSAPYVSNDGLGSSSAPPLE<br>RRSFIGNSDIQSLDNYSTASSHSGGPPQPSAFSESFPSSVAGYGDIYLNAGPMLFSGD<br>KDHRFEYSHGPIAVLANSSDPSTGPESTHPLPAKMHNYNYGGNLQENPSGPSLMH<br>GQTWTSPAQGPGYSQGYRGHISTSTGRGRGRGLPY |
| 38 | XSRHSSYERGGDVSPSPYSSSSWRRSRSPYSPVLRRSGKSRSRSPYSSRHSRSRH<br>RLSRSRSRHSSISPSTLTLKSSLAAELNKNKKARAAEAARAAEAAKAAEATKAAE<br>AAAKAAKASNTSTPTKGNAETSASASQTNHVKDVKKIKIEHAPSPSSGGTLKNDK<br>AKTKPPLQVTKVENNLIVDKATKKAVIVGKESKSAATKEESVSLKEKTKPLTPSIG<br>AKEKEQHVALVTSTLPPLPLPPMLPEDKEADSLRGNISVKAVKKEVEKKLRCLLA<br>DLPLPPELPGGDDLSKSPEEKKTATQLHSKRRPKICGPRYGETKEKDIDWGKRCVD<br>KEDIIGIIGEGTYGQVYKARDKDTGEMVALKKVRLDNEKEGFPITAIREIKILRQLT<br>HQSIINMKEIVTDKEDALDFKKDKGAFYLVFEYMDHDLMGLLESGLVHF'NENHIK<br>SFMRQLMEGLDYCHKKNFLHRDIKCSNILLNNRGQIKLADFGLARLYSSEESRPYT<br>NKVITLWYRPPELLLGEERYTPAIDVWSCGCILGELFTKKPIFQANQELAQLELISRI<br>CGSPCPAVWPDVIKLPYENTMKPKKQYRRKLREEFVFIPAAALDLEDYMLALDPS<br>KRCTAEQALQCEFLRDVEPSKMPPPERFLHAEAMHHSKMAESLPLWQDCHELWS<br>KKRRRQKQMGMTDDVSTIKAPRKDLSLGLDDSRTNTPQGVLPSSQLKSQGSSNVA<br>PGEKQTDPSTPQQESSKPLGGIQPSSQTIQPKVETDAAQAAVQSAFAVLLTQLIKAQ<br>QSKQKDVLLEERENGSGHEASLQLRPPPEPSTPVSGQDDLIQHQDMRILELTPEPDR<br>PRILPPDQRPPEPPEPPPVTEEDLDYRTENQHVPTTSSSLTDPHAGVKAALLQLLAQ<br>HQPDDPKREGGIDYQAGDTYVSTSDYKDNFGSSSFSSAPYVSNDGLGSSSAPPLE<br>RRSFIGNSDIQSLDNYSTASSHSGGPPQPSAFSESFPSSVAGYGDIYLNAGPMLFSGD<br>KDHRFEYSHGPIAVLANSSDPSTGPESTHPLPAKMHNYNYGGNLQENPSGPSLMH<br>GQTWTSPAQGPGYSQGYRGHISTSTGRGRGRGLPY |
| 39 | XQQDGGGGASSGGGVTPLVEYEDVSSQSEQGLLLGGASAATAATAAGGTGGSGG<br>SPASSSGTQRRGEGSERRPRRDRRSSSGRSKERHREHRRRDGQRGGSEASKSRSRH<br>SHSGEERAEVAKSGSSSSSGGRRKSASATSSSSSSRKDRDSKAHRSRTKSSKEPPSA<br>YKEPPKAYREDKTEPKAYRRRRSLSPLGGRDDSPVSHRASQSLRSRKSPSPAGGGS<br>SPYSRRLPRSPSPYSRRRSPSYSRHSSYERGGDVSPSPYSSSSWRRSRSPYSPVFR |
| 40 | IVGKESKSAATKEESVSLKEKTKPLTPSIGAKEKEQHVALVTSTLPPLPLPPMLPED<br>KEADSLRGNISVKAVKKEVEKKLRCLLADLPLPPELPGGDDLSKSPEEKKTATQLH<br>SKRRPKICGPRYGETKEKDIDWGKRCVDKFDIIGIIGEGTYGQVYKARDKDTGEM<br>VALKKVRLDNEKEGFPITAIREIKILRQLTHQSIINMKEIVTDKEDALDFKKDKGAF<br>YLVFEYMDHDLMGLLESGLVHFNENHIKSFMRQLMEGLDYCHKKNFLHRDIKCS<br>NILLNNRGQIKLADFGLARLYSSEESRPYTNKVITLWYRPPELLLGEERYTPAIDVW |

TABLE 6-continued

CDK13 Variants

| SEQ ID NO | Amino Acid Sequence |
|---|---|
|  | SCGCILGELFTKKPIFQANQELAQLELIRALLCCQAGVQWRNLGSLQPLPPRFNRIC GSPCPAVWPDVIKLPYFNTMKPKKQYRRKLREEFVFIPAAALDLFDYMLALDPSK RCTAEQALQCEFLRDVEPSKMPPPDLPLWQDCHELWSKKRRRQKQMGMTDDVS TIKAPRKDLSLGLDDSRTNTPQGVLPSSQLKSQGSSNVAPGEKQTDPSTPQQESSKP LGGIQPSSQTIQPKVETDAAQAAVQSAFAVLLTQLIKAQQSKQKDVLLEERENGSG HEASLQLRPPPEPSTPVSGQDDLIQHQDMRILELTPEPDRPRILPPDQRPPEPPEPPPV TEEDLDYRTENQHVPTTSSSLTDPHAGVKAALLQLLAQHQPQDDPKREGGIDYQA GDTYVSTSDYKDNFGSSSFSSAPYVSNDGLGSSSAPPLERRSFIGNSDIQSLDNYST ASSHSGGPPQPSAFSESFPSSVAGYGDIYLNAGPMLFSGDKDHRFEYSHGPIAVLA NSSDPSTGPESTHPLPAKMHNYNYGGNLQENPSGPSLMHGQTWTSPAQGPGYSQ GYRGHISTSTGRGRGRGLPY |
| 41 | GQRGGSEASKSRSRHSHSGEERAEVAKSGSSSSSGGRRKSASATSSSSSSRKDRDS KAHRSRTKSSKEPPSAYKEPPKAYREDKTEPKAYRRRRSLSPLGGRDDSPVSHRAS QSLRSRKSPSPAGGGSSPYSRRLPRSPSPYSRRRSPSYSRHSSYERGGDVSPSPYSSS SWRRSRSPSYSPVFRRSGKSRSRSPYSSRHSRSRSRHRLSRSRSRHSSISPSTLTLKSSL AAELNKNKKARAAEAARAAEAAKAAEATKAAEAAAKAAKASNTSTPTKGNTET SASASQTNHVKDVKKIKIEHAPSPSSGGTLKNDKAKTKPPLQVTKVENNLIVDKAT KKAVIVGKESKSAATKEESVSLKEKTKPLTPSIGAKEKEQHVALVTSTLPPLPLPPM LPEDKEADSLRGNISVKAVKKEVEKKLRCLLADLPLPPELPGGDDLSKSPEEKKTA TQLHSKRRPKICGPRYGETKEKDIDWGKRCVDKFDIIGIIGEGTYGQVYKARDKDT GEMVALKKVRLDNEKEGFPITAIREIKILRQLTHQSIINMKEIVTDKEDALDFKKDK GAFYLVFEYMDHDLMGLLESGLVHFNENHIKSFMRQLMEGLDYCHKKNFLHRDI KCSNILLNNRGQIKLADFGLARLYSSEESRPYTNKVITLWYRPPELLLGEERYTPAI DVWSCGCILGELFTKKPIFQANQELAQLELISRICGSPCPAVWPDVIKLPYFNTMKP KKQYRRKLREEFVFIPAAALDLFDYMLALDPSKRCTAEQALQCEFLRDVEPSKMP PPERFLHAEAMHHSKMAESLPLWQDCHELWSKKRRRQKQMGMTDDVSTIKAPR KDLSLGLDDSRTNTPQGVLPSSQLKSQGSSNVAPVKTGPGQHLNHSELAILLNLLQ SKTSVNMADFVQVLNIKVNSETQQQLNKINLPAGILATGEKQTDPSTPQQESSKPL GGIQPSSQTIQPKVETDAAQAAVQSAFAVLLTQLIKAQQSKQKDVLLEERENGSGH EASLQLRPPPEPSTPVSGQDDLIQHQDMRILELTPEPDRPRILPPDQRPPEPPEPPPVT EEDLDYRTENQHVPTTSSSLTDPHAGVKAALLQLLAQHQPQDDPKREGGIDYQAG DTYVSTSDYKDNFGSSSFSSAPYVSNDGLGSSSAPPLERRSFIGNSDIQSLDNYSTAS SHSGGPPQPSAFSESFPSSVAGYGDIYLNAGPMLFSGDKDHRFEYSHGPIAVLANSS DPSTGPESTHPLPAKMHNYNYGGNLQENPSGPSLMHGQTWTSPAQGPGYSQGYR GHISTSTGRGRGRGLPY |

Another embodiment provides the modified CDK12 or the modified CDK13 polypeptide wherein the structure of Formula (IV) has the Y group selected from:

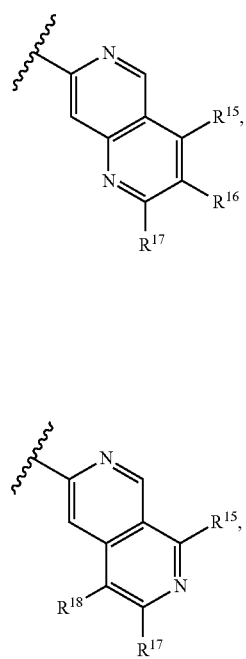
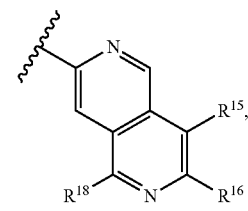
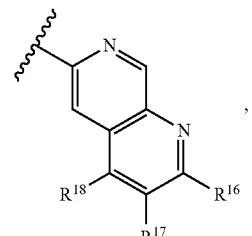
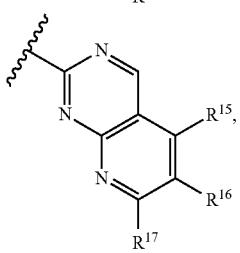
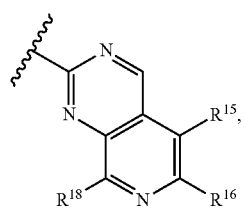
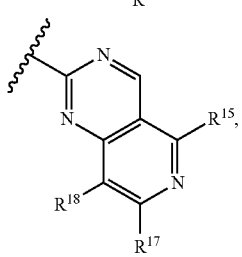

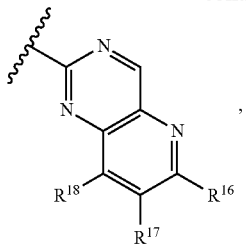

,

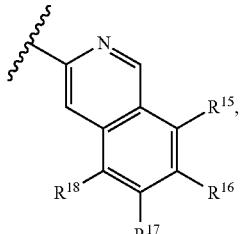

,

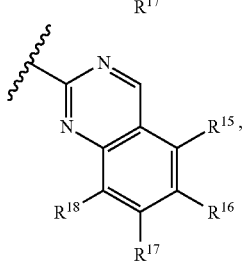

,

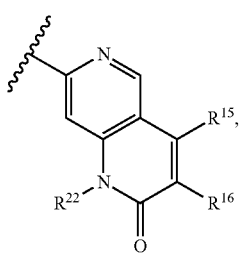

,

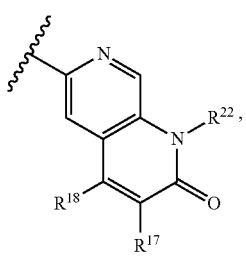

,

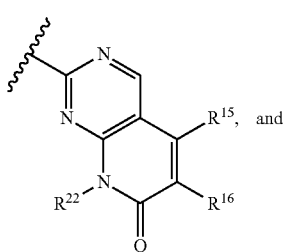

and

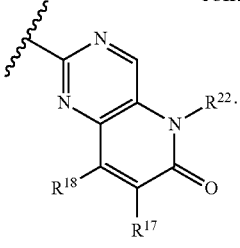

.

wherein, $R^{15}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$) SO$_2$R$^{21}$, —SO$_2$N(R$^{22}$)$_2$, —N(R$^{22}$)SO$_2$N(R$^{22}$)$_2$, —CON (R$^{22}$)$_2$, —N(R$^{22}$)CO$_2$R$^{21}$, —N(R$^{22}$)CON(R$^{22}$)$_2$, —N(R$^{22}$) COR$^{21}$, —OC(O)N(R$^{22}$)$_2$, —OSO$_2$N(R$^{22}$)$_2$, or —N(R$^{22}$) SO$_3$R$^{21}$;

$R^{16}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$) SO$_2$R$^{21}$, —SO$_2$N(R$^{22}$)$_2$, —N(R$^{22}$)SO$_2$N(R$^{22}$)$_2$, —CON (R$^{22}$)$_2$, —N(R$^{22}$)CO$_2$R$^{21}$, —N(R$^{22}$)CON(R$^{22}$)$_2$, —N(R$^{22}$) COR$^{21}$, —OC(O)N(R$^{22}$)$_2$, —OSO$_2$N(R$^{22}$)$_2$, or —N(R$^{22}$) SO$_3$R$^{21}$;

$R^{17}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$) SO$_2$R$^{21}$, —SO$_2$N(R$^{22}$)$_2$, —N(R$^{22}$)SO$_2$N(R$^{22}$)$_2$, —CON (R$^{22}$)$_2$, —N(R$^{22}$)CO$_2$R$^{21}$, —N(R$^{22}$)CON(R$^{22}$)$_2$, —N(R$^{22}$) COR$^{21}$, —OC(O)N(R$^{22}$)$_2$, —OSO$_2$N(R$^{22}$)$_2$, or —N(R$^{22}$) SO$_3$R$^{21}$;

$R^{18}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$) SO$_2$R$^{21}$, —SO$_2$N(R$^{22}$)$_2$, —N(R$^{22}$)SO$_2$N(R$^{22}$)$_2$, —CON (R$^{22}$)$_2$, —N(R$^{22}$)CO$_2$R$^{21}$, —N(R$^{22}$)CON(R$^{22}$)$_2$, —N(R$^{22}$) COR$^{21}$, —OC(O)N(R$^{22}$)$_2$, —OSO$_2$N(R$^{22}$)$_2$, or —N(R$^{22}$) SO$_3$R$^{21}$;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides the modified CDK12 or the modified CDK13 polypeptide wherein the structure of Formula (IV) has A is C—H. Another embodiment provides the modified CDK12 or the modified CDK13 polypeptide wherein the structure of Formula (IV) has A is N.

Another embodiment provides the modified CDK12 or the modified CDK13 polypeptide wherein the structure of Formula (IV) has E is —C(O)—.

Another embodiment provides the modified CDK12 or the modified CDK13 polypeptide wherein the structure of Formula (IV) has n is 1, and m is 2.

Pharmaceutical Compositions

In certain embodiments, the heteroaromatic CDK inhibitory compound described herein is administered as a pure chemical. In other embodiments, the heteroaromatic CDK inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Provided herein is a pharmaceutical composition comprising at least one heteroaromatic CDK inhibitory compound as described herein, or a stereoisomer, pharmaceutically acceptable salt, hydrate, or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and a compound of Formula (I), (II), (Ia), or a compound disclosed in Table 1, or a pharmaceutically acceptable salt or solvate thereof.

One embodiment provides a pharmaceutical composition comprising a pharmaceutically acceptable excipient and a compound of Formula (III), or a compound disclosed in Table 2, or a pharmaceutically acceptable salt or solvate thereof.

One embodiment provides a method of preparing a pharmaceutical composition comprising mixing a compound of Formula (I), (Ia) or (II), or a pharmaceutically acceptable salt or solvate thereof, and a pharmaceutically acceptable carrier.

In certain embodiments, the heteroaromatic CDK inhibitory compound as described by Formula (I), (Ia), or (II), or a compound disclosed in Table 1, is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

In some embodiments, the heteroaromatic CDK inhibitory compound as described by Formula (I), (Ia), (II), or a compound disclosed in Table 1, or pharmaceutically acceptable salt or solvate thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one heteroaromatic CDK inhibitory compound as described herein differs depending upon the subject or patient's (e.g., human) condition. In some embodiments, such factors include general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Methods of Treatment

One embodiment provides a compound of Formula (I), (Ia) or (II), or a pharmaceutically acceptable salt or solvate thereof, for use in a method of treatment of the human or animal body.

One embodiment provides a compound of Formula (I), (Ia) or (II), or a pharmaceutically acceptable salt or solvate thereof, for use in a method of treatment of cancer or neoplastic disease.

One embodiment provides a use of a compound of Formula (I), (Ia) or (II), or a pharmaceutically acceptable salt or solvate thereof, in the manufacture of a medicament for the treatment of cancer or neoplastic disease.

In some embodiments, described herein is a method of treating cancer in a patient in need thereof comprising administering to the patient a compound of Formula (I), or a pharmaceutically acceptable salt or solvate thereof. In some embodiments, described herein is a method of treating cancer in a patient in need thereof comprising administering to the patient a compound of Formula (Ia), or a pharmaceutically acceptable salt or solvate thereof. In some embodiments, described herein is a method of treating cancer in a patient in need thereof comprising administering to the patient a compound of Formula (II), or a pharmaceutically acceptable salt or solvate thereof. In some embodiments, described herein is a method of treating cancer in a patient in need thereof comprising administering to the patient a compound disclosed in Table 1, or a pharmaceutically acceptable salt or solvate thereof. In some embodiments, also described herein is a method of treating cancer in a patient in need thereof comprising administering to the patient a pharmaceutical composition comprising a compound of Formula (I), or a pharmaceutically acceptable salt or solvate thereof, and a pharmaceutically acceptable excipient. In some embodiments, also described herein is a method of treating cancer in a patient in need thereof comprising administering to the patient a pharmaceutical composition comprising a compound of Formula (Ia), or a pharmaceutically acceptable salt or solvate thereof, and a pharmaceutically acceptable excipient. In some embodiments, also described herein is a method of treating cancer in a patient in need thereof comprising administering to the patient a pharmaceutical composition comprising a compound of Formula (II), or a pharmaceutically acceptable salt or solvate thereof, and a pharmaceutically acceptable excipient. In some embodiments, also described herein is a method of treating cancer in a patient in need thereof comprising administering to the patient a pharmaceutical composition comprising a compound disclosed in Table 1, or a pharmaceutically acceptable salt or solvate thereof, and a pharmaceutically acceptable excipient. In some embodiments, the cancer is breast cancer, colorectal cancer, ovarian cancer, pancreatic cancer, prostate cancer, or lung cancer.

One embodiment provides a compound of Formula (III), or a pharmaceutically acceptable salt or solvate thereof, for use in a method of treatment of the human or animal body.

One embodiment provides a compound of Formula (III), or a pharmaceutically acceptable salt or solvate thereof, for use in a method of treatment of cancer or neoplastic disease. In some embodiments, the cancer is breast cancer, colorectal cancer, ovarian cancer, pancreatic cancer, prostate cancer, or lung cancer.

One embodiment provides a use of a compound of Formula (III), or a pharmaceutically acceptable salt or solvate thereof, in the manufacture of a medicament for the treatment of cancer or neoplastic disease. In some embodiments, the cancer is breast cancer, colorectal cancer, ovarian cancer, pancreatic cancer, prostate cancer, or lung cancer.

In some embodiments, described herein is a method of treating myotonic dystrophy type 1 in a patient in need thereof comprising administering to the patient a compound of Formula (I), or a pharmaceutically acceptable salt or solvate thereof.

In some embodiments, described herein is a method of treating myotonic dystrophy type 1 in a patient in need thereof comprising administering to the patient a compound of Formula (Ia), or a pharmaceutically acceptable salt or solvate thereof.

In some embodiments, described herein is a method of treating myotonic dystrophy type 1 in a patient in need thereof comprising administering to the patient a compound of Formula (II), or a pharmaceutically acceptable salt or solvate thereof.

In some embodiments, described herein is a method of treating myotonic dystrophy type 1 in a patient in need thereof comprising administering to the patient a compound of Formula (III), or a pharmaceutically acceptable salt or solvate thereof.

Provided herein is the method wherein the pharmaceutical composition is administered orally.

Provided herein is the method wherein the pharmaceutical composition is administered by injection.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

In some embodiments, the heteroaromatic CDK inhibitory compounds disclosed herein are synthesized according to the following examples. As used below, and throughout the description of the invention, the following abbreviations, unless otherwise indicated, shall be understood to have the following meanings:

° C. degrees Celsius
$\delta_H$ chemical shift in parts per million downfield from tetramethylsilane
DCM dichloromethane ($CH_2Cl_2$)
DMF dimethylformamide
DMSO dimethylsulfoxide
EA ethyl acetate
ESI electrospray ionization
Et ethyl
g gram(s)
h hour(s)
HPLC high performance liquid chromatography
Hz hertz
J coupling constant (in NMR spectrometry)
LCMS liquid chromatography mass spectrometry
μ micro
m multiplet (spectral); meter(s); milli
M molar
$M^+$ parent molecular ion
Me methyl
MHz megahertz
min minute(s)
mol mole(s); molecular (as in mol wt)
mL milliliter
MS mass spectrometry
nm nanometer(s)
NMR nuclear magnetic resonance
pH potential of hydrogen; a measure of the acidity or basicity of an aqueous solution
PE petroleum ether
RT room temperature
s singlet (spectral)
t triplet (spectral)
T temperature
TFA trifluoroacetic acid
THF tetrahydrofuran General Scheme 1 for the synthesis of heteroaromatic CDK inhibitory compounds.

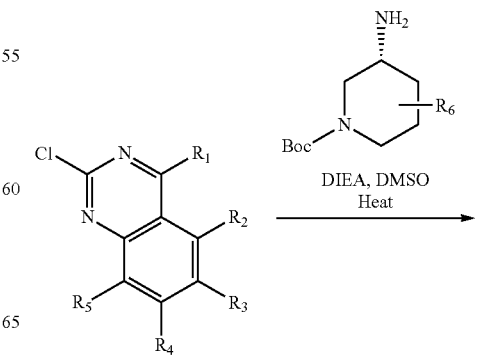

Scheme 1

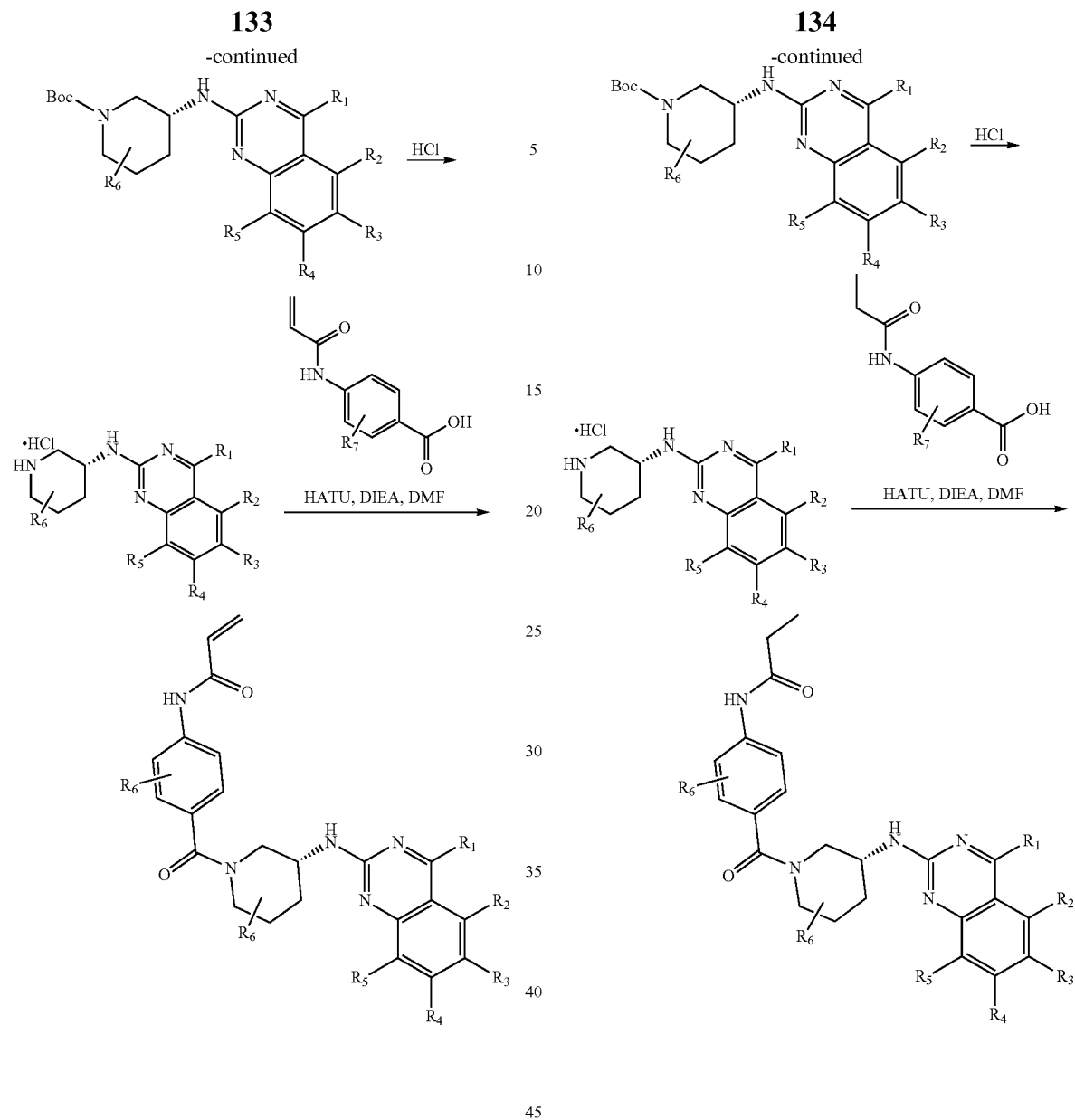
General Scheme 2 for the synthesis of heteroaromatic CDK inhibitory compounds.
General Scheme 3 for the synthesis of heteroaromatic CDK inhibitory compounds.
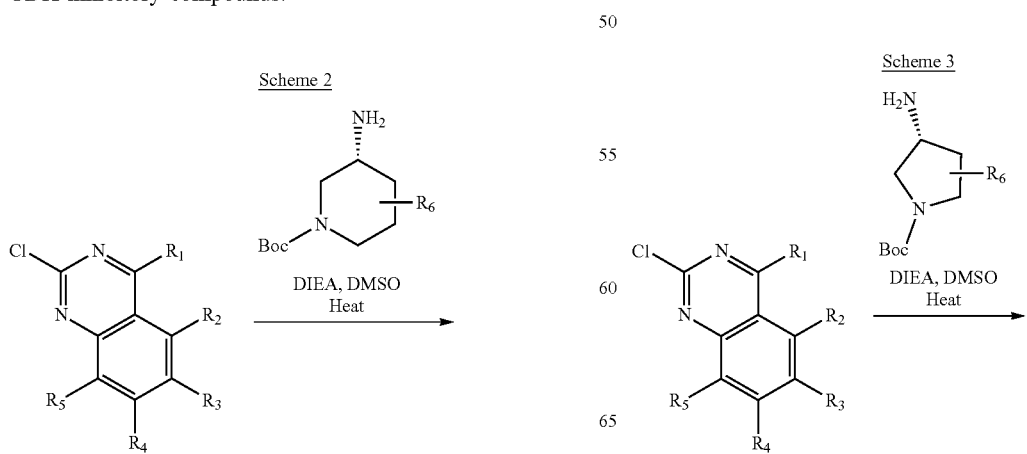

135
-continued
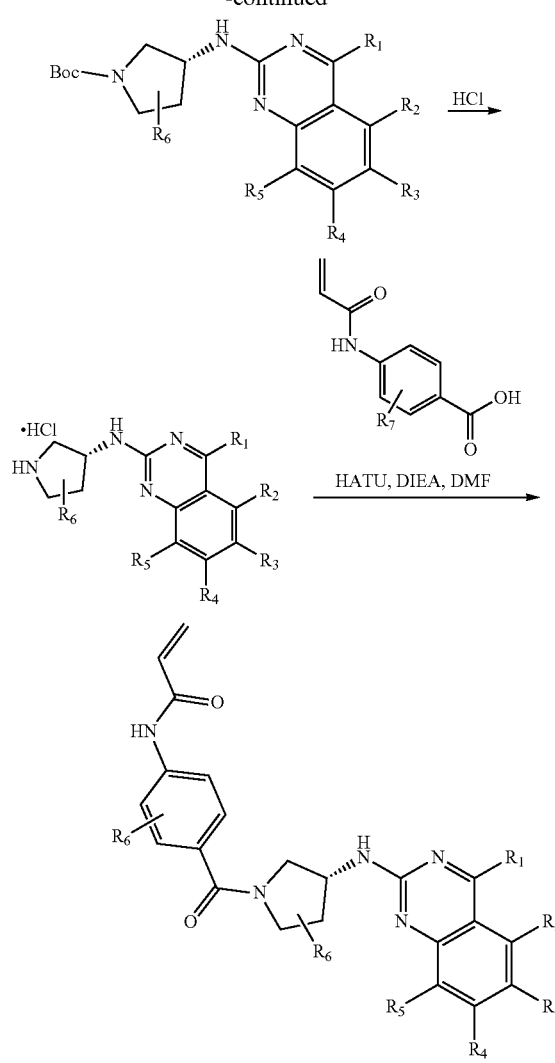
136
-continued
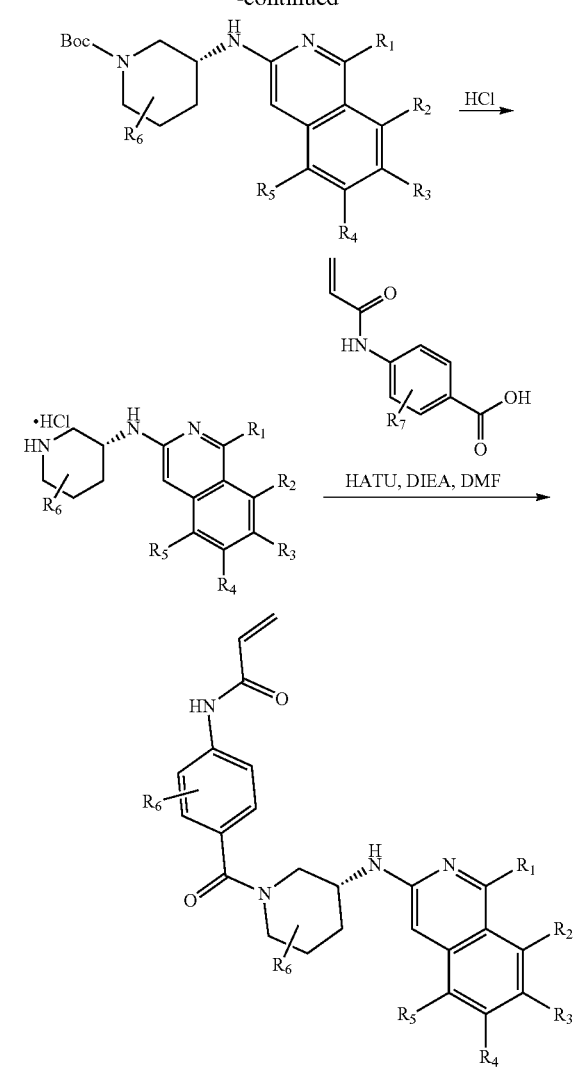
General Scheme 4 for the synthesis of heteroaromatic CDK inhibitory compounds.
Scheme 4
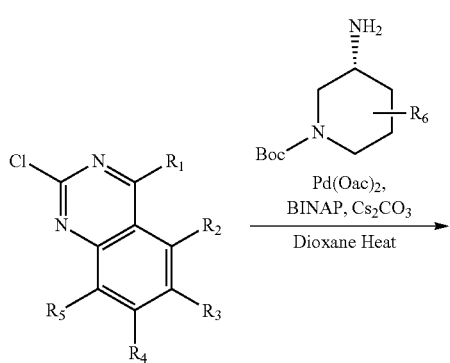
General Scheme 5 for the synthesis of heteroaromatic CDK inhibitory compounds.
Scheme 5
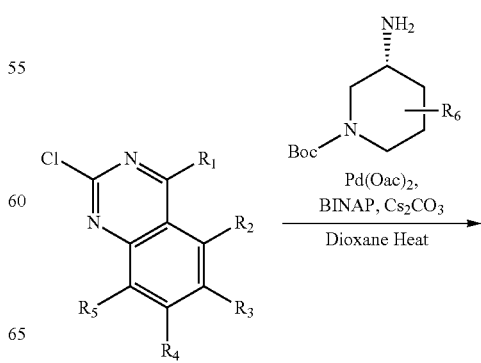

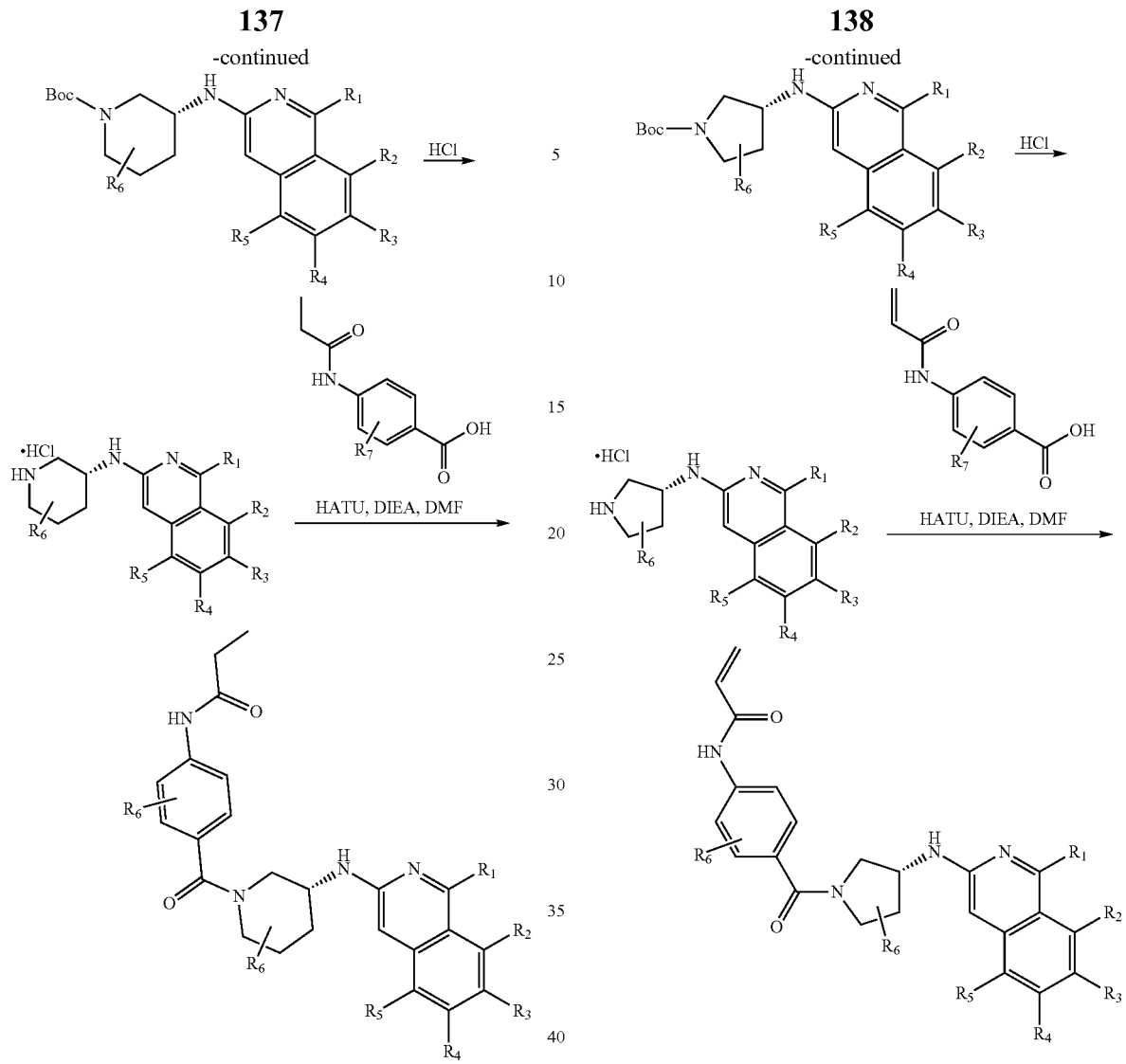

Example A1: Synthesis of Intermediate 1 (4-acrylamidobenzoic Acid)

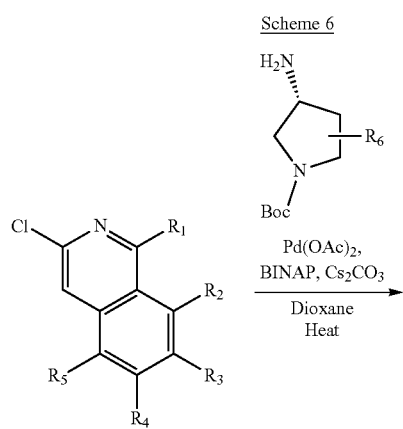

A mixture of 4-amino-benzoic acid (25 g, 181.9 mmol) and pyridine (10 mL) in DMF (200 mL) was cooled to 0° C. Acryloyl chloride (22 mL, 272.8 mmol) was added and the solution was stirred at RT for 3 h. The reaction mixture was poured into water (200 mL) and the precipitate was filtered, washed with water, washed with PE, dried under high vacuum to give 4-acrylamidobenzoic acid as a white solid (22 g, 63%). MS Calcd.: 191, MS Found: 192 ([M+H]$^+$).

General Scheme 6 for the synthesis of heteroaromatic CDK inhibitory compounds.

Example A2: Synthesis of Intermediate 2 (4-propionamidobenzoic Acid)

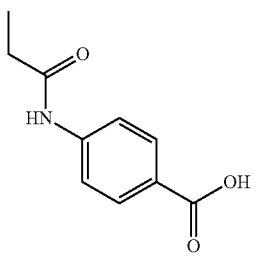

A mixture of 4-amino-benzoic acid (25 g, 181.9 mmol) and pyridine (10 mL) in DMF (200 mL) was cooled to 0° C. Propionyl chloride (23.8 mL, 272.9 mmol) was added and the solution was stirred at RT for 16 h. The reaction mixture was poured into water (200 mL) and the precipitate was filtered, washed with water, washed with PE, dried under high vacuum to give 4-propionamidobenzoic acid as a white solid (22 g, 63%). MS Calcd.: 193, MS Found: 194 ([M+H]$^+$).

Example 1: (R)—N-(4-(3-(quinazolin-2-ylamino)piperidine-1-carbonyl)phenyl)acrylamide

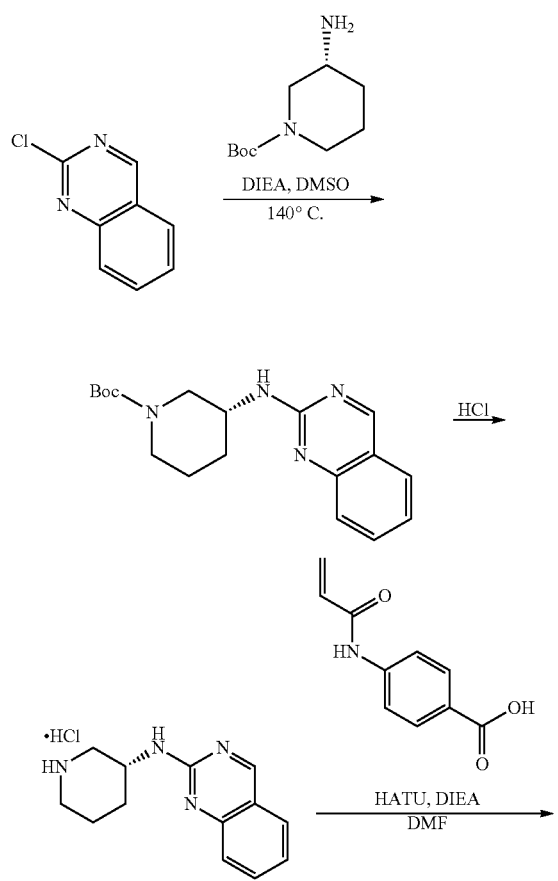

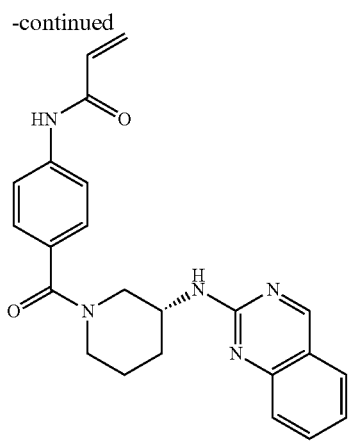

Step 1

To a solution of 2-chloroquinazoline (400 mg, 2.43 mmol), (R)-tert-butyl 3-aminopiperidine-1-carboxylate (582 mg, 2.91 mmol) in DMSO (10 mL) was added DIEA (0.86 mL, 4.86 mmol) at RT and the mixture was stirred at 140° C. for 4 h. The reaction was diluted with water (50 mL), and the precipitate was filtered, washed with PE/EA (5 mL:1 mL) to give (R)-tert-butyl 3-(quinazolin-2-ylamino)piperidine-1-carboxylate (500 mg, 62.7%). MS Calcd.: 328, MS Found: 329 ([M+H]$^+$).

Step 2

A solution of (R)-tert-butyl 3-(quinazolin-2-ylamino)piperidine-1-carboxylate (500 mg, 1.52 mmol) in HCl/EA (10 mL, 2.0 M) was stirred at RT for 3 h. The reaction mixture was filtered to give (R)—N-(piperidin-3-yl)quinazolin-2-amine hydrochloride (600 mg, 100%). MS Calcd.: 228, MS Found: 229 ([M+H]$^+$).

Step 3

To a solution of (R)—N-(piperidin-3-yl)quinazolin-2-amine hydrochloride (300 mg, 1.13 mmol), 4-acrylamidobenzoic acid (238 mg, 1.24 mmol) and DIEA (0.6 mL, 3.40 mmol) in DMF (15 mL) was added HATU (517 mg, 1.36 mmol). The reaction mixture was stirred at RT for 12 h and concentrated. The residue was purified by prep-HPLC to give (R)—N-(4-(3-(quinazolin-2-ylamino)piperidine-1-carbonyl)phenyl)acrylamide (80 mg, 17.7%). $^1$H NMR (400 MHz, CD$_3$OD): δ 1.68-2.11 (m, 4H), 3.29-3.31 (m, 1H), 3.66-3.89 (m, 4H), 5.77 (t, J=5.2 Hz, 1H), 6.34 (s, 2H), 7.15-7.68 (m, 8H), 8.92 (s, 1H). MS Calcd.: 401, MS Found: 402 ([M+H]$^+$).

Example 2: (R)—N-(4-(3-(isoquinolin-3-ylamino)piperidine-1-carbonyl)phenyl)acrylamide

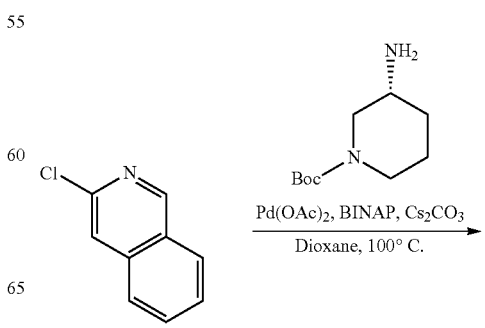

-continued

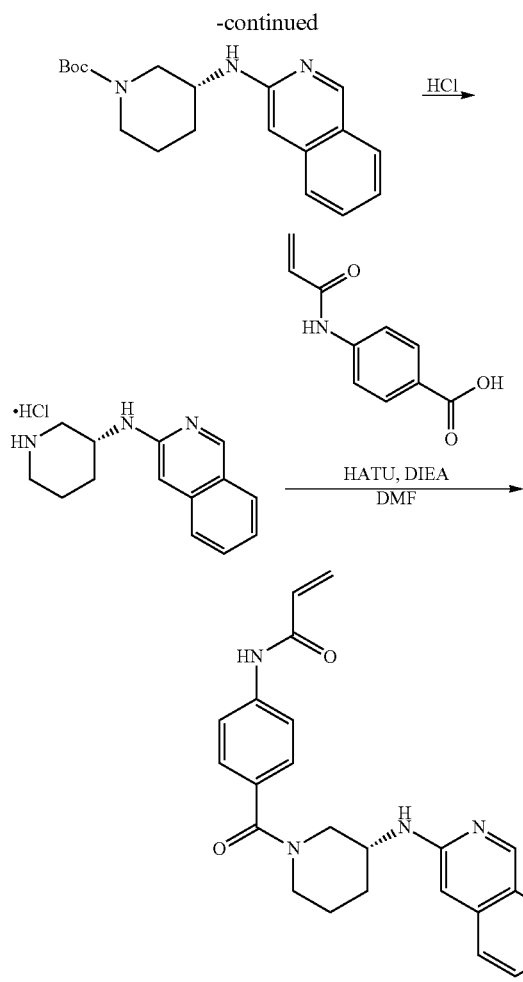

Step 1

To a solution of 3-chloroisoquinoline (200 mg, 1.22 mmol) in dioxane (10 mL) was added (R)-tert-butyl 3-aminopiperidine-1-carboxylate (269 mg, 1.34 mmol), $Cs_2CO_3$ (795 mg, 2.44 mmol), $Pd(OAc)_2$ (27 mg, 0.12 mmol), BINAP (75 mg, 0.12 mmol). The mixture was stirred at 100° C. for 6 h and concentrated in vaccuo. The residue was purified by silica gel chromatography (PE/EA=3/1) to afford (R)-tert-butyl 3-(isoquinolin-3-ylamino)piperidine-1-carboxylate (360 mg, 90%). MS Calcd.: 327, MS Found: 328 ([M+H]$^+$).

Step 2 and 3

The title compound was prepared in 10% yield from (R)-tert-butyl 3-(isoquinolin-3-ylamino)piperidine-1-carboxylate using general procedure of (R)—N-(4-(3-(quinazolin-2-ylamino)piperidine-1-carbonyl)phenyl)acrylamide. $^1$H NMR (400 MHz, DMSO-$d_6$): δ 1.59-1.60 (m, 2H), 1.83 (m, 1H), 2.03-2.08 (m, 1H), 2.85-3.08 (m, 2H), 3.64-3.87 (m, 2H), 4.23-4.46 (m, 1H), 5.79 (d, J=10.0 Hz, 1H), 6.27-6.70 (m, 4H), 7.13 (s, 1H), 7.39-7.44 (m, 4H), 7.71 (d, J=7.2 Hz, 3H), 8.76 (m, 1H), 10.28 (brs, 1H). MS Calcd.: 400, MS Found: 401 ([M+H]$^+$).

Example 3: (R)—N-(4-(3-((6-chloroquinazolin-2-yl)amino)piperidine-1-carbonyl)phenyl)acrylamide

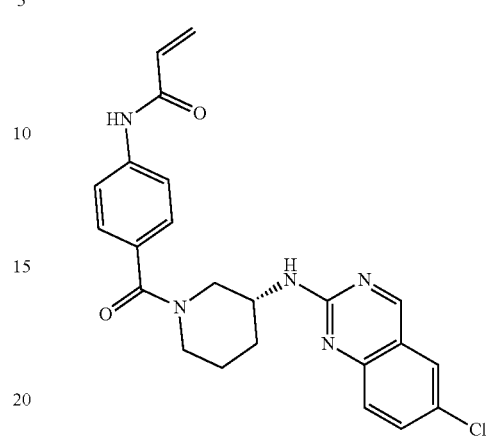

The title compound was prepared in 23.7% yield from (6-chloro-quinazolin-2-yl)-piperidin-3-yl-amine using general procedure of (R)—N-(4-(3-(quinazolin-2-ylamino)piperidine-1-carbonyl)phenyl)acrylamide. $^1$H NMR (400 MHz, CD$_3$OD): δ 1.70-1.73 (m, 4H), 3.72-3.88 (m, 5H), 5.80 (t, J=5.6 Hz, 1H), 6.38 (d, J=4.4 Hz 2H), 7.17-7.50 (m, 7H), 8.91 (s, 1H). MS Calcd.: 435 MS Found: 436 ([M+H]$^+$).

Example 4: (R)—N-(4-(3-((6-fluoroquinazolin-2-yl)amino)piperidine-1-carbonyl)phenyl)acrylamide

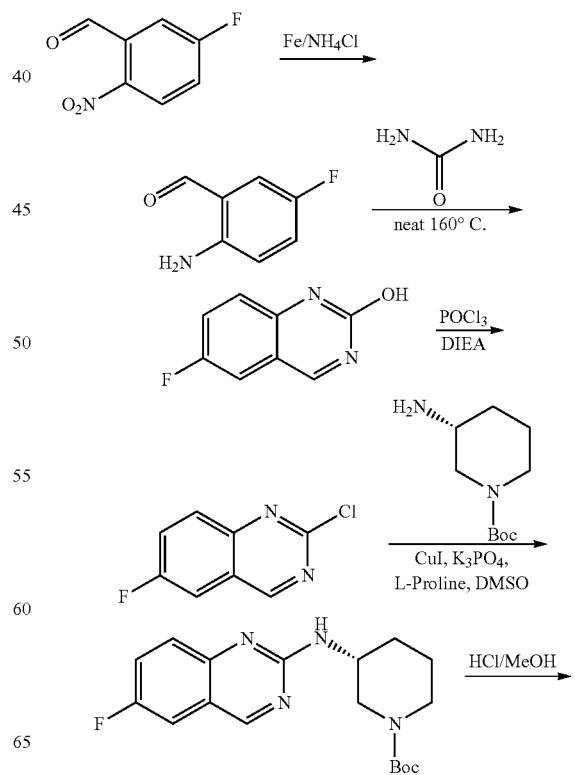

143

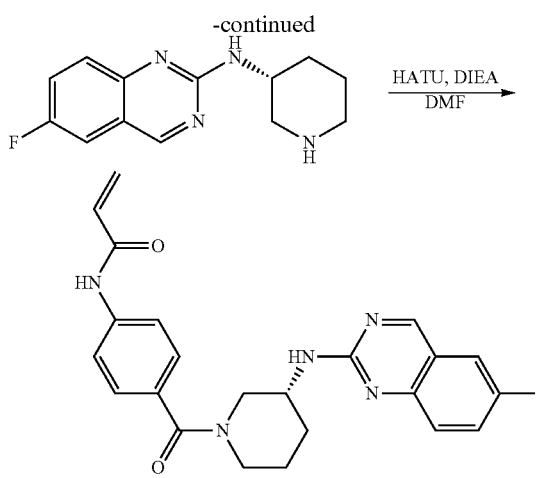

Step 1

A mixture of 5-fluoro-2-nitrobenzaldehyde (2.5 g, 14.8 mmol), Fe (5 g, 89 mmol), acetic acid (15 mL), conc. HCl (2.5 mL) in EtOH (25 mL) and H$_2$O (10 mL) was stirred at 65° C. for 5 h. The mixture was diluted with water (100 mL) and extracted with EA (100 mL*2). The combined organic layers were washed with brine and concentrated to afford 2-amino-5-fluorobenzaldehyde (2.5 g, 100%) as yellow oil. MS Calcd.: 139 MS Found: 140 ([M+H]$^+$).

Step 2

A mixture of 2-amino-5-fluorobenzaldehyde (2 g, 14.4 mmol) and urea (8 g, 133 mmol) was stirred at 140° C. for 3 h. The mixture was diluted with 30 mL of water. The solids were collected by filtration and dried to afford 6-fluoroquinazolin-2-ol (2.3 g, 97%) as a yellow solid. MS Calcd.: 164 MS Found: 165 ([M+H]$^+$).

Step 3

A solution of 6-fluoroquinazolin-2-ol (200 mg, 1.2 mmol) and DIPEA (314 mg, 2.4 mmol) in 2 mL of POCl$_3$ was stirred at 125° C. for 2 h. The mixture was concentrated. The residue was diluted with 20 mL of DCM and washed with 10 mL of water. The organic layer was concentrated and purified by column chromatography on silica gel (PE/EA, 2:1) to afford 2-chloro-6-fluoroquinazoline (150 mg, 68%) as a yellow solid. $^1$H NMR (400 MHz, CDCl$_3$): δ 7.58-7.61 (m, 1H), 7.72-7.77 (m, 1H), 8.02-8.06 (m, 1H), 9.29 (s, 1H). MS Calcd.: 182 MS Found: 183 ([M+H]$^+$).

Step 4

A mixture of 2-chloro-6-fluoroquinazoline (200 mg, 1.1 mmol), (R)-tert-butyl 3-aminopiperidine-1-carboxylate (220 mg, 1.1 mmol) and DIPEA (426 mg, 3.3 mmol) in 2 mL of NMP was stirred at 110° C. for 1 h. The mixture was diluted with water (50 mL) and extracted with DCM (30 mL*2). The combined organic layers were concentrated and the residue was purified by silica column chromatography (PE/EA, 2:1) to afford (R)-tert-butyl 3-((6-fluoroquinazolin-2-yl)amino)piperidine-1-carboxylate (150 mg, 39%) as a yellow oil. $^1$H NMR (400 MHz, DMSO-d$_6$): δ 1.23-1.47 (m, 12H), 1.73-1.78 (m, 1H), 1.91-1.95 (m, 1H), 3.34-3.52 (m, 2H), 3.79-3.84 (m, 2H), 7.40-7.42 (m, 1H), 7.49-7.53 (m, 1H), 7.60-7.65 (m, 2H), 9.13 (s, 1H). MS Calcd.: 346 MS Found: 347 ([M+H]$^+$).

Step 5

To a solution of (R)-tert-butyl 3-((6-fluoroquinazolin-2-yl)amino)piperidine-1-carboxylate (150 mg, 0.43 mmol) in 2 mL of MeOH was added HCl/MeOH (1 mL, 1M). The mixture was stirred at 35° C. for 1 h and concentrated to afford (R)-6-fluoro-N-(piperidin-3-yl)quinazolin-2-amine (107 mg, 100%) as yellow oil. MS Calcd.: 246 MS Found: 247 ([M+H]$^+$).

Step 6

A mixture of (R)-6-fluoro-N-(piperidin-3-yl)quinazolin-2-amine (107 mg, 0.43 mmol), 4-acrylamidobenzoic acid (92 mg, 0.48 mmol), HATU (198 mg, 0.52 mmol), DIPEA (219 mg, 1.7 mmol) in DMF (3 mL) was stirred at 25° C. overnight. The reaction mixture was quenched with water (30 mL) and extracted with EA (30 mL*2). The combined organics were concentrated and the residue was purified by prep-HPLC to afford (R)—N-(4-(3-((6-fluoroquinazolin-2-yl)amino)piperidine-1-carbonyl)phenyl)acrylamide (55 mg, 30%). 1H NMR (400 MHz, DMSO-d6): δ 1.03-2.52 (m, 4H), 3.07-3.20 (m, 2H), 3.31 (s, 1H), 3.79-4.04 (m, 2H), 5.77-5.80 (m, 1H), 6.26-6.30 (m, 1H), 6.39-6.47 (m, 1H), 7.33-7.70 (m, 8H), 9.05 (s, 1H), 10.12 (s, 1H). MS Calcd.: 419 MS Found: 420 ([M+H]+).

Example 5: (R)—N-(4-(3-((7-fluoroquinazolin-2-yl)amino)piperidine-1-carbonyl)phenyl)acrylamide

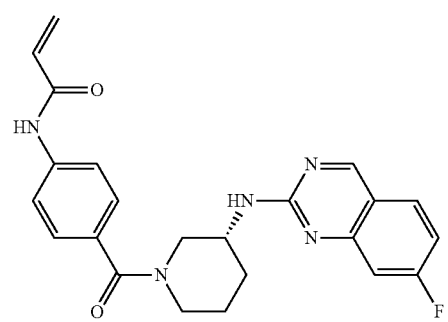 [SMILES: C=CC(=O)Nc1ccc(C(=O)N2CCC[C@@H](Nc3ncc4ccc(F)cc4n3)C2)cc1]

The title compound was prepared in 31% yield from (R)-7-fluoro-N-(piperidin-3-yl)quinazolin-2-amine using general procedure of (R)—N-(4-(3-((6-fluoroquinazolin-2-yl)amino)piperidine-1-carbonyl)phenyl)acrylamide. $^1$H NMR (400 MHz, DMSO-d$_6$): δ 1.51-2.00 (m, 4H), 3.08-3.33 (m, 2H), 3.74-4.41 (m, 3H), 5.77-5.79 (m, 1H), 6.25-6.46 (m, 2H), 6.75-7.42 (m, 3H), 7.77-7.90 (m, 5H), 9.05 (br s, 1H), 10.16-10.41 (m, 1H). MS Calcd.: 419 MS Found: 420 ([M+H]$^+$).

Example 6: (R)—N-(4-(3-((7-methoxyquinazolin-2-yl)amino)piperidine-1-carbonyl)phenyl)acrylamide

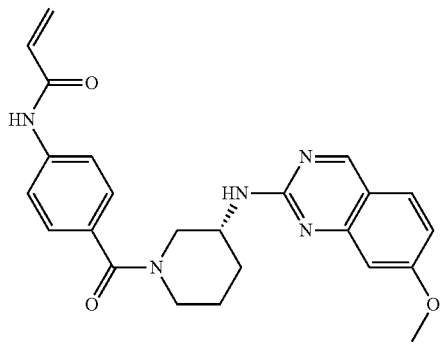 [SMILES: C=CC(=O)Nc1ccc(C(=O)N2CCC[C@@H](Nc3ncc4ccc(OC)cc4n3)C2)cc1]

The title compound was prepared in 7% yield from (R)-7-methoxy-N-(piperidin-3-yl)quinazolin-2-amine using general procedure of (R)—N-(4-(3-((6-fluoroquinazolin-2-yl)amino)piperidine-1-carbonyl)phenyl)acrylamide. $^1$H NMR (400 MHz, CD$_3$OD): δ 1.59-1.99 (m, 4H), 3.37-3.59 (m, 2H), 3.79 (s, 3H), 3.74-3.79 (m, 3H), 5.65-5.68 (m, 1H), 6.23-6.33 (m, 2H), 6.46-6.77 (m, 2H), 7.04-7.24 (m, 3H), 7.36-7.65 (m, 2H), 8.64-8.76 (m, 1H). MS Calcd.: 431 MS Found: 432 ([M+H]$^+$).

Example 7: (R)—N-(4-(3-((6-methoxyquinazolin-2-yl)amino)piperidine-1-carbonyl)phenyl)acrylamide

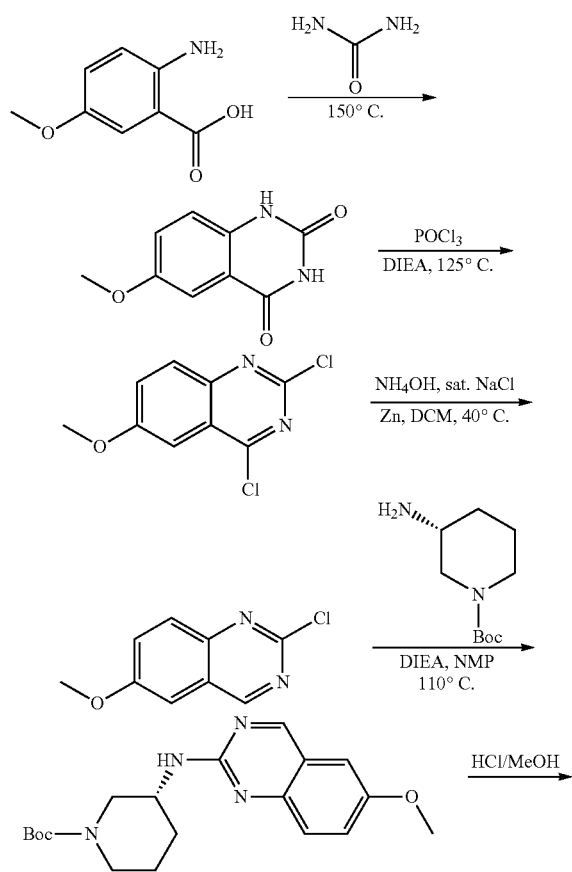

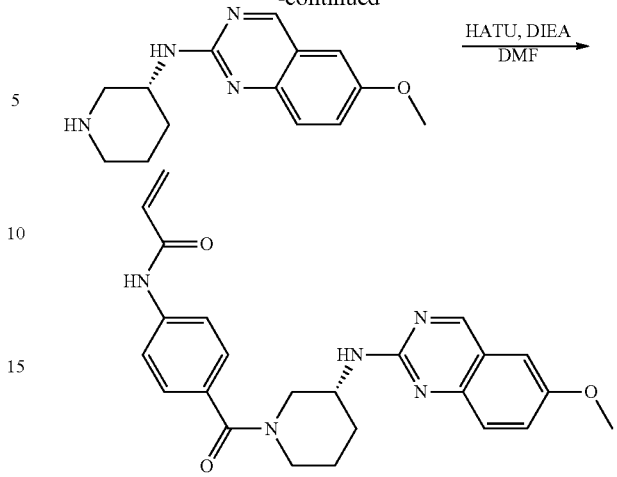

Step 1

A mixture of 2-amino-5-methoxybenzoic acid (5 g, 29.9 mmol) and urea (18 g, 299 mmol) was stirred at 150° C. for 5 h. The mixture was cooled to 100° C. and diluted with of water (50 mL). The precipitate was collected by filtration and rinsed with water. The solid was dissolved in 2 M NaOH (30 mL) and stirred at 100° C. for 30 minutes. After cooling to RT, the reaction mixture was adjusted to pH 1-2 using 2 M HCl. The precipitate was filtered, and the solids were dried to afford 6-methoxyquinazoline-2,4(1H,3H)-dione (3.99 g, 70%) as a yellow solid. MS Calcd.: 192 MS Found: 193 ([M+H]$^+$).

Step 2

A mixture of 6-methoxyquinazoline-2,4(1H,3H)-dione (1 g, 5.2 mmol) and DIPEA (1.34 g, 10.4 mmol) POCl$_3$ (10 mL) was stirred at 125° C. for 3 h. The reaction mixture was cooled to RT, added dropwise to water (100 mL) and extracted with DCM (100 mL*2). The organic layers were dried over Na$_2$SO$_4$, filtered and concentrated to afford 2,4-dichloro-6-methoxyquinazoline (880 mg, 74%) as a yellow solid. MS Calcd.: 228 MS Found: 229 ([M+H]$^+$).

Step 3

To a solution of 2,4-dichloro-6-methoxyquinazoline (880 mg, 3.8 mmol) in sat. NaCl (10 mL) and DCM (15 mL) was added NH$_4$OH (4.5 mL) and Zn (750 mg, 11.5 mmol). The reaction mixture was stirred at 50° C. for 2 days. The mixture was diluted with water (100 mL) and extracted with DCM (100 mL*2). The combined organic layers were dried over Na$_2$SO$_4$, filtered and concentrated. The residue was purified by silica gel chromatography (PE/EA, 5:1) to afford 2-chloro-6-methoxyquinazoline (180 mg, 24%) as a yellow solid. $^1$H NMR (400 MHz, CDCl$_3$): δ 3.97 (s, 3H), 7.17 (d, J=2.8 Hz, 1H), 7.60 (dd, J=3.2, 9.2 Hz 1H), 7.90 (d, J=9.2 Hz, 1H), 9.20 (s, 1H).

Step 4 to 6

The title compound was prepared in 24% yield from (R)-6-methoxy-N-(piperidin-3-yl)quinazolin-2-amine using general procedure of (R)—N-(4-(3-((6-fluoroquinazolin-2-yl)amino)piperidine-1-carbonyl)phenyl)acrylamide. $^1$H NMR (400 MHz, DMSO-d$_6$): δ 1.52-2.02 (m, 4H), 2.86-3.13 (m, 3H), 3.74-4.10 (m, 5H), 5.77-5.80 (m, 1H), 6.25-6.30 (m, 1H), 6.39-6.46 (m, 1H), 7.11-7.75 (m, 8H), 8.95-8.98 (m, 1H), 10.14-10.19 (m, 1H). MS Calcd.: 431 MS Found: 432 ([M+H]$^+$).

Example 8: (R)—N-(4-(3-((6-methylquinazolin-2-yl)amino)piperidine-1-carbonyl)phenyl)acrylamide

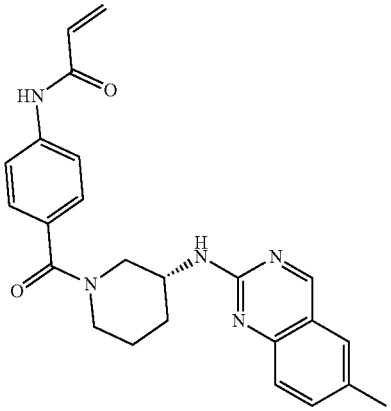 [SMILES: C=CC(=O)Nc1ccc(C(=O)N2CCC[C@@H](Nc3ncc4cc(C)ccc4n3)C2)cc1]

The title compound was prepared in 7% yield from (R)-6-methyl-N-(piperidin-3-yl)quinazolin-2-amine using general procedure of (R)—N-(4-(3-((6-methoxyquinazolin-2-yl)amino)piperidine-1-carbonyl)phenyl)acrylamide. $^1$H NMR (400 MHz, DMSO-d$_6$): δ 1.54-2.00 (m, 4H), 2.36 (br s, 3H), 3.05-3.10 (m, 2H), 3.57-4.41 (m, 3H), 5.77-5.80 (m, 1H), 6.26-6.30 (m, 1H), 6.40-6.47 (m, 1H), 7.11-7.72 (m, 8H), 8.96 (s, 1H), 10.16-10.33 (m, 1H). MS Calcd.: 415 MS Found: 416 ([M+H]$^+$).

Example 9: (R)—N-(4-(3-((7-methylquinazolin-2-yl)amino)piperidine-1-carbonyl)phenyl)acrylamide

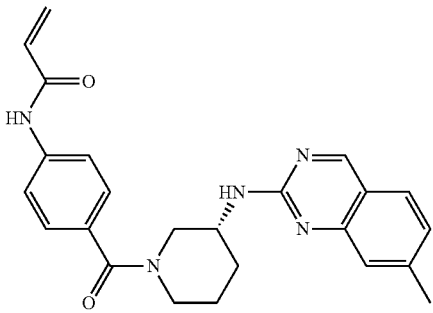 [SMILES: C=CC(=O)Nc1ccc(C(=O)N2CCC[C@@H](Nc3ncc4ccc(C)cc4n3)C2)cc1]

The title compound was prepared in 12% yield from (R)-7-methyl-N-(piperidin-3-yl)quinazolin-2-amine using general procedure of (R)—N-(4-(3-((6-methoxyquinazolin-2-yl)amino)piperidine-1-carbonyl)phenyl)acrylamide. $^1$H NMR (400 MHz, DMSO-d$_6$): δ 1.52-2.05 (m, 4H), 2.39 (s, 3H), 2.95-3.13 (m, 2H), 3.67-4.23 (m, 3H), 5.74-5.80 (m, 1H), 6.24-6.31 (m, 1H), 6.38-6.47 (m, 1H), 6.89-7.81 (m, 8H), 8.92-9.10 (m, 1H), 10.12-10.29 (m, 1H). MS Calcd.: 415 MS Found: 416 ([M+H]$^+$).

Example 10: (R)—N-(4-(3-((7-chloroquinazolin-2-yl)amino)piperidine-1-carbonyl)phenyl)propionamide

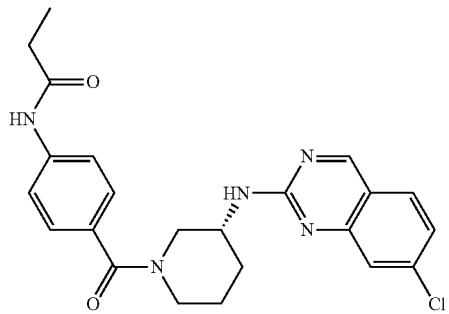 [SMILES: CCC(=O)Nc1ccc(C(=O)N2CCC[C@@H](Nc3ncc4ccc(Cl)cc4n3)C2)cc1]

The title compound was prepared in 33% yield from of (R)-7-chloro-N-(piperidin-3-yl)quinazolin-2-amine and 4-propionamidobenzoic acid using general procedure of (R)—N-(4-(3-((6-fluoroquinazolin-2-yl)amino)piperidine-1-carbonyl)phenyl)acrylamide. $^1$H NMR (400 MHz, DMSO-d$_6$): δ 1.06-1.09 (m, 3H), 1.53-1.99 (m, 4H), 2.30 (s, 2H), 2.93-3.15 (m, 2H), 3.71-4.39 (m, 3H), 7.03-7.79 (m, 8H), 9.08 (s, 1H), 9.88-10.05 (m, 1H). MS Calcd.: 437 MS Found: 438 ([M+H]$^+$).

Example 11: (R)—N-(4-(3-((7-(methylsulfonyl)quinazolin-2-yl)amino)piperidine-1-carbonyl)phenyl)acrylamide

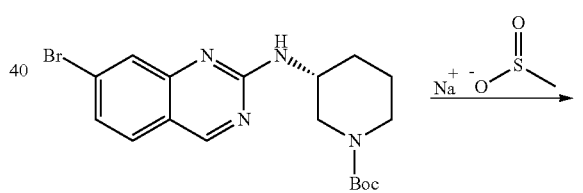

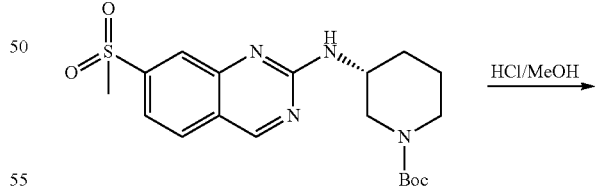

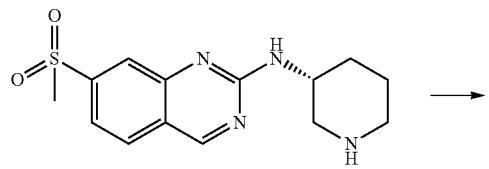

-continued

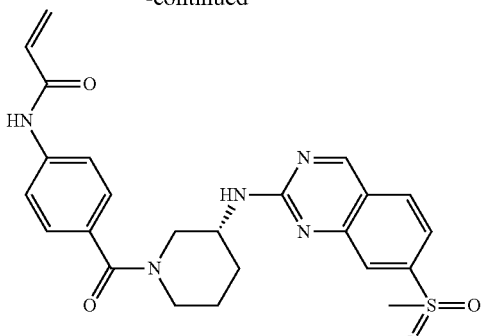

Step 1

A mixture of (R)-tert-butyl 3-((7-bromoquinazolin-2-yl)amino)piperidine-1-carboxylate (406 mg, 1.0 mmol), copper trifluoroacetate (213 mg, 1.0 mmol), CH₃SOONa (638 mg, 6.26 mmol), N,N'-dimethyl-ethane-1,2-diamine (64 mg, 0.7 mmol) in DMSO (4 mL) was stirred at 140° C. for 2 h. The mixture was diluted with EA (100 mL), washed with water (100 mL*3) and concentrated. The crude product was purified by chromatography using PE:EA (2:1-1:1) to give (R)-tert-butyl 3-((7-(methylsulfonyl)quinazolin-2-yl)amino)piperidine-1-carboxylate (400 mg, 98.5%) as a yellow solid. $^1$H NMR (300 MHz, CDCl₃): δ 1.44 (s, 9H), 1.75 (br s, 1H), 1.77-1.79 (m, 2H), 2.01-2.06 (m, 1H), 3.13 (s, 3H), 3.39-3.53 (m, 2H), 3.72-3.87 (m, 2H), 4.12-4.20 (m, 1H), 3.52-3.57 (m, 1H), 7.69 (dd, J=8.4, 1.5 Hz, 1H), 7.86 (d, J=8.1 Hz, 1H), 8.21 (d, J=2.4 Hz, 1H), 9.08 (d, J=2.4 Hz, 1H).

Step 2

To a solution of (R)-tert-butyl 3-((7-(methylsulfonyl)quinazolin-2-yl)amino)piperidine-1-carboxylate (400 mg, 0.98 mmol) in 4 mL of MeOH was added HCl/MeOH (2 mL, 1 M). The mixture was stirred at 35° C. for 1 h and concentrated to afford (R)-7-(methylsulfonyl)-N-(piperidin-3-yl)quinazolin-2-amine (301 mg, 100%) as yellow oil. MS Calcd.: 306 MS Found: 307 ([M+H]⁺).

Step 3

A mixture of (R)-7-(methylsulfonyl)-N-(piperidin-3-yl)quinazolin-2-amine (134 mg, 0.46 mmol), 4-acrylamidobenzoic acid (96 mg, 0.5 mmol), HATU (349 mg, 0.92 mmol), DIPEA (237 mg, 1.8 mmol) in DMF (5 mL) was stirred at 25° C. overnight. The reaction mixture was quenched with water (30 mL) and extracted with EA (30 mL*2). The combined organic layers were concentrated and the residue was purified by prep-HPLC to afford (R)—N-(4-(3-((7-(methylsulfonyl)quinazolin-2-yl)amino)piperidine-1-carbonyl)phenyl)acrylamide (66 mg, 30%). $^1$H NMR (400 MHz, DMSO-d₆): δ 1.51-2.04 (m, 4H), 3.27-3.34 (m, 4H), 3.60-4.53 (m, 4H), 5.74-5.80 (m, 1H), 6.17-6.49 (m, 2H), 7.30-8.16 (m, 8H), 9.23-9.33 (m, 1H), 9.95-10.54 (m, 1H). MS Calcd.: 479; MS Found: 480 ([M+H]⁺).

Example 12: (R)-2-((1-(4-acrylamidobenzoyl)piperidin-3-yl)amino)-N,N-dimethylquinazoline-7-carboxamide

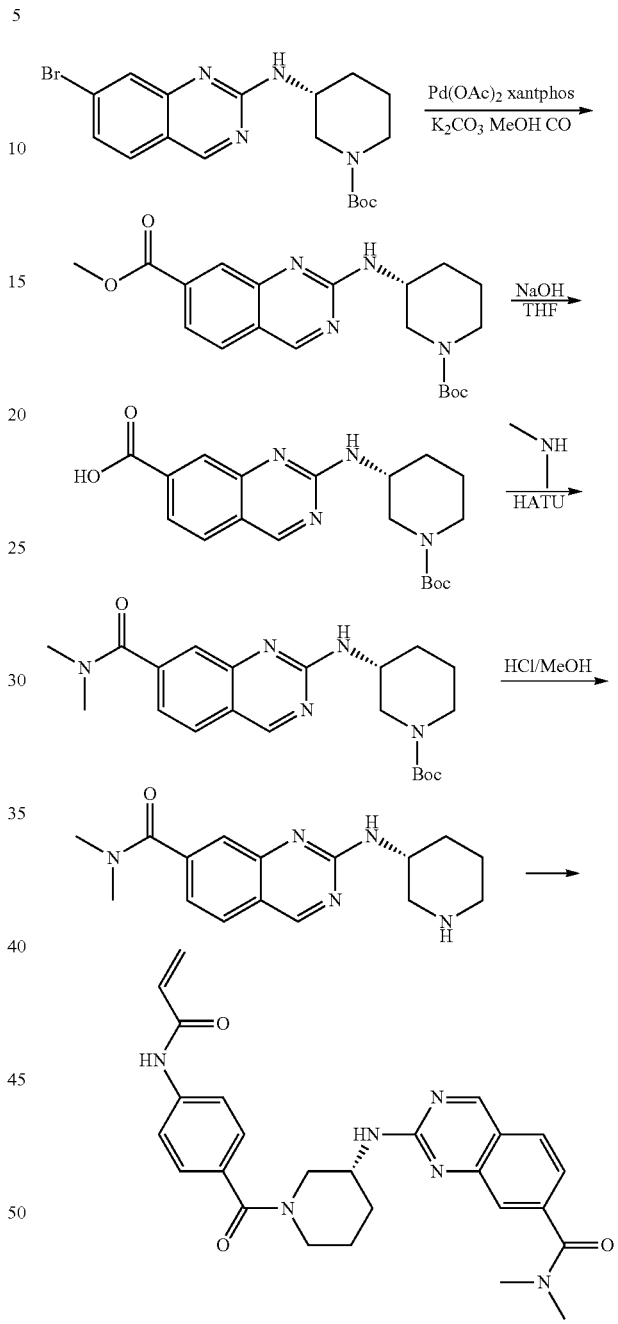

Step 1

A mixture of (R)-tert-butyl 3-((7-bromoquinazolin-2-yl)amino)piperidine-1-carboxylate (4.06 g, 10.0 mmol), Pd(OAc)₂ (896 mg, 4.0 mmol), DCCP.2HBF₄ (900 mg, 1.48 mmol), MeOH (3.2 g, 100 mmol), K₂CO₃ (2.76 g, 20.0 mmol) in DMF (40 mL) was stirred at 90° C. under CO for 6 h. The mixture was diluted with EA (400 mL), washed with water (200 mL). The organic phase was concentrated. The crude product was purified by chromatography using PE:EA (10:1-2:1) to give (R)-methyl 2-((1-(tert-butoxycarbonyl)piperidin-3-yl)amino)quinazoline-7-carboxylate (2.2 g, 57%) as yellow oil. $^1$H NMR (300 MHz, CDCl$_3$): δ 1.37 (s, 9H), 1.66-1.65 (m, 1H), 1.68-1.73 (m, 2H), 2.02-2.06 (m, 1H), 3.33-3.51 (m, 3H), 3.85-3.91 (m, 1H), 3.99 (s, 3H), 4.10-4.17 (m, 1H), 5.40-5.43 (m, 1H), 7.72-7.74 (m, 1H), 7.81-7.85 (m, 1H), 8.31 (s, 1H), 9.03 (s, 1H).

Step 2

A solution of (R)-methyl 2-((1-(tert-butoxycarbonyl)piperidin-3-yl)amino)quinazoline-7-carboxylate (1.2 g, 3.1 mmol) in THF: MeOH (10 mL:10 mL) was added LiOH.H$_2$O (260 mg, 6.2 mmol) in water (5 mL). The mixture was stirred at 25° C. for 2 h. The mixture was concentrated and the mixture was diluted with EA (100 mL), washed with water (200 mL). The aqueous phase was separated and the PH was adjusted to 5 by the addition of HCl (1.0 mmol/L). The mixture was extracted with EA (100 mL*2). The combined organic layers were concentrated to give (R)-2-((1-(tert-butoxycarbonyl)piperidin-3-yl)amino) quinazoline-7-carboxylic acid (1.1 g, 95%) as a yellow solid. $^1$H NMR (300 MHz, DMSO-d$_6$): δ 1.40 (s, 9H), 1.70-1.81 (m, 3H), 1.96-2.02 (m, 1H), 3.61-4.13 (m, 5H), 7.69-7.72 (m, 1H), 7.91-7.95 (m, 1H), 8.03-8.05 (m, 1H), 9.25 (s, 1H).

Step 3

A mixture of (R)-2-((1-(tert-butoxycarbonyl)piperidin-3-yl)amino)quinazoline-7-carboxylic acid (1.0 g, 2.69 mmol), dimethylamine hydrochloride (264 mg, 3.22 mmol), HATU (1.25 g, 3.22 mmol), DIPEA (1.38 g, 10.76 mmol) in DMF (10 mL) was stirred at 25° C. for 3 h. The mixture was added H$_2$O (300 mL), extracted with EtOAc (300 mL). The organic phase was concentrated in vacuo. The residue was purified by chromatography using PE:EA (4:1-0:1) to give (R)-tert-butyl 3-((7-(dimethylcarbamoyl)quinazolin-2-yl)amino)piperidine-1-carboxylate (1.0 g, 93%) as yellow oil. $^1$H NMR (300 MHz, CDCl$_3$): δ 1.27 (s, 9H), 1.64-1.80 (m, 3H), 1.98-2.06 (m, 1H), 3.01 (s, 3H), 3.17 (s, 3H), 3.33-3.56 (m, 3H), 3.79-3.92 (m, 1H), 4.13-4.23 (m, 1H), 5.37 (d, J=9.6 Hz, 1H), 7.25 (s, 1H), 7.58 (s, 1H), 7.72 (d, J=8.1 Hz, 1H), 8.99 (s, 1H).

Step 4

To a solution of (R)-tert-butyl 3-((7-(dimethylcarbamoyl) quinazolin-2-yl)amino)piperidine-1-carboxylate (1.0 g, 2.5 mmol) in 10 mL of MeOH was added HCl/MeOH (5 mL, 1 M). The mixture was stirred at 35° C. for 1 h and concentrated to afford (R)—N,N-dimethyl-2-(piperidin-3-ylamino) quinazoline-7-carboxamide (749 mg, 100%) as yellow oil. MS Calcd.: 299 MS Found: 300 ([M+H]$^+$).

Step 5

A mixture of (R)—N,N-dimethyl-2-(piperidin-3-ylamino)quinazoline-7-carboxamide (560 mg, 1.9 mmol), 4-acrylamidobenzoic acid (358 mg, 1.9 mmol), HATU (747 mg, 2.0 mmol), DIPEA (966 mg, 7.5 mmol) in DMF (5 mL) was stirred at 25° C. overnight. The reaction mixture was quenched with water (50 mL) and extracted with EA (50 mL*2). The combined organic layers were concentrated and the residue was purified by prep-HPLC to afford (R)-2-((1-(4-acrylamidobenzoyl)piperidin-3-yl)amino)-N,N-dimethylquinazoline-7-carboxamide (200 mg, 22%). $^1$H NMR (400 MHz, DMSO-d$_6$): δ 1.54-1.57 (m, 3H), 1.90-2.09 (m, 1H), 2.76-2.88 (m, 3H), 2.95-3.02 (m, 3H), 3.06-3.13 (m, 2H), 3.52-3.46 (m, 3H), 5.78 (d, J=2.0 Hz, 1H), 6.28-6.37 (m, 2H), 7.16-7.82 (m, 8H), 9.12-9.13 (m, 1H), 10.12-10.35 (m, 1H). MS Calcd.: 472; MS Found: 473 ([M+H]$^+$).

Example 13: (R)-2-((1-(4-acrylamidobenzoyl)piperidin-3-yl)amino)quinazoline-7-carboxamide

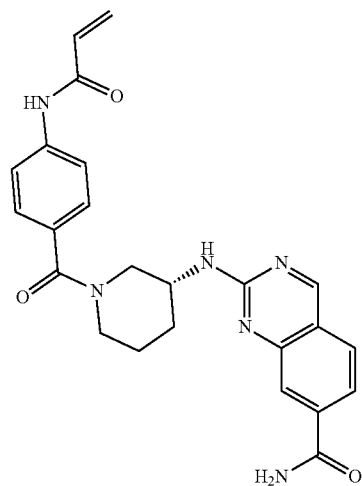 [SMILES: C=CC(=O)Nc1ccc(C(=O)N2CCC[C@@H](Nc3ncc4ccc(C(N)=O)cc4n3)C2)cc1]

The title compound was prepared in 16% yield from (R)-2-(piperidin-3-ylamino)quinazoline-7-carboxamide using general procedure of (R)-2-((1-(4-acrylamidobenzoyl) piperidin-3-yl)amino)-N,N-dimethylquinazoline-7-carboxamide. $^1$H NMR (400 MHz, CD$_3$OD): δ 1.59-2.01 (m, 4H), 3.58-3.82 (m, 4H), 4.01-4.61 (m, 1H), 5.65 (s, 1H), 6.21-6.36 (m, 2H), 7.12-7.95 (m, 7H), 8.90-9.02 (m, 1H). MS Calcd.: 444 MS Found: 445 ([M+H]$^+$).

Example 14: (R)-2-((1-(4-acrylamidobenzoyl)piperidin-3-yl)amino)quinazoline-7-carboxylic Acid

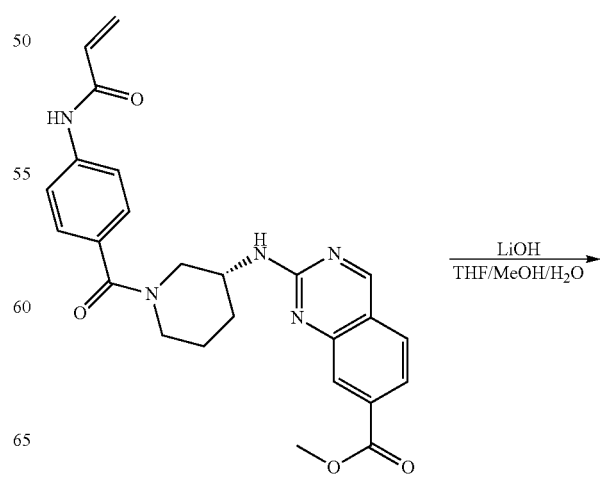

-continued

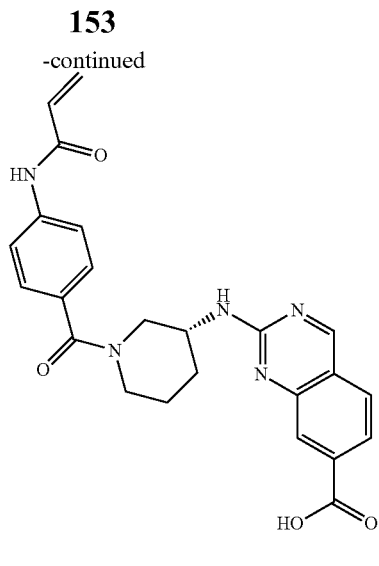

To a mixture of (R)-methyl 2-((1-(4-acrylamidobenzoyl)piperidin-3-yl)amino)quinazoline-7-carboxylate (110 mg, 0.24 mmol) in 1.5 mL of THF and 1.5 mL of MeOH, was added a solution of LiOH.H$_2$O (30 mg, 0.72 mmol) in 0.75 mL of H$_2$O. The reaction was stirred at 30° C. for 0.5 h. The mixture was diluted with 10 mL of water and washed with EA (50 mL*2). The aqueous layer was adjusted pH=4-5 with 0.1% TFA and extracted with EA (50 mL*2). The combined organic layers were concentrated and the residue was purified by prep-HPLC to afford (R)-2-((1-(4-acrylamidobenzoyl)piperidin-3-yl)amino)quinazoline-7-carboxylic acid (25.4 mg, 24%). $^1$H NMR (400 MHz, DMSO-d$_6$): δ 1.57-1.76 (m, 2H), 1.82-2.03 (m, 2H), 3.56-4.51 (m, 5H), 5.76 (s, 1H), 6.27-6.39 (m, 2H), 7.38-7.40 (m, 3H), 7.66 (br s, 3H), 7.86 (br s, 2H), 9.19 (s, 1H), 9.86-10.32 (m, 1H). MS Calcd.: 445; MS Found: 446 ([M+H]$^+$).

Example 15: (R)—N-(4-(3-((8-isopropyl-7-oxo-7,8-dihydropyrido[2,3-d]pyrimidin-2-yl)amino)piperidine-1-carbonyl)phenyl)acrylamide

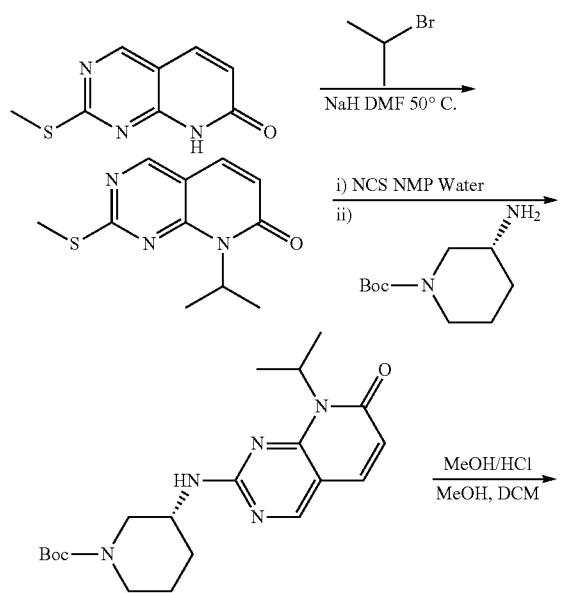

-continued

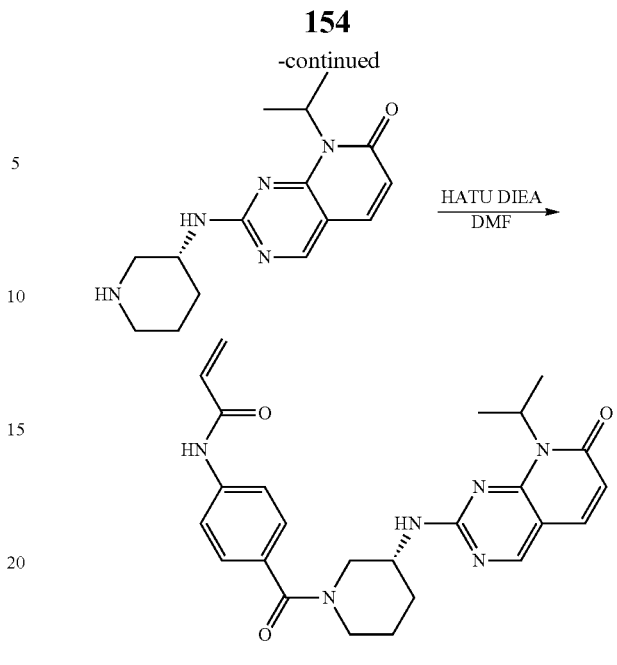

Step 1

To a solution of 2-(methylthio)pyrido[2,3-d]pyrimidin-7(8H)-one (1.93 g, 10.0 mmol) in DMF (40 mL) was added NaH (480 mg, 12.0 mmol, 60% in mineral oil). After stirring at room temperature for 30 minutes, 2-bromopropane (2.44 g, 20.0 mmol) was added to the reaction. The mixture was stirred at 50° C. overnight. The mixture was quenched with 30 mL of saturated aqueous NH$_4$Cl solution and extracted with EtOAc (150 mL). The organic layer was washed with water (200 mL*2), brine (50 mL) and concentrated. The crude product was purified by column chromatography on silica gel (PE/EtOAc, 1:1) to give 8-isopropyl-2-(methylthio)pyrido[2,3-d]pyrimidin-7(8H)-one (1.5 g, 64%) as a yellow solid. $^1$H NMR (400 MHz, DMSO-d$_6$): δ 1.54 (d, J=6.8 Hz, 6H), 2.60 (s, 3H), 5.67 (br s, 1H), 6.57 (d, J=9.2 Hz, 1H), 7.88 (d, J=9.2 Hz, 1H), 8.86 (s, 1H). MS Calcd.: 235; MS Found: 236 ([M+H]$^+$).

Step 2

To a solution of 8-isopropyl-2-(methylthio)pyrido[2,3-d]pyrimidin-7(8H)-one (750 mg, 3.19 mmol) in NMP (10 mL) and water (3 mL) was added NCS (509 mg, 3.83 mmol). After stirring at 80° C. for 30 minutes, the mixture was cooled to 50° C. A solution of (R)-tert-butyl 3-aminopiperidine-1-carboxylate (638 mg, 3.19 mmol) and DIPEA (1.2 g, 9.57 mmol) in NMP (3 mL) was added to the reaction. The mixture was stirred at 80° C. for 2 h. The mixture was poured into water (400 mL) and extracted with EtOAc (300 mL). The organic layer was washed with water (200 mL*3), brine (100 mL) and concentrated. The crude product was purified by column chromatography on silica gel (PE/EtOAc, 1/1) to give (R)-tert-butyl 3-((8-isopropyl-7-oxo-7,8-dihydropyrido[2,3-d]pyrimidin-2-yl)amino)piperidine-1-carboxylate (900 mg, 73%) as yellow oil. $^1$H NMR (300 MHz, CDCl$_3$): δ 1.41 (s, 9H), 1.74-1.76 (m, 6H), 1.94-2.06 (m, 4H), 3.44-3.48 (m, 3H), 4.10-4.15 (m, 2H), 5.48-5.57 (m, 1H), 5.75-5.83 (m, 1H), 6.36 (d, J=17.1 Hz, 1H), 7.42 (d, J=9.3 Hz, 1H), 8.39 (s, 1H). MS Calcd.: 387; MS Found: 388 ([M+H]$^+$).

Step 3

To a solution of (R)-tert-butyl 3-((8-isopropyl-7-oxo-7,8-dihydropyrido[2,3-d]pyrimidin-2-yl)amino)piperidine-1-carboxylate (900 mg, 2.3 mmol) in 10 mL of MeOH was added HCl/MeOH (5 mL, 1 M). The mixture was stirred at 30° C. for 1 h and concentrated to give (R)-8-isopropyl-2-(piperidin-3-ylamino)pyrido[2,3-d]pyrimidin-7(8H)-one (667 mg, 100%) as yellow oil. MS Calcd.: 287 MS Found: 288 ([M+H]$^+$).

Step 4

The title compound was prepared in 13% yield from (R)-8-isopropyl-2-(piperidin-3-ylamino)pyrido[2,3-d]pyrimidin-7(8H)-one using general procedure of (R)—N-(4-(3-((6-fluoroquinazolin-2-yl)amino)piperidine-1-carbonyl)phenyl)acrylamide. $^1$H NMR (400 MHz, DMSO-d$_6$): δ 1.28-1.51 (m, 7H), 1.64-1.73 (m, 1H), 1.87-2.03 (m, 2H), 3.17-3.18 (m, 1H), 3.57-3.68 (m, 2H), 3.83-4.06 (m, 2H), 4.20-4.58 (m, 1H), 5.74-5.78 (m, 1H), 6.17-6.30 (m, 2H), 6.53-6.55 (m, 1H), 7.13-7.52 (m, 2H), 7.65-7.87 (m, 4H), 8.50-8.57 (m, 1H), 10.32-10.72 (m, 1H). MS Calcd.: 460; MS Found: 461 ([M+H]$^+$).

Example 16: (R)—N-(4-(3-((7-oxo-7,8-dihydropyrido[2,3-d]pyrimidin-2-yl)amino)piperidine-1-carbonyl)phenyl)acrylamide

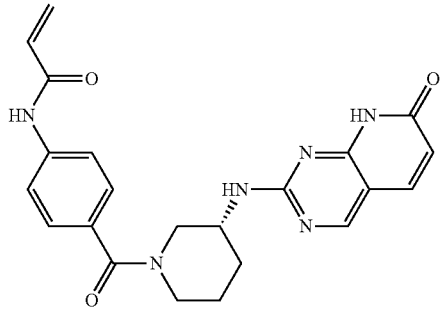 [SMILES: C=CC(=O)Nc1ccc(C(=O)N2CCC[C@@H](Nc3ncc4ccc(=O)[nH]c4n3)C2)cc1]

The title compound was prepared in 5% yield from (R)-2-(piperidin-3-ylamino)pyrido[2,3-d]pyrimidin-7(8H)-one using general procedure of (R)—N-(4-(3-((8-isopropyl-7-oxo-7,8-dihydropyrido[2,3-d]pyrimidin-2-yl)amino)piperidine-1-carbonyl)phenyl)acrylamide. $^1$H NMR (400 MHz, DMSO-d$_6$): δ 1.45-1.98 (m, 4H), 3.00-3.29 (m, 3H), 3.48-4.05 (m, 2H), 5.77-5.80 (m, 1H), 6.13-6.45 (m, 3H), 7.28-7.74 (m, 6H), 8.45-8.62 (m, 1H), 10.18-10.42 (m, 1H), 11.64-11.79 (m, 1H). MS Calcd.: 418; MS Found: 419 ([M+H]$^+$).

Example 17: (R)—N-(4-(3-(quinazolin-2-ylamino)piperidine-1-carbonyl)phenyl)propionamide

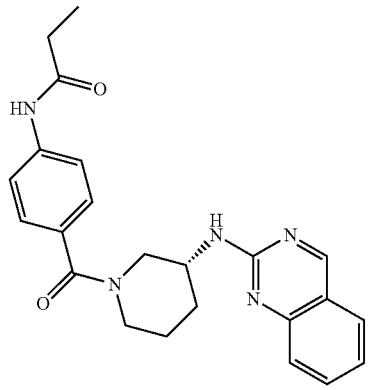 [SMILES: CCC(=O)Nc1ccc(C(=O)N2CCC[C@@H](Nc3ncc4ccccc4n3)C2)cc1]

The title compound was prepared in 32% yield from (R)—N-(piperidin-3-yl)quinazolin-2-amine and 4-propionamidobenzoic acid using general procedure of (R)—N-(4-(3-((6-fluoroquinazolin-2-yl)amino)piperidine-1-carbonyl)phenyl)acrylamide. 1H NMR (400 MHz, DMSO-d6): δ 1.05-1.09 (m, 3H), 1.53-1.56 (m, 4H), 2.30-2.33 (m, 2H), 3.01-3.017 (m, 2H), 3.86-4.12 (m, 3H), 7.20-7.77 (m, 9H), 9.06 (s, 1H), 9.87 (s, 0.5H), 10.05 (s, 0.5H). MS Calcd.: 403 MS Found: 404 ([M+H]+).

Example 18: (R)—N-(4-(3-(isoquinolin-3-ylamino)piperidine-1-carbonyl)phenyl)propionamide

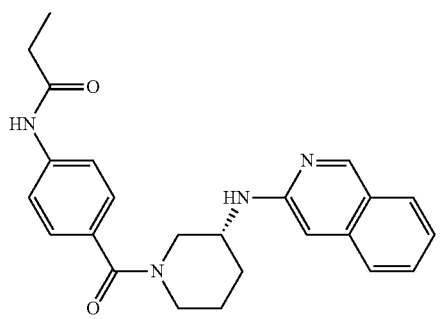 [SMILES: CCC(=O)Nc1ccc(C(=O)N2CCC[C@@H](Nc3cc4ccccc4cn3)C2)cc1]

The title compound was prepared in 16% yield from (R)—N-(piperidin-3-yl)isoquinolin-3-amine and 4-propionamidobenzoic acid using general procedure of (R)—N-(4-(3-(isoquinolin-3-ylamino)piperidine-1-carbonyl)phenyl)acrylamide. $^1$H NMR (400 MHz, DMSO-d$_6$): δ 1.07 (t, J=7.8 Hz, 3H), 1.59 (m, 2H), 1.80-1.83 (m, 1H), 2.03 (m, 1H), 2.30-2.36 (m, 2H), 2.81-3.23 (m, 3H), 3.45-4.50 (m, 2H), 6.43 (m, 2H), 7.15-7.16 (m, 1H), 7.38-7.40 (m, 4H), 7.62-7.64 (m, 2H), 7.75 (brs, 1H), 8.76-8.78 (m, 1H), 10.01 (brs, 1H). MS Calcd.: 402 MS Found: 403 ([M+H]$^+$).

Example 19: (R)—N-(4-(3-((6-chloroquinazolin-2-yl)amino)piperidine-1-carbonyl)phenyl)propionamide

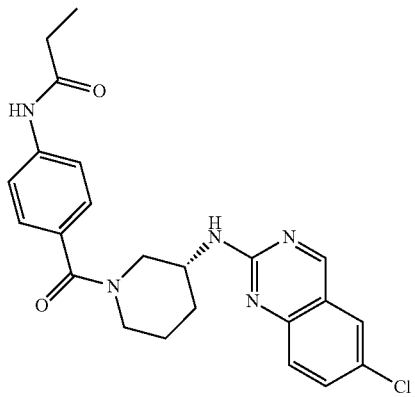 [SMILES: CCC(=O)Nc1ccc(C(=O)N2CCC[C@@H](Nc3ncc4cc(Cl)ccc4n3)C2)cc1]

The title compound was prepared as the TFA salt in 28% yield from (6-chloro-quinazolin-2-yl)-piperidin-3-yl-amine using general procedure of (R)—N-(4-(3-(quinazolin-2-ylamino)piperidine-1-carbonyl)phenyl)propionamide. $^1$H NMR (400 MHz, DMSO-d$_6$): δ 1.06-1.10 (m, 3H), 1.55-1.99 (m, 4H), 2.31 (d, J=7.2 Hz 2H), 3.16 (m, 2H), 3.73-4.10 (m, 3H), 7.29-7.89 (m, 8H), 9.07 (s, 1H), 9.86 (s, 1H). MS Calcd.: 437 MS Found: 438 ([M+H]$^+$).

Example 20: (R)—N-(4-(3-((7-methoxyquinazolin-2-yl)amino)piperidine-1-carbonyl)phenyl)propionamide

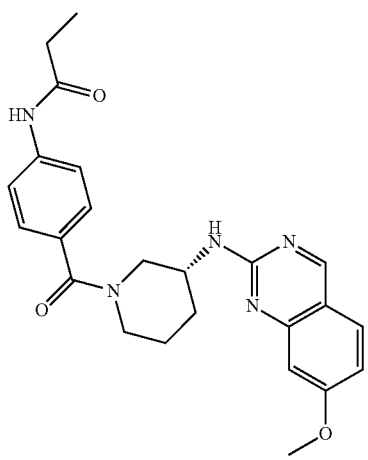 [SMILES: CCC(=O)Nc1ccc(C(=O)N2CCC[C@@H](Nc3ncc4ccc(OC)cc4n3)C2)cc1]

The title compound was prepared in 15% yield from (R)-7-methoxy-N-(piperidin-3-yl)quinazolin-2-amine using general procedure of (R)—N-(4-(3-(quinazolin-2-ylamino)piperidine-1-carbonyl)phenyl)propionamide. $^1$H NMR (400 MHz, CD$_3$OD): δ 1.07 (t, J=12.4 Hz, 3H), 1.59-1.99 (m, 4H), 2.15-2.33 (m, 2H), 3.35-3.55 (m, 2H), 3.74-4.08 (m, 6H), 6.44-6.50 (m, 1H), 6.71-6.75 (m, 1H), 6.99-7.58 (m, 5H), 8.65 (s, 1H). MS Calcd.: 433 MS Found: 434 ([M+H]$^+$).

Example 21: (R)—N-(4-(3-((7-(methylsulfonyl)quinazolin-2-yl)amino)piperidine-1-carbonyl)phenyl)propionamide

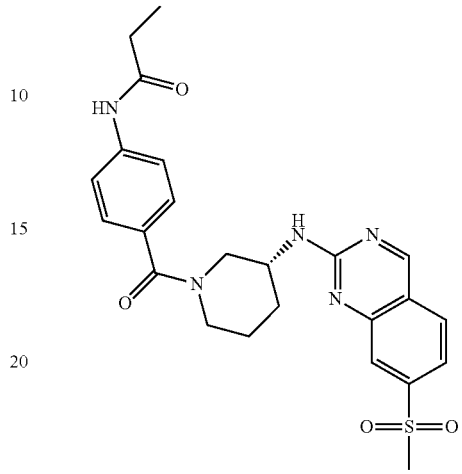

The title compound was prepared in 16% yield from (R)-7-(methylsulfonyl)-N-(piperidin-3-yl)quinazolin-2-amine using general procedure of (R)—N-(4-(3-(quinazolin-2-ylamino)piperidine-1-carbonyl)phenyl)propionamide. $^1$H NMR (400 MHz, DMSO-d$_6$): δ 1.05 (s, 3H), 1.48-1.70 (m, 2H), 1.78-2.02 (m, 1H), 2.16-2.17 (m, 1H), 2.32-2.40 (m, 2H), 2.67-3.22 (m, 4H), 3.46-3.90 (m, 4H), 7.21-7.43 (m, 3H), 7.56-7.64 (m, 2H), 7.78-8.10 (m, 3H), 9.27-9.31 (m, 1H), 9.67-9.99 (m, 1H). MS Calcd.: 481 MS Found: 482 ([M+H]$^+$).

Example 22: (R)—N-(4-(3-((7-chloroquinazolin-2-yl)amino)piperidine-1-carbonyl)phenyl)propionamide

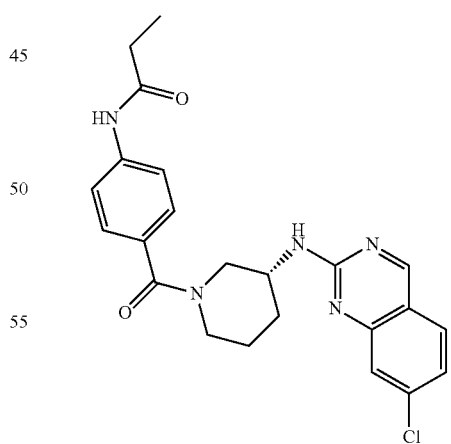

The title compound was prepared in 33% yield from (R)-7-chloro-N-(piperidin-3-yl)quinazolin-2-amine using general procedure of (R)—N-(4-(3-(quinazolin-2-ylamino) piperidine-1-carbonyl)phenyl)propionamide. $^1$H NMR (400 MHz, DMSO-d$_6$): δ 1.06-1.09 (m, 3H), 1.53-1.99 (m, 4H), 2.30 (s, 2H), 2.93-3.15 (m, 2H), 3.71-4.39 (m, 3H), 7.03-

7.79 (m, 8H), 9.08 (s, 1H), 9.88-10.05 (m, 1H). MS Calcd.: 437 MS Found: 438 ([M+H]⁺).

Example 23: (R)—N-(4-(3-((7-fluoroquinazolin-2-yl)amino)piperidine-1-carbonyl)phenyl)propionamide

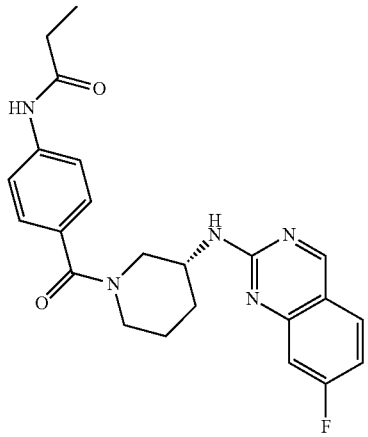 [SMILES: CCC(=O)Nc1ccc(C(=O)N2CCC[C@@H](Nc3ncc4ccc(F)cc4n3)C2)cc1]

The title compound was prepared in 19% yield from (R)-7-fluoro-N-(piperidin-3-yl)quinazolin-2-amine using general procedure of (R)—N-(4-(3-(quinazolin-2-ylamino)piperidine-1-carbonyl)phenyl)propionamide. ¹H NMR (400 MHz, CD₃OD): δ 1.18 (t, J=8 Hz, 3H), 1.71-2.12 (m, 4H), 2.28-2.37 (m, 2H), 3.68-4.18 (m, 5H), 6.71-6.82 (m, 1H), 6.99-7.43 (m, 5H), 7.67-7.81 (m, 1H), 7.90-8.99 (m, 1H). MS Calcd.: 421 MS Found: 422 ([M+H]⁺).

Example 24: (R)—N-(4-(3-((8-isopropyl-7-oxo-7,8-dihydropyrido[2,3-d]pyrimidin-2-yl)amino)piperidine-1-carbonyl)phenyl)propionamide

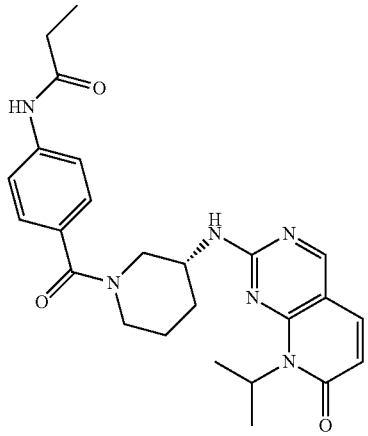 [SMILES: CCC(=O)Nc1ccc(C(=O)N2CCC[C@@H](Nc3ncc4ccc(=O)n(C(C)C)c4n3)C2)cc1]

The title compound was prepared in 16% yield from give (R)-8-isopropyl-2-(piperidin-3-ylamino)pyrido[2,3-d]pyrimidin-7(8H)-one using general procedure of (R)—N-(4-(3-(quinazolin-2-ylamino)piperidine-1-carbonyl)phenyl)propionamide. ¹H NMR (400 MHz, DMSO-d₆): δ 1.06-1.08 (m, 3H), 1.36-1.51 (m, 7H), 1.68-1.72 (m, 1H), 1.90-2.01 (m, 2H), 2.32-2.36 (m, 2H), 3.02-3.17 (m, 1H), 3.50-3.62 (m, 2H), 3.83-4.02 (m, 2H), 5.40-5.74 (m, 1H), 6.17-6.19 (m, 1H), 7.08-7.32 (m, 2H), 7.58-7.90 (m, 4H), 8.52-8.62 (m, 1H), 10.01-10.35 (m, 1H). MS Calcd.: 462 MS Found: 463 ([M+H]⁺).

Example 25: (R)—N-(4-(3-((6-chloroquinazolin-2-yl)amino)pyrrolidine-1-carbonyl)phenyl)acrylamide

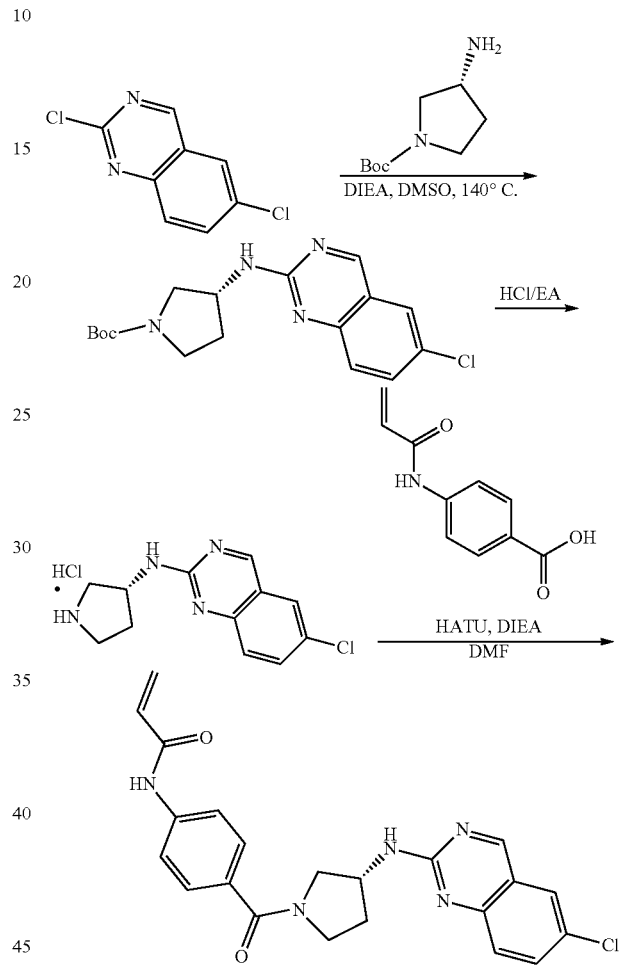

Step 1

To a solution of 2,6-dichloroquinazoline (250 mg, 1.27 mmol), (R)-tert-butyl 3-aminopyrrolidine-1-carboxylate (280 mg, 1.51 mmol) in DMSO (10 mL) was added DIEA (328 mg, 2.54 mmol) at RT. The mixture was stirred at 140° C. for 4 h. The reaction was diluted with water (50 mL). The precipitate was filtered, washed with PE/EA (5 mL:1 mL) to give (R)-tert-butyl 3-((6-chloroquinazolin-2-yl)amino)pyrrolidine-1-carboxylate (340 mg, 77%). MS Calcd.: 348 MS Found: 349 ([M+H]⁺).

Step 2

A solution of (R)-tert-butyl 3-((6-chloroquinazolin-2-yl)amino)pyrrolidine-1-carboxylate (340 mg, 0.98 mmol) in HCl/EA (10 mL, 2.0 M) was stirred at RT for 2 h. The reaction mixture was filtered to give (R)-6-chloro-N-(pyrrolidin-3-yl)quinazolin-2-amine hydrochloride (260 mg, 93%). MS Calcd.: 248 MS Found: 249 ([M+H]⁺).

Step 3

To a solution of (R)-6-chloro-N-(pyrrolidin-3-yl)quinazolin-2-amine hydrochloride (250 mg, 0.88 mmol), 4-acrylamidobenzoic acid (168 mg, 0.88 mmol) and DIEA (340 mg, 2.64 mmol) in DMF (15 mL) was added HATU (401 mg, 1.06 mmol) at RT. The mixture was stirred at RT for 12 h. The reaction mixture was purified by prep-HPLC to give (R)—N-(4-(3-((6-chloroquinazolin-2-yl)amino)pyrrolidine-1-carbonyl)phenyl)acrylamide (57 mg, 15%). ¹H NMR (400 MHz, DMSO-d₆): δ 1.95-2.08 (m, 1H), 2.17-2.25 (m, 1H), 3.43-3.61 (m, 2H), 3.66-3.75 (m, 1H), 3.83-3.87 (m, 1H), 4.45-4.59 (m, 1H), 5.79 (t, J=8.0 Hz, 1H), 6.25-6.31 (m, 1H), 6.40-6.49 (m, 1H), 7.43-7.56 (m, 3H), 7.65-7.75 (m, 3H), 7.90-7.97 (m, 2H), 9.10-9.16 (m, 1H), 10.31 (s, 0.5H), 10.35 (s, 0.5H). MS Calcd.: 421 MS Found: 422 ([M+H]⁺).

Example 26: (R)—N-(4-(3-(quinazolin-2-ylamino)pyrrolidine-1-carbonyl)phenyl)acrylamide

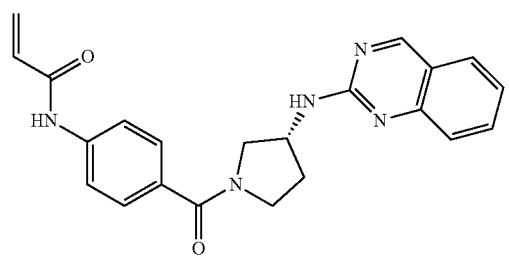 [SMILES: C=CC(=O)Nc1ccc(C(=O)N2CC[C@@H](Nc3ncc4ccccc4n3)C2)cc1]

The title compound was prepared in 12% yield from (R)—N-(pyrrolidin-3-yl)quinazolin-2-amine using general procedure of (R)—N-(4-(3-((6-chloroquinazolin-2-yl)amino)pyrrolidine-1-carbonyl)phenyl)acrylamide. ¹H NMR (400 MHz, CD₃OD): δ 2.03-2.08 (m, 1H), 2.31-2.46 (m, 1H), 3.51-3.81 (m, 3H), 4.12-4.20 (m, 1H), 4.56-4.79 (m, 1H), 5.73-5.83 (m, 1H), 6.30-6.54 (m, 2H), 7.18-7.27 (m, 1H), 7.36-7.54 (m, 3H), 7.63-7.87 (m, 4H), 9.01 (s, 0.5H), 9.07 (s, 0.5H). MS Calcd.: 387 MS Found: 388 ([M+H]⁺).

Example 27: (R)—N-(4-(3-(isoquinolin-3-ylamino)pyrrolidine-1-carbonyl)phenyl)acrylamide

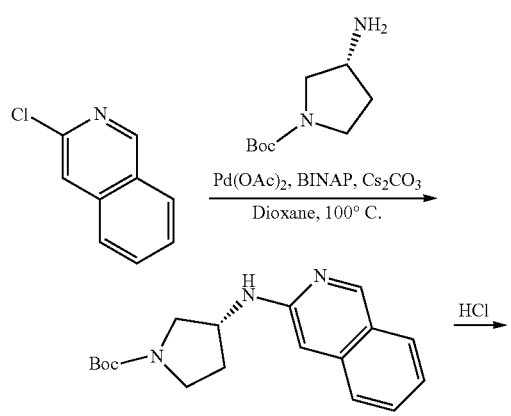

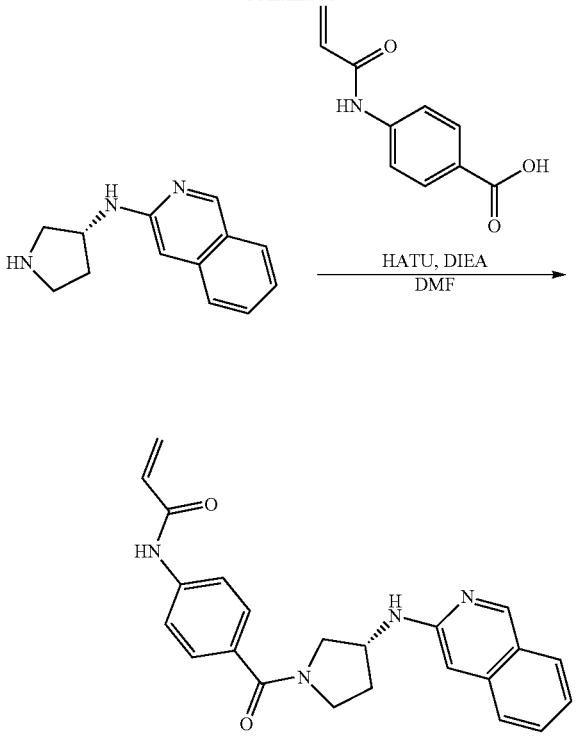

Step 1

To a solution of 3-chloroisoquinoline (250 mg, 1.53 mmol) in dioxane (10 mL) was added (R)-tert-butyl 3-aminopyrrolidine-1-carboxylate (285 mg, 1.53 mmol), Cs₂CO₃ (997 mg, 3.06 mmol), Pd(OAc)₂ (35 mg, 0.153 mmol) and BINAP (188 mg, 0.306 mmol). The mixture was stirred at 100° C. for 6 h and concentrated. The residue was purified by silica gel chromatography (PE/EA=3:1) to afford (R)-tert-butyl 3-(isoquinolin-3-ylamino)pyrrolidine-1-carboxylate (400 mg, 84%). MS Calcd.: 313 MS Found: 314 ([M+H]⁺).

Step 2 to 3

The title compound was prepared in 18% yield from (R)-tert-butyl 3-(isoquinolin-3-ylamino)pyrrolidine-1-carboxylate using general procedure of (R)—N-(4-(3-((6-chloroquinazolin-2-yl)amino)pyrrolidine-1-carbonyl)phenyl) acrylamide. ¹H NMR (400 MHz, DMSO-d₆): δ 1.86-2.03 (m, 1H), 2.05-2.28 (m, 1H), 3.39-3.61 (m, 2H), 3.66-3.73 (m, 1H), 3.84-3.89 (m, 1H), 4.29-4.38 (m, 1H), 5.78 (t, J=7.8 Hz, 1H), 6.24-6.39 (m, 1H), 6.42-6.50 (m, 1H), 6.65 (s, 1H), 6.76-6.78 (m, 1H), 7.11-7.20 (m, 1H), 7.42-7.58 (m, 4H), 7.68-7.83 (m, 3H), 8.86 (s, 1H), 10.32 (s, 1H). MS Calcd.: 386 MS Found: 387 ([M+H]⁺).

Example 28: (R)—N-(4-(3-((6-fluoroquinazolin-2-yl)amino)pyrrolidine-1-carbonyl)phenyl)acrylamide

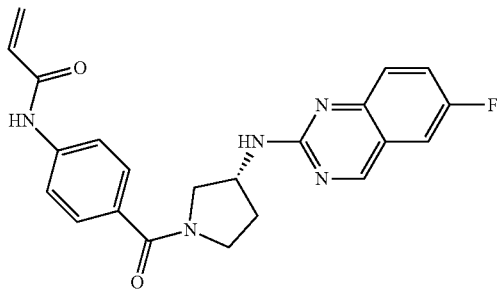 [SMILES: C=CC(=O)Nc1ccc(C(=O)N2CC[C@@H](Nc3ncc4cc(F)ccc4n3)C2)cc1]

The title compound was prepared in 21% yield from (R)-6-fluoro-N-(pyrrolidin-3-yl)quinazolin-2-amine using general procedure of (R)—N-(4-(3-((6-chloroquinazolin-2-yl)amino)pyrrolidine-1-carbonyl)phenyl)acrylamide. $^1$H NMR (400 MHz, DMSO-d$_6$): δ 2.06-2.21 (m, 2H), 3.42-3.73 (m, 3H), 3.83-3.87 (m, 1H), 4.44-4.57 (m, 1H), 5.75-5.80 (m, 1H), 6.24-6.46 (m, 2H), 7.50-7.78 (m, 8H), 9.10-9.16 (m, 1H), 10.27-10.31 (m, 1H). MS Calcd.: 405 MS Found: 406 ([M+H]$^+$).

Example 29: (R)—N-(4-(3-((6-methoxyquinazolin-2-yl)amino)pyrrolidine-1-carbonyl)phenyl)acrylamide

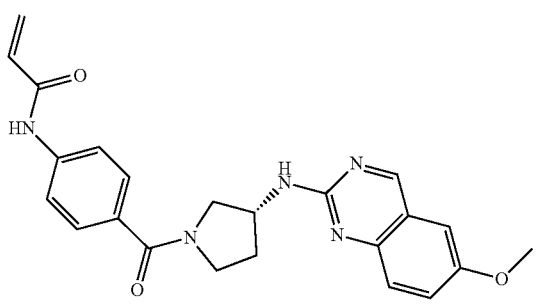 [SMILES: C=CC(=O)Nc1ccc(C(=O)N2CC[C@@H](Nc3ncc4cc(OC)ccc4n3)C2)cc1]

The title compound was prepared in 39% yield from (R)-6-methoxy-N-(pyrrolidin-3-yl)quinazolin-2-amine using general procedure of (R)—N-(4-(3-((6-chloroquinazolin-2-yl)amino)pyrrolidine-1-carbonyl)phenyl)acrylamide. $^1$H NMR (400 MHz, DMSO-d$_6$): δ 1.94-2.24 (m, 2H), 3.38-3.87 (m, 7H), 4.40-4.56 (m, 1H), 5.76-5.80 (m, 1H), 6.24-6.49 (m, 2H), 7.23-7.74 (m, 8H), 9.03-9.09 (m, 1H), 10.23-10.32 (m, 1H). MS Calcd.: 417 MS Found: 418 ([M+H]$^+$).

Example 30: (R)—N-(4-(3-((6-methylquinazolin-2-yl)amino)pyrrolidine-1-carbonyl)phenyl)acrylamide

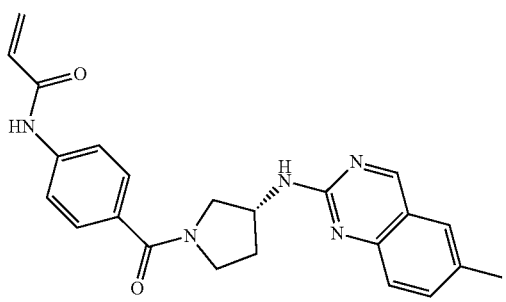 [SMILES: C=CC(=O)Nc1ccc(C(=O)N2CC[C@@H](Nc3ncc4cc(C)ccc4n3)C2)cc1]

The title compound was prepared in 46% yield from (R)-6-methyl-N-(pyrrolidin-3-yl)quinazolin-2-amine using general procedure of (R)—N-(4-(3-((6-chloroquinazolin-2-yl)amino)pyrrolidine-1-carbonyl)phenyl)acrylamide. $^1$H NMR (400 MHz, DMSO-d$_6$): δ 1.93-2.07 (m, 1H), 2.16-2.04 (m, 1H), 2.37-2.40 (m, 3H), 3.40-3.87 (m, 4H), 4.42-4.57 (m, 1H), 5.76-5.80 (m, 1H), 6.24-6.31 (m, 1H), 6.41-6.51 (m, 1H), 7.34-7.45 (m, 1H), 7.50-7.60 (m, 4H), 7.65-7.76 (m, 3H), 9.02-9.08 (m, 1H), 10.36-10.40 (m, 1H). MS Calcd.: 401 MS Found: 402 ([M+H]$^+$).

Example 31: (R)—N-(4-(3-(pyrido[3,4-d]pyrimidin-2-ylamino)pyrrolidine-1-carbonyl)phenyl)acrylamide

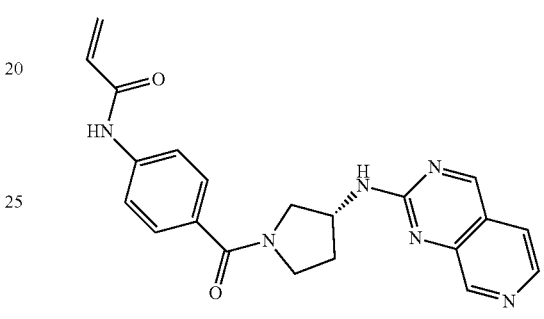

The title compound was prepared in 19% yield from (R)—N-(pyrrolidin-3-yl)pyrido[3,4-d]pyrimidin-2-amine using general procedure of (R)—N-(4-(3-((6-chloroquinazolin-2-yl)amino)pyrrolidine-1-carbonyl)phenyl)acrylamide. $^1$H NMR (400 MHz, DMSO-d$_6$): δ 1.99-2.18 (m, 1H), 2.23-2.33 (m, 1H), 3.48-3.58 (m, 2H), 3.70 (br s, 1H), 3.86-3.89 (m, 1H), 4.49-4.61 (m, 1H), 5.78 (br s, 1H), 6.24-6.31 (m, 1H), 6.40-6.46 (m, 1H), 7.48-7.56 (m, 2H), 7.70 (d, J=18.0 Hz, 3H), 8.15 (br s, 1H), 8.34 (d, J=10.4 Hz, 1H), 8.92 (d, J=35.6 Hz, 1H), 9.30 (d, J=19.6 Hz, 1H), 10.29 (d, J=14.4 Hz, 1H). MS Calcd.: 388 MS Found: 389 ([M+H]$^+$).

Example 32: (R)—N-(4-(3-((7-methylquinazolin-2-yl)amino)pyrrolidine-1-carbonyl)phenyl)acrylamide

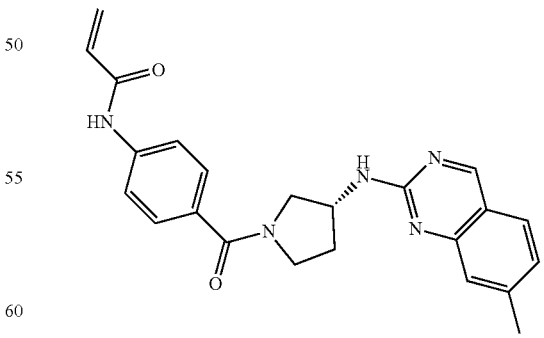

The title compound was prepared in 25% yield from (R)-7-methyl-N-(pyrrolidin-3-yl)quinazolin-2-amine using general procedure of (R)—N-(4-(3-((6-chloroquinazolin-2-yl)amino)pyrrolidine-1-carbonyl)phenyl)acrylamide. $^1$H NMR (400 MHz, DMSO-d$_6$): δ 1.93-2.08 (m, 1H), 2.16-

2.24 (m, 1H), 2.33-2.44 (m, 3H), 3.39-3.60 (m, 2H), 3.65-3.73 (m, 1H), 3.83-3.89 (m, 1H), 4.42-4.57 (m, 1H), 5.76-5.80 (m, 1H), 6.24-6.49 (m, 2H), 7.05-7.74 (m, 8H), 9.02-9.07 (m, 1H), 10.23-10.33 (m, 1H). MS Calcd.: 401 MS Found: 402 ([M+H]+).

Example 33: (R)—N-(4-(3-((7-(methylsulfonyl)quinazolin-2-yl)amino)pyrrolidine-1-carbonyl)phenyl)acrylamide

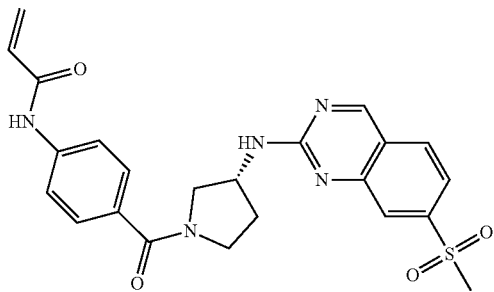 [SMILES: C=CC(=O)Nc1ccc(C(=O)N2CC[C@@H](Nc3ncc4ccc(S(C)(=O)=O)cc4n3)C2)cc1]

The title compound was prepared in 25% yield from (R)-7-(methylsulfonyl)-N-(pyrrolidin-3-yl)quinazolin-2-amine using general procedure of (R)—N-(4-(3-((6-chloroquinazolin-2-yl)amino)pyrrolidine-1-carbonyl)phenyl)acrylamide. ¹H NMR (400 MHz, DMSO-d₆): δ 1.97-2.09 (m, 1H), 2.24-2.33 (m, 1H), 3.29 (s, 3H), 3.46-3.58 (m, 2H), 3.71-3.90 (m, 2H), 4.50-4.60 (m, 1H), 5.76-5.80 (m, 1H), 6.24-6.49 (m, 2H), 7.51-8.18 (m, 8H), 9.29-9.33 (m, 1H), 10.27-10.31 (m, 1H). MS Calcd.: 465 MS Found: 466 ([M+H]+).

Example 34: (R)—N-(4-(3-((7-methoxyquinazolin-2-yl)amino)pyrrolidine-1-carbonyl)phenyl)acrylamide

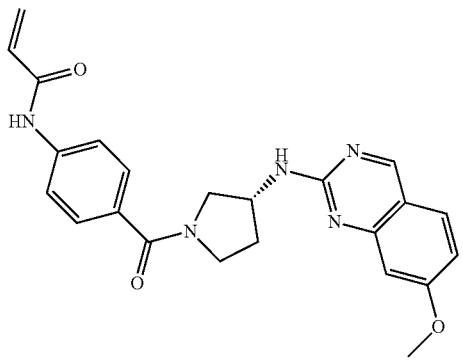 [SMILES: C=CC(=O)Nc1ccc(C(=O)N2CC[C@@H](Nc3ncc4ccc(OC)cc4n3)C2)cc1]

The title compound was prepared in 25% yield from (R)-7-methoxy-N-(pyrrolidin-3-yl)quinazolin-2-amine using general procedure of (R)—N-(4-(3-((6-chloroquinazolin-2-yl)amino)pyrrolidine-1-carbonyl)phenyl)acrylamide. ¹H NMR (400 MHz, DMSO-d₆): δ 1.97-2.08 (m, 1H), 2.20-2.21 (m, 1H), 3.44-3.89 (m, 7H), 4.46-4.58 (m, 1H), 5.76-5.80 (m, 1H), 6.25-6.49 (m, 2H), 6.79-6.88 (m, 2H), 7.51-7.75 (m, 6H), 8.91-8.97 (m, 1H), 10.28-10.31 (m, 1H). MS Calcd.: 417 MS Found: 418 ([M+H]+).

Example 35: (R)—N-(4-(3-((7-fluoroquinazolin-2-yl)amino)pyrrolidine-1-carbonyl)phenyl)acrylamide

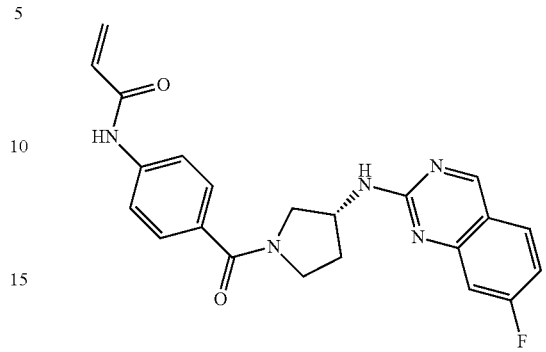

The title compound was prepared in 7% yield from (R)-7-fluoro-N-(pyrrolidin-3-yl)quinazolin-2-amine using general procedure of (R)—N-(4-(3-((6-chloroquinazolin-2-yl)amino)pyrrolidine-1-carbonyl)phenyl)acrylamide. ¹H NMR (400 MHz, CD₃OD): δ 2.06-2.19 (m, 1H), 2.27-2.42 (m, 1H), 3.54-3.76 (m, 3H), 3.84-4.04 (m, 1H), 4.59-4.74 (m, 1H), 5.77-5.81 (m, 1H), 6.34-6.48 (m, 2H), 7.01-7.21 (m, 2H), 7.52-7.59 (m, 2H), 7.69-7.87 (m, 3H), 8.96-9.04 (m, 1H). MS Calcd.: 405 MS Found: 406 ([M+H]+).

Example 36: (R)—N-(4-(3-((7-chloroquinazolin-2-yl)amino)pyrrolidine-1-carbonyl)phenyl)acrylamide

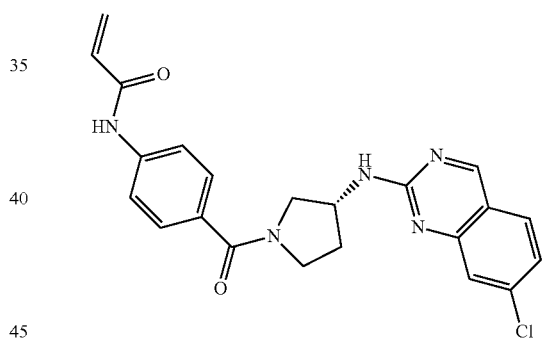

The title compound was prepared in 22% yield from (R)-7-chloro-N-(pyrrolidin-3-yl)quinazolin-2-amine using general procedure of (R)—N-(4-(3-((6-chloroquinazolin-2-yl)amino)pyrrolidine-1-carbonyl)phenyl)acrylamide. ¹H NMR (400 MHz, CDCl₃): δ 2.03-2.09 (m, 1H), 2.31-2.44 (m, 1H), 3.45-4.13 (m, 4H), 4.65-4.78 (m, 1H), 5.42-5.52 (m, 1H), 5.79 (t, J=9.2 Hz, 1H), 6.23-6.32 (m, 1H), 6.43-6.49 (m, 1H), 7.20 (t, J=10.4 Hz, 1H), 7.49-7.73 (m, 7H), 8.91-8.96 (d, J=20.0 Hz, 1H). MS Calcd.: 421 MS Found: 422 ([M+H]+).

Example 37: (R)—N-(4-(3-((7-cyanoquinazolin-2-yl)amino)pyrrolidine-1-carbonyl)phenyl)acrylamide

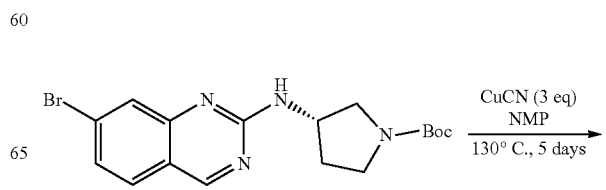

167

-continued

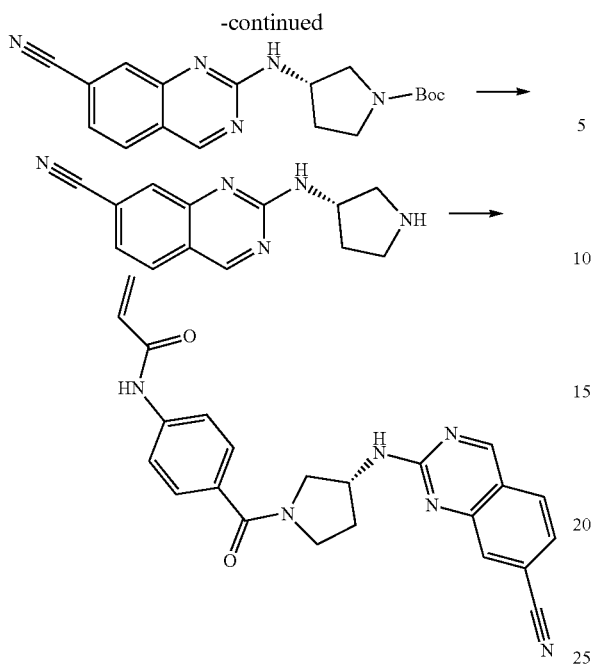

Step 1

A mixture of (S)-tert-butyl 3-((7-bromoquinazolin-2-yl)amino)pyrrolidine-1-carboxylate (1.4 g, 3.5 mmol), CuCN (951 mg, 10.7 mmol), in NMP (20 mL) was stirred at 130° C. for 2 days. CuCN (475 mg, 5.4 mmol) was added and the mixture was stirred at 130° C. for another 2 days. The mixture was diluted with EA (200 mL), washed with $NH_3 \cdot H_2O$ (200 mL*3, 10%), water (200 mL), brine (100 mL) and concentrated. The crude product was purified by chromatography using PE:EA (5:1-1:1) to give 3-(7-cyano-quinazolin-2-ylamino)-pyrrolidine-1-carboxylic acid tert-butyl ester (300 mg, 25%) as a yellow solid. $^1$H NMR (400 MHz, CDCl$_3$): δ 1.47 (s, 9H), 1.95 (br s, 1H), 2.28-2.32 (m, 1H), 3.26-3.52 (m, 3H), 3.76-3.80 (m, 1H), 4.67 (br s, 1H), 5.50 (d, J=10.0 Hz, 1H), 7.39 (d, J=8.0 Hz, 1H), 7.75 (d, J=8.4 Hz, 1H), 7.94 (s, 1H), 9.04 (s, 1H).

Step 2

To a solution of 3-(7-cyano-quinazolin-2-ylamino)-pyrrolidine-1-carboxylic acid tert-butyl ester (100 mg, 0.29 mmol) in 2 mL of MeOH was added HCl/MeOH (1.5 mL, 1 M). The mixture was stirred at RT for 1 h and concentrated to afford 2-(pyrrolidin-3-ylamino)-quinazoline-7-carbonitrile (70 mg, 100%) as yellow oil. MS Calcd.: 239 MS Found: 240 ([M+H]$^+$).

Step 3

The title compound was prepared in 25% yield from (R)-2-(pyrrolidin-3-ylamino)quinazoline-7-carbonitrile using general procedure of (R)—N-(4-(3-((6-chloroquinazolin-2-yl)amino)pyrrolidine-1-carbonyl)phenyl)acrylamide. $^1$H NMR (400 MHz, CD$_3$OD): δ 2.14-2.41 (m, 2H), 3.60-3.88 (m, 3H), 3.96-4.04 (m, 1H), 4.60-4.76 (m, 1H), 5.81 (t, J=8.0 Hz, 1H), 6.40-6.46 (m, 2H), 7.41-7.46 (m, 1H), 7.53-7.61 (m, 2H), 7.70-7.79 (m, 2H), 7.85-7.95 (m, 2H), 9.12-9.18 (m, 1H). MS Calcd.: 412 MS Found: 413 ([M+H]$^+$).

168

Example 38: (R)-2-((1-(4-acrylamidobenzoyl)pyrrolidin-3-yl)amino)quinazoline-7-carboxylic Acid

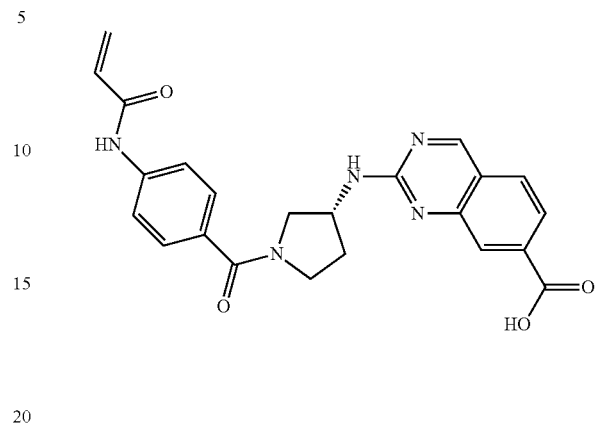

The title compound was prepared in 28% yield from (R)-2-(pyrrolidin-3-ylamino)quinazoline-7-carboxylic acid using general procedure of (R)-2-((1-(4-acrylamidobenzoyl)piperidin-3-yl)amino)quinazoline-7-carboxylic acid. $^1$H NMR (400 MHz, DMSO-d$_6$): 1.99-2.08 (m, 1H), 2.23-2.33 (m, 1H), 3.69-3.89 (m, 4H), 4.48-4.61 (m, 1H), 5.78 (br s, 1H), 6.25-6.31 (m, 1H), 6.40-6.50 (m, 1H), 7.51-7.57 (m, 2H), 7.69-7.73 (m, 3H), 7.79-8.04 (m, 3H), 9.22 (d, J=22.0 Hz, 1H), 10.32 (d, J=18.4 Hz, 1H). MS Calcd.: 431 MS Found: 432 ([M+H]$^+$).

Example 39: (R)-2-((1-(4-acrylamidobenzoyl)pyrrolidin-3-yl)amino)quinazoline-7-carboxamide

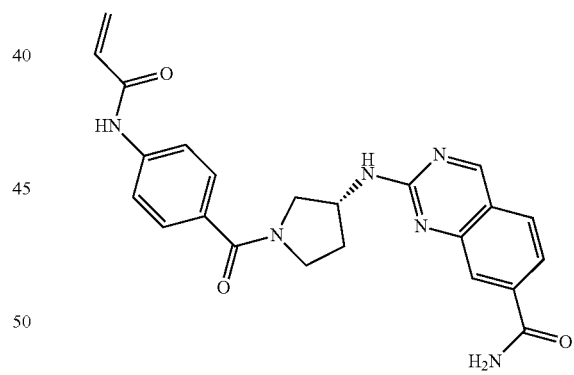

The title compound was prepared in 23% yield from (R)-2-(pyrrolidin-3-ylamino)quinazoline-7-carboxamide using general procedure of (R)-2-((1-(4-acrylamidobenzoyl)piperidin-3-yl)amino)quinazoline-7-carboxamide. $^1$H NMR (400 MHz, DMSO-d$_6$): 1.99-2.08 (m, 1H), 2.23-2.33 (m, 1H), 3.47-3.65 (m, 2H), 3.72-3.78 (m, 1H), 3.87-3.89 (m, 1H), 4.45-4.59 (m, 1H), 5.79 (br s, 1H), 6.26-6.32 (m, 1H), 6.40-6.47 (m, 1H), 7.48-7.57 (m, 3H), 7.69-8.04 (m, 6H), 8.22 (d, J=22.0 Hz, 1H), 9.21 (d, J=18.4 Hz, 1H), 10.32 (d, J=14.8 Hz, 1H). MS Calcd.: 430 MS Found: 431 ([M+H]$^+$).

Example 40: (R)-2-((1-(4-acrylamidobenzoyl)pyrrolidin-3-yl)amino)-N-methylquinazoline-7-carboxamide

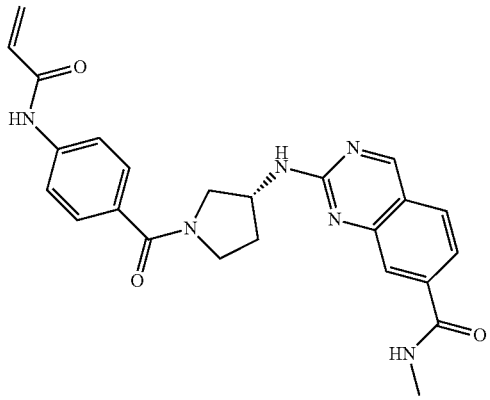 [SMILES: C=CC(=O)Nc1ccc(C(=O)N2CC[C@@H](Nc3ncc4ccc(C(=O)NC)cc4n3)C2)cc1]

The title compound was prepared in 29% yield from (R)—N-methyl-2-(pyrrolidin-3-ylamino)quinazoline-7-carboxamide using general procedure of (R)-2-((1-(4-acrylamidobenzoyl)piperidin-3-yl)amino)-N,N-dimethylquinazoline-7-carboxamide. $^1$H NMR (400 MHz, DMSO-d$_6$): δ 1.98-2.08 (m, 1H), 2.19-2.33 (m, 1H), 2.79-2.82 (m, 3H), 3.44-3.59 (m, 2H), 3.68-3.74 (m, 1H), 3.86-3.89 (m, 1H), 4.45-4.58 (m, 1H), 5.78 (t, J=10. Hz, 1H), 6.24-6.31 (m, 1H), 6.39-6.46 (m, 1H), 7.51-7.56 (m, 2H), 7.60-7.45 (m, 3H), 7.83-7.98 (m, 3H), 8.66 (d, J=27.2 Hz, 1H), 9.19 (d, J=20.4 Hz, 1H), 10.29 (d, J=15.6 Hz, 1H). MS Calcd.: 444 MS Found: 445 ([M+H]$^+$).

Example 41: (R)-2-((1-(4-acrylamidobenzoyl)pyrrolidin-3-yl)amino)-N,N-dimethylquinazoline-7-carboxamide

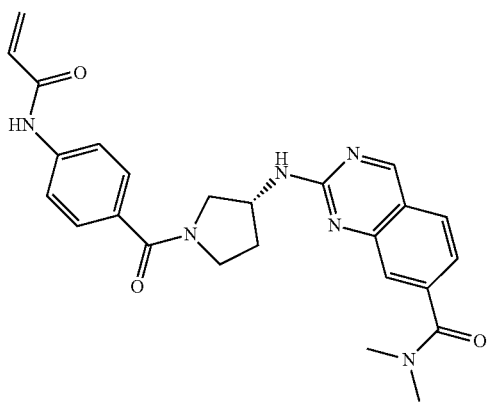 [SMILES: C=CC(=O)Nc1ccc(C(=O)N2CC[C@@H](Nc3ncc4ccc(C(=O)N(C)C)cc4n3)C2)cc1]

The title compound was prepared in 18% yield from (R)—N,N-dimethyl-2-(pyrrolidin-3-ylamino)quinazoline-7-carboxamide using general procedure of (R)-2-((1-(4-acrylamidobenzoyl)piperidin-3-yl)amino)-N,N-dimethylquinazoline-7-carboxamide. $^1$H NMR (400 MHz, DMSO-d$_6$): δ 1.97-2.07 (m, 1H), 2.20-2.33 (m, 1H), 2.83-3.00 (m, 6H), 3.43-3.56 (m, 2H), 3.65-3.75 (m, 1H), 3.80-3.86 (m, 1H), 4.47-4.59 (m, 1H), 5.78 (br s, 1H), 6.24-0.30 (m, 1H), 6.38-6.49 (m, 1H), 7.17-7.22 (m, 1H), 7.31-7.52 (m, 3H), 7.65-7.78 (m, 2H), 7.90-7.94 (m, 2H), 9.16-9.20 (m, 1H), 10.25-10.28 (m, 1H). MS Calcd.: 458 MS Found: 459 ([M+H]$^+$).

Example 42: (R)—N-(4-(3-((7-oxo-7,8-dihydropyrido[2,3-d]pyrimidin-2-yl)amino)pyrrolidine-1-carbonyl)phenyl)acrylamide

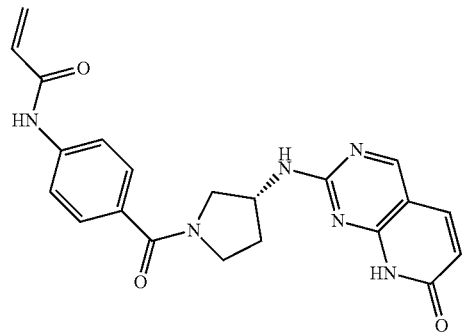 [SMILES: C=CC(=O)Nc1ccc(C(=O)N2CC[C@@H](Nc3ncc4ccc(=O)[nH]c4n3)C2)cc1]

The title compound was prepared in 7% yield from (R)-2-(pyrrolidin-3-ylamino)pyrido[2,3-d]pyrimidin-7(8H)-one using general procedure of (R)—N-(4-(3-((8-isopropyl-7-oxo-7,8-dihydropyrido[2,3-d]pyrimidin-2-yl)amino)piperidine-1-carbonyl)phenyl)acrylamide. $^1$H NMR (400 MHz, DMSO-d$_6$): δ 1.93-2.01 (m, 1H), 2.16-2.17 (m, 1H), 3.37-3.42 (m, 1H), 3.53 (br s, 1H), 3.66-3.68 (m, 1H), 3.82-3.83 (m, 1H), 4.35-4.48 (m, 1H), 5.78 (d, J=8.8 Hz, 1H), 6.14 (t, J=12.8 Hz, 1H), 6.25-6.29 (m, 1H), 6.40-6.44 (m, 1H), 7.52 (t, J=8.8 Hz, 2H), 7.65-7.71 (m, 3H), 7.88-8.05 (m, 1H), 8.53-8.61 (m, 1H), 10.29 (d, J=7.6 Hz, 1H), 11.75-11.84 (m, 1H). MS Calcd.: 404 MS Found: 405 ([M+H]$^+$).

Example 43: (R)—N-(4-(3-((8-isopropyl-7-oxo-7,8-dihydropyrido[2,3-d]pyrimidin-2-yl)amino)pyrrolidine-1-carbonyl)phenyl)acrylamide

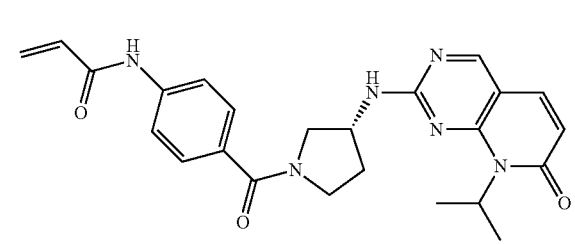 [SMILES: C=CC(=O)Nc1ccc(C(=O)N2CC[C@@H](Nc3ncc4ccc(=O)n(C(C)C)c4n3)C2)cc1]

The title compound was prepared in 28% yield from (R)-8-isopropyl-2-(pyrrolidin-3-ylamino)pyrido[2,3-d]pyrimidin-7(8H)-one using general procedure of (R)—N-(4-(3-((8-isopropyl-7-oxo-7,8-dihydropyrido[2,3-d]pyrimidin-2-yl)amino)piperidine-1-carbonyl)phenyl)acrylamide. $^1$H NMR (400 MHz, CD$_3$OD): δ 1.47 (s, 3H), 1.61-1.63 (m, 3H), 2.07-2.18 (m, 1H), 2.25-2.43 (m, 1H), 3.54-3.86 (m, 3H), 3.97-4.02 (m, 1H), 4.47-4.70 (m, 1H), 5.66-5.88 (m, 2H), 6.24-6.31 (m, 1H), 6.37-6.48 (m, 2H), 7.51-7.77 (m, 5H), 8.49-8.56 (m, 1H). MS Calcd.: 446 MS Found: 447 ([M+H]$^+$).

Example 44: (R)—N-(4-(3-(quinazolin-2-ylamino)pyrrolidine-1-carbonyl)phenyl)propionamide

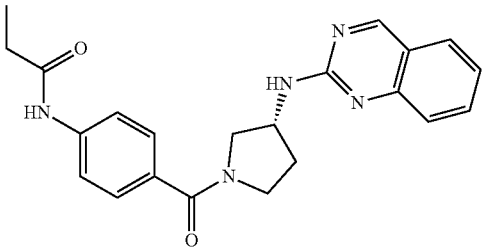 [SMILES: CCC(=O)Nc1ccc(C(=O)N2CC[C@@H](Nc3ncc4ccccc4n3)C2)cc1]

The title compound was prepared in 21% yield from (R)—N-(pyrrolidin-3-yl)quinazolin-2-amine and 4-propionamidobenzoic acid using general procedure of (R)—N-(4-(3-(quinazolin-2-ylamino)pyrrolidine-1-carbonyl)phenyl)acrylamide. $^1$H NMR (400 MHz, DMSO-d$_6$): δ 1.04-1.10 (m, 3H), 1.92-2.05 (m, 1H), 2.20-2.22 (m, 1H), 2.28-2.36 (m, 2H), 3.45-3.70 (m, 3H), 3.83-3.87 (m, 1H), 4.45-4.55 (m, 1H), 7.22-7.26 (m, 1H), 7.41-7.5 (m, 3H), 7.63-7.87 (m, 5H), 9.15 (m, 1H), 10.02 (m, 1H). MS Calcd.: 389 MS Found: 390 ([M+H]$^+$).

Example 45: (R)—N-(4-(3-(isoquinolin-3-ylamino)pyrrolidine-1-carbonyl)phenyl)propionamide

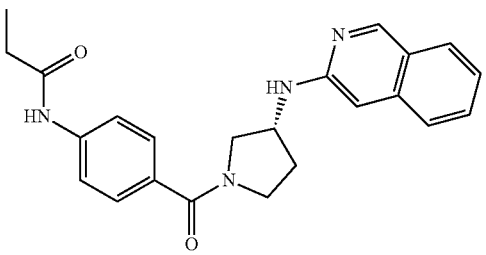 [SMILES: CCC(=O)Nc1ccc(C(=O)N2CC[C@@H](Nc3cc4ccccc4cn3)C2)cc1]

The title compound was prepared in 14% yield from (R)—N-(pyrrolidin-3-yl)isoquinolin-3-amine using general procedure of (R)—N-(4-(3-(isoquinolin-3-ylamino)pyrrolidine-1-carbonyl)phenyl)acrylamide. $^1$H NMR (400 MHz, DMSO-d$_6$): δ 1.08 (t, J=7.8 Hz, 3H), 1.87-2.04 (m, 1H), 2.15-2.26 (m, 1H), 2.30-2.35 (m, 2H), 3.34-3.39 (m, 1H), 3.48-3.50 (m, 1H), 3.61-3.69 (m, 1H), 3.86-3.88 (m, 1H), 4.28-4.40 (m, 1H), 6.65 (d, J=27.2 Hz, 1H), 6.77 (t, J=6.4 Hz, 1H), 7.14-7.16 (m, 1H), 7.44-7.62 (m, 6H), 7.75-7.77 (m, 1H), 8.86 (d, J=30.8 Hz, 1H), 10.04 (d, J=15.6 Hz, 1H). MS Calcd.: 388 MS Found: 389 ([M+H]$^+$).

Example 46: (R)—N-(4-(3-((6-fluoroquinazolin-2-yl)amino)pyrrolidine-1-carbonyl)phenyl)propionamide

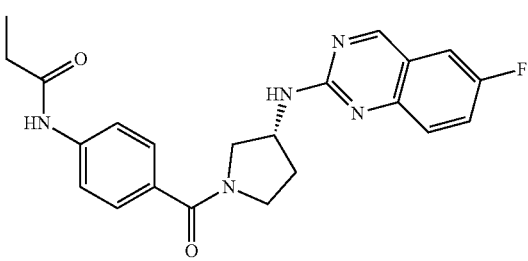 [SMILES: CCC(=O)Nc1ccc(C(=O)N2CC[C@@H](Nc3ncc4cc(F)ccc4n3)C2)cc1]

The title compound was prepared in 31% yield from (R)-6-fluoro-N-(pyrrolidin-3-yl)quinazolin-2-amine and 4-propionamidobenzoic acid using general procedure of (R)—N-(4-(3-(quinazolin-2-ylamino)pyrrolidine-1-carbonyl)phenyl)acrylamide. $^1$H NMR (400 MHz, DMSO-d$_6$): δ 1.04-1.07 (m, 3H), 2.08-2.28 (m, 2H), 2.30-2.35 (m, 2H), 3.29-3.69 (m, 4H), 4.42-4.50 (m, 1H), 7.48-7.77 (m, 8H), 9.13 (d, J=22.0 Hz, 1H), 10.01 (d, J=10.8 Hz, 1H). MS Calcd.: 407 MS Found: 408 ([M+H]$^+$).

Example 47: (R)—N-(4-(3-((6-chloroquinazolin-2-yl)amino)pyrrolidine-1-carbonyl)phenyl)propionamide

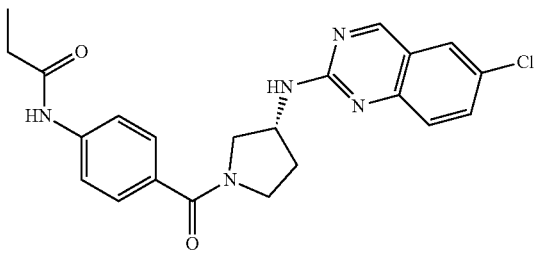 [SMILES: CCC(=O)Nc1ccc(C(=O)N2CC[C@@H](Nc3ncc4cc(Cl)ccc4n3)C2)cc1]

The title compound was prepared in 18% yield from (R)-6-chloro-N-(pyrrolidin-3-yl)quinazolin-2-amine and 4-propionamidobenzoic acid using general procedure of (R)—N-(4-(3-(quinazolin-2-ylamino)pyrrolidine-1-carbonyl)phenyl)acrylamide. $^1$H NMR (400 MHz, DMSO-d$_6$): δ 1.05-1.11 (m, 3H), 1.93-2.06 (m, 1H), 2.16-2.24 (m, 1H), 2.29-2.38 (m, 2H), 3.37-3.60 (m, 2H), 3.64-3.73 (m, 1H), 3.83-3.87 (m, 1H), 4.44-4.58 (m, 1H), 7.43-7.52 (m, 3H), 7.60-7.73 (m, 3H), 7.90-7.96 (m, 2H), 9.10-9.15 (m, 1H), 10.02 (s, 0.5H), 10.06 (s, 0.5H). MS Calcd.: 423 MS Found: 424 ([M+H]$^+$).

Example 48: (R)—N-(4-(3-((6-methoxyquinazolin-2-yl)amino)pyrrolidine-1-carbonyl)phenyl)propionamide

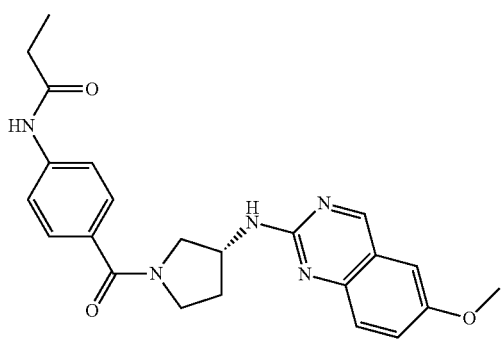 [SMILES: CCC(=O)Nc1ccc(C(=O)N2CC[C@@H](Nc3ncc4cc(OC)ccc4n3)C2)cc1]

The title compound was prepared in 16% yield from (R)-6-methoxy-N-(pyrrolidin-3-yl)quinazolin-2-amine and 4-propionamidobenzoic acid using general procedure of (R)—N-(4-(3-(quinazolin-2-ylamino)pyrrolidine-1-carbonyl)phenyl)acrylamide. $^1$H NMR (400 MHz, CDCl$_3$): δ 1.19-1.30 (m, 3H), 2.26-2.27 (m, 2H), 2.40-2.42 (m, 2H), 3.57-3.58 (m, 1H), 3.71-4.04 (m, 5H), 4.69-4.89 (m, 1H), 7.13-7.22 (m, 1H), 7.29-7.36 (m, 1H), 7.49-7.57 (m, 4H), 7.74-7.76 (m, 1H), 9.13-9.20 (m, 1H), 11.10-11.20 (m, 1H). MS Calcd.: 419 MS Found: 420 ([M+H]+).

Example 49: (R)—N-(4-(3-((6-methylquinazolin-2-yl)amino)pyrrolidine-1-carbonyl)phenyl)propionamide

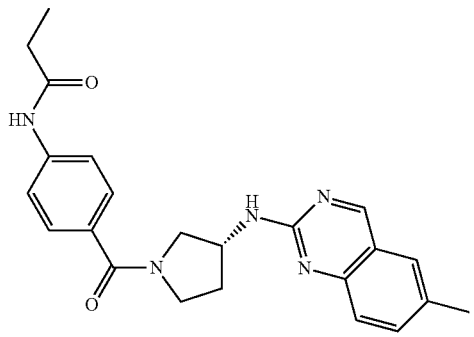 [SMILES: CCC(=O)Nc1ccc(C(=O)N2CC[C@@H](Nc3ncc4cc(C)ccc4n3)C2)cc1]

The title compound was prepared in 40% yield from (R)-6-methyl-N-(pyrrolidin-3-yl)quinazolin-2-amine and 4-propionamidobenzoic acid using general procedure of (R)—N-(4-(3-(quinazolin-2-ylamino)pyrrolidine-1-carbonyl)phenyl)acrylamide. $^1$H NMR (400 MHz, DMSO-$d_6$): δ 1.05-1.11 (m, 3H), 1.92-2.40 (m, 7H), 3.41-3.86 (m, 4H), 4.41-4.57 (m, 1H), 7.34-7.67 (m, 8H), 9.02-9.08 (m, 1H), 10.02-10.05 (m, 1H). MS Calcd.: 403 MS Found: 404 ([M+H]+).

Example 50: (R)—N-(4-(3-(pyrido[3,4-d]pyrimidin-2-ylamino)pyrrolidine-1-carbonyl)phenyl)propionamide

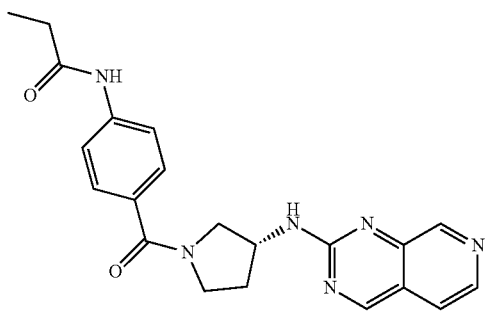 [SMILES: CCC(=O)Nc1ccc(C(=O)N2CC[C@@H](Nc3ncc4ccncc4n3)C2)cc1]

The title compound was prepared in 31% yield from (R)—N-(pyrrolidin-3-yl)pyrido[3,4-d]pyrimidin-2-amine and 4-propionamidobenzoic acid using general procedure of (R)—N-(4-(3-(quinazolin-2-ylamino)pyrrolidine-1-carbonyl)phenyl)acrylamide. $^1$H NMR (400 MHz, DMSO-$d_6$): 1.08 (dd, J=18.0, 7.6 Hz, 3H), 1.98-2.08 (m, 1H), 2.22-2.25 (m, 1H), 2.29-2.38 (m, 2H), 3.45-3.61 (m, 2H), 3.66-3.74 (m, 1H), 3.85-3.89 (m, 1H), 4.47-4.61 (m, 1H), 7.48-7.53 (m, 2H), 7.61-7.74 (m, 3H), 8.19 (br s, 1H), 8.34 (dd, J=14.8, 4.8 Hz, 1H), 8.92 (d, J=36.0 Hz, 1H), 9.30 (d, J=19.2 Hz, 1H), 10.02 (d, J=15.2 Hz, 1H). MS Calcd.: 390 MS Found: 391 ([M+H]+).

Example 51: (R)—N-(4-(3-((7-methoxyquinazolin-2-yl)amino)pyrrolidine-1-carbonyl)phenyl)propionamide

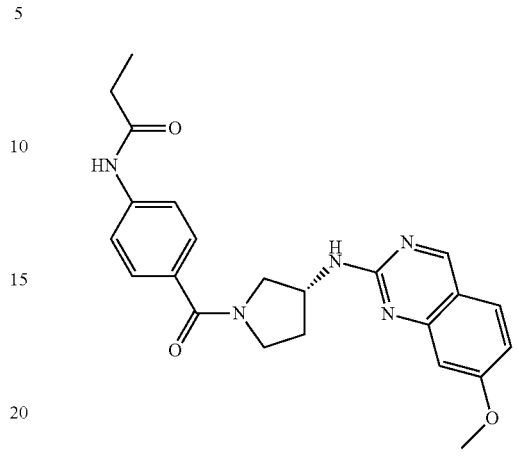

The title compound was prepared in 15% yield from (R)-7-methoxy-N-(pyrrolidin-3-yl)quinazolin-2-amine and 4-propionamidobenzoic acid using general procedure of (R)—N-(4-(3-(quinazolin-2-ylamino)pyrrolidine-1-carbonyl)phenyl)acrylamide. $^1$H NMR (400 MHz, DMSO-$d_6$): δ 1.04-1.11 (m, 3H), 1.93-1.97 (m, 1H), 2.03-2.08 (m, 1H), 2.17-2.24 (m, 2H), 2.29-2.44 (m, 3H), 3.41-3.57 (m, 2H), 3.64-3.73 (m, 1H), 3.82-3.86 (m, 1H), 4.42-4.56 (m, 1H), 7.05-7.72 (m, 8H), 9.02-9.07 (m, 1H), 10.00-10.04 (m, 1H). MS Calcd.: 419 MS Found: 420 ([M+H]+).

Example 52: (R)—N-(4-(3-((7-(methylsulfonyl)quinazolin-2-yl)amino)pyrrolidine-1-carbonyl)phenyl)propionamide

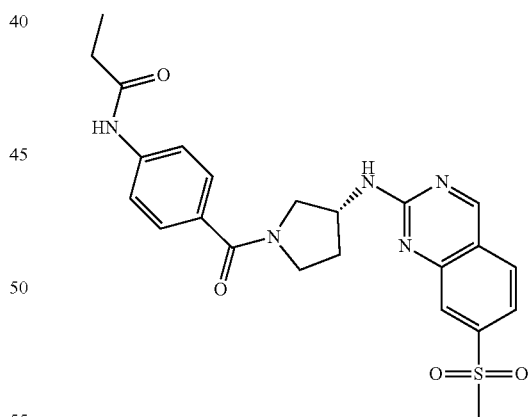

The title compound was prepared in 39% yield from (R)-7-(methylsulfonyl)-N-(pyrrolidin-3-yl)quinazolin-2-amine and 4-propionamidobenzoic acid using general procedure of (R)—N-(4-(3-(quinazolin-2-ylamino)pyrrolidine-1-carbonyl)phenyl)acrylamide. $^1$H NMR (400 MHz, DMSO-$d_6$): δ 1.05-1.11 (m, 3H), 1.96-2.09 (m, 1H), 2.18-2.23 (m, 1H), 2.25-2.38 (m, 2H), 3.30-3.34 (m, 3H), 3.41-3.61 (m, 2H), 3.66-3.77 (m, 1H), 3.85-3.90 (m, 1H), 4.45-4.61 (m, 1H), 7.46-7.71 (m, 5H), 7.90-8.11 (m, 2H), 8.20 (s, 1H), 9.29-9.33 (m, 1H), 10.01-10.06 (m, 1H). MS Calcd.: 467 MS Found: 468 ([M+H]+).

Example 53: (R)—N-(4-(3-((7-chloroquinazolin-2-yl)amino)pyrrolidine-1-carbonyl)phenyl)propionamide

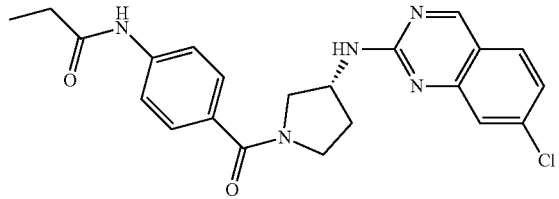 [SMILES: CCC(=O)Nc1ccc(C(=O)N2CC[C@@H](Nc3ncc4ccc(Cl)cc4n3)C2)cc1]

The title compound was prepared in 20% yield from (R)-7-chloro-N-(pyrrolidin-3-yl)quinazolin-2-amine and 4-propionamidobenzoic acid using general procedure of (R)—N-(4-(3-(quinazolin-2-ylamino)pyrrolidine-1-carbonyl)phenyl)acrylamide. $^1$H NMR (400 MHz, CDCl$_3$): δ 1.20-1.26 (m, 3H), 2.01-2.07 (m, 1H), 2.2.29-2.42 (m, 3H), 3.45-4.12 (m, 4H), 4.56-4.76 (m, 1H), 5.47-5.59 (m, 1H), 7.18-7.27 (m, 1H), 7.44-7.67 (m, 7H), 8.93 (d, J=20.0 Hz, 1H). MS Calcd.: 423 MS Found: 424 ([M+H]$^+$).

Example 54: (R)—N-(4-(3-((7-fluoroquinazolin-2-yl)amino)pyrrolidine-1-carbonyl)phenyl)propionamide

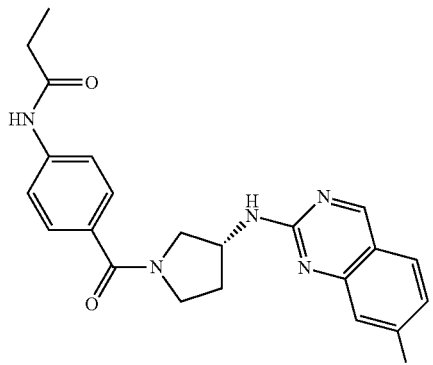

The title compound was prepared in 21% yield from (R)-7-fluoro-N-(pyrrolidin-3-yl)quinazolin-2-amine and 4-propionamidobenzoic acid using general procedure of (R)—N-(4-(3-(quinazolin-2-ylamino)pyrrolidine-1-carbonyl)phenyl)acrylamide. $^1$H NMR (400 MHz, DMSO-d$_6$): δ 1.05-1.11 (m, 3H), 1.95-2.35 (m, 4H), 3.38-3.86 (m, 4H), 4.55 (d, J=4.8 Hz, 1H), 7.09-7.23 (m, 2H), 7.47-7.67 (m, 4H), 7.86-7.92 (m, 2H), 9.10-9.15 (m, 1H), 9.99-10.03 (m, 1H). MS Calcd.: 407 MS Found: 408 ([M+H]$^+$).

Example 55: (R)—N-(4-(3-((7-cyanoquinazolin-2-yl)amino)pyrrolidine-1-carbonyl)phenyl)propionamide

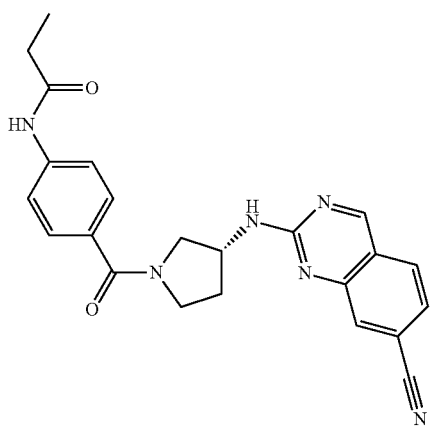 [SMILES: CCC(=O)Nc1ccc(C(=O)N2CC[C@@H](Nc3ncc4ccc(C#N)cc4n3)C2)cc1]

The title compound was prepared in 29% yield from (R)-2-(pyrrolidin-3-ylamino)quinazoline-7-carbonitrile and 4-propionamidobenzoic acid using general procedure of (R)—N-(4-(3-(quinazolin-2-ylamino)pyrrolidine-1-carbonyl)phenyl)acrylamide. $^1$H NMR (400 MHz, DMSO-d$_6$): δ 1.07 (q, J=8.0 Hz, 3H), 1.97-2.09 (m, 1H), 2.21-2.22 (m, 1H), 2.29-2.35 (m, 2H), 3.43-3.58 (m, 3H), 3.83-3.87 (m, 1H), 4.46-4.59 (m, 1H), 7.46-7.52 (m, 3H), 7.56-7.67 (m, 2H), 7.91-8.02 (m, 2H), 8.17 (br s, 1H), 9.26-9.30 (m, 1H), 9.99-10.03 (m, 1H). MS Calcd.: 414 MS Found: 415 ([M+H]$^+$).

Example 56: (R)-2-((1-(4-propionamidobenzoyl)pyrrolidin-3-yl)amino)quinazoline-7-carboxylic Acid

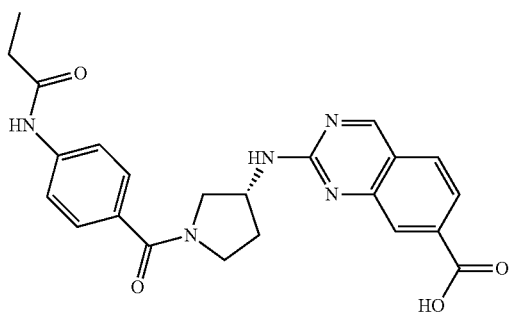 [SMILES: CCC(=O)Nc1ccc(C(=O)N2CC[C@@H](Nc3ncc4ccc(C(=O)O)cc4n3)C2)cc1]

The title compound was prepared in 34% yield from methyl-(R)-2-(pyrrolidin-3-ylamino)quinazoline-7-carboxylate and 4-propionamidobenzoic acid using general procedure of (R)-2-((1-(4-acrylamidobenzoyl)piperidin-3-yl)amino)quinazoline-7-carboxylic acid. $^1$H NMR (400 MHz, DMSO-d$_6$): δ 1.04-1.09 (m, 3H), 1.96-2.07 (m, 1H), 2.21-2.23 (m, 1H), 2.29-2.38 (m, 2H), 3.44-3.58 (m, 2H), 3.67-3.73 (m, 1H), 3.85-3.88 (m, 1H), 4.45-4.60 (m, 1H), 7.47-7.52 (m, 2H), 7.60-7.80 (m, 5H), 7.94 (d, J=36.8 Hz, 1H), 9.16 (d, J=24.0 Hz, 1H), 10.03 (d, J=19.2 Hz, 1H). MS Calcd.: 433 MS Found: 434 ([M+H]$^+$).

Example 57: (R)-2-((1-(4-propionamidobenzoyl)pyrrolidin-3-yl)amino)quinazoline-7-carboxamide

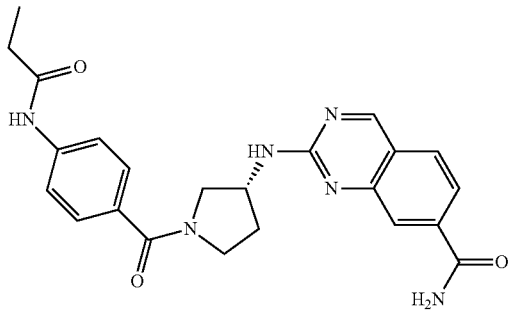 [SMILES: CCC(=O)Nc1ccc(C(=O)N2CC[C@@H](Nc3ncc4ccc(C(N)=O)cc4n3)C2)cc1]

The title compound was prepared in 25% yield from (R)-2-(pyrrolidin-3-ylamino)quinazoline-7-carboxamide and 4-propionamidobenzoic acid using general procedure of (R)-2-((1-(4-acrylamidobenzoyl)piperidin-3-yl)amino)quinazoline-7-carboxamide $^1$H NMR (400 MHz, DMSO-$d_6$): δ 1.05-1.12 (m, 3H), 1.99-2.10 (m, 1H), 2.22-2.25 (m, 1H), 2.29-2.38 (m, 2H), 3.45-3.61 (m, 2H), 3.67-3.77 (m, 1H), 3.85-3.88 (m, 1H), 4.46-4.58 (m, 1H), 7.48-7.53 (m, 3H), 7.61-7.67 (m, 3H), 7.83-8.03 (m, 3H), 8.20 (d, J=20.0 Hz, 1H), 9.20 (d, J=20.4 Hz, 1H), 10.01 (d, J=16.0 Hz, 1H). MS Calcd.: 432 MS Found: 433 ([M+H]$^+$).

Example 58: (R)-2-((1-(4-acrylamidobenzoyl)pyrrolidin-3-yl)amino)-N-methylquinazoline-7-carboxamide

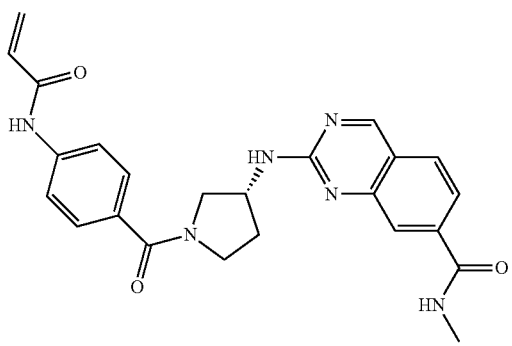 [SMILES: C=CC(=O)Nc1ccc(C(=O)N2CC[C@@H](Nc3ncc4ccc(C(=O)NC)cc4n3)C2)cc1]

The title compound was prepared in 29% yield from (R)—N-methyl-2-(pyrrolidin-3-ylamino)quinazoline-7-carboxamide using general procedure of (R)-2-((1-(4-acrylamidobenzoyl)piperidin-3-yl)amino)-N,N-dimethylquinazoline-7-carboxamide. $^1$H NMR (400 MHz, DMSO-$d_6$): δ 1.98-2.08 (m, 1H), 2.19-2.33 (m, 1H), 2.79-2.82 (m, 3H), 3.44-3.59 (m, 2H), 3.68-3.74 (m, 1H), 3.86-3.89 (m, 1H), 4.45-4.58 (m, 1H), 5.78 (t, J=10. Hz, 1H), 6.24-6.31 (m, 1H), 6.39-6.46 (m, 1H), 7.51-7.56 (m, 2H), 7.60-7.45 (m, 3H), 7.83-7.98 (m, 3H), 8.66 (d, J=27.2 Hz, 1H), 9.19 (d, J=20.4 Hz, 1H), 10.29 (d, J=15.6 Hz, 1H). MS Calcd.: 444 MS Found: 445 ([M+H]$^+$).

Example 59: (R)—N,N-dimethyl-2-((1-(4-propionamidobenzoyl)pyrrolidin-3-yl)amino)quinazoline-7-carboxamide

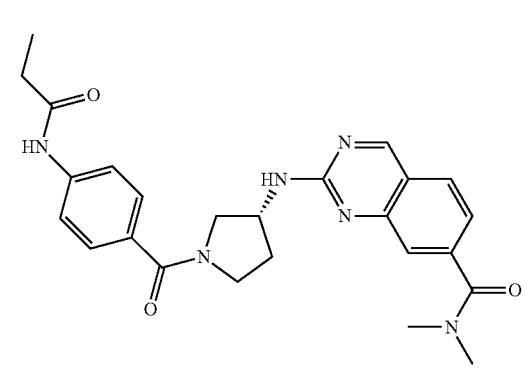 [SMILES: CCC(=O)Nc1ccc(C(=O)N2CC[C@@H](Nc3ncc4ccc(C(=O)N(C)C)cc4n3)C2)cc1]

The title compound was prepared in 46% yield from (R)—N,N-dimethyl-2-(pyrrolidin-3-ylamino)quinazoline-7-carboxamide and 4-propionamidobenzoic acid using general procedure of (R)-2-((1-(4-acrylamidobenzoyl)piperidin-3-yl)amino)-N,N-dimethylquinazoline-7-carboxamide. $^1$H NMR (400 MHz, DMSO-$d_6$): δ 1.05-1.11 (m, 3H), 1.96-2.10 (m, 1H), 2.18-2.25 (m, 1H), 2.29-2.38 (m, 2H), 2.90 (d, J=17.6 Hz, 3H), 3.01 (d, J=8.8 Hz, 3H), 3.42-3.60 (m, 2H), 3.66-3.84 (m, 1H), 3.85-3.88 (m, 1H), 4.45-4.60 (m, 1H), 7.17-7.23 (m, 1H), 7.35-7.53 (m, 3H), 7.60-7.68 (m, 2H), 7.83-7.91 (m, 2H), 9.17 (d, J=20.4 Hz, 1H), 10.03 (d, J=16.4 Hz, 1H). MS Calcd.: 460 MS Found: 461 ([M+H]$^+$).

Example 60: (R)—N-(4-(3-((7-oxo-7,8-dihydropyrido[2,3-d]pyrimidin-2-yl)amino)pyrrolidine-1-carbonyl)phenyl)propionamide

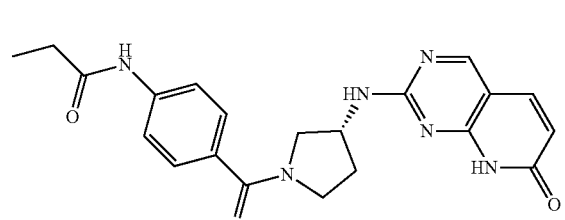

The title compound was prepared in 7% yield from (R)-2-(pyrrolidin-3-ylamino)pyrido[2,3-d]pyrimidin-7(8H)-one and 4-propionamidobenzoic acid using general procedure of (R)—N-(4-(3-((8-isopropyl-7-oxo-7,8-dihydropyrido[2,3-d]pyrimidin-2-yl)amino)piperidine-1-carbonyl)phenyl)acrylamide. $^1$H NMR (400 MHz, DMSO-$d_6$): δ 1.07-1.09 (m, 3H), 1.91-2.01 (m, 1H), 2.08-2.17 (m, 1H), 2.31-2.35 (m, 2H), 3.37-3.66 (m, 4H), 4.37-4.51 (m, 1H), 6.14 (t, J=12.4 Hz, 1H), 7.48 (t, J=8.4 Hz, 2H), 7.61-7.73 (m, 3H), 7.85-8.04 (m, 1H), 8.55-8.60 (m, 1H), 10.01 (d, J=6.8 Hz, 1H), 11.75 (br s, 1H). MS Calcd.: 406 MS Found: 407 ([M+H]$^+$).

Example 61: (R)—N-(4-(3-((8-isopropyl-7-oxo-7,8-dihydropyrido[2,3-d]pyrimidin-2-yl)amino)pyrrolidine-1-carbonyl)phenyl)propionamide

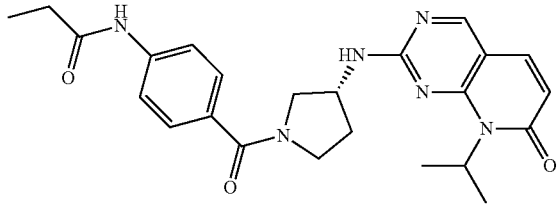 [SMILES: CCC(=O)Nc1ccc(C(=O)N2CC[C@@H](Nc3ncc4ccc(=O)n(C(C)C)c4n3)C2)cc1]

The title compound was prepared in 56% yield from (R)-8-isopropyl-2-(pyrrolidin-3-ylamino)pyrido[2,3-d]pyrimidin-7(8H)-one and 4-propionamidobenzoic acid using general procedure of (R)—N-(4-(3-((8-isopropyl-7-oxo-7,8-dihydropyrido[2,3-d]pyrimidin-2-yl)amino)piperidine-1-carbonyl)phenyl)acrylamide. $^1$H NMR (400 MHz, CD$_3$OD): δ 1.17-1.23 (m, 3H), 1.47 (s, 3H), 1.61-1.62 (m, 3H), 2.08-2.19 (m, 1H), 2.27-2.44 (m, 3H), 3.55-3.89 (m, 3H), 3.97-4.02 (m, 1H), 4.40-4.76 (m, 1H), 5.63-5.96 (m, 1H), 6.22-6.31 (m, 1H), 7.49-7.69 (m, 5H), 8.46-8.56 (m, 1H). MS Calcd.: 448 MS Found: 449 ([M+H]$^+$).

Example 62: Synthesis of (R)—N-(2-fluoro-4-(3-(quinazolin-2-ylamino)pyrrolidine-1-carbonyl)phenyl)acrylamide

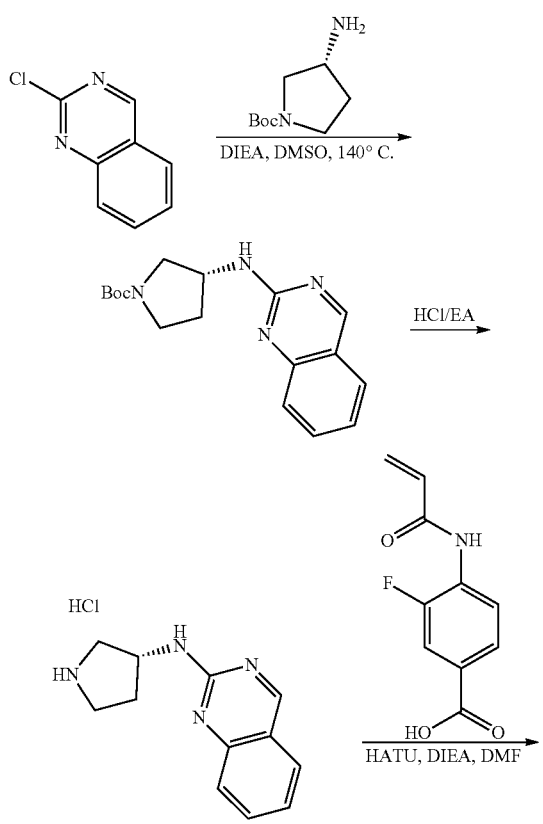

Step 1: (R)-tert-butyl 3-(quinazolin-2-ylamino)pyrrolidine-1-carboxylate

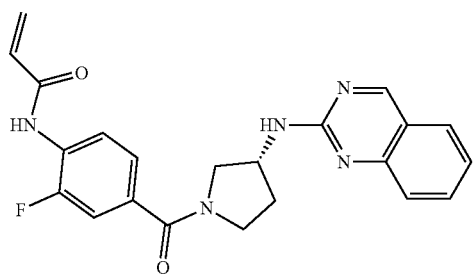

To a solution of 2-chloroquinazoline (2.0 g, 12.2 mmol) and (R)-tert-butyl 3-aminopyrrolidine-1-carboxylate (2.7 g, 14.6 mmol) in DMSO (30 mL) was added DIEA (3.1 g, 24.3 mmol) at rt. The mixture was stirred at 140° C. for 2 h. The reaction mixture was cooled to rt, poured into 30 mL of H$_2$O and extracted with DCM (20 mL*3). The combined organic layers were dried over Na$_2$SO$_4$, filtered and concentrated in vacuo to afford (R)-tert-butyl 3-(quinazolin-2-ylamino)pyrrolidine-1-carboxylate (3.8 g, crude) as a yellow solid. [M+H] Calc'd for C$_{17}$H$_{23}$N$_4$O$_2$, 315.1; Found, 315.1.

Step 2: (R)—N-(pyrrolidin-3-yl)quinazolin-2-amine hydrochloride

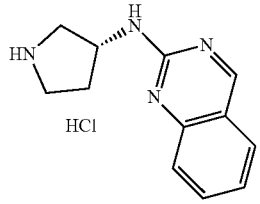 [SMILES: c1ccc2nc(N[C@@H]3CCNC3)ncc2c1 ; Cl]

A solution of (R)-tert-butyl 3-(quinazolin-2-ylamino)pyrrolidine-1-carboxylate (3.8 g, 12.2 mmol) in EA/HCl (20.0 mL, 1.0 M, 20.0 mmol) was stirred at rt for 1 h. The mixture was concentrated to afford (R)—N-(pyrrolidin-3-yl)quinazolin-2-amine hydrochloride (2.6 g, crude) as a white solid. [M+H] Calc'd for C$_{12}$H$_{15}$N$_4$, 215.1; Found, 215.1.

Step 3: (R)—N-(2-fluoro-4-(3-(quinazolin-2-ylamino)pyrrolidine-1-carbonyl)phenyl)acrylamide

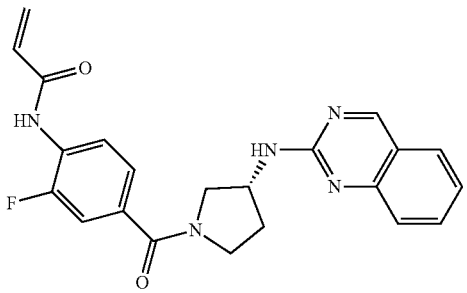 [SMILES: C=CC(=O)Nc1ccc(C(=O)N2CC[C@@H](Nc3ncc4ccccc4n3)C2)cc1F]

A mixture of 4-acrylamido-3-fluorobenzoic acid (150 mg, 0.72 mmol), (R)—N-(pyrrolidin-3-yl)quinazolin-2-amine hydrochloride (184 mg, 0.86 mmol), HATU (410 mg, 1.08 mmol) and DIEA (278 mg, 2.16 mmol) in DMF (15 mL) was stirred at rt overnight. The mixture was diluted with water (10 mL) and extracted with DCM (10 mL*3). The combined organic layer was washed with brine (20 mL), dried over $Na_2SO_4$, filtered and concentrated in vacuo. The residue was purified by prep-HPLC to afford (R)—N-(2-fluoro-4-(3-(quinazolin-2-ylamino)pyrrolidine-1-carbonyl)phenyl)acrylamide (89.41 mg, 31%) as a white solid. $^1$H NMR (400 MHz, DMSO-$d_6$): δ 1.93-2.09 (m, 1H), 2.09-2.31 (m, 1H), 3.47-3.88 (m, 4H), 4.48-4.60 (m, 1H), 5.79 (t, J=8.8 Hz, 1H), 6.26-6.36 (m, 1H), 6.62-6.67 (m, 1H), 7.23-7.26 (m, 1H), 7.36-7.52 (m, 3H), 7.62-7.83 (m, 3H), 8.11-8.15 (m, 1H), 9.11 (s, 0.5H), 9.16 (s, 0.5H), 10.05 (s, 0.5H), 10.09 (s, 0.5H). [M+H] Calc'd for $C_{22}H_{21}FN_5O_2$, 406.1; Found, 406.1.

Example 63: Synthesis of N-(4-((3S,4S)-3-fluoro-4-(quinazolin-2-ylamino)pyrrolidine-1-carbonyl)phenyl)acrylamide

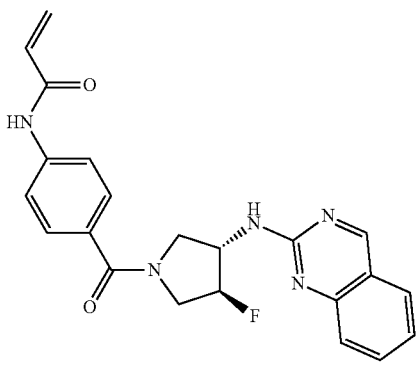 [SMILES: C=CC(=O)Nc1ccc(C(=O)N2C[C@H](Nc3ncc4ccccc4n3)[C@@H](F)C2)cc1]

The title compound was prepared in 21% yield from N-((3S,4S)-4-fluoropyrrolidin-3-yl)quinazolin-2-amine hydrochloride using general procedure of (R)—N-(2-fluoro-4-(3-(quinazolin-2-ylamino)pyrrolidine-1-carbonyl)phenyl)acrylamide. $^1$H NMR (400 MHz, DMSO-$d_6$): δ 3.31-3.53 (m, 2H), 3.86-4.11 (m, 2H), 4.55-4.71 (m, 1H), 5.13-5.38 (m, 1H), 5.78-5.80 (m, 1H), 6.31 (d, J=8.0 Hz, 1H), 6.42-6.48 (m, 1H), 7.25-7.35 (m, 1H), 7.48-7.60 (m, 3H), 7.72-7.74 (m, 3H), 7.80-7.99 (m, 2H), 9.17-9.21 (m, 1H), 10.31 (br s, 1H). [M+H] Calc'd for $C_{22}H_{20}FN_5O_2$, 406.1; Found, 406.1.

Example 64: Synthesis of N-(4-(3-(quinazolin-2-ylamino)azetidine-1-carbonyl)phenyl)acrylamide

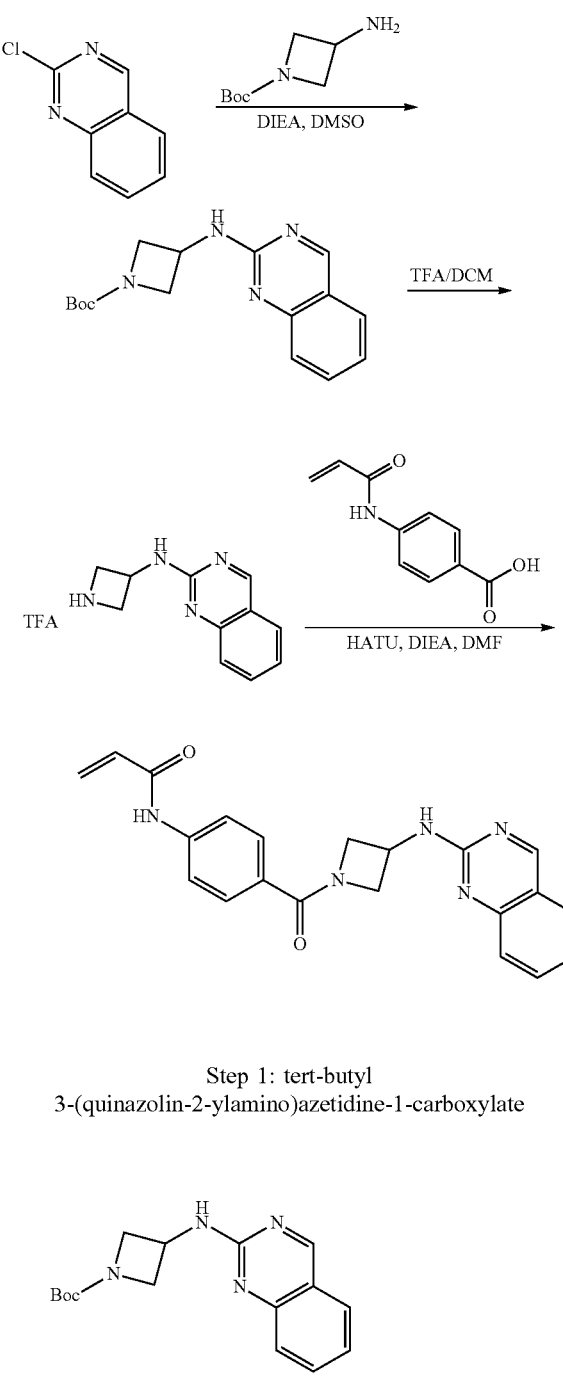

Step 1: tert-butyl 3-(quinazolin-2-ylamino)azetidine-1-carboxylate

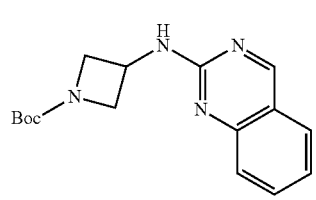 [SMILES: CC(C)(C)OC(=O)N1CC(Nc2ncc3ccccc3n2)C1]

The title compound was prepared in 73% yield from 2-chloroquinazoline using general procedure of (R)-tert-butyl 3-(quinazolin-2-ylamino)pyrrolidine-1-carboxylate. [M+H] Calc'd for $C_{16}H_{20}N_4O_2$, 301.1; Found, 301.1.

Step 2: N-(azetidin-3-yl)quinazolin-2-amine (TFA salt)

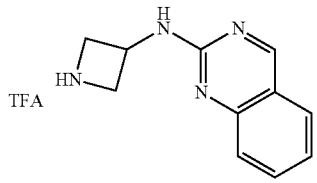 [SMILES: c1ccc2nc(NC3CNC3)ncc2c1]

A solution of tert-butyl 3-(quinazolin-2-ylamino)azetidine-1-carboxylate (283 mg, 0.943 mmol) in TFA/DCM (2 mL/10 mL) was stirred at rt for 1 h. The mixture was concentrated to afford N-(azetidin-3-yl)quinazolin-2-amine (200 mg, crude) as a green oil. [M+H] Calc'd for $C_{11}H_{12}N_4$, 201.1; Found, 201.1.

Step 3: N-(4-(3-(quinazolin-2-ylamino)azetidine-1-carbonyl)phenyl)acrylamide

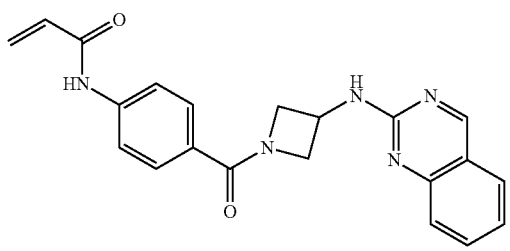 [SMILES: C=CC(=O)Nc1ccc(C(=O)N2CC(Nc3ncc4ccccc4n3)C2)cc1]

The title compound was prepared in 21% yield from N-(azetidin-3-yl)quinazolin-2-amine using general procedure of (R)—N-(2-fluoro-4-(3-(quinazolin-2-ylamino)pyrrolidine-1-carbonyl)phenyl)acrylamide. $^1$H NMR (400 MHz, DMSO-$d_6$): δ 4.08 (s, 1H), 4.26-4.39 (m, 2H), 4.70-4.77 (m, 2H), 5.78-5.81 (m, 1H), 6.27-6.31 (m, 1H), 6.42-6.49 (m, 1H), 7.26-7.30 (m, 1H), 7.48 (d, J=8.4 Hz, 1H), 7.65-7.67 (m, 2H), 7.70-7.76 (m, 3H), 7.83 (d, J=8.0 Hz, 1H), 8.08-8.11 (m, 1H), 9.17 (s, 1H), 10.35 (s, 1H). [M+H] Calc'd for $C_{21}H_{19}N_5O_2$, 374.0; Found, 374.0.

Example 65: Synthesis of (R)—N-(2-fluoro-4-(3-(quinazolin-2-ylamino)pyrrolidine-1-carbonyl)phenyl)acrylamide

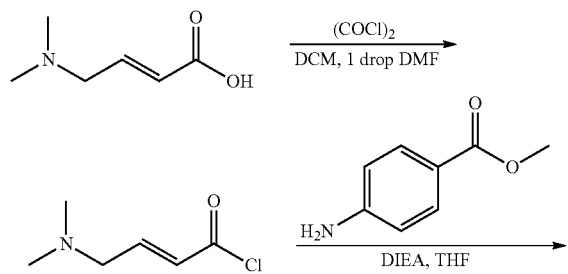

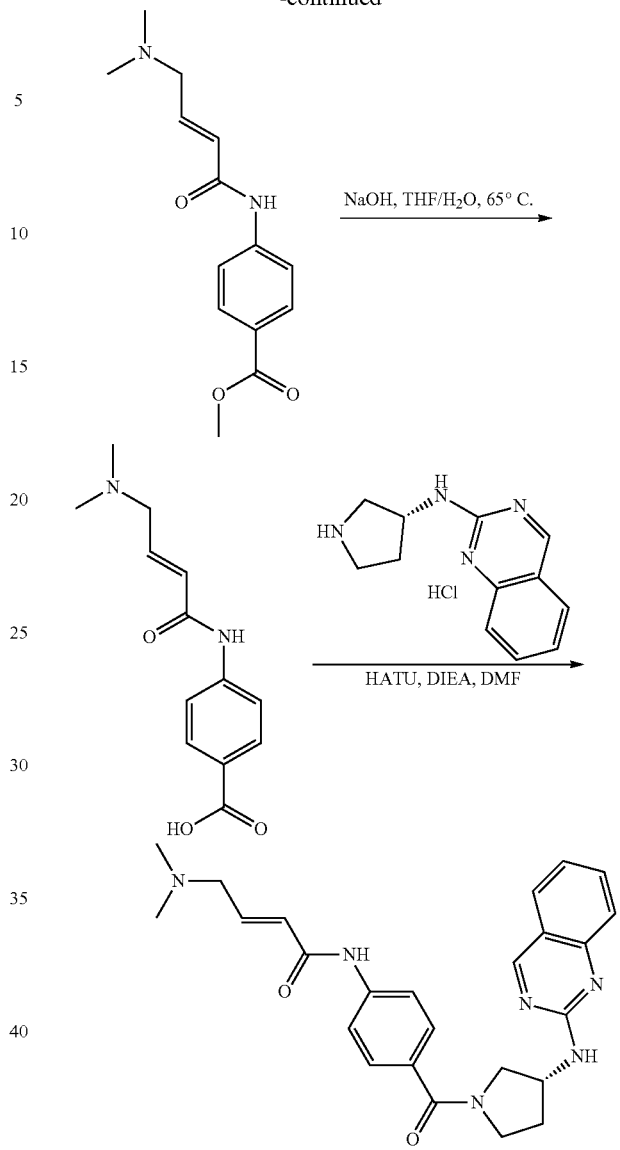

Step 1: (E)-4-(dimethylamino)but-2-enoyl chloride

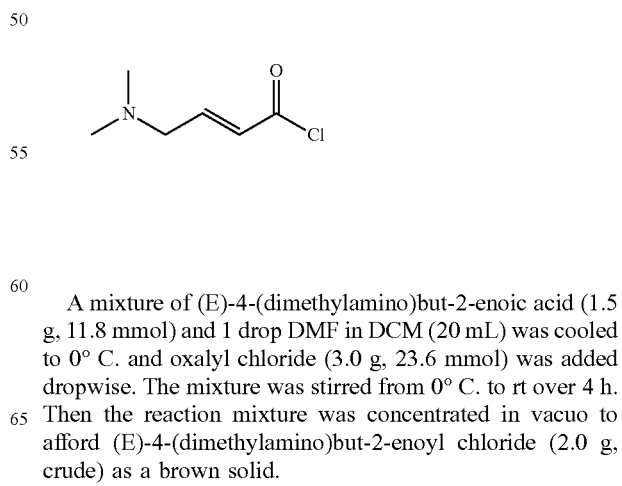

A mixture of (E)-4-(dimethylamino)but-2-enoic acid (1.5 g, 11.8 mmol) and 1 drop DMF in DCM (20 mL) was cooled to 0° C. and oxalyl chloride (3.0 g, 23.6 mmol) was added dropwise. The mixture was stirred from 0° C. to rt over 4 h. Then the reaction mixture was concentrated in vacuo to afford (E)-4-(dimethylamino)but-2-enoyl chloride (2.0 g, crude) as a brown solid.

Step 2: (E)-methyl 4-(4-(dimethylamino)but-2-enamido)benzoate

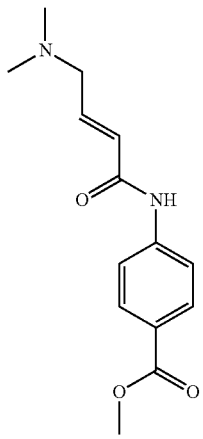 [SMILES: COC(=O)c1ccc(NC(=O)/C=C/CN(C)C)cc1]

To a solution of methyl 4-aminobenzoate (830 mg, 5.5 mmol) and DIEA (1.4 g, 11.0 mmol) in THF (15 mL) was added (E)-4-(dimethylamino)but-2-enoyl chloride (2.0 g, crude) in THF (5 mL) dropwise at ice-bath. The mixture was diluted with water (10 mL) and extracted with DCM (10 mL*3). The combined organic layer was washed with brine (20 mL), dried over $Na_2SO_4$, filtered and concentrated in vacuo. The residue was purified by column (DCM: MeOH=10:1) to afford (E)-methyl 4-(4-(dimethylamino) but-2-enamido)benzoate (500 mg, 35%) as a brown solid. [M+H] Calc'd for $C_{14}H_{19}FN_2O_3$, 263.1; Found, 263.1.

Step 3: Sodium (E)-4-(4-(dimethylamino)but-2-enamido)benzoate

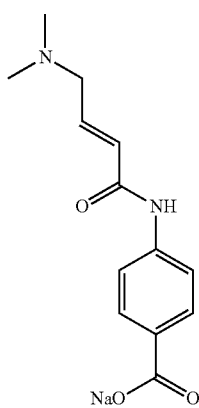

A mixture of (E)-methyl 4-(4-(dimethylamino)but-2-enamido)benzoate (300 mg, 1.14 mmol) and NaOH (46 mg, 1.14 mmol) in THF (10 mL) and $H_2O$ (10 mL) was stirred at 65° C. for 6 h. Then the reaction mixture was concentrated in vacuo to afford sodium (E)-4-(4-(dimethylamino)but-2-enamido)benzoate (250 mg, crude) as a brown solid. [M+H] Calc'd for $C_{13}H_{15}N_2NaO_3$, 271.0; Found, 249.1.

Step 4: (R,E)-4-(dimethylamino)-N-(4-(3-(quinazolin-2-ylamino)pyrrolidine-1-carbonyl)phenyl)but-2-enamide

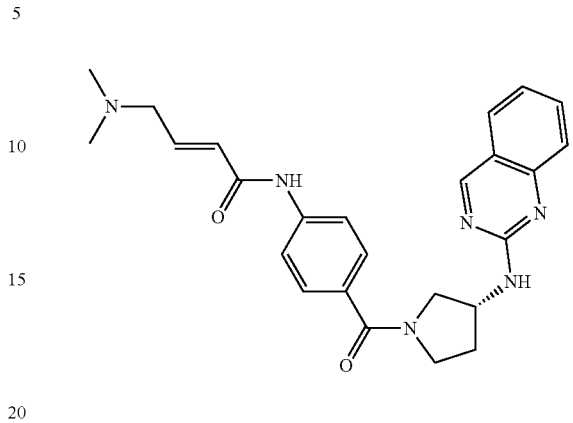

A mixture of sodium (E)-4-(4-(dimethylamino)but-2-enamido)benzoate (90 mg, 0.33 mmol), (R)—N-(pyrrolidin-3-yl)quinazolin-2-amine hydrochloride (85 mg, 0.39 mmol), HATU (188 mg, 0.49 mmol) and DIEA (128 mg, 0.99 mmol) in DMF (10 mL) was stirred at rt overnight. The mixture was diluted with water (10 mL) and extracted with DCM (10 mL*3). The combined organic layer was washed with brine (20 mL), dried over $Na_2SO_4$, filtered and concentrated in vacuo. The residue was purified by prep-HPLC to afford (R,E)-4-(dimethylamino)-N-(4-(3-(quinazolin-2-ylamino) pyrrolidine-1-carbonyl)phenyl)but-2-enamide (23.66 mg, 16%) as white solid. $^1$H NMR (400 MHz, DMSO-d$_6$): δ 1.93-2.09 (m, 1H), 2.09-2.31 (m, 7H), 3.04-3.05 (m, 2H), 3.42-3.88 (m, 4H), 4.48-4.60 (m, 1H), 6.27 (t, J=14.8 Hz, 1H), 6.71-6.76 (m, 1H), 7.20-7.28 (m, 1H), 7.41-7.54 (m, 3H), 7.66-7.83 (m, 5H), 9.10 (s, 0.5H), 9.16 (s, 0.5H), 10.05 (s, 0.5H), 10.09 (s, 0.5H). [M+H] Calc'd for $C_{25}H_{29}N_6O_2$, 445.2; Found, 445.2.

Example 66: Synthesis of (R,E)-4-(dimethylamino)-N-(4-(3-(quinazolin-2-ylamino)piperidine-1-carbonyl)phenyl)but-2-enamide

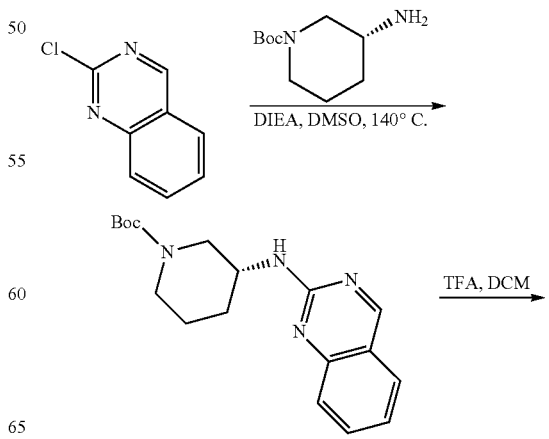

187
-continued

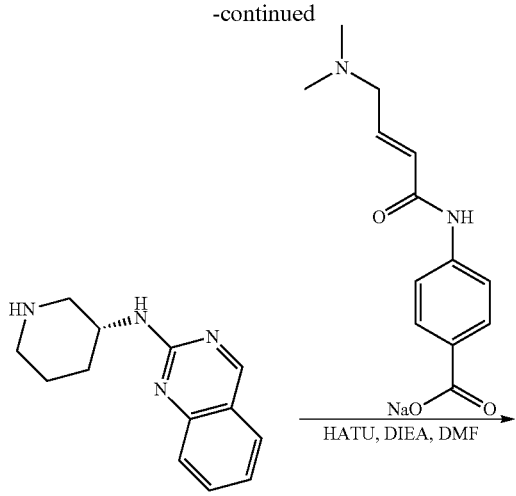

Step 1: (R)-tert-butyl 3-(quinazolin-2-ylamino)piperidine-1-carboxylate

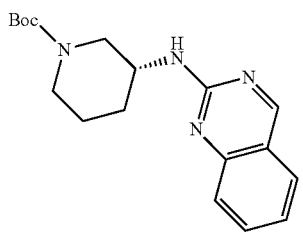 [SMILES: CC(C)(C)OC(=O)N1CCC[C@@H](Nc2ncc3ccccc3n2)C1]

The title compound was prepared in 91% yield from (R)-tert-butyl 3-aminopiperidine-1-carboxylate using general procedure of (R)-tert-butyl 3-(quinazolin-2-ylamino) pyrrolidine-1-carboxylate. [M+H] Calc'd for $C_{18}H_{25}N_4O_2$, 329.2; Found, 329.2.

188

Step 2: (R)—N-(piperidin-3-yl)quinazolin-2-amine (TFA salt)

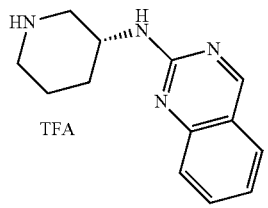 [SMILES: c1ccc2nc(N[C@@H]3CCCNC3)ncc2c1]

A solution of (R)-tert-butyl 3-(quinazolin-2-ylamino)piperidine-1-carboxylate (450 mg, 1.37 mmol) and TFA (3 mL) in DCM (10 mL) was stirred at r.t. for 2 hrs. The mixture was concentrated to afford crude (R)—N-(piperidin-3-yl)quinazolin-2-amine (TFA salt) (300 mg, 96%) as brown oil. [M+H] Calc'd for $C_{13}H_{17}N_4$, 229.1; Found, 229.1.

Step 3: (R,E)-4-(dimethylamino)-N-(4-(3-(quinazolin-2-ylamino)piperidine-1-carbonyl)phenyl)but-2-enamide

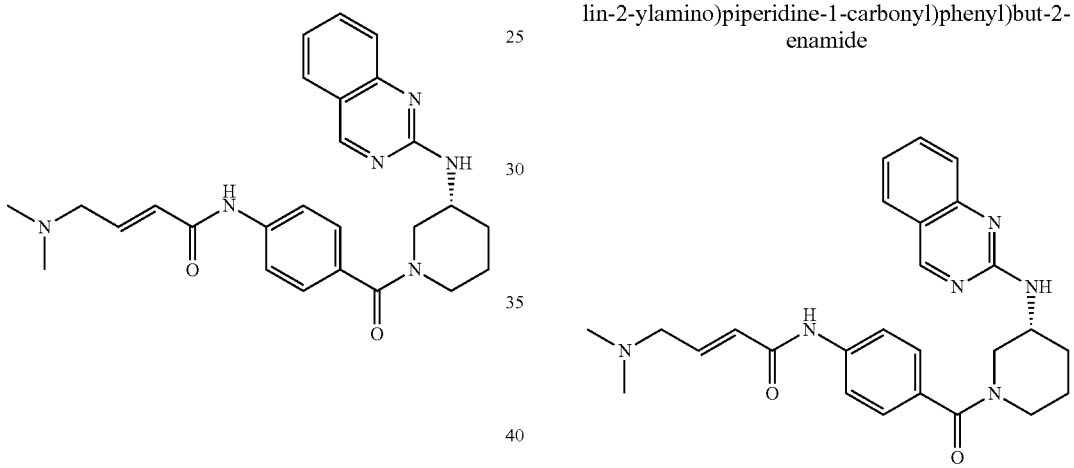

The title compound was prepared in 5% yield from (R)—N-(piperidin-3-yl)quinazolin-2-amine (TFA salt) using general procedure of (R,E)-4-(dimethylamino)-N-(4-(3-(quinazolin-2-ylamino)pyrrolidine-1-carbonyl)phenyl)but-2-enamide. $^1$H NMR (400 MHz, CD$_3$OD): δ 1.71-2.15 (m, 4H), 2.32 (s, 6H), 3.20 (dd, J=0.8, 6.4 Hz, 2H), 3.72-3.91 (m, 5H), 6.18 (d, J=14.0 Hz, 1H), 6.87-6.90 (m, 1H), 7.17-7.73 (m, 8H), 8.93 (s, 1H). [M+H] Calc'd for $C_{26}H_{31}N_6O_2$, 459.2; Found, 459.2.

Example 67: (R)—N-(5-(3-(quinazolin-2-ylamino) pyrrolidine-1-carbonyl)pyridin-2-yl)acrylamide

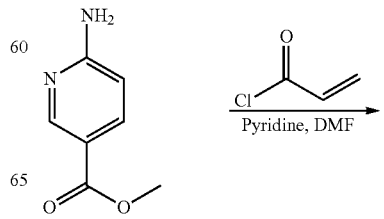

Step 1: methyl 6-acrylamidonicotinate

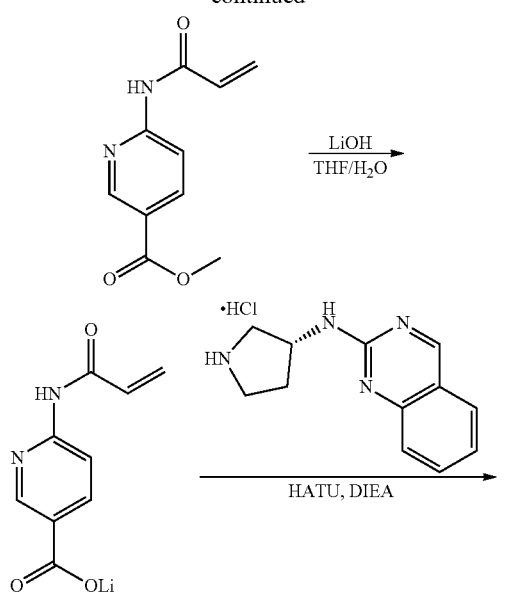

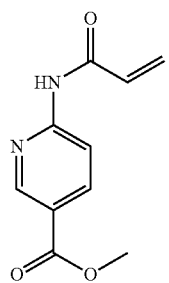

To a solution of methyl 6-aminonicotinate (4.0 g, 26.2 mmol) and Py (2 mL) in DMF (30 mL) was added acryloyl chloride (3.1 mL, 39.4 mmol) dropwise at 0° C. The mixture was stirred at rt for 16 h. The reaction mixture was diluted with water (50 mL) and extracted with DCM (50 mL*3). The combined organic layer was washed with brine (20 mL), dried over $Na_2SO_4$, filtered and concentrated in vacuo. The residue was purified by column (PE:EA=2:1) to afford methyl 6-acrylamidonicotinate (340 mg, 6.0%) as a white solid. [M+H] Calc'd for $C_{10}H_{10}N_2O_3$, 207.2; Found, 207.2.

Step 2: Lithium 6-acrylamidonicotinate

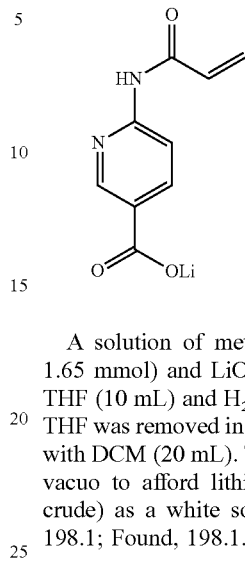

A solution of methyl 6-acrylamidonicotinate (340 mg, 1.65 mmol) and LiOH (69 mg, 1.65 mmol) in mixture of THF (10 mL) and $H_2O$ (10 mL) was stirred at RT for 16 h. THF was removed in vacuo and aqueous layer was extracted with DCM (20 mL). The aqueous layer was concentrated in vacuo to afford lithium 6-acrylamidonicotinate (310 mg, crude) as a white solid. [M+H] Calc'd for $C_9H_7LiN_2O_3$, 198.1; Found, 198.1.

Step 3: (R)—N-(5-(3-(quinazolin-2-ylamino)pyrrolidine-1-carbonyl)pyridin-2-yl)acrylamide

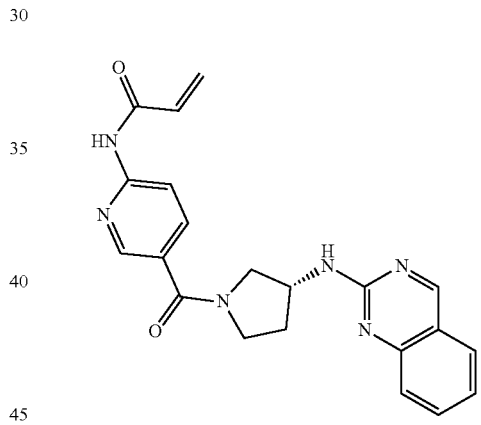

A mixture of lithium 6-acrylamidonicotinate (100 mg, 0.50 mmol), (R)—N-(pyrrolidin-3-yl)quinazolin-2-amine hydrochloride (151 mg, 0.71 mmol), HATU (231 mg, 0.60 mmol) and DIEA (4.19 mL, 2.53 mmol) in DMF (8 mL) was stirred at rt overnight. The mixture was diluted with water (10 mL) and extracted with DCM (10 mL*3). The combined organic layer was washed with brine (20 mL), dried over $Na_2SO_4$, filtered and concentrated in vacuo. The residue was purified by prep-HPLC to afford (R)—N-(5-(3-(quinazolin-2-ylamino)pyrrolidine-1-carbonyl)pyridin-2-yl)acrylamide (70.5 mg, 36%) as an off white solid. $^1$H NMR (400 MHz, DMSO-$d_6$): 2.01-2.20 (m, 2H), 3.49-3.89 (m, 4H), 4.55 (d, J=10.5 Hz, 1H), 5.80 (m, 1H), 6.337 (m, 1H), 6.59 (m, 1H), 7.25 (m, 1H), 7.48 (dd, J=8, J=8 Hz, 1H), 7.77 (m, 3H), 8.00 (m, 1H), 8.52 (m, 1H), 9.13 (m, 1H), 10.91 (m, 1H). [M+H] Calc'd for $C_{21}H_{20}N_6O_2$, 389.1; Found, 389.1.

Example 68: Synthesis of (R,E)-4-(dimethylamino)-N-(2-fluoro-4-(3-(quinazolin-2-ylamino)pyrrolidine-1-carbonyl)phenyl)but-2-enamide

Step 1: (R)-(3-fluoro-4-nitrophenyl)(3-(quinazolin-2-ylamino)pyrrolidin-1-yl)methanone

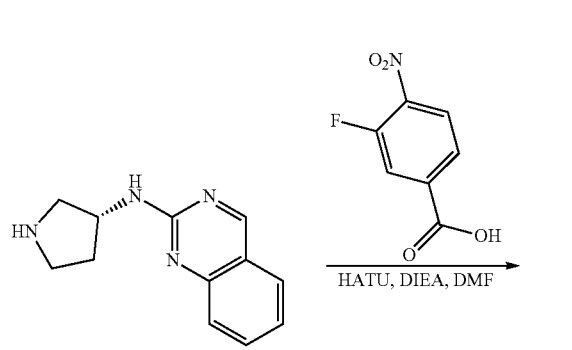

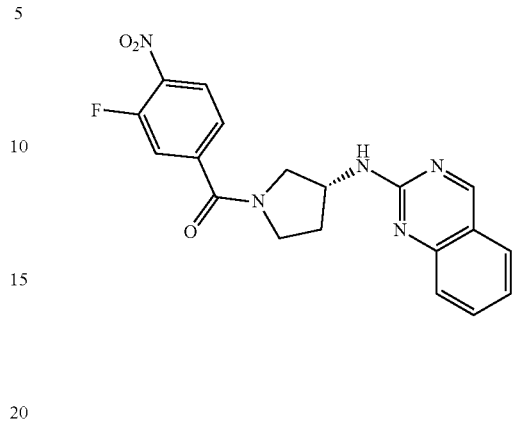

A mixture of (R)—N-(pyrrolidin-3-yl)quinazolin-2-amine (500 mg, 2.34 mmol), 3-fluoro-4-nitrobenzoic acid (519 mg, 2.81 mmol), HATU (1232 mg, 3.24 mmol) and DIEA (1507 mg, 11.7 mmol) in DMF (20 mL) was stirred at RT overnight. The mixture was diluted with water (100 mL) and extracted with DCM (50 mL*3). The combined organic layer was washed with brine (50 mL), dried over $Na_2SO_4$, filtered and concentrated in vacuo. The residue was purified by column (PE:EA=1:1) to afford (R)-(3-fluoro-4-nitrophenyl)(3-(quinazolin-2-ylamino)pyrrolidin-1-yl)methanone (280 mg, 31%) as a yellow solid. [M+H] Calc'd for $C_9H_{16}FN_5O_3$, 382.1; Found, 382.1.

Step 2: (R)-(4-amino-3-fluorophenyl)(3-(quinazolin-2-ylamino)pyrrolidin-1-yl)methanone

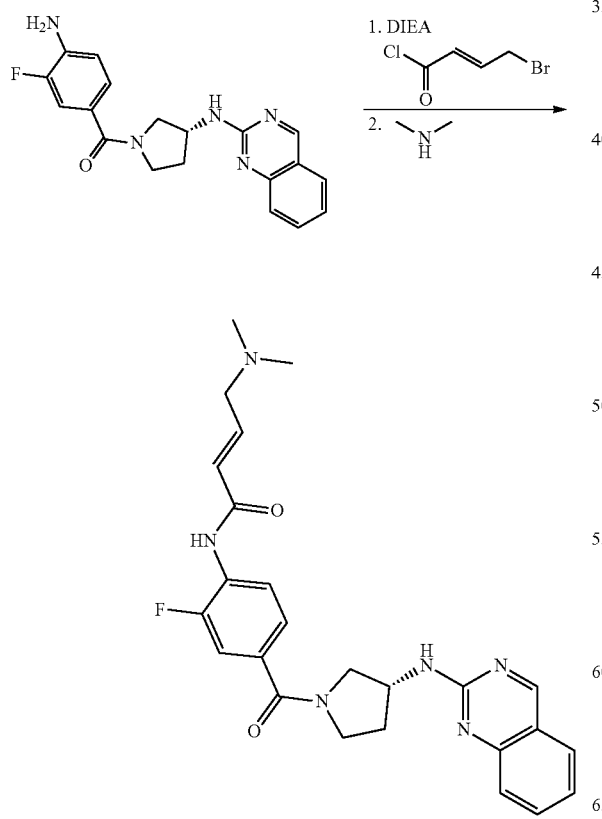

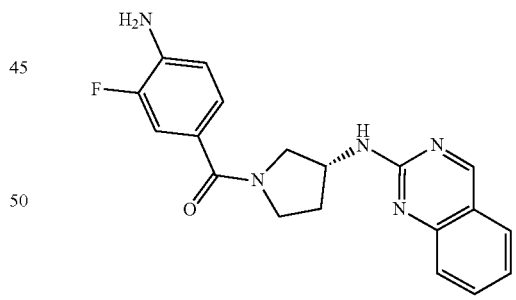

A mixture of (R)-(3-fluoro-4-nitrophenyl)(3-(quinazolin-2-ylamino)pyrrolidin-1-yl)methanone (175 mg, 0.459 mmol) and Pd/C (88 mg) in MeOH (20 mL) was stirred at 50° C. for 6 h under 50 psi $H_2$ atmosphere. Filtered and concentrated in vacuo to afford (R)-(4-amino-3-fluorophenyl)(3-(quinazolin-2-ylamino)pyrrolidin-1-yl)methanone (150 mg, 93%) as a yellow solid. [M+H] Calc'd for $C_9H_{18}FN_5O$, 352.2; Found, 352.2.

Step 3: (R,E)-4-(dimethylamino)-N-(2-fluoro-4-(3-(quinazolin-2-ylamino)pyrrolidine-1-carbonyl)phenyl)but-2-enamide

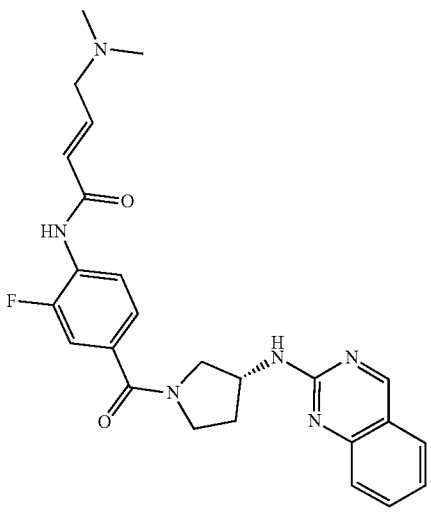 [SMILES: CN(C)C/C=C/C(=O)Nc1ccc(C(=O)N2CC[C@@H](Nc3ncc4ccccc4n3)C2)cc1F]

To a mixture of (R)-(4-amino-3-fluorophenyl)(3-(quinazolin-2-ylamino)pyrrolidin-1-yl)methanone (150 mg, 0.427 mmol) and DIEA (138 mg, 1.07 mmol) in DMF (20 mL) was added (E)-4-bromobut-2-enoyl chloride (130 mg, 0.71 mmol) at 0° C. The mixture was stirred at rt for 30 min. Dimethylamine (2.14 mL, 1.0 M in THF, 2.14 mmol) was added and the mixture was stirred at rt overnight. The reaction mixture was concentrated in vacuo and purified by prep-HPLC to afford (R,E)-4-(dimethylamino)-N-(2-fluoro-4-(3-(quinazolin-2-ylamino)pyrrolidine-1-carbonyl)phenyl)but-2-enamide (25 mg, 15%) as a white solid. $^1$H NMR (400 MHz, CD$_3$OD): δ 2.13-2.16 (m, 1H), 2.30 (s, 3H), 2.32 (s, 3H), 2.33-2.44 (m, 1H), 3.17-3.20 (m, 2H), 3.55-3.84 (m, 3H), 3.94-4.01 (m, 1H), 4.60-4.77 (m, 1H), 6.36-6.43 (m, 1H), 6.90-6.99 (m, 1H), 7.24-7.29 (m, 1H), 7.36-7.42 (m, 2H), 7.44-7.60 (m, 1H), 7.67-7.80 (m, 2H), 8.14-8.25 (m, 1H), 9.02-9.07 (m, 1H). [M+H] Calc'd for C$_{25}$H$_{27}$FN$_6$O$_2$, 463.0; Found, 463.0.

Example 69: Synthesis of (R)—N-(2-fluoro-4-(3-((6-fluoroquinazolin-2-yl)amino)pyrrolidine-1-carbonyl)phenyl)acrylamide

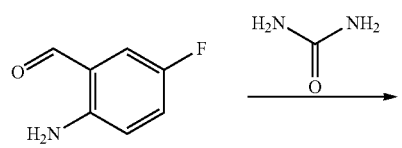

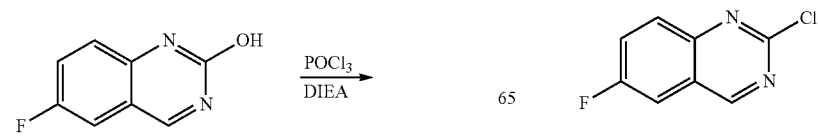

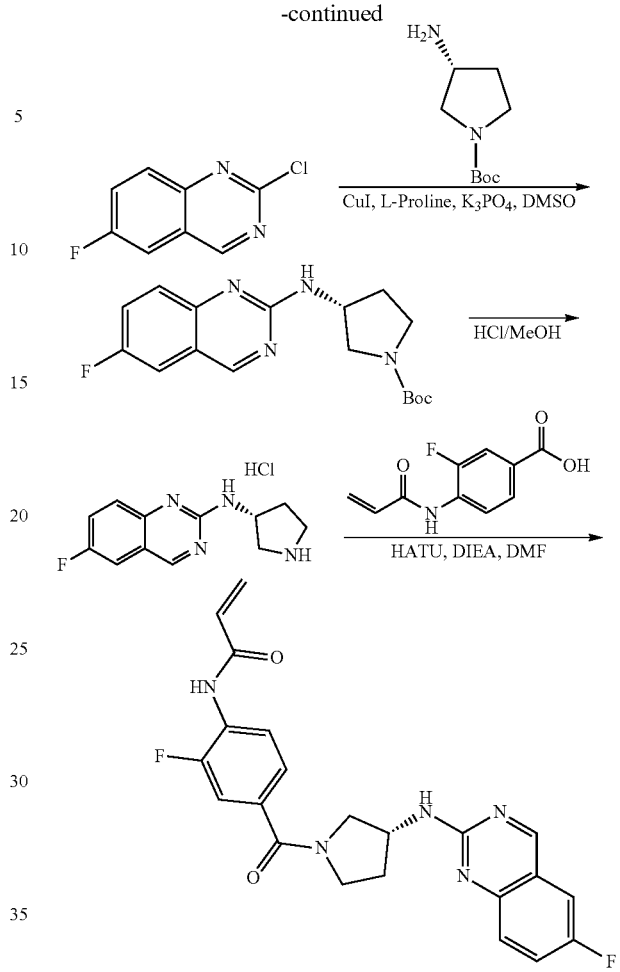

Step 1: 6-fluoroquinazolin-2-ol

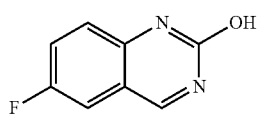

A mixture of 2-amino-5-fluorobenzaldehyde (5.7 g, 41.1 mmol) and urea (24.0 g, 40.2 mmol) was stirred at 140° C. overnight in a sealed tube. The reaction mixture was cooled to 100° C. and diluted with H$_2$O (100 mL) and filtered. The filtered cake was dried to afford 6-fluoroquinazolin-2-ol (6.7 g, 100%) as a yellow solid. [M+H] Calc'd for C$_8$H$_5$FN$_2$O, 165.0; Found, 165.0.

Step 2: 2-chloro-6-fluoroquinazoline

A mixture of 6-fluoroquinazolin-2-ol (2.0 g, 12.2 mmol) and DIPEA (3.1 g, 24.4 mmol) in POCl$_3$ (20 mL) was stirred at 125° C. for 2 hours. The reaction mixture was cooled to r.t and concentrated in vacuo. The residue was diluted with DCM (100 mL) and poured into hot water (100 mL) and separated. The aqueous was extracted with DCM (100 mL). The combined organic phase was concentrated to afford 2-chloro-6-fluoroquinazoline (1.8 g, 82%) as a yellow solid. [M+H] Calc'd for C$_8$H$_4$ClFN$_2$, 183.0; Found, 183.0.

Step 3: (R)-tert-butyl 3-((6-fluoroquinazolin-2-yl)amino)pyrrolidine-1-carboxylate

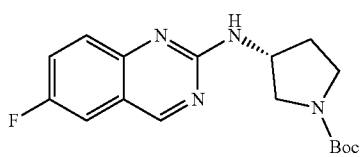 [SMILES: CC(C)(C)OC(=O)N1CC[C@@H](Nc2ncc3cc(F)ccc3n2)C1]

A mixture of 2-chloro-6-fluoroquinazoline (800 mg, 4.4 mmol), (R)-tert-butyl 3-aminopyrrolidine-1-carboxylate (818 mg, 4.4 mmol), CuI (418 mg, 2.2 mmol), K$_3$PO$_4$ (1.9 g, 8.8 mmol) and L-proline (506 mg, 4.4 mmol) in DMSO (10 mL) was stirred at 50° C. for 18 hours. The reaction mixture was cooled to r.t, diluted with water (50 mL) and extracted with EA (50*2 mL). The combined organic phase was washed with NH$_3$H$_2$O (50 mL) and concentrated. The residue was purified by flash chromatography on silica gel (petroleum ether/EtOAc=2/1) to afford (R)-tert-butyl 3-((6-fluoroquinazolin-2-yl)amino)pyrrolidine-1-carboxylate (100 mg, 7%) as a white solid. [M+H] Calc'd for C$_{17}$H$_{21}$FN$_4$O$_2$, 333.1; Found, 333.1.

Step 4: (R)-6-fluoro-N-(pyrrolidin-3-yl)quinazolin-2-amine hydrochloride

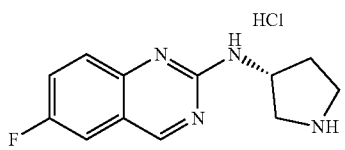 [SMILES: Cl ; Fc1ccc2nc(N[C@@H]3CCNC3)ncc2c1]

To a solution of (R)-tert-butyl 3-((6-fluoroquinazolin-2-yl)amino)pyrrolidine-1-carboxylate (100 mg, 0.3 mmol) in MeOH (2 mL) was added HCl/MeOH (1 M, 2 mL). The reaction mixture was stirred at rt for 2 hours. Then the mixture was concentrated to afford (R)-6-fluoro-N-(pyrrolidin-3-yl)quinazolin-2-amine hydrochloride (70 mg, 100%) as yellow oil. [M+H] Calc'd for C$_{12}$H$_{13}$FN$_4$, 233.1; Found, 233.1.

Step 5: (R)—N-(2-fluoro-4-(3-((6-fluoroquinazolin-2-yl)amino)pyrrolidine-1-carbonyl)phenyl)acrylamide

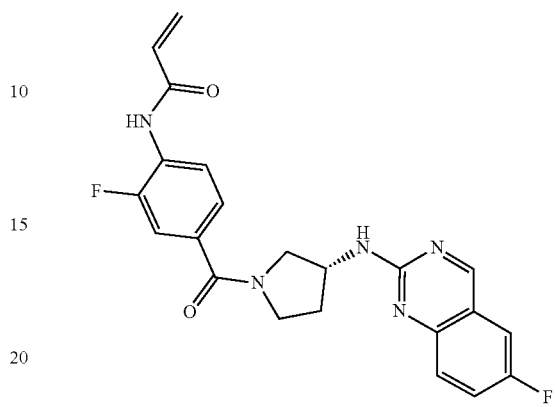

A mixture of (R)-6-fluoro-N-(pyrrolidin-3-yl)quinazolin-2-amine hydrochloride (100 mg, 0.43 mmol), 4-acrylamido-3-fluorobenzoic acid (90 mg, 0.43 mmol), HATU (179 mg, 0.47 mmol) and DIPEA (445 mg, 3.45 mmol) in DMF (2 mL) was stirred at 25° C. overnight. The mixture was concentrated and the residue was by flash chromatography on silica gel (DCM/MeOH=20/1) to afford (R)—N-(2-fluoro-4-(3-((6-fluoroquinazolin-2-yl)amino)pyrrolidine-1-carbonyl)phenyl)acrylamide (63 mg, 35%) as a white solid. $^1$H NMR (400 MHz, CD$_3$OD): δ 2.07-2.19 (m, 1H), 2.29-2.41 (m, 1H), 3.54-4.04 (m, 4H), 4.55-4.73 (m, 1H), 5.78-5.83 (m, 1H), 6.36-6.60 (m, 2H), 7.35-7.64 (m, 5H), 8.13-8.24 (m, 1H), 9.01 (s, 0.5H), 9.06 (s, 0.5H). [M+H] Calc'd for C$_{22}$H$_{19}$F$_2$N$_5$O$_2$, 424.1; Found, 424.1.

Example 70: Synthesis of (R)—N-(4-(3-(quinazolin-2-ylamino)pyrrolidine-1-carbonyl)phenyl)propiolamide

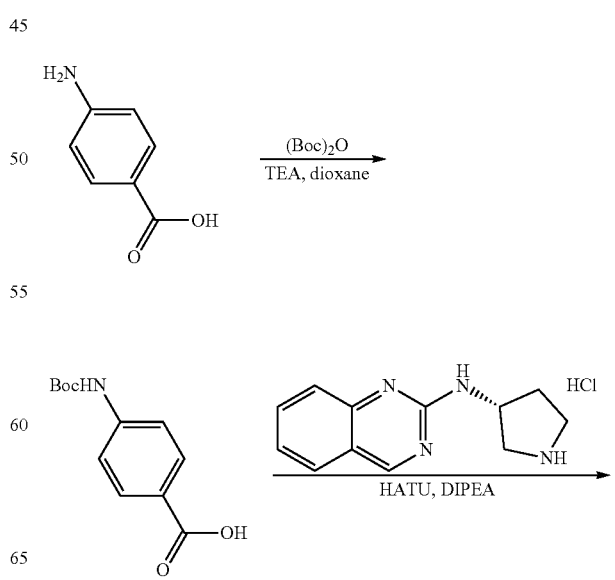

-continued

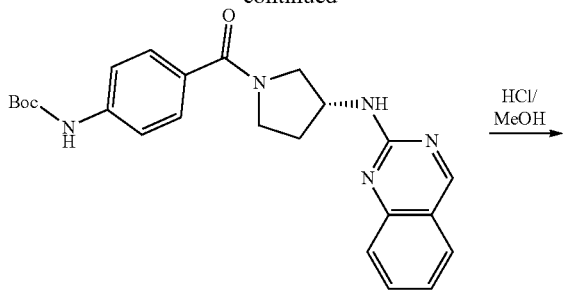

Step 2: (R)-tert-butyl (4-(3-(quinazolin-2-ylamino)pyrrolidine-1-carbonyl)phenyl)carbamate

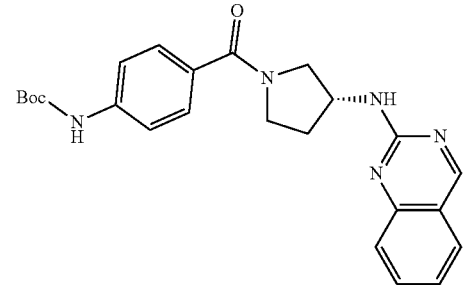 [SMILES: CC(C)(C)OC(=O)Nc1ccc(C(=O)N2CC[C@@H](Nc3ncc4ccccc4n3)C2)cc1]

The title compound was prepared in 86% yield from 4-((tert-butoxycarbonyl)amino)benzoic acid using general procedure of (R)—N-(2-fluoro-4-(3-((6-fluoroquinazolin-2-yl)amino)pyrrolidine-1-carbonyl)phenyl)acrylamide. [M+H] Calc'd for $C_{24}H_{27}N_5O_3$, 434.2; Found, 434.2.

Step 3: (R)-(4-aminophenyl)(3-(quinazolin-2-ylamino)pyrrolidin-1-yl)methanone

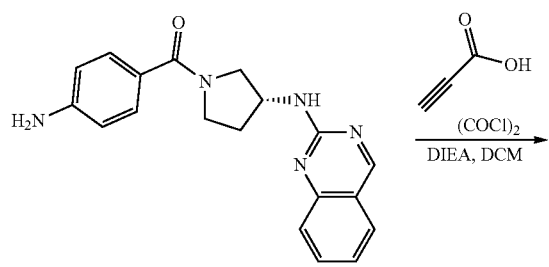

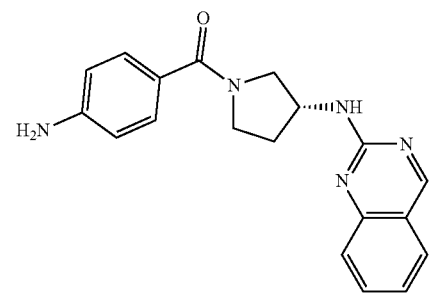 [SMILES: Nc1ccc(C(=O)N2CC[C@@H](Nc3ncc4ccccc4n3)C2)cc1]

The title compound was prepared in 90% yield from (R)-tert-butyl (4-(3-(quinazolin-2-ylamino)pyrrolidine-1-carbonyl)phenyl)carbamate using general procedure of (R)-6-fluoro-N-(pyrrolidin-3-yl)quinazolin-2-amine hydrochloride. [M+H] Calc'd for $C_{19}H_{19}N_5O$, 334.2; Found, 334.2.

Step 4: (R)—N-(4-(3-(quinazolin-2-ylamino)pyrrolidine-1-carbonyl)phenyl)propiolamide

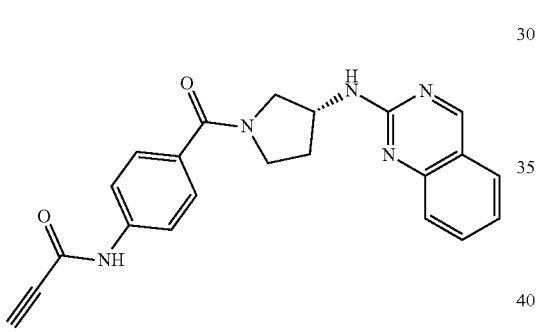

Step 1: 4-((tert-butoxycarbonyl)amino)benzoic Acid

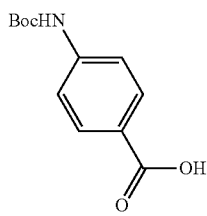

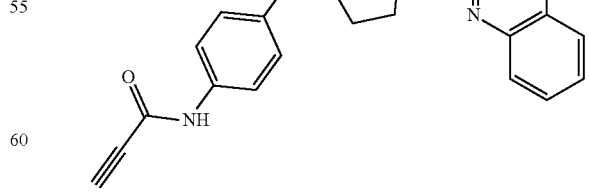

To a solution of 4-aminobenzoic acid (5.0 g, 36.5 mmol) and TEA (7.4 g, 73.0 mmol) in dioxane (45 mL) and $H_2O$ (20 mL) was added di-tert-butyl dicarbonate (15.9 g, 73.0 mmol) at rt. The solution was stirred at RT overnight. The solution was concentrated to afford 4-((tert-butoxycarbonyl)amino)benzoic acid (7.0 g, 81%) as a white solid. [M+H] Calc'd for $C_{12}H_{15}NO_4$, 238.1; Found, 238.1.

To a solution of propiolic acid (13 mg, 0.18 mmol) in DCM (1 mL) was added Oxalyl chloride (25 mg, 0.2 mmol) and 1 drop of DMF at 0° C. The solution was stirred at 0° C. for 5 minutes to afford B1. To a solution of (R)-(4- aminophenyl)(3-(quinazolin-2-ylamino)pyrrolidin-1-yl)methanone (30 mg, 0.09 mmol) and DIPEA (23 mg, 0.18 mmol) in DCM (0.5 mL) was added a solution of B1 at 0° C. The solution was stirred at 0° C. for 5 minutes. The solution was diluted with EtOAc (80 mL), washed with water (20*3 mL) and brine (200 mL), dried over $Na_2SO_4$ and filtered. The filtrate was concentrated and the residue was purified by prep-TLC (DCM/MeOH=15/1) and prep-HPLC to afford (R)—N-(4-(3-(quinazolin-2-ylamino)pyrrolidine-1-carbonyl)phenyl)propiolamide (7 mg, 20%) as a white solid. $^1$H NMR (400 MHz, DMSO-$d_6$): δ 1.96-2.07 (m, 1H), 2.16-2.32 (m, 1H), 3.38-3.58 (m, 2H), 3.64-3.71 (m, 1H), 3.82-3.85 (m, 1H), 4.43-4.58 (m, 2H), 7.20-7.28 (m, 1H), 7.40-7.55 (m, 3H), 7.60-7.83 (m, 5H), 9.11 (s, 0.5H), 9.16 (s, 0.5H), 10.94 (br s, 1H). [M+H] Calc'd for $C_{22}H_{19}N_5O_2$, 386.1; Found, 386.1.

Example 71: Synthesis of (R)—N-(2-methoxy-4-(3-(quinazolin-2-ylamino)pyrrolidine-1-carbonyl)phenyl)acrylamide

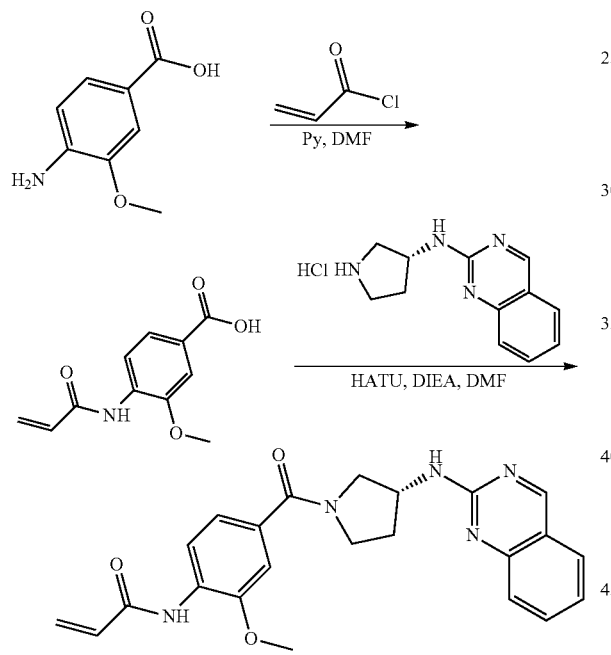

Step 1: 4-acrylamido-3-methoxybenzoic Acid

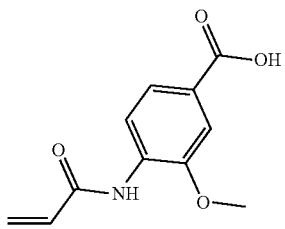 [SMILES: C=CC(=O)Nc1ccc(C(=O)O)cc1OC]

The title compound was prepared in 31% yield from 4-amino-3-methoxybenzoic acid using general procedure of 4-acrylamido-3-methoxybenzoic acid. [M+H] Calc'd for $C_{11}H_{11}NO_4$, 221.0; Found, 222.1.

Step 2: (R)—N-(2-methoxy-4-(3-(quinazolin-2-ylamino)pyrrolidine-1-carbonyl)phenyl)acrylamide

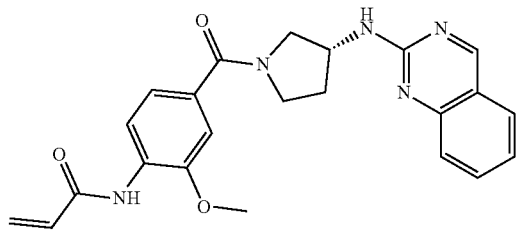 [SMILES: C=CC(=O)Nc1ccc(C(=O)N2CC[C@@H](Nc3ncc4ccccc4n3)C2)cc1OC]

The title compound was prepared in 14% yield from 4-acrylamido-3-methoxybenzoic acid using general procedure of (R)—N-(2-methoxy-4-(3-(quinazolin-2-ylamino)pyrrolidine-1-carbonyl)phenyl)acrylamide. $^1$H NMR (400 MHz, DMSO-$d_6$): δ 1.86-1.92 (m, 1H), 2.23-2.50 (m, 1H), 3.49-3.69 (m, 3H), 3.70-3.85 (m, 4H), 4.45-4.46 (m, 1H), 568-5.74 (m, 1H), 6.23-6.27 (m, 1H), 6.70-6.74 (m, 1H), 7.07-7.52 (m, 7H), 8.12-8.24 (m, 1H), 9.11-9.31 (m, 1H). 9.47-9.51 (m, 1H). [M+H] Calc'd for $C_{23}H_{23}N_5O_3$, 418.18; Found, 418.2.

Example 72: Synthesis of (R)—N-(2-methyl-4-(3-(quinazolin-2-ylamino)pyrrolidine-1-carbonyl)phenyl)acrylamide

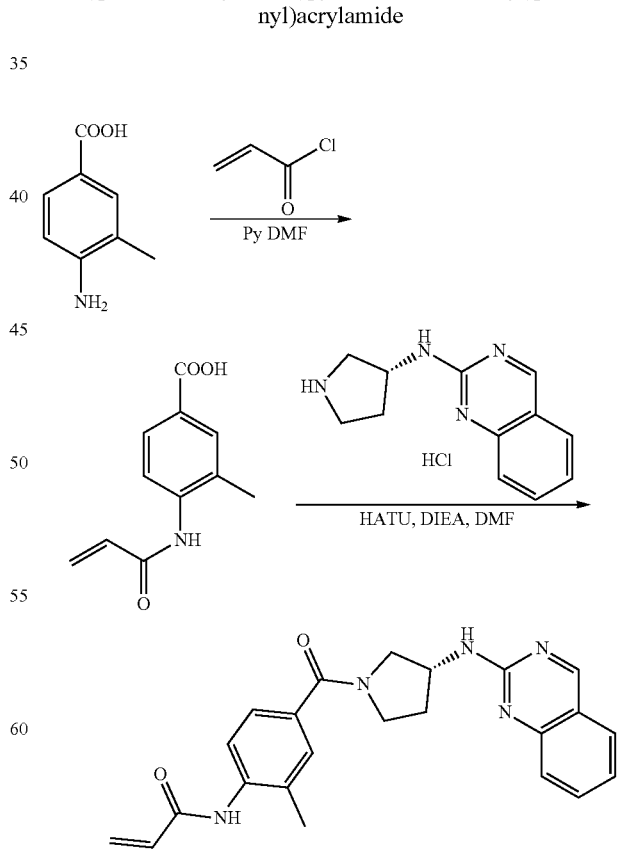

201

Step 1: 4-acrylamido-3-methylbenzoic Acid

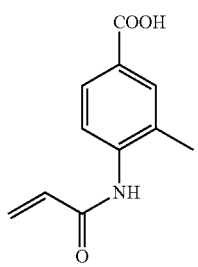

To a solution of 4-amino-3-methylbenzoic acid (1.0 g, 6.6 mmol) and Py (1 mL) in DMF (15 mL) was dropwised acryloyl chloride (1.7 g, 13.2 mmol). The mixture was stirred at RT for 3 h. The residue was diluted with water (30 mL) and extracted with DCM (30 mL*3). The combined organic layer was washed with brine (20 mL), dried over $Na_2SO_4$, filtered and concentrated in vacuo. The residue was purified by column (PE:EA=1:1) to afford 4-acrylamido-3-methylbenzoic acid (400 mg, 29%) as a white solid. [M+H] Calc'd for $C_{11}H_{12}NO_3$, 206.0; Found, 206.0.

Step 2: (R)-tert-butyl 3-(quinazolin-2-ylamino)piperidine-1-carboxylate

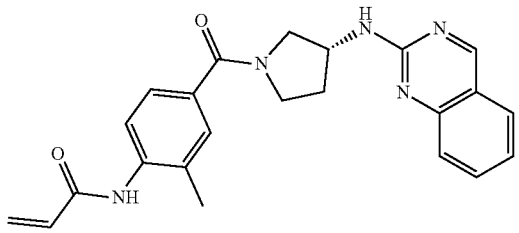 [SMILES: C=CC(=O)Nc1ccc(C(=O)N2CC[C@@H](Nc3ncc4ccccc4n3)C2)cc1C]

A mixture of 4-acrylamido-3-methylbenzoic acid (100 mg, 0.49 mmol), (R)—N-(pyrrolidin-3-yl)quinazolin-2-amine hydrochloride (171 mg, 0.49 mmol), HATU (223 mg, 0.59 mmol) and DIEA (189 mg, 1.47 mmol) in DMF (5 mL) was stirred at RT overnight. The mixture was diluted with water (10 mL) and extracted with DCM (10 mL*3). The combined organic layer was washed with brine (20 mL), dried over $Na_2SO_4$, filtered and concentrated in vacuo. The residue was purified by prep-HPLC to afford (R)-tert-butyl 3-(quinazolin-2-ylamino)piperidine-1-carboxylate (101.52 mg, 51%) as a white solid. $^1$H NMR (400 MHz, DMSO-$d_6$): δ 1.93-2.08 (m, 1H), 2.20-2.26 (m, 4H), 3.42-3.87 (m, 4H), 4.46-4.60 (m, 1H), 5.76 (t, J=9.2 Hz, 1H), 6.22-6.30 (m, 1H), 6.51-6.58 (m, 1H), 7.21-7.82 (m, 8H), 9.11 (s, 0.5H), 9.16 (s, 0.5H), 9.47 (s, 0.5H), 9.52 (s, 0.5H). [M+H] Calc'd for $C_{23}H_{24}N_5O_2$, 402.1; Found, 402.1.

202

Example 73: Synthesis of (R)—N-(3-methoxy-4-(3-(quinazolin-2-ylamino)pyrrolidine-1-carbonyl)phenyl)acrylamide

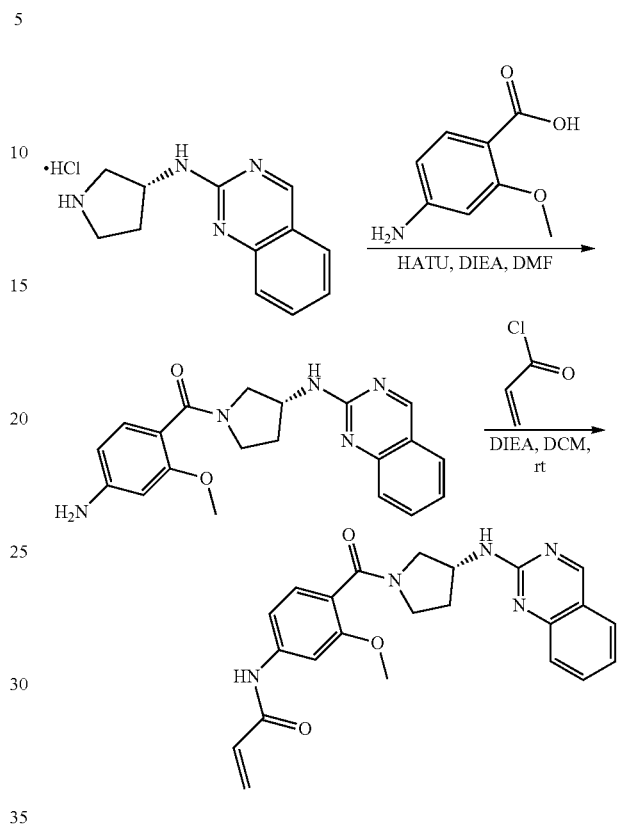

Step 1: (R)-(4-amino-2-methoxyphenyl)(3-(quinazolin-2-ylamino)pyrrolidin-1-yl)methanone

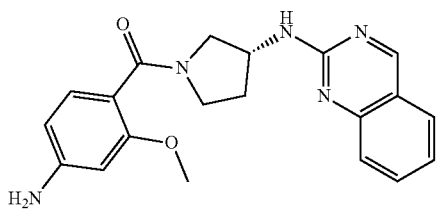 [SMILES: COc1cc(N)ccc1C(=O)N1CC[C@@H](Nc2ncc3ccccc3n2)C1]

A mixture of 4-amino-2-methoxybenzoic acid (500 mg, 2.99 mmol), (R)—N-(pyrrolidin-3-yl)quinazolin-2-amine hydrochloride (824 mg, 3.29 mmol), HATU (1.36 g, 3.58 mmol) and DIEA (2.46 mL, 14.95 mmol) in DMF (20 mL) was stirred at rt overnight. The mixture was diluted with water (20 mL) and extracted with DCM (20 mL*3). The combined organic layer was washed with brine (30 mL), dried over $Na_2SO_4$, filtered and concentrated in vacuo. The residue was purified by by silica gel chromatography (DCM/MeOH=20/1) to afford (R)-(4-amino-2-methoxyphenyl)(3-(quinazolin-2-ylamino)pyrrolidin-1-yl)methanone (750 mg, 69%) as a yellow solid. [M+H] Calc'd for $C_{20}H_{21}N_5O_2$, 364.1; Found, 364.1.

Step 2: (R)—N-(3-methoxy-4-(3-(quinazolin-2-ylamino)pyrrolidine-1-carbonyl)phenyl)acrylamide

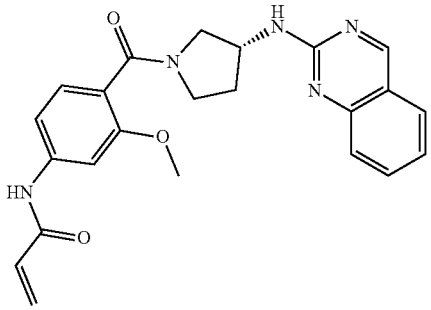 [SMILES: C=CC(=O)Nc1ccc(C(=O)N2CC[C@@H](Nc3ncc4ccccc4n3)C2)c(OC)c1]

A mixture of (R)-(4-amino-2-methoxyphenyl)(3-(quinazolin-2-ylamino)pyrrolidin-1-yl)methanone (200 mg, 0.55 mmol) and DIEA (0.45 mL, 2.75 mmol) in DCM (30 mL) was stirred at 0° C. under nitrogen atmosphere. A solution of acryloyl chloride (45 mg, 0.49.00 mmol) in DCM was added dropwise and the mixture was warmed to rt, and stirred for 3 h. The mixture was concentrated and purified by prep-HPLC to afford (R)—N-(3-methoxy-4-(3-(quinazolin-2-ylamino)pyrrolidine-1-carbonyl)phenyl)acrylamide (36.2 mg, 15.7%) as a white solid. $^1$H NMR (400 MHz, DMSO-d$_6$): δ 1.94-2.04 (m, 1H), 2.14-2.25 (m, 1H), 3.19-3.21 (m, 1H), 3.37-3.54 (m, 2H), 3.66-3.88 (m, 4H), 4.41-4.55 (m, 1H), 5.72-5.80 (m, 1H), 6.23-6.49 (m, 2H), 7.10-7.28 (m, 3H), 7.40-7.52 (m, 2H), 7.36-7.85 (m, 3H), 9.09-9.157 (m, 1H), 10.22-10.29 (m, 1H). [M+H] Calc'd for $C_{23}H_{23}N_5O_3$, 418.1; Found, 418.1.

Example 74: Synthesis of (R)—N-methyl-N-(4-(3-(quinazolin-2-ylamino)pyrrolidine-1-carbonyl)phenyl)acrylamide

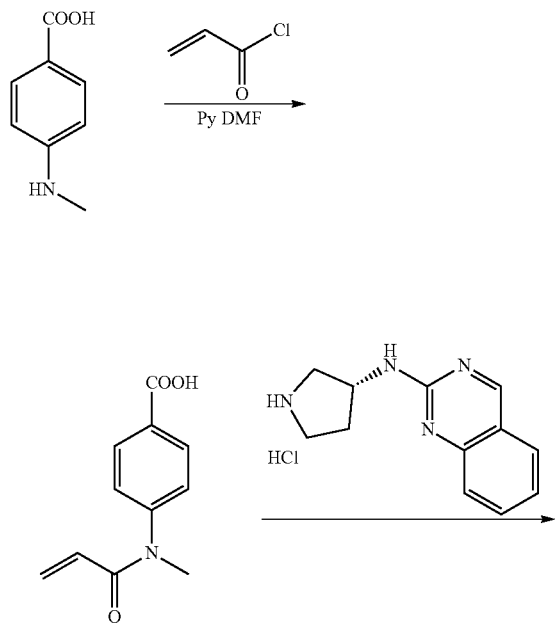

Step 1: 4-(N-methylacrylamido)benzoic Acid

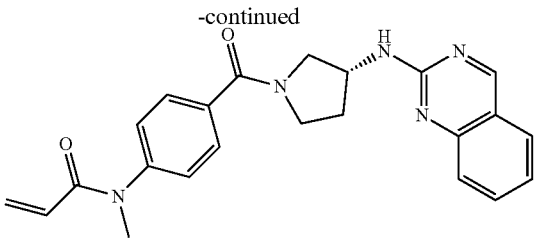

The title compound was prepared in 24% yield from 4-(methylamino)benzoic acid using general procedure of 4-acrylamido-3-methylbenzoic acid. [M+H] Calc'd for $C_{11}H_{12}NO_3$, 206.0; Found, 206.0.

Step 2: (R)—N-methyl-N-(4-(3-(quinazolin-2-ylamino)pyrrolidine-1-carbonyl)phenyl)acrylamide

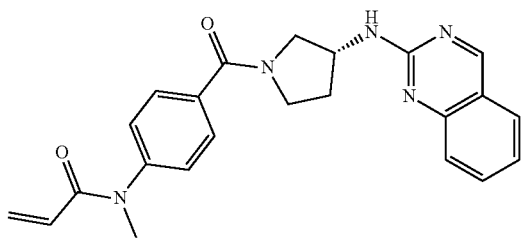 [SMILES: C=CC(=O)N(C)c1ccc(C(=O)N2CC[C@@H](Nc3ncc4ccccc4n3)C2)cc1]

The title compound was prepared in 67% yield from 4-(N-methylacrylamido)benzoic acid using general procedure of (R)-tert-butyl 3-(quinazolin-2-ylamino)piperidine-1-carboxylate. $^1$H NMR (400 MHz, DMSO-d$_6$): δ 1.98-2.14 (m, 1H), 2.20-2.29 (m, 1H), 3.26 (d, J=16.0 Hz, 3H), 3.45-3.92 (m, 4H), 4.47-4.69 (m, 1H), 5.54-5.63 (m, 1H), 5.99-6.21 (m, 2H), 7.31-7.38 (m, 3H), 7.51-7.64 (m, 3H), 7.75-7.93 (m, 2H), 8.43 (br s, 1H), 9.24 (s, 0.5H), 9.28 (s, 0.5H). [M+H] Calc'd for $C_{23}H_{24}N_5O_2$, 402.1; Found, 402.1.

Example 75: Synthesis of (R)—N-(2-fluoro-6-methyl-4-(3-(quinazolin-2-ylamino)pyrrolidine-1-carbonyl)phenyl)acrylamide

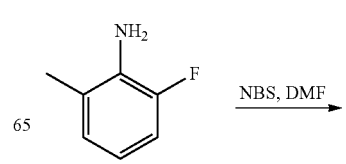

205

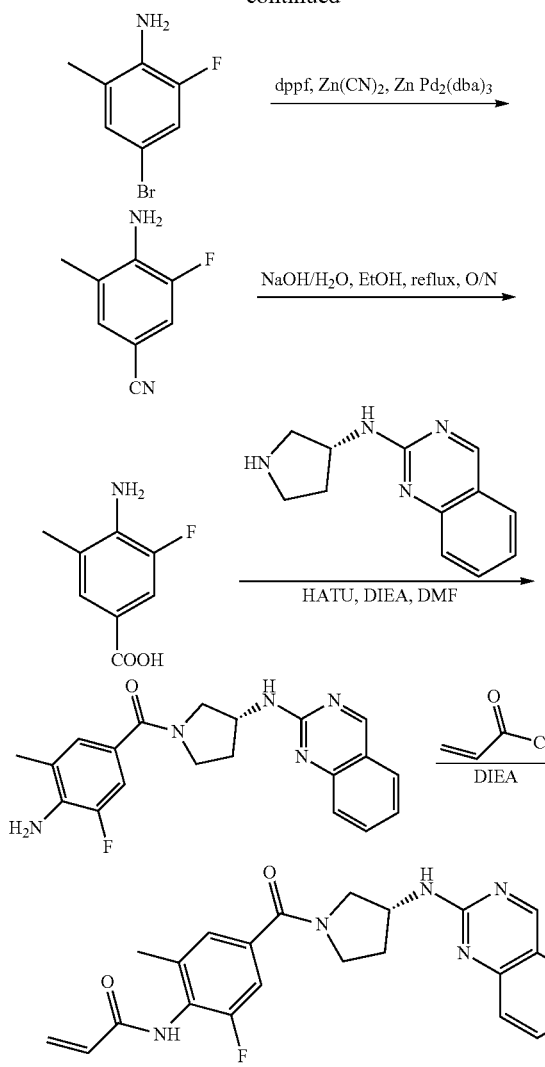

Step 1: 4-bromo-2-fluoro-6-methylaniline

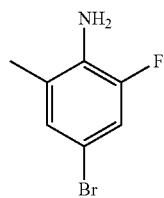

A mixture of 2-fluoro-6-methylaniline (5.0 g, 40.0 mmol) and NBS (7.8 g, 44.0 mmol) in DMF (45 mL) was stirred at rt for 1 h. The mixture was diluted with water (100 mL) and extracted with DCM (50 mL*3). The combined organic layer was washed with brine (50 mL), dried over Na$_2$SO$_4$, filtered and concentrated in vacuo. The residue was purified by column (PE:EA=1:4/1) to afford 4-bromo-2-fluoro-6-methylaniline (6.8 g, 84%) as a brown solid.

206

Step 2: 4-amino-3-fluoro-5-methylbenzonitrile

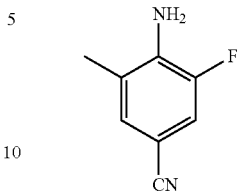

A mixture of 4-bromo-2-fluoro-6-methylaniline (300 mg, 1.48 mmol), Zn(CN)$_2$ (432 mg, 3.69 mmol), Zn (24 mg, 0.37 mmol), dppf (123 mg, 0.22 mmol) and Pd$_2$(dba)$_3$ (68 mg, 0.12 mmol) in DMA (4 mL) was stirred at 130° C. overnight. The mixture was cooled, diluted with water (50 mL) and extracted with EA (15 mL*3). The combined organic layer was washed with brine (50 mL), dried over Na$_2$SO$_4$, filtered and concentrated in vacuo. The residue was purified by column (PE:EA=1~9/1) to afford 4-amino-3-fluoro-5-methylbenzonitrile (171 mg, 80%) as a white solid.

Step 3: 4-amino-3-fluoro-5-methylbenzoic Acid

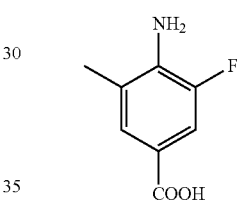

A mixture of 4-amino-3-fluoro-5-methylbenzonitrile (176 mg, 1.17 mmol) in NaOH/H$_2$O (3.00 mL, 1M, 3.00 mmol) and EtOH (0.3 mL) was stirred at reflux overnight. The solution was cooled and washed with MTBE (10 mL). The aqueous phase was adjusted to pH 3-4 with 2M HCl and filtered to afford 4-amino-3-fluoro-5-methylbenzoic acid (198 mg, 100%) as a white solid.

Step 4: (R)-(4-amino-3-fluoro-5-methylphenyl)(3-(quinazolin-2-ylamino)pyrrolidin-1-yl)methanone

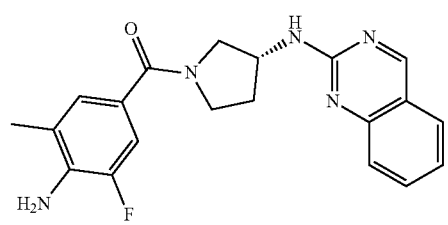 [SMILES: Cc1cc(C(=O)N2CC[C@@H](Nc3ncc4ccccc4n3)C2)cc(F)c1N]

A mixture of 4-amino-3-fluoro-5-methylbenzoic acid (200 mg, 1.18 mmol), (R)—N-(pyrrolidin-3-yl)quinazolin-2-amine (296 mg, 1.18 mmol), HATU (495 mg, 1.30 mmol) and DIEA (458 mg, 3.55 mmol) in DMF (5 mL) was stirred at RT overnight. The mixture was diluted with water (50 mL) and extracted with DCM (20 mL*3). The combined organic layer was washed with brine (20 mL), dried over Na$_2$SO$_4$, filtered and concentrated in vacuo. The residue was purified by column (PE:EA=1/2) to afford (R)-(4-amino-3-fluoro-5-methylphenyl)(3-(quinazolin-2-ylamino)pyrrolidin-1-yl)methanone (295 mg, 68%) as yellow oil. [M+H] Calc'd for $C_{20}H_{20}FN_5O$, 366.1; Found, 366.1.

Step 5: (R)—N-(2-fluoro-6-methyl-4-(3-(quinazolin-2-ylamino)pyrrolidine-1-carbonyl)phenyl)acrylamide

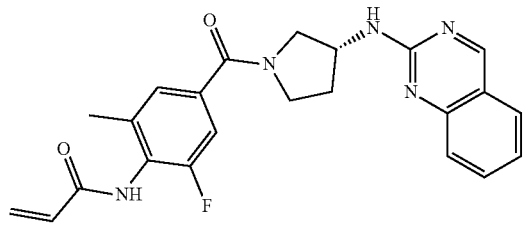 [SMILES: C=CC(=O)Nc1c(C)cc(C(=O)N2CC[C@@H](Nc3ncc4ccccc4n3)C2)cc1F]

To a solution of (R)-(4-amino-3-fluoro-5-methylphenyl)(3-(quinazolin-2-ylamino)pyrrolidin-1-yl)methanone (295 mg, 0.81 mmol) and DIEA (0.5 mL) in DCM (30 mL) was added dropwise acryloyl chloride (73 mg, 0.808 mmol) at 0° C. The mixture was stirred at rt for 4 h. The mixture concentrated in vacuo. The residue was purified by prep-HPLC to afford (R)—N-(2-fluoro-6-methyl-4-(3-(quinazolin-2-ylamino)pyrrolidine-1-carbonyl)phenyl)acrylamide (110 mg, 40%) as white solid. $^1$H NMR (400 MHz, CD$_3$OD): δ 2.03-2.37 (m, 4H), 2.40 (s, 1H), 3.58-3.72 (m, 3H), 3.81-3.88 (m, 1H), 4.57-4.78 (m, 1H), 5.79-5.84 (m, 1H), 6.43-6.62 (m, 2H), 7.05 (s, 1H), 7.09-7.15 (m, 1H), 7.24-7.30 (m, 1H), 7.53-7.58 (m, 1H), 7.68-7.79 (m, 2H), 9.02-9.06 (m, 1H). [M+H] Calc'd for $C_{23}H_{22}FN_5O_2$, 420.1; Found, 420.1.

Example 76: Synthesis of (R)—N-(2-fluoro-4-(3-((6-fluoroquinazolin-2-yl)amino)pyrrolidine-1-carbonyl)phenyl)acrylamide

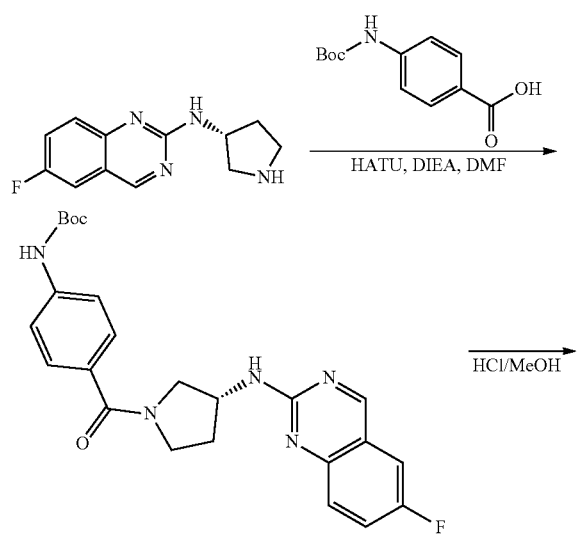

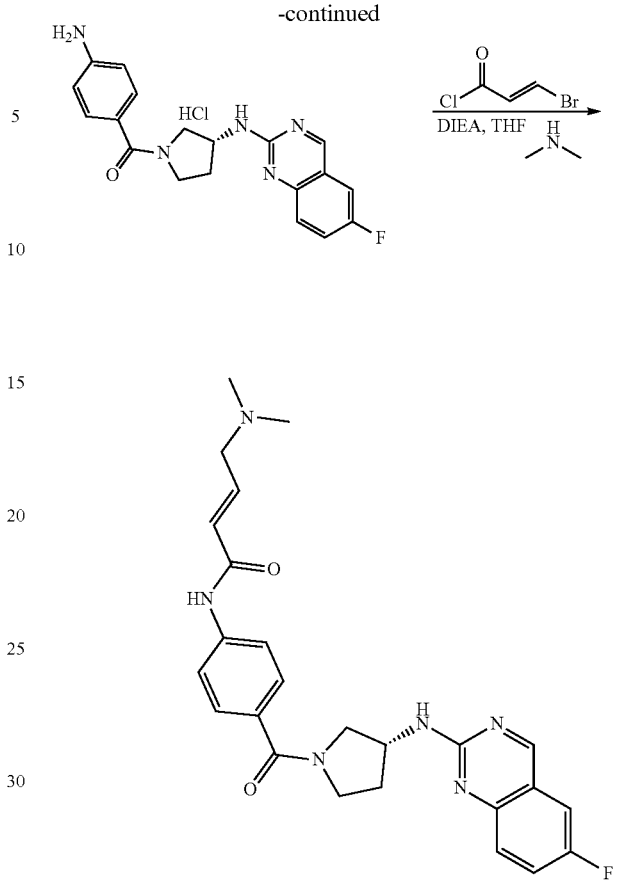

Step 1: (R)-tert-butyl (4-(3-((6-fluoroquinazolin-2-yl)amino)pyrrolidine-1-carbonyl)phenyl)carbamate

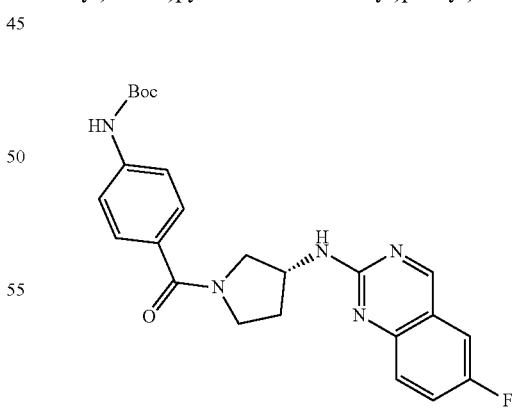

The title compound was prepared in 96% yield from (R)-6-fluoro-N-(pyrrolidin-3-yl)quinazolin-2-amine using general procedure of (R)—N-(2-fluoro-4-(3-((6-fluoroquinazolin-2-yl)amino)pyrrolidine-1-carbonyl)phenyl)acrylamide. [M+H] Calc'd for $C_{24}H_{26}FN_5O_3$, 452.2; Found, 452.2.

Step 2: (R)-(4-aminophenyl)(3-((6-fluoroquinazolin-2-yl)amino)pyrrolidin-1-yl)methanone hydrochloride

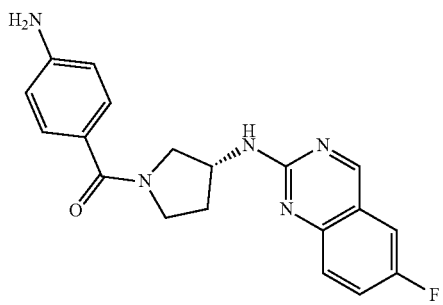 [SMILES: Nc1ccc(C(=O)N2CC[C@@H](Nc3ncc4cc(F)ccc4n3)C2)cc1]

The title compound was prepared in 99% yield from (R)-tert-butyl (4-(3-((6-fluoroquinazolin-2-yl)amino)pyrrolidine-1-carbonyl)phenyl)carbamate using general procedure of (R)-6-fluoro-N-(pyrrolidin-3-yl)quinazolin-2-amine hydrochloride. [M+H] Calc'd for $C_{19}H_{18}FN_5O$, 352.1; Found, 352.1.

Step 3: (R,E)-4-(dimethylamino)-N-(4-(3-((6-fluoroquinazolin-2-yl)amino)pyrrolidine-1-carbonyl)phenyl)but-2-enamide

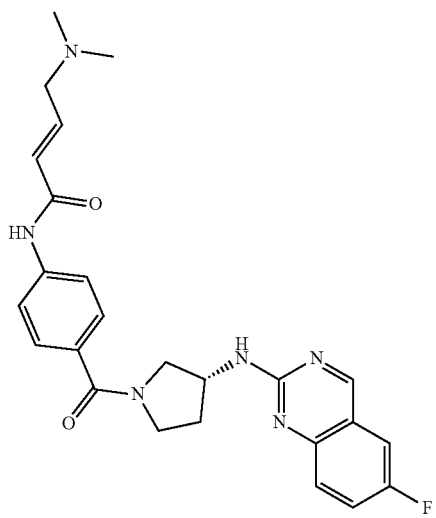 [SMILES: CN(C)C/C=C/C(=O)Nc1ccc(C(=O)N2CC[C@@H](Nc3ncc4cc(F)ccc4n3)C2)cc1]

To a solution of (R)-(4-aminophenyl)(3-((6-fluoroquinazolin-2-yl)amino)pyrrolidin-1-yl)methanone hydrochloride (100 mg, 0.3 mmol) and DIPEA (310 mg, 2.4 mmol) in THF (2 mL) was added (E)-3-bromoacryloyl chloride (110 mg, 0.6 mmol). The mixture was stirred at rt for 2 hours. A solution of dimethylamine (27 mg, 0.6 mmol) in THF (1 mL) was added to the mixture. The mixture was stirred at rt overnight. The reaction mixture concentrated and the residue was purified by prep-TLC to afford (R,E)-4-(dimethylamino)-N-(4-(3-((6-fluoroquinazolin-2-yl)amino)pyrrolidine-1-carbonyl)phenyl)but-2-enamide (14 mg, 10%) as a white solid. $^1$H NMR (400 MHz, DMSO-$d_6$): δ 2.03-2.07 (m, 1H), 2.21-2.32 (m, 7H), 3.12-3.24 (m, 2H), 3.41-3.56 (m, 2H), 3.64-3.71 (m, 1H), 3.82-3.87 (m, 1H), 4.42-4.57 (m, 1H), 6.29-6.35 (m, 1H), 6.72-6.76 (m, 1H), 7.48-7.77 (m, 8H), 9.10 (s, 0.5H), 9.15 (s, 0.5H), 10.30-10.33 (m, 1H). [M+H] Calc'd for $C_{25}H_{27}FN_6O_2$, 463.2; Found, 463.2.

Example 77: Synthesis of (R)—N-(4-(3-(quinazolin-2-ylamino)pyrrolidine-1-carbonyl)phenyl)but-2-ynamide

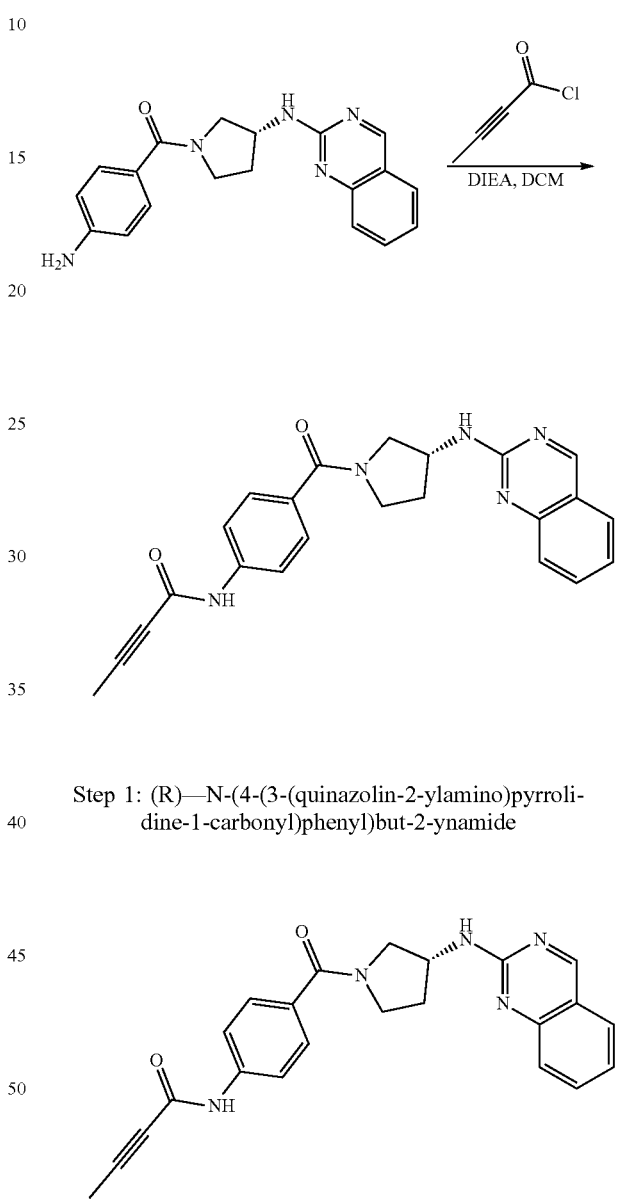

Step 1: (R)—N-(4-(3-(quinazolin-2-ylamino)pyrrolidine-1-carbonyl)phenyl)but-2-ynamide The title compound was prepared in 8% yield from (R)-(4-aminophenyl)(3-(quinazolin-2-ylamino)pyrrolidin-1-yl)methanone using general procedure of (R)—N-(4-(3-(quinazolin-2-ylamino)pyrrolidine-1-carbonyl)phenyl)propiolamide. $^1$H NMR (400 MHz, DMSO-$d_6$): δ 1.93-2.07 (m, 4H), 2.18-2.21 (m, 1H), 3.50-3.56 (m, 2H), 3.65-3.74 (m, 1H), 3.83-3.85 (m, 1H), 4.43-4.61 (m, 1H), 7.22-7.26 (m, 1H), 7.41-7.53 (m, 3H), 7.59-7.83 (m, 5H), 9.10 (s, 0.5H), 9.16 (s, 0.5H), 10.74 (s, 0.5H), 10.77 (s, 0.5H). [M+H] Calc'd for $C_{23}H_{21}N_5O_2$, 400.1; Found, 400.1.

Example 78: Synthesis of (R)—N-(4-(3-(quinazolin-2-ylamino)pyrrolidine-1-carbonyl)phenyl)but-2-ynamide

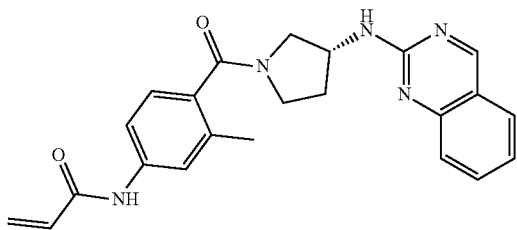 [SMILES: C=CC(=O)Nc1ccc(C(=O)N2CC[C@@H](Nc3ncc4ccccc4n3)C2)c(C)c1]

The title compound was prepared in 26% yield from 4-acrylamido-2-methylbenzoic acid using general procedure of (R)—N-(2-fluoro-4-(3-(quinazolin-2-ylamino)pyrrolidine-1-carbonyl)phenyl)acrylamide. $^1$H NMR (400 MHz, DMSO-$d_6$): δ 1.94-2.07 (m, 1H), 2.20-2.25 (m, 4H), 3.11-3.14 (m, 1H), 3.34-3.36 (m, 1H), 3.48-3.59 (m, 1H), 3.71-3.88 (m, 1H), 4.43-4.58 (m, 1H), 5.73-5.78 (m, 1H), 6.21-6.29 (m, 1H), 6.45-6.48 (m, 1H), 7.14-7.26 (m, 2H), 7.40-7.56 (m, 3H), 7.65-7.83 (m, 3H), 9.11 (s, 0.5H), 9.16 (s, 0.5H), 10.14 (s, 0.5H), 10.19 (s, 0.5H). [M+H] Calc'd for $C_{23}H_{21}N_5O_2$, 402.0; Found, 402.0.

Example 79: (R)-1-(6-(3-(quinazolin-2-ylamino)pyrrolidine-1-carbonyl)-3,4-dihydroquinolin-1(2H)-yl)prop-2-en-1-one

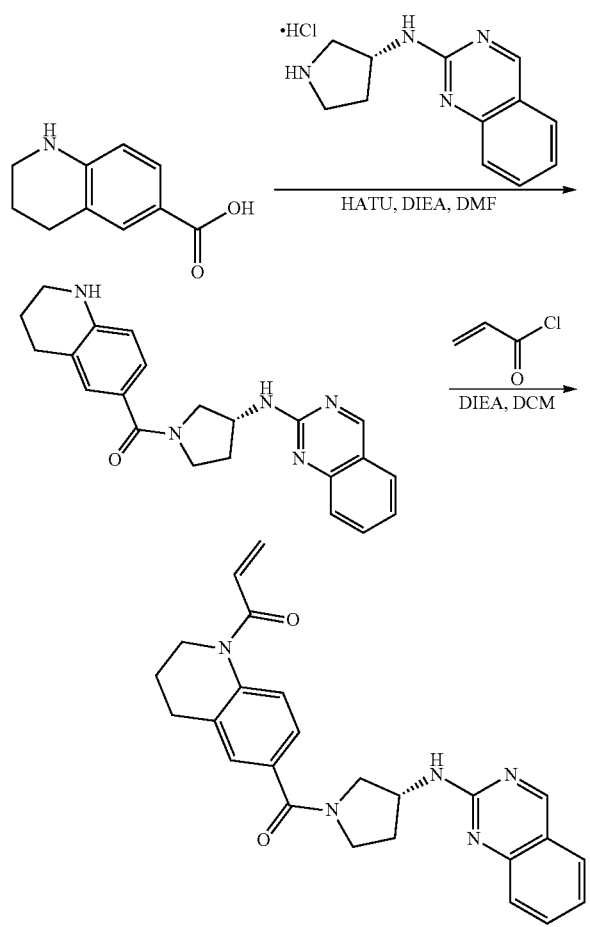

Step 1: (R)-(3-(quinazolin-2-ylamino)pyrrolidin-1-yl)(1,2,3,4-tetrahydroquinolin-6-yl)methanone

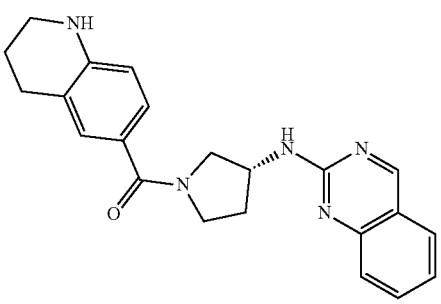 [SMILES: O=C(c1ccc2c(c1)CCCN2)N1CC[C@@H](Nc2ncc3ccccc3n2)C1]

A mixture of 1,2,3,4-tetrahydroquinoline-6-carboxylic acid (500 mg, 2.82 mmol), (R)—N-(pyrrolidin-3-yl)quinazolin-2-amine hydrochloride (848 mg, 3.38 mmol), HATU (1.28 g, 3.38 mmol) and DIEA (1.09 mL, 8.46 mmol) in DMF (50 mL) was stirred at rt overnight. The mixture was diluted with water (20 mL) and extracted with DCM (20 mL*3). The combined organic layer was washed with brine (20 mL), dried over $Na_2SO_4$, filtered and concentrated in vacuo. The residue was purified by column chromatography (PE:EA=1:1) to afford (R)-(3-(quinazolin-2-ylamino)pyrrolidin-1-yl)(1,2,3,4-tetrahydroquinolin-6-yl)methanone (230 mg, 23%) as light yellow solid. [M+H] Calc'd for $C_{22}H_{23}N_5O$, 374.4; Found, 374.4.

Step 2: TFA salt of (R)-1-(6-(3-(quinazolin-2-ylamino)pyrrolidine-1-carbonyl)-3,4-dihydroquinolin-1(2H)-yl)prop-2-en-1-one

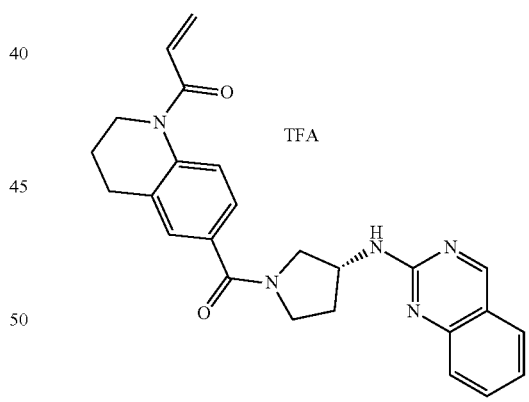

A mixture of (R)-(3-(quinazolin-2-ylamino)pyrrolidin-1-yl)(1,2,3,4-tetrahydroquinolin-6-yl)methanone (130 mg, 0.34 mmol) and DIEA (0.11 mL, 0.69 mmol) in DCM (40 mL) was stirred at 0° C. under nitrogen atmosphere. A solution of acryloyl chloride (0.02 mL, 0.31 mmol) in DCM (5 mL) was added dropwise and the mixture was warmed to r.t. The reaction was stirred at rt for 3 h. The mixture was concentrated and purified by prep-HPLC to afford TFA salt of (R)-1-(6-(3-(quinazolin-2-ylamino)pyrrolidine-1-carbonyl)-3,4-dihydroquinolin-1(2H)-yl)prop-2-en-1-one (9.0 mg, 47%) as a light yellow solid. [M+H] Calc'd for $C_{25}H_{25}N_5O_2$, 427.51; Found, 427.5. $^1$H NMR (400 MHz, DMSO-$d_6$): 1.85-2.22 (m, 3H), 2.67-2.76 (m, 3H), 3.48-3.88

(m, 6H), 4.50-4.61 (m, 1H), 5.67-5.76 (m, 1H), 6.17-6.26 (m, 1H), 6.53-6.66 (m, 1H), 7.17-7.54 (m, 5H), 7.71-7.87 (m, 3H), 9.17-9.22 (m, 1H).

Example 80: Synthesis of (R)-1-(7-(3-(quinazolin-2-ylamino)pyrrolidine-1-carbonyl)-2H-benzo[b][1,4]oxazin-4(3H)-yl)prop-2-en-1-one

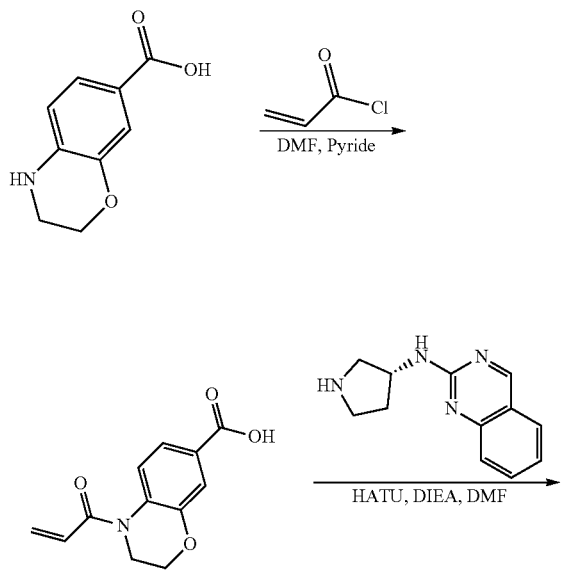

Step 1: 4-acryloyl-3,4-dihydro-2H-benzo[b][1,4]oxazine-7-carboxylic Acid

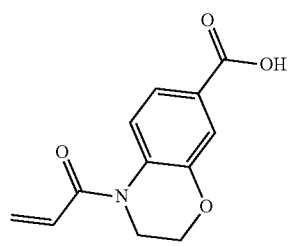 [SMILES: C=CC(=O)N1CCOc2cc(C(=O)O)ccc21]

The title compound was prepared in 44% yield from 4-acryloyl-3,4-dihydro-2H-benzo[b][1,4]oxazine-7-carboxylic acid. [M+H] Calc'd for $C_{12}H_{11}NO_4$, 234.0; Found, 234.0.

Step 2: (R)-1-(7-(3-(quinazolin-2-ylamino)pyrrolidine-1-carbonyl)-2H-benzo[b][1,4]oxazin-4(3H)-yl)prop-2-en-1-one

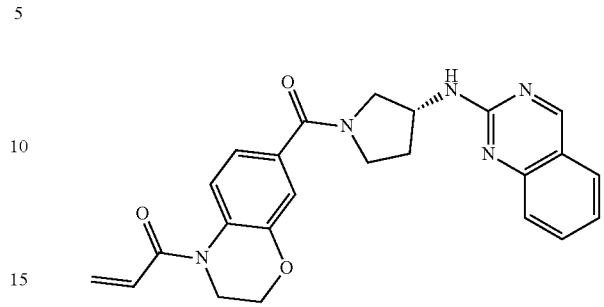

The title compound was prepared in 5% yield from 4-acryloyl-3,4-dihydro-2H-benzo[b][1,4]oxazine-7-carboxylic acid using general procedure of (R)-1-(7-(3-(quinazolin-2-ylamino)pyrrolidine-1-carbonyl)-2H-benzo[b][1,4]oxazin-4(3H)-yl)prop-2-en-1-one. $^1$H NMR (400 MHz, DMSO-$d_6$): δ 2.00-2.21 (m, 2H), 3.54-3.96 (m, 8H), 4.27-4.63 (m, 2H), 5.80-6.27 (m, 2H), 6.76-6.78 (m, 1H), 7.04-7.09 (m, 2H), 7.32-7.56 (m, 3H), 7.75-7.85 (m, 2H), 9.22 (s, 1H). [M+H] Calc'd for $C_{24}H_{23}N_5O_3$, 430.1; Found, 430.1.

Example 81: Synthesis of (R,E)-4-(dimethylamino)-N-(2-methoxy-4-(3-(quinazolin-2-ylamino)pyrrolidine-1-carbonyl)phenyl)but-2-enamide

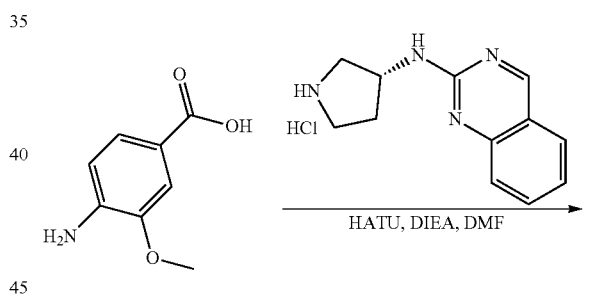

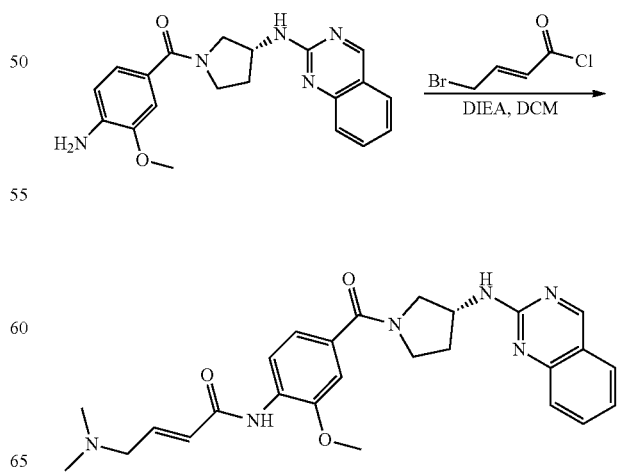

Step 1: (R)-(4-amino-3-methoxyphenyl)(3-(quinazo-lin-2-ylamino)pyrrolidin-1-yl)methanone

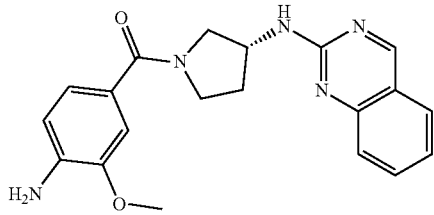 [SMILES: COc1cc(C(=O)N2CC[C@@H](Nc3ncc4ccccc4n3)C2)ccc1N]

The title compound was prepared in 69% yield from 4-amino-3-methoxybenzoic acid using general procedure of (R)-(4-amino-3-methoxyphenyl)(3-(quinazolin-2-ylamino)pyrrolidin-1-yl)methanone. [M+H] Calc'd for $C_{20}H_{21}N_5O_2$, 364.1; Found, 364.1.

Step 2: (R,E)-4-(dimethylamino)-N-(2-methoxy-4-(3-(quinazolin-2-ylamino)pyrrolidine-1-carbonyl)phenyl)but-2-enamide

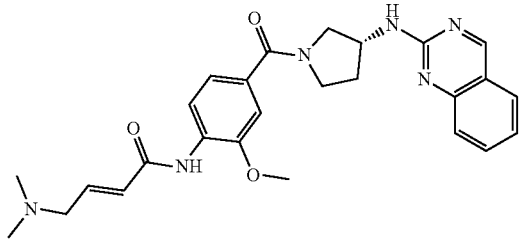 [SMILES: COc1cc(C(=O)N2CC[C@@H](Nc3ncc4ccccc4n3)C2)ccc1NC(=O)/C=C/CN(C)C]

The title compound was prepared in 7% yield from (R)-(4-amino-3-methoxyphenyl)(3-(quinazolin-2-ylamino)pyrrolidin-1-yl)methanone using general procedure of (R,E)-4-(dimethylamino)-N-(2-methoxy-4-(3-(quinazolin-2-ylamino)pyrrolidine-1-carbonyl)phenyl)but-2-enamide.
$^1$H NMR (400 MHz, DMSO-$d_6$): δ 1.94-2.09 (m, 1H), 2.21-2.31 (m, 1H), 2.80 (s, 6H), 3.84-3.90 (m, 9H), 4.47-4.48 (m, 1H), 6.70-6.71 (m, 1H), 7.10-7.14 (m, 3H), 7.51-7.53 (m, 1H), 7.66-7.85 (m, 3H), 8.07-8.13 (m, 1H), 9.13-9.18 (m, 1H), 9.67-9.69 (m, 1H). [M+H] Calc'd for $C_{26}H_{30}N_6O_3$, 474.2; Found, 475.2.

Example 82: Synthesis of (R,E)-N-(2-chloro-4-(3-(quinazolin-2-ylamino)pyrrolidine-1-carbonyl)phenyl)-4-(dimethylamino)but-2-enamide

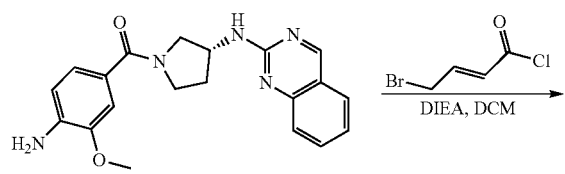

Step 1: (R,E)-N-(2-chloro-4-(3-(quinazolin-2-ylamino)pyrrolidine-1-carbonyl)phenyl)-4-(dimethylamino)but-2-enamide

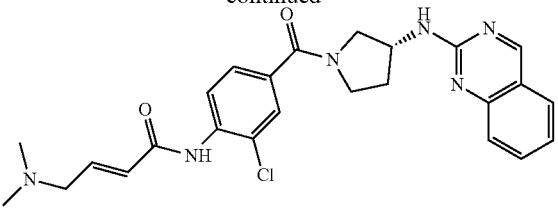

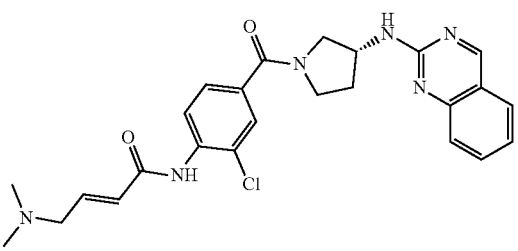 [SMILES: CN(C)C/C=C/C(=O)Nc1ccc(C(=O)N2CC[C@@H](Nc3ncc4ccccc4n3)C2)cc1Cl]

The title compound was prepared in 15% yield from (R)-(4-amino-3-chlorophenyl)(3-(quinazolin-2-ylamino)pyrrolidin-1-yl)methanone using general procedure of (R,E)-4-(dimethylamino)-N-(2-methoxy-4-(3-(quinazolin-2-ylamino)pyrrolidine-1-carbonyl)phenyl)but-2-enamide.
$^1$H NMR (400 MHz, DMSO-$d_6$): δ 1.93-2.09 (m, 1H), 2.17 (s, 6H), 2.18-2.22 (m, 1H), 3.05-3.08 (m, 2H), 3.40-3.87 (m, 4H), 4.48-4.63 (m, 1H), 6.46-6.55 (m, 1H), 6.72-6.83 (m, 1H), 7.20-7.30 (m, 1H), 7.42-7.52 (m, 2H), 7.56-7.78 (m, 4H), 7.85-7.97 (m, 1H), 9.12-9.16 (m, 1H), 9.66-9.70 (m, 1H). [M+H] Calc'd for $C_{25}H_{27}ClN_6O_2$, 479.2; Found, 479.2.

Example 83: Synthesis of (R,E)-4-(dimethylamino)-N-(2-methyl-4-(3-(quinazolin-2-ylamino)pyrrolidine-1-carbonyl)phenyl)but-2-enamide

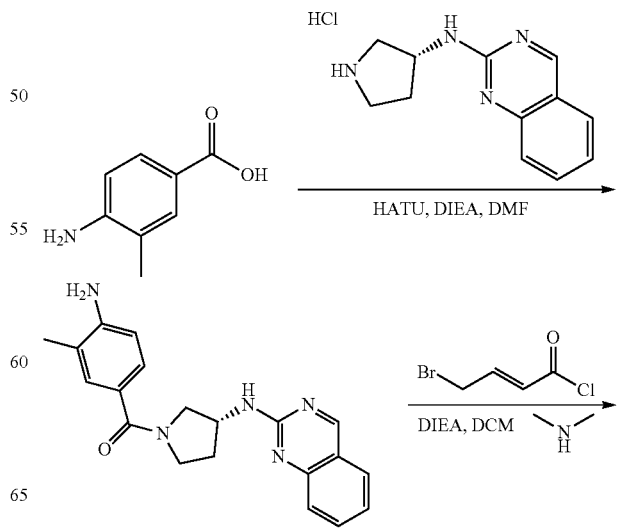

-continued

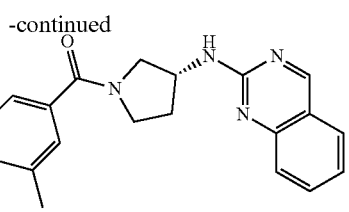

Step 1: (R)-(4-amino-3-methylphenyl)(3-(quinazolin-2-ylamino)pyrrolidin-1-yl)methanone

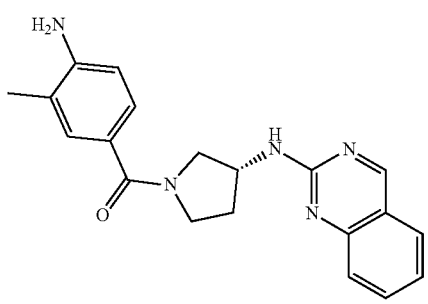 [SMILES: Cc1cc(C(=O)N2CC[C@@H](Nc3ncc4ccccc4n3)C2)ccc1N]

A mixture of 4-amino-3-methylbenzoic acid (250 mg, 1.66 mmol), (R)—N-(pyrrolidin-3-yl)quinazolin-2-amine hydrochloride (579 mg, 1.66 mmol), HATU (756 mg, 1.99 mmol) and DIEA (642 mg, 4.98 mmol) in DMF (15 mL) was stirred at RT overnight. The mixture was diluted with water (10 mL) and extracted with DCM (10 mL*3). The combined organic layer was washed with brine (20 mL), dried over $Na_2SO_4$, filtered and concentrated in vacuo. The residue was purified by column (PE:EA=0:1) to afford (R)-(4-amino-3-methylphenyl)(3-(quinazolin-2-ylamino)pyrrolidin-1-yl)methanone (340 mg, 59%) as a yellow solid. [M+H] Calc'd for $C_{20}H_{22}N_5O$, 348.1; Found, 348.1.

Step 2: (R,E)-4-(dimethylamino)-N-(2-methyl-4-(3-(quinazolin-2-ylamino)pyrrolidine-1-carbonyl)phenyl)but-2-enamide

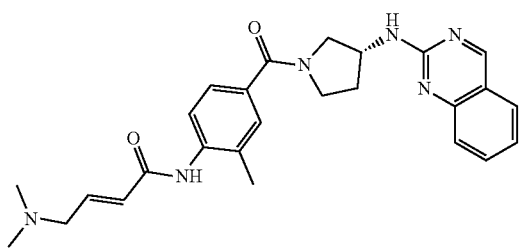 [SMILES: Cc1cc(C(=O)N2CC[C@@H](Nc3ncc4ccccc4n3)C2)ccc1NC(=O)/C=C/CN(C)C]

The title compound was prepared in 15% yield from (R)-(4-amino-3-methylphenyl)(3-(quinazolin-2-ylamino) pyrrolidin-1-yl)methanone using general procedure of (R,E)-N-(2-chloro-4-(3-(quinazolin-2-ylamino)pyrrolidine-1-carbonyl)phenyl)-4-(dimethylamino)but-2-enamide. $^1$H NMR (400 MHz, DMSO-$d_6$): δ 1.95-2.09 (m, 1H), 2.21-2.27 (m, 4H), 2.80 (s, 6H), 3.42-3.94 (m, 6H), 4.47-4.60 (m, 1H), 6.56-6.78 (m, 2H), 7.23-7.93 (m, 7H), 9.14 (s, 0.5H), 9.19 (s, 0.5H), 9.67 (s, 0.5H), 9.73 (s, 0.5H), 9.82 (s, 1H). [M+H] Calc'd for $C_{26}H_{31}N_6O_2$, 459.2; Found, 459.2.

Example 84: Synthesis of (R,E)-4-(dimethylamino)-1-(7-(3-(quinazolin-2-ylamino)pyrrolidine-1-carbonyl)-2H-benzo[b][1,4]oxazin-4(3H)-yl)but-2-en-1-one

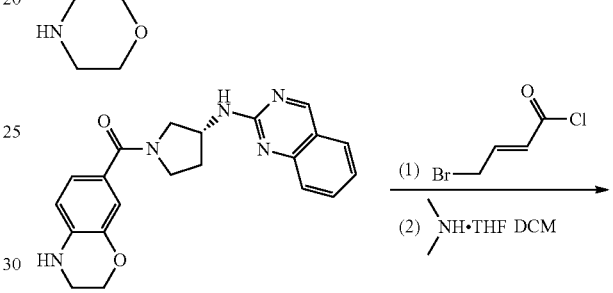

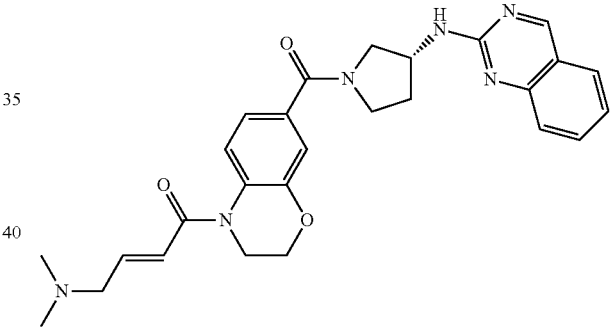

Step 1: (R)-(3,4-dihydro-2H-benzo[b][1,4]oxazin-7-yl)(3-(quinazolin-2-ylamino)pyrrolidin-1-yl)methanone

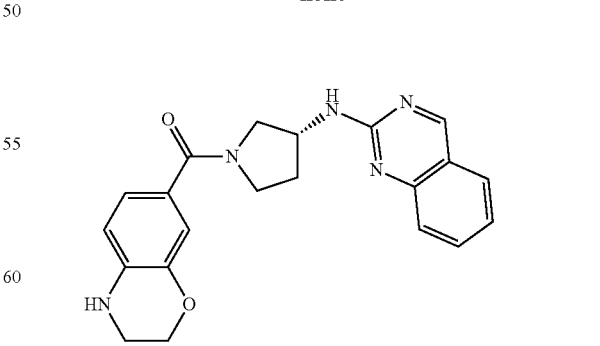

The title compound was prepared in 36% yield from 3,4-dihydro-2H-benzo[b][1,4]oxazine-7-carboxylic acid. [M+H] Calc'd for $C_{21}H_{21}N_5O_2$, 376.1; Found, 376.1.

Step 2: (R,E)-4-(dimethylamino)-1-(7-(3-(quinazolin-2-ylamino)pyrrolidine-1-carbonyl)-2H-benzo[b][1,4]oxazin-4(3H)-yl)but-2-en-1-one

Step 1: (R,E)-4-(dimethylamino)-N-(3-methoxy-4-(3-(quinazolin-2-ylamino)pyrrolidine-1-carbonyl)phenyl)but-2-enamide

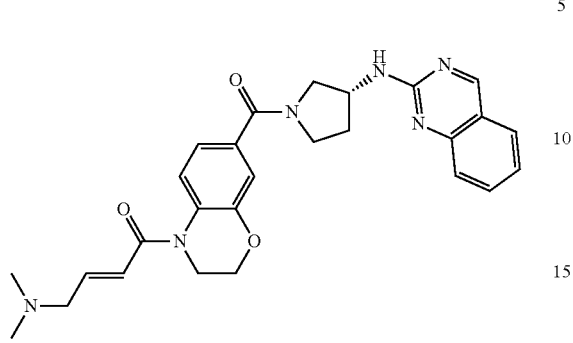

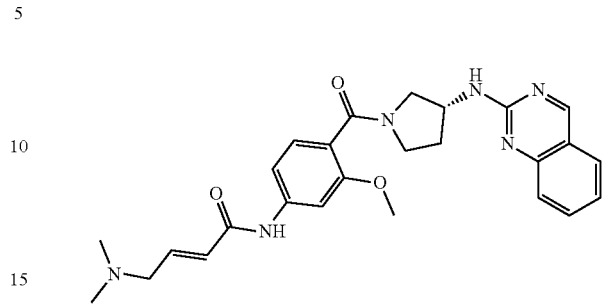

The title compound was prepared in 16% yield from (4-Amino-2-methoxy-phenyl)-[3-(quinazolin-2-ylamino)-pyrrolidin-1-yl]-methanone using general procedure of (R,E)-4-(dimethylamino)-1-(6-(3-(quinazolin-2-ylamino)pyrrolidine-1-carbonyl)-3,4-dihydroquinolin-1(2H)-yl)but-2-en-1-one $^1$H NMR (400 MHz, CD$_3$OD): δ 2.07-2.16 (m, 1H), 2.19-2.31 (m, 7H), 3.19-3.22 (m, 2H), 3.44-3.91 (m, 7H), 4.58-4.79 (m, 1H), 6.24-6.32 (m, 1H), 6.89-6.97 (m, 1H), 7.12-7.49 (m, 3H), 7.65-7.81 (m, 4H), 9.04-9.08 (m, 1H), [M+H] Calc'd for C$_{26}$H$_{30}$N$_6$O$_3$, 475.2; Found, 475.2.

The title compound was prepared in 13.2% yield from (R)-(3,4-dihydro-2H-benzo[b][1,4]oxazin-7-yl)(3-(quinazolin-2-ylamino)pyrrolidin-1-yl)methanone using general procedure of (R,E)-4-(dimethylamino)-1-(7-(3-(quinazolin-2-ylamino)pyrrolidine-1-carbonyl)-2H-benzo[b][1,4]oxazin-4(3H)-yl)but-2-en-1-one. $^1$H NMR (400 MHz, DMSO-d$_6$): δ 1.96-2.23 (m, 2H), 2.78-2.80 (m, 6H), 3.45-3.97 (m, 7H), 4.29-4.3 (m, 4H), 6.70-6.88 (m, 2H), 7.05-7.12 (m, 2H), 7.25-7.32 (m, 1H), 7.45-7.54 (m, 1H), 7.69-7.87 (m, 2H), 7.98 (br s, 1H), 9.15-9.20 (m, 1H), 9.90 (br s, 1H). [M+H] Calc'd for C$_{27}$H$_{30}$N$_6$O$_3$, 487.2; Found, 487.2.

Example 86: Synthesis of (R,E)-4-(dimethylamino)-N-methyl-N-(4-(3-(quinazolin-2-ylamino)pyrrolidine-1-carbonyl)phenylbut-2-enamide

Example 85: Synthesis of 4-Dimethylamino-but-2-enoic acid {3-methoxy-4-[3-(quinazolin-2-ylamino)-pyrrolidine-1-carbonyl]-phenyl}-amide

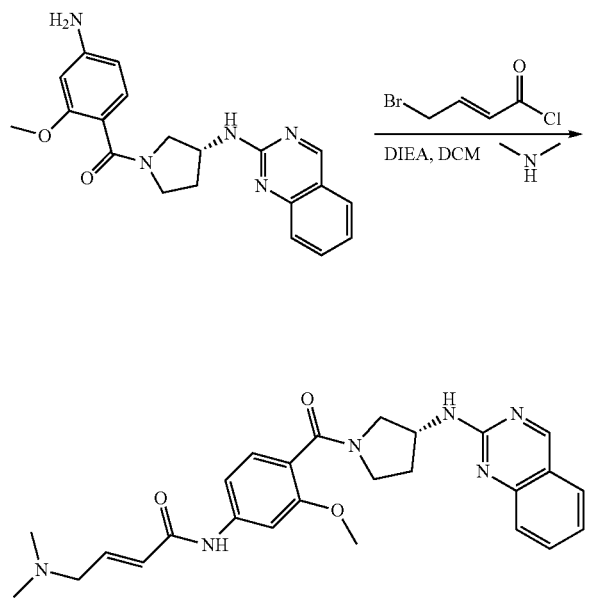

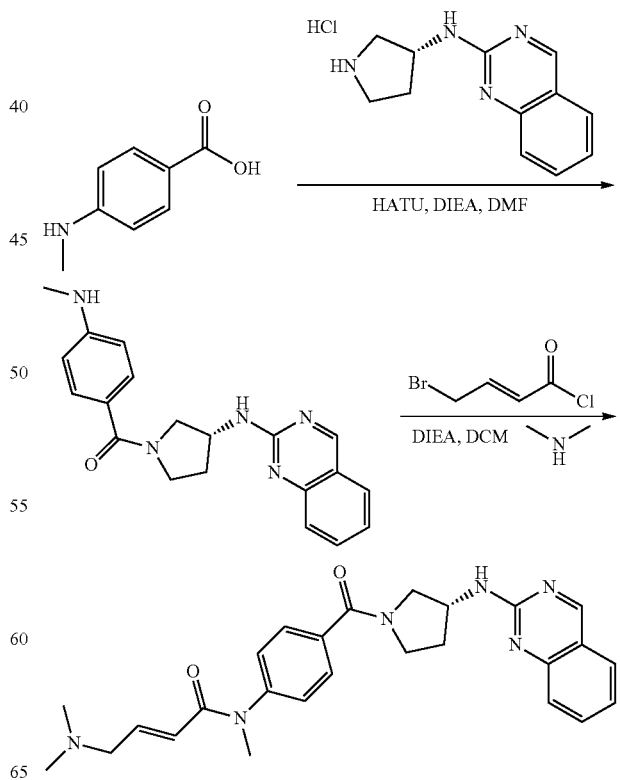

221

Step 1: (R)-(4-(methylamino)phenyl)(3-(quinazolin-2-ylamino)pyrrolidin-1-yl)methanone

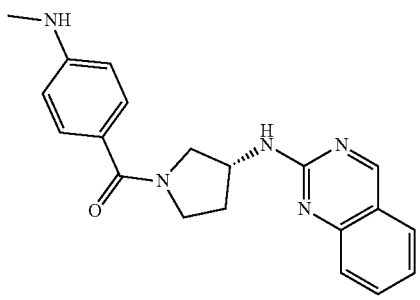 [SMILES: CNc1ccc(C(=O)N2CC[C@@H](Nc3ncc4ccccc4n3)C2)cc1]

The title compound was prepared in 44% yield from 4-(methylamino)benzoic acid using general procedure of (R)-(4-amino-3-methylphenyl)(3-(quinazolin-2-ylamino) pyrrolidin-1-yl)methanone. [M+H] Calc'd for $C_{20}H_{22}N_5O$, 348.1; Found, 348.1.

Step 2: (R,E)-4-(dimethylamino)-N-methyl-N-(4-(3-(quinazolin-2-ylamino)pyrrolidine-1-carbonyl)phenyl)but-2-enamide

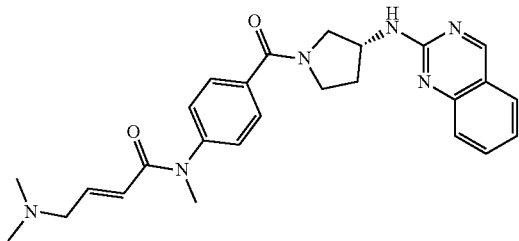 [SMILES: CN(C)C/C=C/C(=O)N(C)c1ccc(C(=O)N2CC[C@@H](Nc3ncc4ccccc4n3)C2)cc1]

The title compound was prepared in 21% yield from (R)-(4-(methylamino)phenyl)(3-(quinazolin-2-ylamino)pyrrolidin-1-yl)methanone using general procedure of (R,E)-N-(2-chloro-4-(3-(quinazolin-2-ylamino)pyrrolidine-1-carbonyl)phenyl)-4-(dimethylamino)but-2-enamide. $^1$H NMR (400 MHz, DMSO-$d_6$): δ 2.07-2.18 (m, 7H), 2.29-2.45 (m, 1H), 2.86-2.94 (m, 1H), 3.00 (d, J=6.4 Hz, 1H), 3.36 (s, 3H), 3.50-4.07 (m, 4H), 4.62-4.77 (m, 1H), 5.90-6.01 (m, 1H), 6.71-6.85 (m, 1H), 7.24-7.80 (m, 9H), 9.02 (s, 0.5H), 9.07 (s, 0.5H). [M+H] Calc'd for $C_{26}H_{31}N_6O_2$, 459.2; Found, 459.2.

Example 87: Synthesis of (R)—N-(3-(3-(quinazolin-2-ylamino)pyrrolidine-1-carbonyl)phenyl)acrylamide

222

-continued

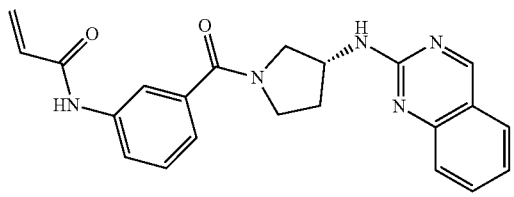

Step 1: (R)—N-(3-(3-(quinazolin-2-ylamino)pyrrolidine-1-carbonyl)phenyl)acrylamide

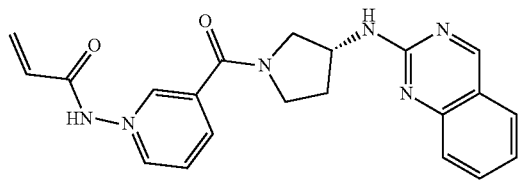

The title compound was prepared in 22% yield from 3-acrylamidobenzoic acid using general procedure of (R)—N-(3-(3-(quinazolin-2-ylamino)pyrrolidine-1-carbonyl)phenyl)acrylamide. $^1$H NMR (400 MHz, DMSO-$d_6$): δ 2.49-2.51 (m, 2H), 3.31-3.82 (m, 4H), 4.49-4.80 (m, 1H), 5.77-5.78 (m, 1H), 6.27-6.28 (m, 2H), 7.21-7.43 (m, 4H), 7.64-7.78 (m, 4H), 7.90-7.93 (m, 1H), 9.10-9.16 (m, 1H), 10.23-0.27 (m, 1H). [M+H] Calc'd for $C_{22}H_{21}N_5O_2$, 388.1; Found, 388.1.

Example 88: Synthesis of (R)—N-(2-chloro-4-(3-(quinazolin-2-ylamino)pyrrolidine-1-carbonyl)phenyl)acrylamide

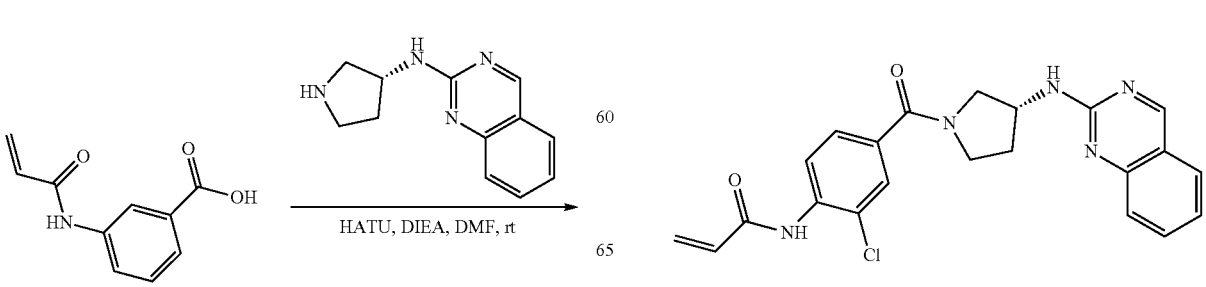

223

Step 1: (R)—N-(2-chloro-4-(3-(quinazolin-2-ylamino)pyrrolidine-1-carbonyl)phenyl)acrylamide

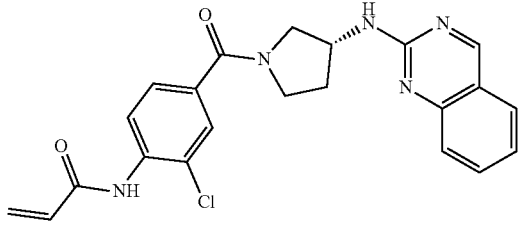 [SMILES: C=CC(=O)Nc1ccc(C(=O)N2CC[C@@H](Nc3ncc4ccccc4n3)C2)cc1Cl]

The title compound was prepared in 6% yield from 4-acrylamido-3-chlorobenzoic acid using general procedure of (R)—N-(2-methyl-4-(3-(quinazolin-2-ylamino)pyrrolidine-1-carbonyl)phenyl)acrylamide. $^1$H NMR (400 MHz, DMSO-d$_6$): δ 2.22-2.33 (m, 2H), 3.67-3.85 (m, 4H), 4.50-4.64 (m, 1H), 5.79-5.81 (m, 1H), 6.31-6.35 (m, 1H), 6.64-6.68 (m, 1H), 7.31 (br s, 1H), 7.51-7.96 (m, 7H), 9.22 (br s, 1H), 9.81-9.85 (m, 1H). [M+H] Calc'd for $C_{22}H_{20}ClN_5O_2$, 422.1; Found, 422.1.

Example 89: (R,E)-4-(dimethylamino)-1-(6-(3-(quinazolin-2-ylamino)pyrrolidine-1-carbonyl)-3,4-dihydroquinolin-1(2H)-yl)but-2-en-1-one

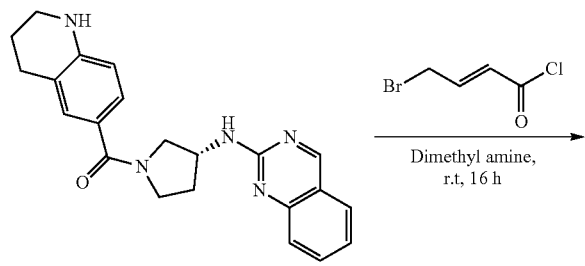

224

Step 1: (R,E)-4-(dimethylamino)-1-(6-(3-(quinazolin-2-ylamino)pyrrolidine-1-carbonyl)-3,4-dihydroquinolin-1(2H)-yl)but-2-en-1-one

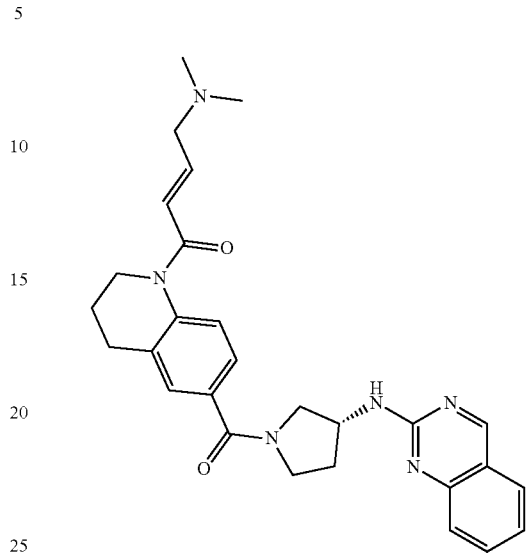

A mixture of (R)-(3-(quinazolin-2-ylamino)pyrrolidin-1-yl)(1,2,3,4-tetrahydroquinolin-6-yl)methanone (100 mg, 0.26 mmol) and DIEA (0.08 mL, 0.53 mmol) in DCM (30 mL) was stirred at 0° C. under nitrogen atmosphere. A solution of (E)-4-bromobut-2-enoyl chloride (98 mg, 0.532 mmol) in DCM (30 mL) was added dropwise and the mixture was warmed to r.t. and stirred for 2 hrs. After stirring for 2 hrs, the reaction mixture was cooled 0° C. and added 2 M a solution of dimethyl amine solution (5 mL) in THF and the mixture was warmed to r.t. and stirred for 16 hrs. The mixture was concentrated and submitted to prep-hplc to afford (R,E)-4-(dimethylamino)-1-(6-(3-(quinazolin-2-ylamino)pyrrolidine-1-carbonyl)-3,4-dihydroquinolin-1(2H)-yl)but-2-en-1-one (4.0 mg, 3.1%) as a light brown solid. HNMR (400 MHz, DMSO-d$_6$): 1.82-2.30 (m, 10H), 2.67-2.73 (m, 2H), 3.07-3.13 (m, 2H), 3.47-3.86 (m, 6H), 6.37-6.43 (m, 1H), 6.64-6.76 (m, 1H), 7.15-7.52 (m, 5H), 7.65-7.83 (m, 3H), 9.14-9.16 (m, 1H). [M+H] Calc'd for $C_{28}H_{32}N_6O_2$, 485.1; Found, 485.1.

Example 90: Synthesis of (R)—N-(4-(3-((8-fluoroquinazolin-2-yl)amino)pyrrolidine-1-carbonyl)phenyl)acrylamide

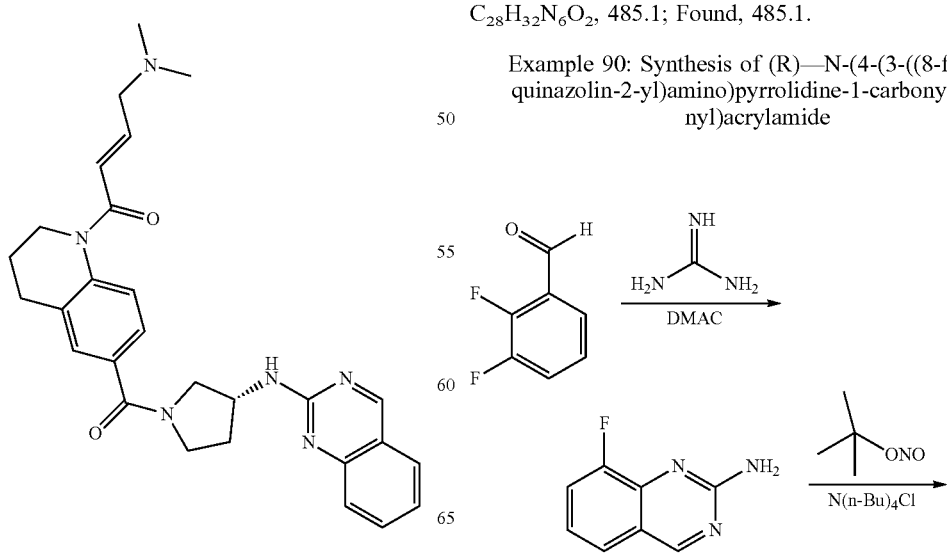

-continued

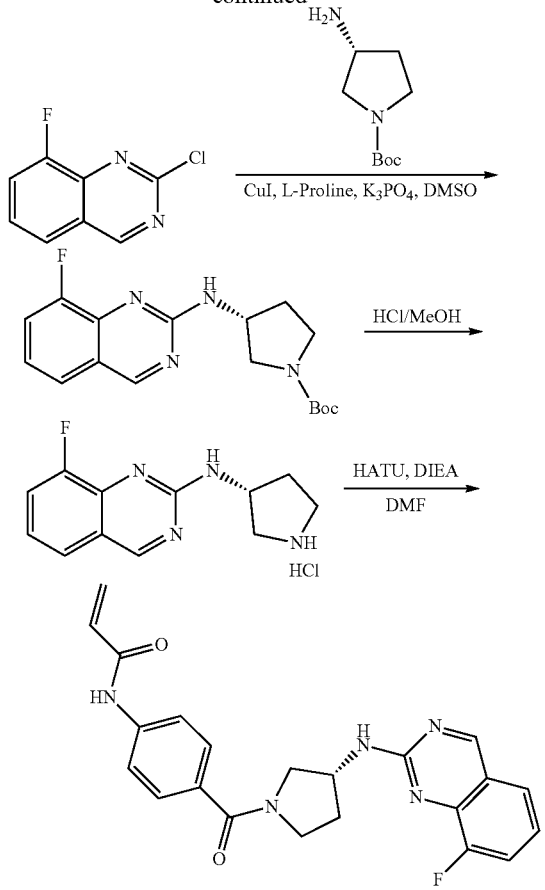

Step 1: 8-fluoroquinazolin-2-amine

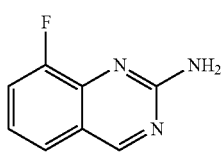 [SMILES: Nc1ncc2cccc(F)c2n1]

The title compound was prepared in 18% yield from 2,3-difluorobenzaldehyde using general procedure of 5-fluoroquinazolin-2-amine. [M+H] Calc'd for $C_8H_6FN_3$, 164.0; Found, 164.0.

Step 2: 2-chloro-8-fluoroquinazoline

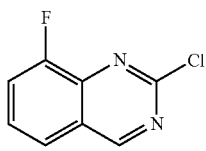 [SMILES: Fc1cccc2cnc(Cl)nc12]

The title compound was prepared in 73% yield from 8-fluoroquinazolin-2-amine using general procedure of 2-chloro-5-fluoroquinazoline. [M+H] Calc'd for $C_8H_4ClFN_2$, 183.0; Found, 183.0.

Step 3: (R)-tert-butyl 3-((8-fluoroquinazolin-2-yl)amino)pyrrolidine-1-carboxylate

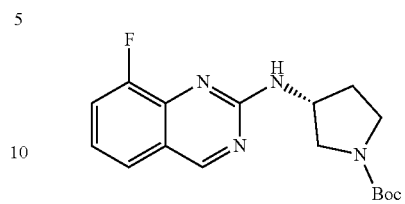

The title compound was prepared in 14% yield from 2-chloro-8-fluoroquinazoline using general procedure of (R)-tert-butyl 3-((6-fluoroquinazolin-2-yl)amino)pyrrolidine-1-carboxylate. [M+H] Calc'd for $C_{17}H_{21}FN_4O_2$, 333.1; Found, 333.1.

Step 4: (R)-8-fluoro-N-(pyrrolidin-3-yl)quinazolin-2-amine hydrochloride

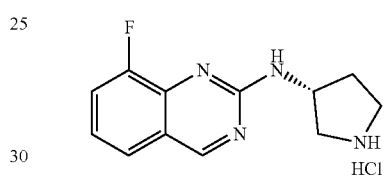

The title compound was prepared in 100% yield from (R)-tert-butyl 3-((8-fluoroquinazolin-2-yl)amino)pyrrolidine-1-carboxylate using general procedure of (R)-6-fluoro-N-(pyrrolidin-3-yl)quinazolin-2-amine hydrochloride. [M+H] Calc'd for $C_{12}H_{13}FN_4$, 233.1; Found, 233.1.

Step 5: (R)—N-(4-(3-((8-fluoroquinazolin-2-yl)amino)pyrrolidine-1-carbonyl)phenyl)acrylamide

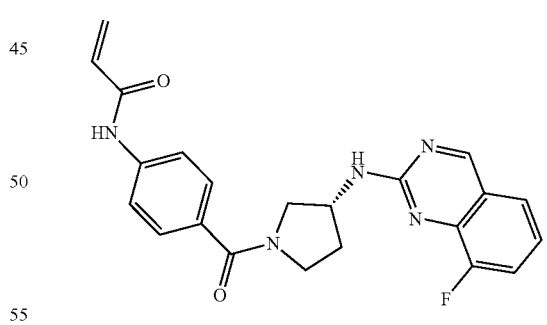

The title compound was prepared in 21% yield from (R)-8-fluoro-N-(pyrrolidin-3-yl)quinazolin-2-amine hydrochloride using general procedure of (R)—N-(2-fluoro-4-(3-((6-fluoroquinazolin-2-yl)amino)pyrrolidine-1-carbonyl)phenyl)acrylamide. $^1$H NMR (400 MHz, $CD_3OD$): δ 2.07-2.18 (m, 1H), 2.32-2.43 (m, 1H), 3.58-3.80 (m, 3H), 3.89-4.06 (m, 1H), 4.55-4.65 (m, 1H), 5.76-5.81 (m, 1H), 6.33-6.48 (m, 2H), 7.15-7.24 (m, 1H), 7.38-7.48 (m, 1H), 7.52-7.61 (m, 3H), 7.69-7.76 (m, 2H), 9.06 (s, 0.5H), 9.11 (s, 0.5H). [M+H] Calc'd for $C_{22}H_{20}FN_5O_2$, 406.1; Found, 406.1.

Example 91: Synthesis of (R)—N-(4-(3-((5-fluoroquinazolin-2-yl)amino)pyrrolidine-1-carbonyl)phenyl)acrylamide

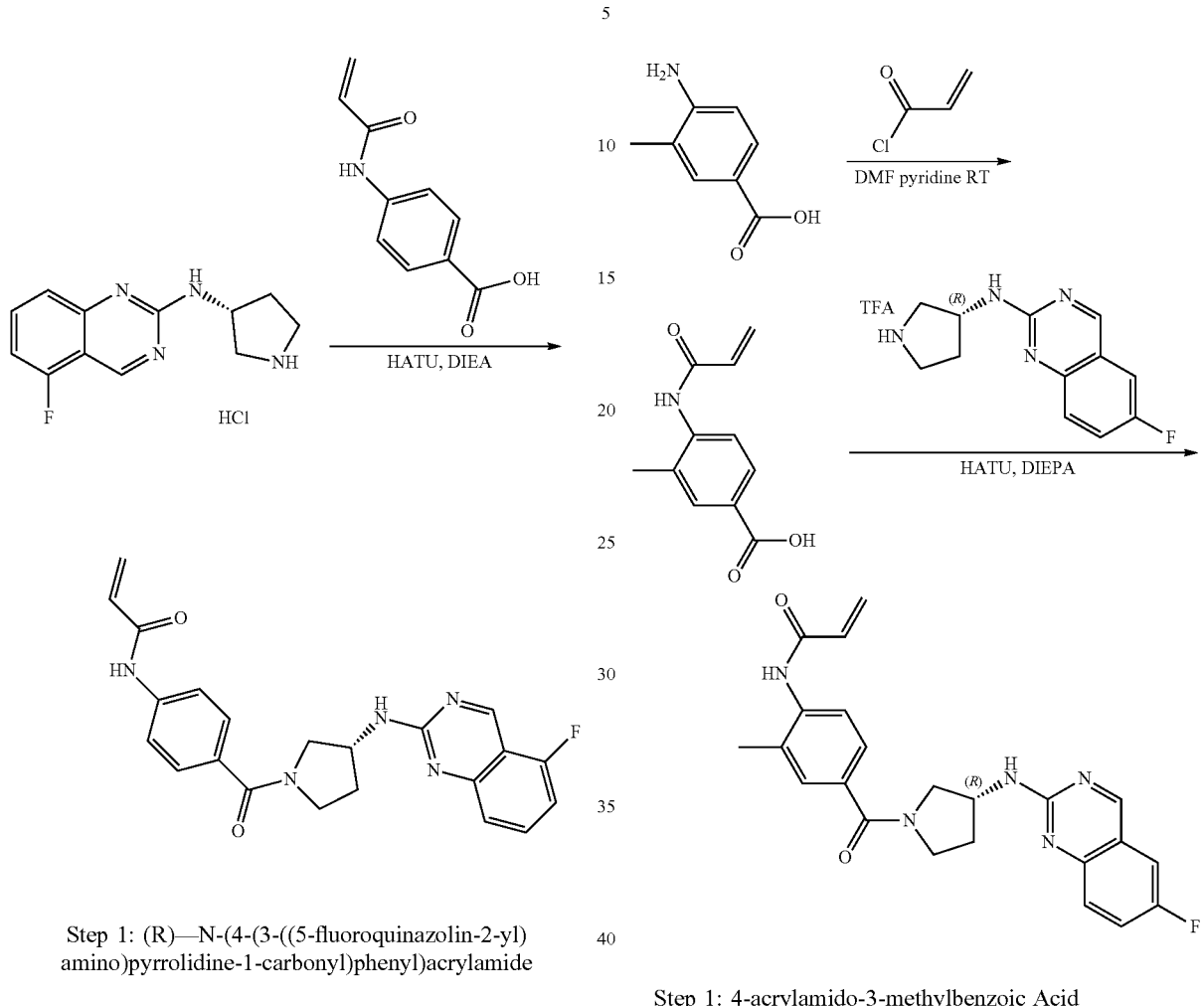

Step 1: (R)—N-(4-(3-((5-fluoroquinazolin-2-yl)amino)pyrrolidine-1-carbonyl)phenyl)acrylamide The title compound was prepared in 32% yield from (R)-5-fluoro-N-(pyrrolidin-3-yl)quinazolin-2-amine using general procedure of (R)—N-(2-fluoro-4-(3-((6-fluoroquinazolin-2-yl)amino)pyrrolidine-1-carbonyl)phenyl)acrylamide. $^1$H NMR (400 MHz, CD$_3$OD): δ 2.07-2.19 (m, 1H), 2.28-2.41 (m, 1H), 3.55-3.86 (m, 3H), 3.93-4.04 (m, 1H), 4.57-4.75 (m, 1H), 5.76-5.81 (m, 1H), 6.32-6.48 (m, 2H), 6.87-6.95 (m, 1H), 7.28-7.40 (m, 1H), 7.52-7.77 (m, 5H), 9.22 (s, 0.6H), 9.28 (s, 0.4H). [M+H] Calc'd for C$_{22}$H$_{20}$FN$_5$O$_2$, 406.1; Found, 406.1.

Example 92: Synthesis of (R)—N-(4-(3-((6-fluoroquinazolin-2-yl)amino)pyrrolidine-1-carbonyl)-2-methylphenyl)acrylamide

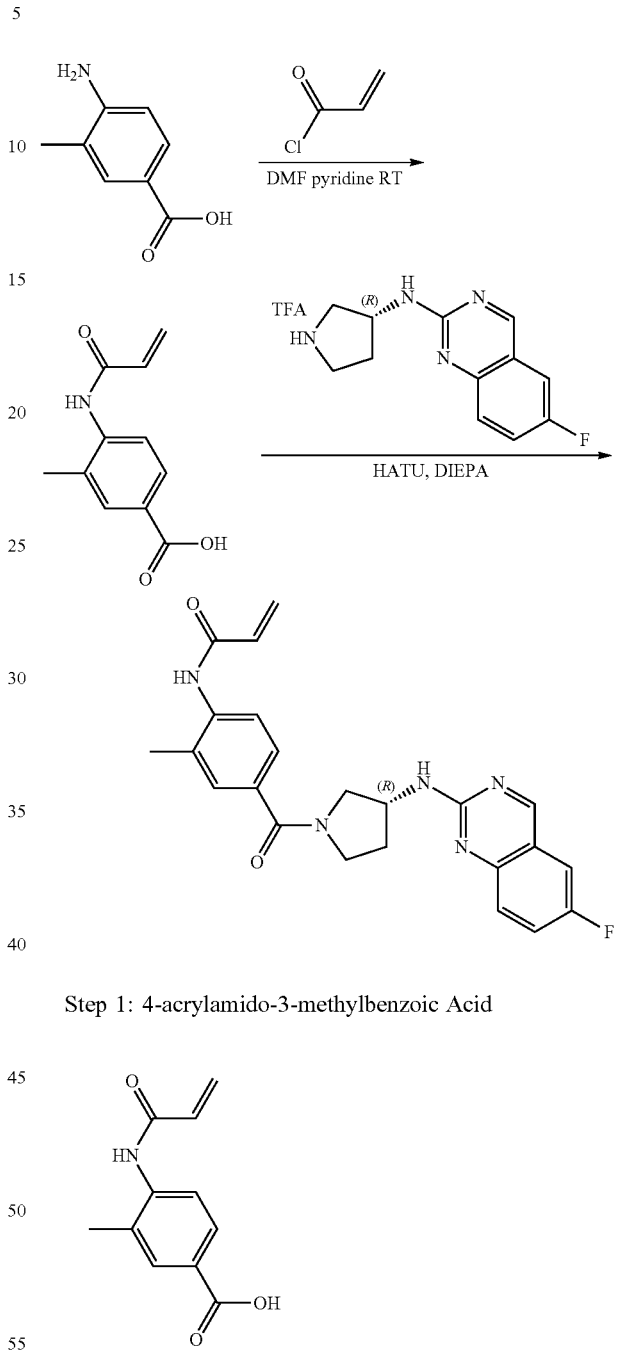

Step 1: 4-acrylamido-3-methylbenzoic Acid

To a mixture of 4-amino-3-methylbenzoic acid (13.7 g, 91.0 mmol) in DMF (100 mL) was added pyridine (5 mL) at 0° C., followed by added acryloyl chloride (11 mL) slowly. The mixture was stirred at RT for 4 hours. The mixture was added water (1000 mL). The mixture was filtered, the residue was triturate with water (200 mL*2). The mixture was filtered and the filtered cake was concentrated to give 4-acrylamido-3-methylbenzoic acid (15.1 g, 81%) as a white solid. [M+H] Calc'd for C$_{11}$H$_{11}$NO$_3$, 206.0; Found, 206.0.

Step 2: (R)—N-(4-(3-((6-fluoroquinazolin-2-yl)amino)pyrrolidine-1-carbonyl)-2-methylphenyl)acrylamide

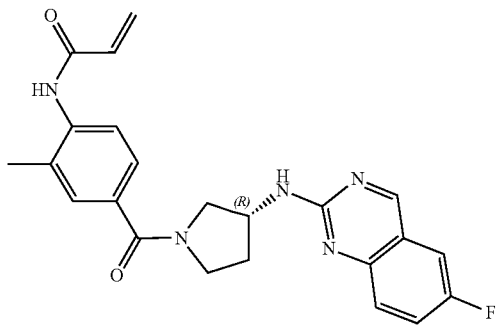

The title compound was prepared in 18% yield from 4-acrylamido-3-methylbenzoic acid using general procedure of (R)—N-(2-fluoro-4-(3-((6-fluoroquinazolin-2-yl)amino)pyrrolidine-1-carbonyl)phenyl)acrylamide. $^1$H NMR (400 MHz, DMSO-$d_6$): δ 1.96-2.07 (m, 1H), 2.17-2.26 (m, 4H), 3.41-3.73 (m, 3H), 3.81-3.87 (m, 1H), 4.43-4.58 (m, 1H), 5.76 (t, J=8.8 Hz, 1H), 6.22-6.29 (m, 1H), 6.52-6.58 (m, 1H), 7.32-7.66 (m, 6H), 7.76-7.78 (m, 1H), 9.11 (s, 0.5H), 9.16 (s, 0.5H), 9.48 (s, 0.5H), 9.53 (s, 0.5H). [M+H] Calc'd for $C_{23}H_{22}FN_5O_2$, 420.0; Found, 420.0.

Example 93: Synthesis of (R)—N-(2-methyl-4-(3-((7-(methylsulfonyl)quinazolin-2-yl)amino)pyrrolidine-1-carbonyl)phenyl)acrylamide

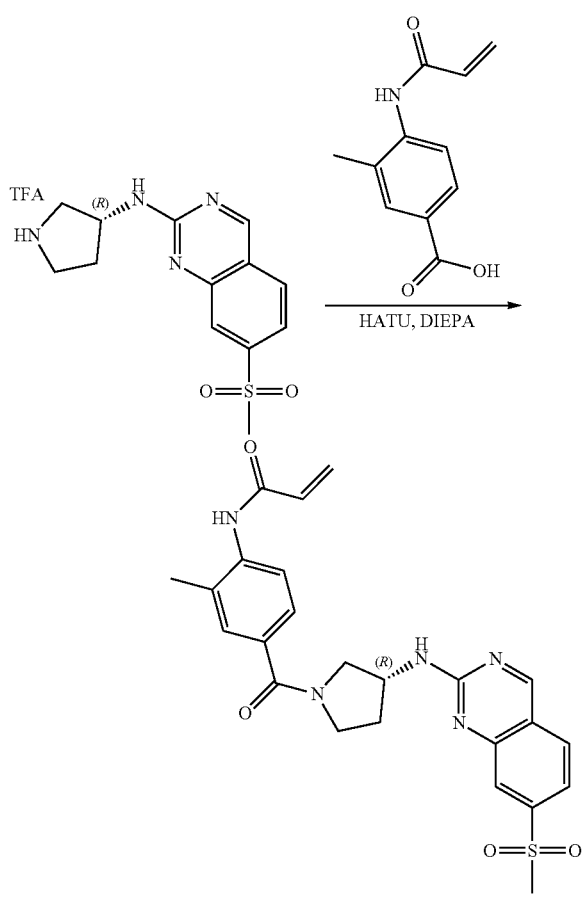

Step 1: (R)—N-(2-methyl-4-(3-((7-(methylsulfonyl)quinazolin-2-yl)amino)pyrrolidine-1-carbonyl)phenyl)acrylamide

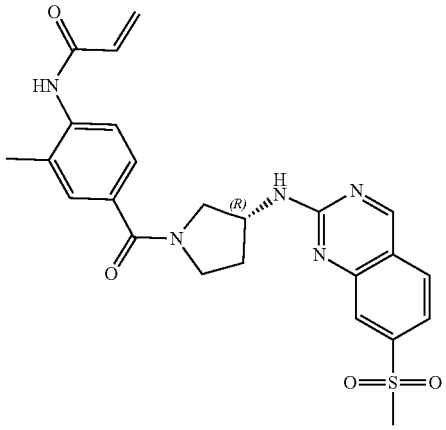

The title compound was prepared in 28% yield from (R)-7-(methylsulfonyl)-N-(pyrrolidin-3-yl)quinazolin-2-amine 2,2,2-trifluoroacetate using general procedure of (R)—N-(2-fluoro-4-(3-((6-fluoroquinazolin-2-yl)amino)pyrrolidine-1-carbonyl)phenyl)acrylamide. $^1$H NMR (400 MHz, DMSO-$d_6$): δ 1.97-2.10 (m, 1H), 2.21-2.27 (m, 4H), 3.30 (s, 3H), 3.47-3.74 (m, 3H), 3.85-3.87 (m, 1H), 4.48-4.59 (m, 1H), 5.76 (t, J=9.2 Hz, 1H), 6.22-6.29 (m, 1H), 6.54-6.61 (m, 1H), 7.33-7.43 (m, 2H), 7.59-7.70 (m, 2H), 7.91-8.10 (m, 2H), 8.20 (br s, 1H), 9.29 (s, 0.5H), 9.33 (s, 0.5H), 9.50 (s, 0.5H), 9.55 (s, 0.5H). [M+H] Calc'd for $C_{24}H_{25}N_5O_4S$, 480.0; Found, 480.0.

Example 94: Synthesis of (R)-2-methylene-N-(4-(3-(quinazolin-2-ylamino)pyrrolidine-1-carbonyl)phenyl)butanamide

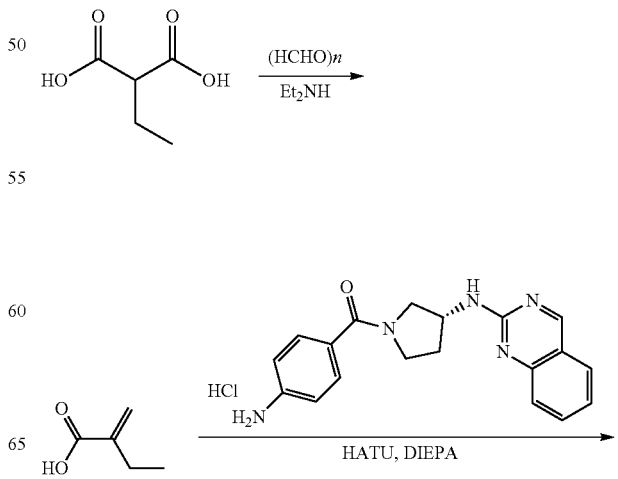

231

-continued

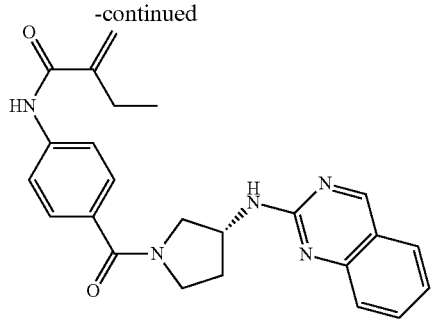

Step 1: 2-methylenebutanoic Acid

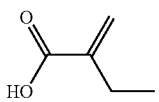

To a solution of 2-ethylmalonic acid (1.5 g, 11.4 mmol) in EtOAc (114 mL) was added Paraformaldehyde (682 mg, 22.7 mmol) and diethylamine (1.2 g, 17.0 mmol) at 0° C. The mixture was refluxed for 4 hours. The solution was cooled to RT and concentrated. The residue was quenched with ice-water (20 mL) and acidified to pH 1.0 by con. HCl. The solution was extracted with DCM (30 mL*2). The combined organic phase was washed with brine (100 mL), dried over $Na_2SO_4$ and filtered. The filtrate was concentrated, and the residue was purified by flash chromatography on silica gel (petroleum ether/EtOAc=1/1) to afford 2-methylenebutanoic acid (700 mg, 64%) as a colorless oil. [M+H] Calc'd for $C_5H_8O_2$, 101.0; Found, 101.0.

Step 2: (R)-2-methylene-N-(4-(3-(quinazolin-2-ylamino)pyrrolidine-1-carbonyl)phenyl)butanamide

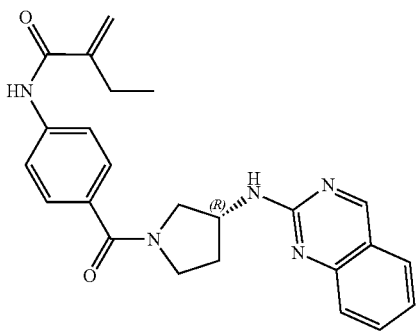

The title compound was prepared in 31% yield from (R)-(4-aminophenyl)(3-(quinazolin-2-ylamino)pyrrolidin-1-yl)methanone hydrochloride using general procedure of (R)—N-(2-fluoro-4-(3-((6-fluoroquinazolin-2-yl)amino) pyrrolidine-1-carbonyl)phenyl)acrylamide. $^1$H NMR (400 MHz, DMSO-$d_6$): δ 0.99-1.05 (m, 3H), 1.90-2.07 (m, 1H), 2.15-2.23 (m, 1H), 2.29-2.37 (m, 2H), 3.41-3.60 (m, 2H), 3.65-3.72 (m, 1H), 3.84-3.88 (m, 1H), 4.46-4.59 (m, 1H), 5.46 (d, J=10.8 Hz, 1H), 5.75 (d, J=13.6 Hz, 1H), 7.20-7.28 (m, 1H), 7.41-7.54 (m, 3H), 7.64-7.83 (m, 5H), 9.11 (s, 0.5H), 9.16 (s, 0.5H), 10.00 (s, 0.5H), 10.04 (s, 0.5H). [M+H] Calc'd for $C_{24}H_{25}N_5O_4S$, 416.4; Found, 416.4.

Example 95: Synthesis of (R)—N-(4-(3-(quinazolin-2-ylamino)pyrrolidine-1-carbonyl)phenyl)ethenesulfonamide

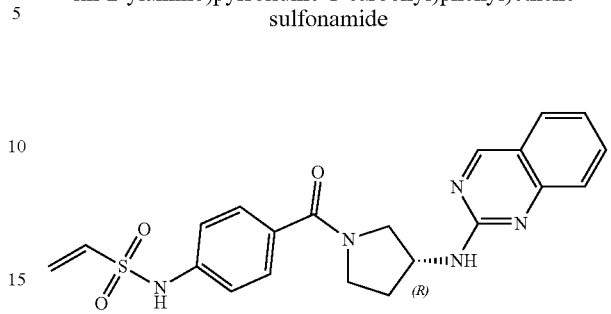

To a solution of (R)-(4-aminophenyl)(3-(quinazolin-2-ylamino)pyrrolidin-1-yl)methanone hydrochloride (69 mg, 0.21 mmol) in DCM (1 mL) was added DIPEA (135 mg, 1.05 mmol) and a solution of 2-chloroethanesulfonyl chloride (34 mg, 0.21 mmol) in DCM (1 mL) dropwise at 0° C. The solution was stirred at 0° C. for 5 h. The solution was concentrated and the residue was purified by prep-HPLC to afford (R)—N-(4-(3-(quinazolin-2-ylamino)pyrrolidine-1-carbonyl)phenyl)ethenesulfonamide (5.8 mg, 8%) as a white solid. $^1$H NMR (400 MHz, DMSO-$d_6$): δ 1.90-2.07 (m, 1H), 2.16-2.22 (m, 1H), 3.37-3.70 (m, 3H), 3.80-3.86 (m, 1H), 4.45-4.58 (m, 1H), 6.00-6.19 (m, 2H), 6.75-6.86 (m, 1H), 7.12-7.27 (m, 3H), 7.41-7.51 (m, 3H), 7.65-7.83 (m, 3H), 9.11 (s, 0.5H), 9.16 (s, 0.5H), 10.26 (br s, 1H). [M+H] Calc'd for $C_{21}H_{21}N_5O_3S$, 424.1; Found, 424.1.

Example 96: Synthesis of N-(4-((3S,4R)-3-methyl-4-(quinazolin-2-ylamino)pyrrolidine-1-carbonyl) phenyl)acrylamide

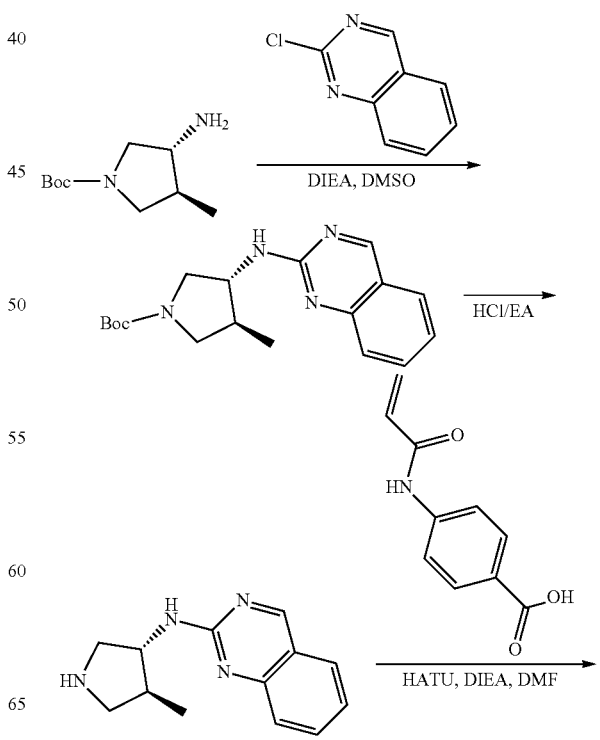

-continued

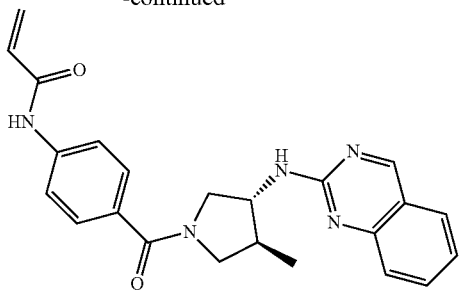

Step 1: (3S,4R)-tert-butyl 3-methyl-4-(quinazolin-2-ylamino)pyrrolidine-1-carboxylate

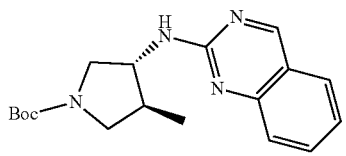 [SMILES: C[C@H]1CN(C(=O)OC(C)(C)C)C[C@@H]1Nc1ncc2ccccc2n1]

The title compound was prepared in 54% yield from (R)-tert-butyl 3-aminopyrrolidine-1-carboxylate and 2-chloroquinazoline using general procedure of (3S,4R)-tert-butyl 3-methyl-4-(quinazolin-2-ylamino)pyrrolidine-1-carboxylate. [M+H] Calc'd for $C_{18}H_{24}N_4O_2$, 329.1; Found, 329.1.

Step 2: N-((3R,4S)-4-methylpyrrolidin-3-yl)quinazolin-2-amine

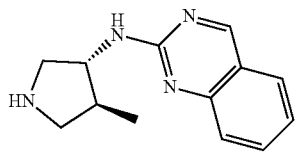 [SMILES: C[C@H]1CNC[C@@H]1Nc1ncc2ccccc2n1]

The title compound was prepared in 93% yield from (3S,4R)-tert-butyl 3-methyl-4-(quinazolin-2-ylamino)pyrrolidine-1-carboxylate using general procedure of N-((3R,4S)-4-methylpyrrolidin-3-yl)quinazolin-2-amine. [M+H] Calc'd for $C_{13}H_{16}N_4$, 229.2; Found, 229.2.

Step 3: N-(4-((3S,4R)-3-methyl-4-(quinazolin-2-ylamino)pyrrolidine-1-carbonyl)phenyl)acrylamide

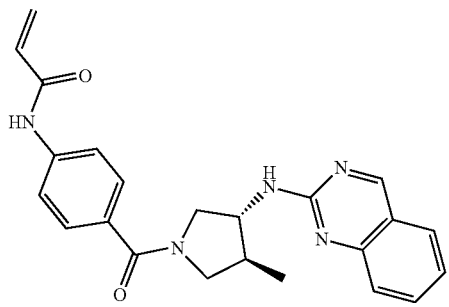 [SMILES: C=CC(=O)Nc1ccc(C(=O)N2C[C@H](Nc3ncc4ccccc4n3)[C@@H](C)C2)cc1]

The title compound was prepared in 39% yield from N-((3R,4S)-4-methylpyrrolidin-3-yl)quinazolin-2-amine using general procedure of N-(4-((3S,4R)-3-methyl-4-(quinazolin-2-ylamino)pyrrolidine-1-carbonyl)phenyl)acrylamide. $^1$H NMR (400 MHz, DMSO-d$_6$): δ 0.96-1.13 (d, J=8.0 Hz, 3H), 2.28-2.30 (m, 1H), 3.17-3.22 (m, 2H), 3.68-4.27 (m, 3H), 5.77-5.80 (m, 1H), 6.23-6.44 (m, 2H), 7.23-7.25 (m, 1H), 7.38-7.40 (m, 3H), 7.52-7.81 (m, 5H), 9.10-9.14 (m, 1H), 10.27-10.31 (m, 1H). [M+H] Calc'd for $C_{23}H_{23}N_5O_2$, 402.2; Found, 402.2.

II. Biological Evaluation

Example 1—Assay Condition A (Thiol Containing Conditions)

Objective:

The IC$_{50}$ profile of test compounds was determined using three protein kinases. IC$_{50}$ values were measured by testing 10 concentrations ($1\times10^{-04}$M, $3\times10^{-05}$M, $1\times10^{-05}$M, $3\times10^{-06}$M, $1\times10^{-06}$M, $3\times10^{-07}$M, $1\times10^{-07}$M, $3\times10^{-08}$M, $1\times10^{-08}$M, and $3\times10^{-09}$M) of each compound in singlicate.

Test Compounds:

The compounds were provided as pre-weighed powders in vials. The compounds were dissolved to $1\times10^{-02}$M by adding DMSO. 100 µl of each of the resulting stock solutions were transferred into column 2 of four 96 well "master plates".

Prior to testing, the $1\times10^{-02}$M stock solutions in column 2 of the master plates were subjected to a serial, semi-logarithmic dilution using 100% DMSO as a solvent. This resulted in 10 distinct concentrations, with a dilution endpoint of $3\times10^{-07}$M/100% DMSO in column 12. Column 1 and 7 were filled with 100% DMSO as controls. Subsequently, 2×10 µl from each well of the serial diluted copy plates were aliquoted with a 96 channel pipettor into two identical sets of "compound dilution plates".

In the process, 90 µl H$_2$O were added to each well of a set of compound dilution plates. To minimize potential precipitation, the H$_2$O was added to each plate only a few minutes before the transfer of the compound solutions into the assay plates. Each plate was shaken thoroughly, resulting in a "compound dilution plate/10% DMSO".

For the assays, 5 µl solution from each well of the compound dilution plates/10% DMSO were transferred into the assay plates. The final volume of the assay was 50 µl. All compounds were tested at 10 final assay concentrations in the range from $1\times10^{-04}$M to $3\times10^{-09}$M, in singlicate. The final DMSO concentration in the reaction cocktails was 1% in all cases.

Recombinant Protein Kinases:

All protein kinases were expressed in Sf9 insect cells or in E. coli as recombinant GST-fusion proteins or His-tagged proteins, either as full-length or enzymatically active fragments. All kinases were produced from human cDNAs and purified by either GSH-affinity chromatography or immobilized metal. Affinity tags were removed from a number of kinases during purification. The purity of the protein kinases was examined by SDS-PAGE/Coomassie staining, the identity was checked by mass spectroscopy.

Protein Kinase Assay:

A radiometric protein kinase assay ($^{33}$PanQinase® Activity Assay) was used for measuring the kinase activity of the three protein kinases. All kinase assays were performed in 96-well FlashPlates™ from PerkinElmer (Boston, Mass., USA) in a 50 µl reaction volume. The reaction cocktail was pipetted in four steps in the following order:

20 µl of assay buffer (standard buffer)
5 µl of ATP solution (in H$_2$O)
5 µl of test compound (in 10% DMSO)
20 µl enzyme/substrate mix The assay for all protein kinases contained 70 mM HEPES-NaOH pH 7.5, 3 mM MgCl$_2$, 3 mM MnCl$_2$, 3 µM Na-orthovanadate, 1.2 mM DTT, 50 µg/ml PEG$_{20000}$, ATP (variable concentrations, corresponding to the apparent ATP-K$_m$ of the respective kinase), [γ-$^{33}$P]-ATP (approx. 9×10$^{05}$ cpm per well), protein kinase (variable amounts), and substrate (variable amounts).

The following amounts of enzyme and substrate were used per well:

| Kinase Name | Kinase Conc. ng/50 µl | Kinase Conc. nM * | ATP Conc. µM | Substrate Name | Substrate Lot | Substrate µg/50 µl |
|---|---|---|---|---|---|---|
| CDK12 wt/CycK | 100 | 14.7 | 0.3 | RBER-IRStide | 036 | 2 |
| CDK2/CycA2 | 25 | 3.7 | 0.3 | RBER-CHKtide | 076 | 1 |
| CDK7/CycH/MAT1 | 25 | 3.3 | 3.0 | RBER-CHKtide | 076 | 2 |

* Maximal molar enzyme assay concentrations, implying enzyme preparations exclusively containing 100% active enzyme The reaction cocktails were incubated at 30° C. for 60 minutes. The reaction was stopped with 50 µl of 2% (v/v) H$_3$PO$_4$, plates were aspirated and washed two times with 200 µl 0.9% (w/v) NaCl. Incorporation of $^{33}$Pi was determined with a microplate scintillation counter (Microbeta, Wallac). All assays were performed with a BeckmanCoulter/SAGIAN™ Core System.

Evaluation of Raw Data:

The median value of the counts in column 1 (n=8) of each assay plate was defined as "low control". This value reflects unspecific binding of radioactivity to the plate in the absence of a protein kinase but in the presence of the substrate. The median value of the counts in column 7 of each assay plate (n=8) was taken as the "high control", i.e. full activity in the absence of any inhibitor. The difference between high and low control was taken as 100% activity.

As part of the data evaluation the low control value from a particular plate was subtracted from the high control value as well as from all 80 "compound values" of the corresponding plate. The residual activity (in %) for each well of a particular plate was calculated by using the following formula:

Res. Activity (%)=100×[(cpm of compound−low control)/(high control−low control)]

The residual activities for each concentration and the compound IC$_{50}$ values were calculated using Quattro Workflow V3.1.1 (Quattro Research GmbH, Munich, Germany). The fitting model for the IC$_{50}$ determinations was "Sigmoidal response (variable slope)" with parameters "top" fixed at 100% and "bottom" at 0%. The fitting method used was a least-squares fit.

Results: The IC$_{50}$ values for all compounds are compiled in Table 1. This table shows all IC$_{50}$ values calculated, as well as the Hill slopes of the corresponding curves. All IC$_{50}$ values that were out of range of the tested concentrations (<3×10$^{-09}$ M; >1×10$^{-04}$M) are marked grey. A Hill slope higher than −0.4 is indicative that the curve is not sigmoidal, very flat or not descending.

Example 2—Assay Condition B (Thiol-Free Conditions)

The IC$_{50}$ profile of compounds was determined using one protein kinase in a customized, thiol free assay. IC$_{50}$ values were measured by testing 10 concentrations (1×10$^{-05}$M to 3×10$^{-10}$ M) of each test compound in singlicate against each kinase of interest. Prior to testing, the 1×10$^{-03}$ M stock solutions in column 2 of the master plates were subjected to a serial, semi-logarithmic dilution using 100% DMSO as a solvent. This resulted in 10 distinct concentrations, with a dilution endpoint of 3×10$^{-08}$ M/100% DMSO in column 12. Column 1 and 7 were filled with 100% DMSO as controls. Subsequently, 2×10 microliter from each well of the serial diluted copy plates were aliquoted with a 96 channel pipettor into two identical sets of "compound dilution plates". All plates were barcoded for automated identification and tracking purposes. IC$_{50}$ values were measured by testing 10 concentrations (1×10$^{-05}$M to 3×10$^{-10}$ M) of each compound in singlicate. All compounds were stored as powder until being solubilized in DMSO. Solubilized compounds were stored as 1×10$^{-02}$M/100% DMSO stock solutions. Prior to the assay process, 90 microliters of H$_2$O were added to each well of a set of compound dilution plates. To minimize potential precipitation, the H$_2$O was added to each plate only a few minutes before the transfer of the compound solutions into the assay plates. Each plate was shaken thoroughly, resulting in compound dilution plates with a final of 10% DMSO. For each assay, 5 microliters of solution from each well of the compound dilution plates/10% DMSO were transferred into the assay plate. The final volume of the assay was 50 µl. All compounds were tested at 10 final assay concentrations in the range from 1×10$^{-05}$M to 3×10$^{-10}$ M, in singlicate. The final DMSO concentration in the reaction cocktails was 1% in all cases. A radiometric protein kinase assay (33PanQinase® Activity Assay) was used for measuring the kinase activity of the protein kinase. All kinase assays were performed in 96-well FlashPlates™ from PerkinElmer (Boston, Mass., USA) in a 50 microliter reaction volume. The reaction cocktail was pipetted in four steps in the following order: 20 microliter of assay buffer (standard buffer)•5 microliter of ATP solution (in H$_2$O)•5 microliter of test compound (in 10% DMSO)•20 microliter enzyme/substrate mix. Each assay for the protein kinase contained 70 mM HEPES-NaOH pH 7.5, 3 mM MgCl$_2$, 3 mM MnCl$_2$, 3 microM Na-orthovanadate, 1 mM TCEP, 50 µg/ml PEG20000, ATP (corresponding to the apparent ATP-Km of the kinase, see Table A), [gamma-33P]-ATP (approx. 6×10× E5 cpm per well), with the protein kinase and relevant substrate being used in pre-determined amounts, depending on the kinase in question. For all experiments labeled as "Thiol-free", all glutathione was exchanged from protein preparations so as to be removed from the assay and final buffer conditions contained no thiol-containing reagents. In addition, the DTT in the thiol-containing assays is replaced by TCEP in the thiol-free assays and all enzymes and substrates are produced under thiol-free conditions for the thiol-free assays. This was done so there would be no interference with the key cysteines in the proteins of interest.

For data analysis, the median value of the counts in column 1 (n=8) of each assay plate was defined as "low control". This value reflects unspecific binding of radioactivity to the plate in the absence of a protein kinase but in the presence of the substrate. The median value of the counts in column 7 of each assay plate (n=8) was taken as the "high control", i.e. full activity in the absence of any inhibitor. The difference between high and low control was taken as 100% activity. As part of the data evaluation the low control value from a particular plate was subtracted from the high control value as well as from all 80 "compound values" of the corresponding plate. The residual activity (in %) for each well of a particular plate was calculated by using the following formula:

Res. Activity (%)=100×[(cpm of compound−low control)/(high control−low control)]

The residual activities for each concentration and the compound $IC_{50}$ values were calculated using Quattro Workflow V3.1.1 (Quattro Research GmbH, Munich, Germany; www.quattro-research.com). The fitting model for the $IC_{50}$ determinations was "Sigmoidal response (variable slope)" with parameters "top" fixed at 100% and "bottom" at 0%. The fitting method used was a least-squares fit. As a parameter for assay quality, the Z'-factor (Zhang et al., J. Biomol. Screen. 2: 67-73, 1999) for the low and high controls of each assay plate (n=8) was used. ProQinase's criterion for repetition of an assay plate is a Z'-factor below 0.4 (Iversen et al., J. Biomol. Screen. 3: 247-252, 2006).

Representative data for exemplary compounds disclosed in Tables 1 or 2 are presented in the following Table 7.

TABLE 7

| Synthetic Chemistry Example | CDK12 $IC_{50}$ A/B | CDK2 $IC_{50}$ A/B | CDK7 $IC_{50}$ A/B |
| --- | --- | --- | --- |
| 1 | C/— | E/— | E/— |
| 2 | C/— | E/— | E/— |
| 3 | C/— | E/— | E/— |
| 4 | C/— | E/— | E/— |
| 5 | C/— | E/— | E/— |
| 6 | D/— | E/— | E/— |
| 7 | E/— | E/— | E/— |
| 8 | D/— | E/— | E/— |
| 9 | D/— | E/— | E/— |
| 10 | C/— | E/— | E/— |
| 11 | C/— | D/— | E/— |
| 12 | C/— | D/— | E/— |
| 13 | B/— | C/— | D/— |
| 14 | B/— | C/— | D/— |
| 15 | C/— | D/— | E/— |
| 16 | D/— | E/— | E/— |
| 17 | E/— | E/— | E/— |
| 18 | D/— | E/— | E/— |
| 19 | E/— | E/— | E/— |
| 20 | E/— | E/— | E/— |
| 21 | D/— | D/— | E/— |
| 22 | E/— | E/— | E/— |
| 23 | E/— | E/— | E/— |
| 24 | D/— | D/— | E/— |
| 25 | A/— | B/— | C/— |
| 26 | A/A | B/C | B/B |
| 27 | A/B | B/C | B/C |
| 28 | A/A | B/C | B/C |
| 29 | B/— | D/— | E/— |
| 30 | B/— | C/— | C/— |
| 31 | A/— | B/— | C/— |
| 32 | A/— | B/— | C/— |
| 33 | A/A | B/B | B/B |
| 34 | A/A | B/C | B/B |
| 35 | A/— | C/— | C/— |
| 36 | B/— | B/— | C/— |
| 37 | A/A | B/B | B/C |
| 38 | A/— | A/— | B/— |
| 39 | A/— | A/— | B/— |
| 40 | A/— | A/— | B/— |
| 41 | A/— | B/— | C/— |
| 42 | A/— | B/— | C/— |
| 43 | A/A | A/B | B/B |
| 44 | B/B | C/C | C/C |
| 45 | B/— | C/— | C/— |
| 46 | B/— | C/— | C/— |
| 47 | B/— | C/— | C/— |
| 48 | C/— | D/— | E/— |
| 49 | C/— | C/— | C/— |
| 50 | B/— | C/— | C/— |
| 51 | B/— | B/— | B/— |
| 52 | B/— | B/— | C/— |
| 53 | B/— | B/— | C/— |
| 54 | B/— | C/— | C/— |
| 55 | B/— | B/— | C/— |
| 56 | A/— | A/— | B/— |
| 57 | A/— | A/— | A/— |
| 58 | A/— | A/— | B/— |
| 59 | A/— | A/— | B/— |
| 60 | A/— | C/— | C/— |
| 61 | A/B | B/B | B/C |
| 62 | A/A | B/C | B/B |
| 63 | B/— | D/— | C/— |
| 64 | C/— | C/— | D/— |
| 65 | B/— | B/— | B/— |
| 66 | C/— | E/— | E/— |
| 67 | A/B | B/D | B/C |
| 68 | B/— | C/— | B/— |
| 69 | A/— | C/— | B/— |
| 70 | A/— | B/— | A/— |
| 71 | A/— | B/— | B/— |
| 72 | A/A | C/C | C/C |
| 73 | B/— | C/— | C/— |
| 74 | B/B | C/C | B/B |
| 75 | C/— | D/— | D/— |
| 76 | C/— | C/— | C/— |
| 77 | A/— | B/— | B/— |
| 78 | B/— | C/— | C/— |
| 79 | A/— | C/— | B/— |
| 80 | A/— | B/— | B/— |
| 81 | B/— | C/— | B/— |
| 82 | B/— | C/— | B/— |
| 83 | C/— | C/— | C/— |
| 84 | B/— | C/— | B/— |
| 85 | C/— | C/— | C/— |
| 86 | B/— | C/— | C/— |
| 87 | B/— | B/— | B/— |
| 88 | A/A | C/C | B/B |
| 89 | B/— | C/— | B/— |
| 90 | B/— | C/— | C/— |
| 91 | B/— | C/— | C/— |
| 92 | A/— | C/— | C/— |
| 93 | A/— | B/— | C/— |
| 94 | B/— | C/— | C/— |
| 95 | B/— | C/— | B/— |
| 96 | C/— | E/— | D/— |

Note:
Biochemical assay $IC_{50}$ data are designated within the following ranges:
A: ≤0.10 μM
B: >0.10 μM to ≤1.0 μM
C: >1.0 μM to ≤10 μM
D: >10 μM to ≤30 μM
E: >30 uM to ≤100 uM III. Preparation of Pharmaceutical Dosage Forms Example 1: Oral Capsule The active ingredient is a compound of Table 1, or a pharmaceutically acceptable salt thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example 2: Solution for Injection

The active ingredient is a compound of Table 1, or a pharmaceutically acceptable salt thereof, and is formulated as a solution in sesame oil at a concentration of 50 mg-eq/mL.

The examples and embodiments described herein are for illustrative purposes only and various modifications or changes suggested to persons skilled in the art are to be included within the spirit and purview of this application and scope of the appended claims.

We claim:

1. A compound, or pharmaceutically acceptable salt or solvate thereof, having the structure of Formula (I):

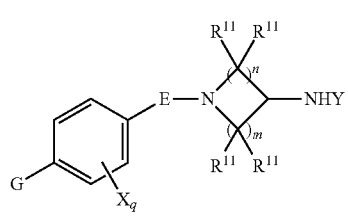

(I)

wherein,

E is selected from —C(O)—;

G is selected from a group having the structure:

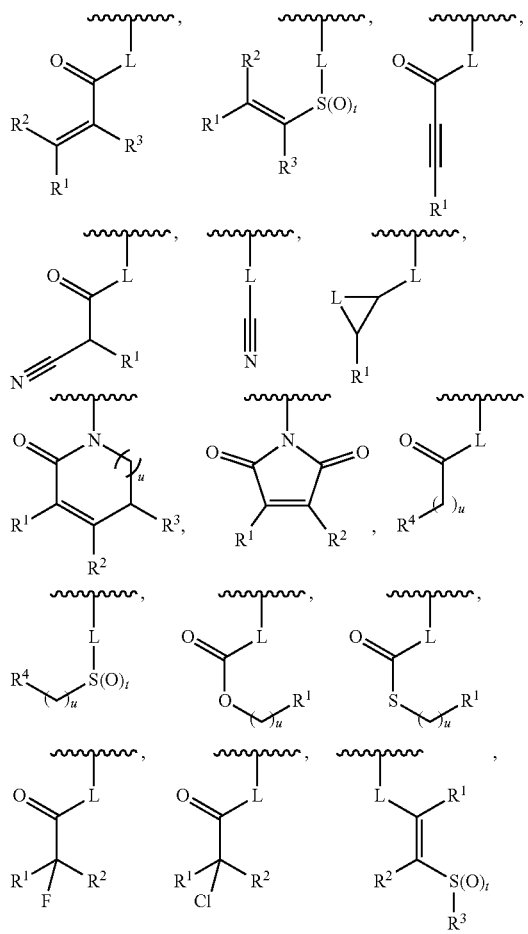

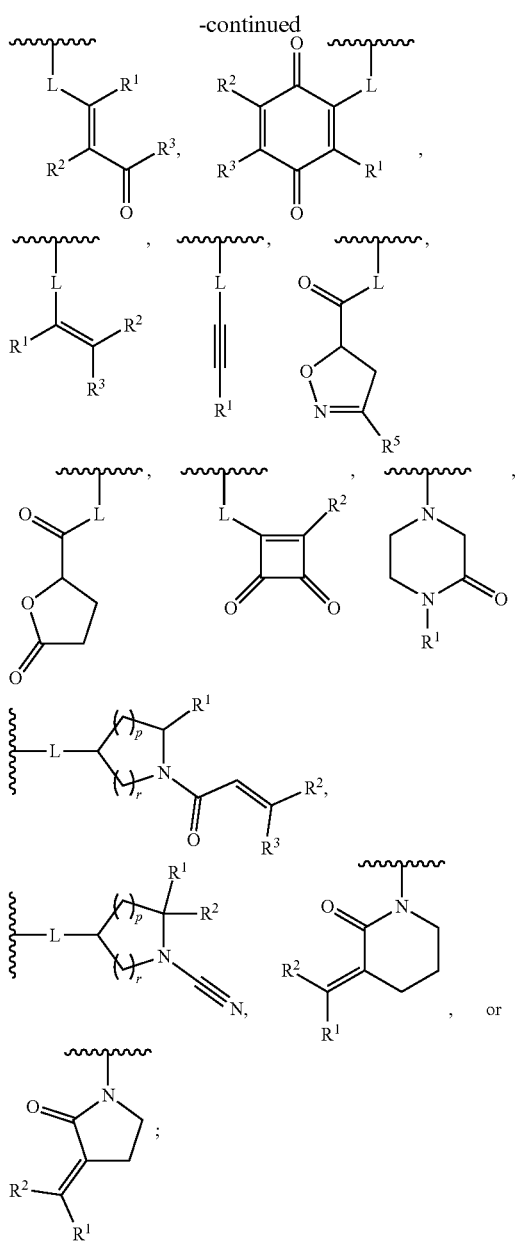

wherein,

L is O, NH, or N (optionally substituted C1-C4 alkyl);

t is 0, 1, or 2;

u is 1, or 2;

p is 0, 1, or 2;

r is 0, 1, or 2;

$R^1$ is selected from hydrogen, optionally substituted C1-C4 alkyl, or optionally substituted heterocyclylalkyl;

$R^2$ is selected from hydrogen, or optionally substituted C1-C4 alkyl;

$R^3$ is selected from hydrogen, —CN, or optionally substituted C1-C4 alkyl;

each $R^4$ is independently selected from optionally substituted C1-C4 alkyl, or optionally substituted heterocyclylalkyl;

$R^5$ is optionally substituted C1-C4 alkyl, or optionally substituted heterocyclylalkyl;

each $R^{11}$ is independently selected from hydrogen, halogen, optionally substituted C1-C6 alkyl, or both $R^{11}$ groups form an oxo;

q is 0, 1, 2, or 3; n is 0, 1, 2, or 3; m is 0, 1, 2, or 3;

X is halogen, optionally substituted C1-C4 alkyl, or optionally substituted C1-C4 alkoxy;

Y is a group selected from:

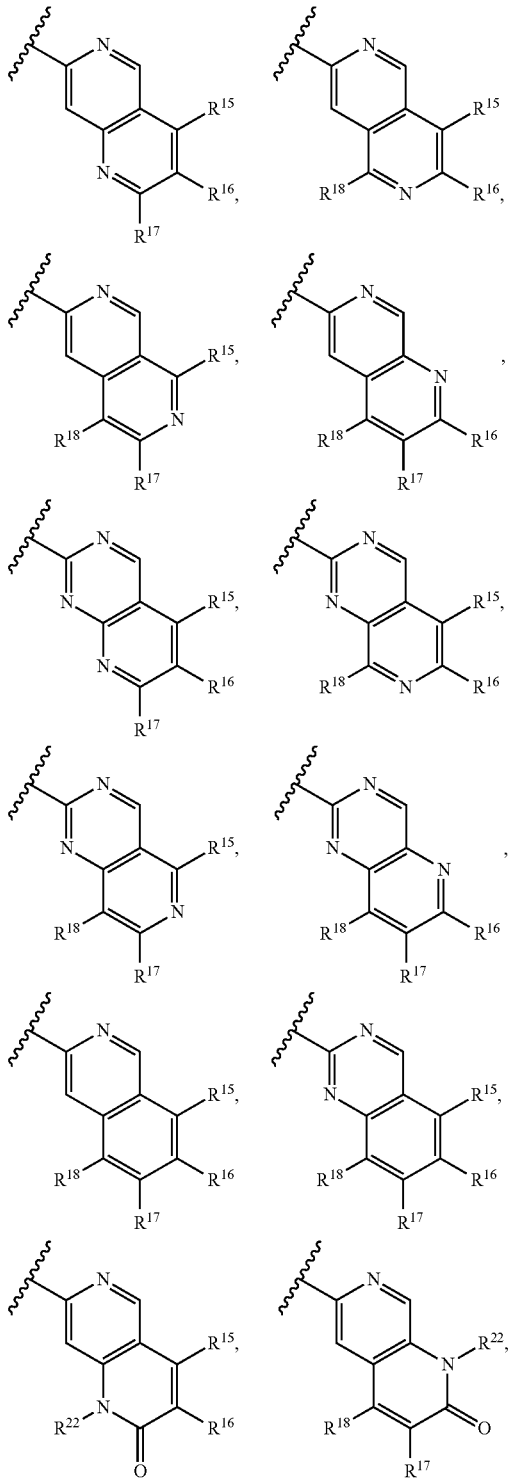

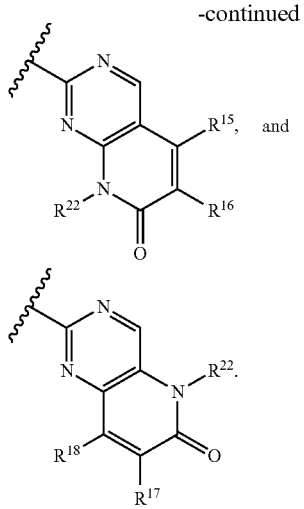

wherein, $R^{15}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

$R^{16}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

$R^{17}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

$R^{18}$ is selected from hydrogen, halogen, —CN, optionally substituted alkyl, optionally substituted alkoxy, optionally substituted cycloalkyl, optionally substituted cycloalkylalkyl, optionally substituted cycloalkyl-O—, optionally substituted aryl, optionally substituted aralkyl, optionally substituted heteroaryl, optionally substituted heteroaralkyl, optionally substituted aryloxy, optionally substituted aralkyloxy, optionally substituted heteroaryloxy, optionally substituted heteroaralkyloxy, —N(R$^{22}$)$_2$, —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{2'}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

each R$^{21}$ is independently selected from alkyl, cycloalkyl, cycloalkylalkyl, aryl, aralkyl, heterocyclyl, heterocyclylalkyl, heteroaryl, or heteroarylalkyl; and each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

2. The compound of claim 1, or pharmaceutically acceptable salt or solvate thereof, wherein G is

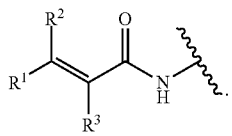

3. The compound of claim 1, or pharmaceutically acceptable salt or solvate thereof, wherein q is 0, 1, or 2.

4. The compound of claim 1, or pharmaceutically acceptable salt or solvate thereof, wherein n is 1 and m is 1.

5. The compound of claim 1, or pharmaceutically acceptable salt or solvate thereof, wherein n is 1 and m is 2.

6. The compound of claim 1, or pharmaceutically acceptable salt or solvate thereof, wherein n is 1 and m is 3.

7. The compound of claim 1, or pharmaceutically acceptable salt or solvate thereof, wherein Y is selected from:

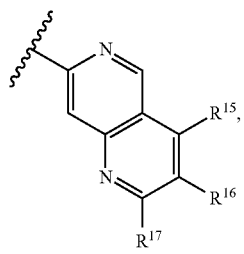

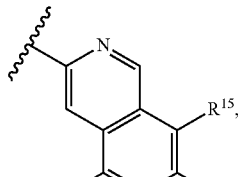

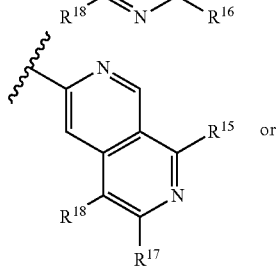

8. The compound of claim 1, or pharmaceutically acceptable salt or solvate thereof, wherein Y is selected from:

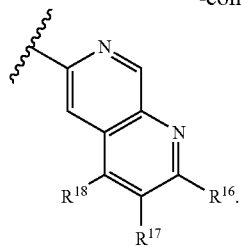

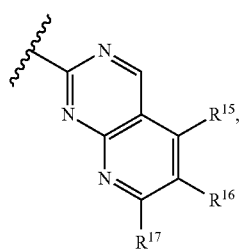

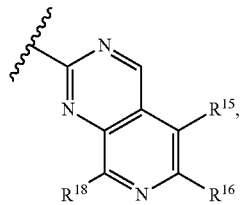

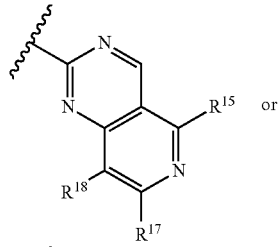

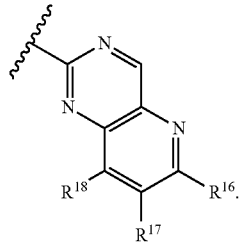

9. The compound of claim 1, or pharmaceutically acceptable salt or solvate thereof, wherein Y is:

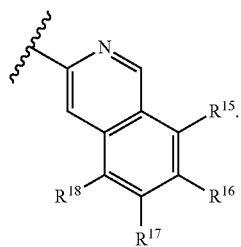

10. The compound of claim 1, or pharmaceutically acceptable salt or solvate thereof, wherein Y is:

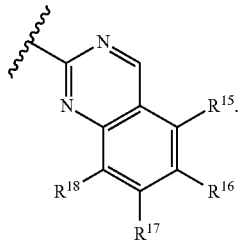

11. The compound of claim 1, or pharmaceutically acceptable salt or solvate thereof, wherein $R^{15}$ is hydrogen.
12. The compound of claim 1, or pharmaceutically acceptable salt or solvate thereof, wherein $R^{16}$ is hydrogen.
13. The compound of claim 1, or pharmaceutically acceptable salt or solvate thereof, wherein $R^{17}$ is hydrogen.
14. The compound of claim 1, or pharmaceutically acceptable salt or solvate thereof, wherein $R^{18}$ is hydrogen.
15. The compound of claim 1, or pharmaceutically acceptable salt or solvate thereof, wherein $R^{15}$ and $R^{16}$ are hydrogen.
16. A compound, or pharmaceutically acceptable salt or solvate thereof, selected from:
- (R)—N-(4-(3-(quinazolin-2-ylamino)piperidine-1-carbonyl)phenyl)acrylamide,
- (R)—N-(4-(3-(isoquinolin-3-ylamino)piperidine-1-carbonyl)phenyl)acrylamide,
- (R)—N-(4-(3-((6-chloroquinazolin-2-yl)amino)piperidine-1-carbonyl)phenyl)acrylamide,
- (R)—N-(4-(3-((6-fluoroquinazolin-2-yl)amino)piperidine-1-carbonyl)phenyl)acrylamide,
- (R)—N-(4-(3-((7-fluoroquinazolin-2-yl)amino)piperidine-1-carbonyl)phenyl)acrylamide,
- (R)—N-(4-(3-((7-methoxyquinazolin-2-yl)amino)piperidine-1-carbonyl)phenyl)acrylamide,
- (R)—N-(4-(3-((6-methoxyquinazolin-2-yl)amino)piperidine-1-carbonyl)phenyl)acrylamide,
- (R)—N-(4-(3-((6-methylquinazolin-2-yl)amino)piperidine-1-carbonyl)phenyl)acrylamide,
- (R)—N-(4-(3-((7-methylquinazolin-2-yl)amino)piperidine-1-carbonyl)phenyl)acrylamide,
- (R)—N-(4-(3-((7-chloroquinazolin-2-yl)amino)piperidine-1-carbonyl)phenyl)acrylamide,
- (R)—N-(4-(3-((7-(methyl sulfonyl)quinazolin-2-yl)amino)piperidine-1-carbonyl)phenyl)acrylamide,
- (R)-2-((1-(4-acrylamidobenzoyl)piperidin-3-yl)amino)-N,N-dimethylquinazoline-7-carboxamide,
- (R)-2-((1-(4-acrylamidobenzoyl)piperidin-3-yl)amino)quinazoline-7-carboxamide,
- (R)-2-((1-(4-acrylamidobenzoyl)piperidin-3-yl)amino)quinazoline-7-carboxylic acid,
- (R)—N-(4-(3-((8-isopropyl-7-oxo-7,8-dihydropyrido[2,3-d]pyrimidin-2-yl)amino)piperidine-1-carbonyl)phenyl)acrylamide,
- (R)—N-(4-(3-((7-oxo-7,8-dihydropyrido[2,3-d]pyrimidin-2-yl)amino)piperidine-1-carbonyl)phenyl)acrylamide,
- (R)—N-(4-(3-((6-chloroquinazolin-2-yl)amino)pyrrolidine-1-carbonyl)phenyl)acrylamide,
- (R)—N-(4-(3-(quinazolin-2-ylamino)pyrrolidine-1-carbonyl)phenyl)acrylamide,
- (R)—N-(4-(3-(isoquinolin-3-ylamino)pyrrolidine-1-carbonyl)phenyl)acrylamide,
- (R)—N-(4-(3-((6-fluoroquinazolin-2-yl)amino)pyrrolidine-1-carbonyl)phenyl)acrylamide,
- (R)—N-(4-(3-((6-methoxyquinazolin-2-yl)amino)pyrrolidine-1-carbonyl)phenyl)acrylamide,
- (R)—N-(4-(3-((6-methylquinazolin-2-yl)amino)pyrrolidine-1-carbonyl)phenyl)acrylamide,
- (R)—N-(4-(3-(pyrido[3,4-d]pyrimidin-2-ylamino)pyrrolidine-1-carbonyl)phenyl)acrylamide,
- (R)—N-(4-(3-((7-methylquinazolin-2-yl)amino)pyrrolidine-1-carbonyl)phenyl)acrylamide,
- (R)—N-(4-(3-((7-(methylsulfonyl)quinazolin-2-yl)amino)pyrrolidine-1-carbonyl)phenyl)acrylamide,
- (R)—N-(4-(3-((7-methoxyquinazolin-2-yl)amino)pyrrolidine-1-carbonyl)phenyl)acrylamide,
- (R)—N-(4-(3-((7-fluoroquinazolin-2-yl)amino)pyrrolidine-1-carbonyl)phenyl)acrylamide,
- (R)—N-(4-(3-((7-chloroquinazolin-2-yl)amino)pyrrolidine-1-carbonyl)phenyl)acrylamide,
- (R)—N-(4-(3-((7-cyanoquinazolin-2-yl)amino)pyrrolidine-1-carbonyl)phenyl)acrylamide,
- (R)-2-((1-(4-acrylamidobenzoyl)pyrrolidin-3-yl)amino)quinazoline-7-carboxylic acid,
- (R)-2-((1-(4-acrylamidobenzoyl)pyrrolidin-3-yl)amino)quinazoline-7-carboxamide,
- (R)-2-((1-(4-acrylamidobenzoyl)pyrrolidin-3-yl)amino)-N-methylquinazoline-7-carboxamide,
- (R)-2-((1-(4-acrylamidobenzoyl)pyrrolidin-3-yl)amino)-N,N-dimethylquinazoline-7-carboxamide,
- (R)—N-(4-(3-((7-oxo-7,8-dihydropyrido[2,3-d]pyrimidin-2-yl)amino)pyrrolidine-1-carbonyl)phenyl)acrylamide,
- (R)—N-(4-(3-((8-isopropyl-7-oxo-7,8-dihydropyrido[2,3-d]pyrimidin-2-yl)amino)pyrrolidine-1-carbonyl)phenyl)acrylamide,
- (R)-2-((1-(4-acrylamidobenzoyl)pyrrolidin-3-yl)amino)-N-methylquinazoline-7-carboxamide, (R)—N-(2-fluoro-4-(3-(quinazolin-2-ylamino)pyrrolidine-1-carbonyl)phenyl)acrylamide,
- N-(4-((3 S,4S)-3-fluoro-4-(quinazolin-2-ylamino)pyrrolidine-1-carbonyl)phenyl)acrylamide,
- N-(4-(3-(quinazolin-2-ylamino)azetidine-1-carbonyl)phenyl)acrylamide, (R,E)-4-(dimethylamino)-N-(4-(3-(quinazolin-2-ylamino)pyrrolidine-1-carbonyl)phenyl)but-2-enamide,
- (R,E)-4-(dimethylamino)-N-(4-(3-(quinazolin-2-ylamino)piperidine-1-carbonyl)phenyl)but-2-enamide,
- (R)—N-(5-(3-(quinazolin-2-ylamino)pyrrolidine-1-carbonyl)pyridin-2-yl)acrylamide,
- (R,E)-4-(dimethylamino)-N-(2-fluoro-4-(3-(quinazolin-2-ylamino)pyrrolidine-1-carbonyl)phenyl)but-2-enamide,
- (R)—N-(2-fluoro-4-(3-((6-fluoroquinazolin-2-yl)amino)pyrrolidine-1-carbonyl)phenyl)acrylamide,
- (R)—N-(4-(3-(quinazolin-2-ylamino)pyrrolidine-1-carbonyl)phenyl)propiolamide,
- (R)—N-(2-methoxy-4-(3-(quinazolin-2-ylamino)pyrrolidine-1-carbonyl)phenyl)acrylamide,
- (R)—N-(2-methyl-4-(3-(quinazolin-2-ylamino)pyrrolidine-1-carbonyl)phenyl)acrylamide,
- N-{3-Methoxy-4-[3-(quinazolin-2-yl amino)-pyrrolidine-1-carbonyl]-phenyl}-acrylamide,
- (R)—N-methyl-N-(4-(3-(quinazolin-2-ylamino)pyrrolidine-1-carbonyl)phenyl)acrylamide,
- (R)—N-(2-fluoro-6-methyl-4-(3-(quinazolin-2-ylamino)pyrrolidine-1-carbonyl)phenyl)acrylamide,

- (R,E)-4-(dimethylamino)-N-(4-(3-((6-fluoroquinazolin-2-yl)amino)pyrrolidine-1-carbonyl)phenyl)but-2-enamide,
- (R)—N-(4-(3-(quinazolin-2-ylamino)pyrrolidine-1-carbonyl)phenyl)but-2-ynamide,
- (R)—N-(3-methyl-4-(3-(quinazolin-2-ylamino)pyrrolidine-1-carbonyl)phenyl)acrylamide,
- (R)-1-(6-(3-(quinazolin-2-ylamino)pyrrolidine-1-carbonyl)-3,4-dihydroquinolin-1(2H)-yl)prop-2-en-1-one,
- (R)-1-(7-(3-(quinazolin-2-ylamino)pyrrolidine-1-carbonyl)-2H-benzo[b][1,4]oxazin-4(3H)-yl)prop-2-en-1-one,
- (R,E)-4-(dimethylamino)-N-(2-methoxy-4-(3-(quinazolin-2-ylamino)pyrrolidine-1-carbonyl)phenyl)but-2-enamide,
- (R,E)-N-(2-chloro-4-(3-(quinazolin-2-ylamino)pyrrolidine-1-carbonyl)phenyl)-4-(dimethylamino)but-2-enamide,
- (R,E)-4-(dimethylamino)-N-(2-methyl-4-(3-(quinazolin-2-ylamino)pyrrolidine-1-carbonyl)phenyl)but-2-enamide,
- (R,E)-4-(dimethylamino)-1-(7-(3-(quinazolin-2-ylamino)pyrrolidine-1-carbonyl)-2H-benzo[b][1,4]oxazin-4(3H)-yl)but-2-en-1-one,
- 4-Dimethylamino-but-2-enoic acid {3-methoxy-4-[3-(quinazolin-2-ylamino)-pyrrolidine-1-carbonyl]-phenyl}-amide,
- (R,E)-4-(dimethylamino)-N-methyl-N-(4-(3-(quinazolin-2-ylamino)pyrrolidine-1-carbonyl)phenyl)but-2-enamide,
- (R)—N-(3-(3-(quinazolin-2-ylamino)pyrrolidine-1-carbonyl)phenyl)acrylamide,
- (R)—N-(2-chloro-4-(3-(quinazolin-2-ylamino)pyrrolidine-1-carbonyl)phenyl)acrylamide,
- (R,E)-4-(dimethylamino)-1-(6-(3-(quinazolin-2-ylamino)pyrrolidine-1-carbonyl)-3,4-dihydroquinolin-1(2H)-yl)but-2-en-1-one,
- (R)—N-(4-(3-((8-fluoroquinazolin-2-yl)amino)pyrrolidine-1-carbonyl)phenyl)acrylamide,
- (R)—N-(4-(3-((5-fluoroquinazolin-2-yl)amino)pyrrolidine-1-carbonyl)phenyl)acrylamide,
- (R)—N-(4-(3-((6-fluoroquinazolin-2-yl)amino)pyrrolidine-1-carbonyl)-2-methylphenyl)acrylamide,
- (R)—N-(2-methyl-4-(3-((7-(methylsulfonyl)quinazolin-2-yl)amino)pyrrolidine-1-carbonyl)phenyl)acrylamide,
- (R)-2-methylene-N-(4-(3-(quinazolin-2-ylamino)pyrrolidine-1-carbonyl)phenyl)butanamide,
- (R)—N-(4-(3-(quinazolin-2-ylamino)pyrrolidine-1-carbonyl)phenyl)ethenesulfonamide, or
- N-(4-((3S,4R)-3-methyl-4-(quinazolin-2-ylamino)pyrrolidine-1-carbonyl)phenyl)acrylamide.

17. A pharmaceutical composition comprising a compound of Formula (I) as described in claim 1, or pharmaceutically acceptable salt or solvate thereof, and a pharmaceutically acceptable excipient.

18. A pharmaceutical composition comprising a compound as described in claim 16, or pharmaceutically acceptable salt or solvate thereof, and a pharmaceutically acceptable excipient.

19. A method of inhibiting a CDK2, CDK7, or CDK12 enzyme, or a combination thereof, comprising contacting the enzyme with a compound of claim 1.

* * * * *